US011555021B2

(12) United States Patent
Ramsden et al.

(10) Patent No.: US 11,555,021 B2
(45) Date of Patent: Jan. 17, 2023

(54) FATTY ACID DERIVATIVES AND THEIR USE

(71) Applicant: THE UNITED STATES OF AMERICA, as represented by the Secretary, Department of Health and Human Services, Bethesda, MD (US)

(72) Inventors: Christopher Ramsden, Baltimore, MD (US); Gregory Keyes, Baltimore, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 21 days.

(21) Appl. No.: 16/622,697

(22) PCT Filed: Jul. 6, 2018

(86) PCT No.: PCT/US2018/041086
§ 371 (c)(1),
(2) Date: Dec. 13, 2019

(87) PCT Pub. No.: WO2019/010414
PCT Pub. Date: Jan. 10, 2019

(65) Prior Publication Data
US 2021/0139440 A1     May 13, 2021

Related U.S. Application Data

(60) Provisional application No. 62/529,846, filed on Jul. 7, 2017.

(51) Int. Cl.
C07D 303/42     (2006.01)
A61P 3/06       (2006.01)
(Continued)

(52) U.S. Cl.
CPC .............. *C07D 303/42* (2013.01); *A61P 3/06* (2018.01); *A61P 17/00* (2018.01); *A61P 25/00* (2018.01); *C07C 59/42* (2013.01); *G01N 33/92* (2013.01)

(58) Field of Classification Search
CPC ....... C07D 303/42; C07D 303/38; A61P 3/06; A61P 17/00; A61P 25/00; A61P 29/00;
(Continued)

(56) References Cited

U.S. PATENT DOCUMENTS 7,550,613 B2     6/2009   Bryhn et al.
2002/0037876 A1*  3/2002  Bar-Tana ............... A61K 31/69
                                                 514/625

FOREIGN PATENT DOCUMENTS

JP     2006-513251 A    4/2006
JP     2012-502035 A    1/2012
(Continued)

OTHER PUBLICATIONS

Bui et al., "Human CYP2S1 Metabolizes Cyclooxygenase- and Lipoxygenase-Derived Eicosanoids," *Drug Metabolism & Disposition* 39.2: 180-190, Feb. 2011.
(Continued)

*Primary Examiner* — Taylor V Oh
(74) *Attorney, Agent, or Firm* — Klarquist Sparkman, LLP

(57) ABSTRACT

This disclosure concerns fatty acid derivatives, pharmaceutical compositions comprising the fatty acid derivatives, and methods of using the fatty acid derivatives, for example, to treat inflammation, chronic itch, chronic pain, an autoimmune disorder, atherosclerosis, a skin disorder, arthritis, a neurodegenerative disorder, or a psychiatric disorder in a subject. In some embodiments, the fatty acid derivative is a
(Continued)

compound, or a stereoisomer, tautomer, or pharmaceutically acceptable salt thereof, having a structure according to:

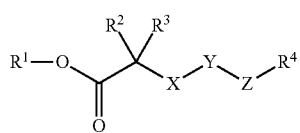

(I)

wherein X is from 1-16 carbons in length, Z is aliphatic from 1-16 carbons in length, or is not present, Y is selected from:

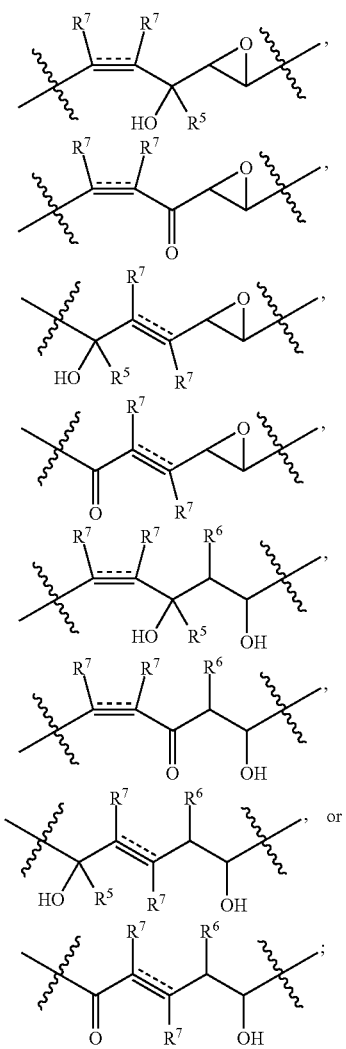

$R^1$, $R^2$, and $R^3$ are independently hydrogen or lower alkyl, $R^4$ is lower alkyl, hydroxyl, carboxyl, or amine, $R^5$ is hydrogen, lower alkyl, or halide, $R^6$ is hydroxyl or substituted thiol, and each $R^7$ is independently hydrogen or fluoride or is not present and the adjacent carbons form alkyne.

16 Claims, 24 Drawing Sheets

(51) Int. Cl.
G01N 33/92 (2006.01)
A61P 25/00 (2006.01)
C07C 59/42 (2006.01)
A61P 17/00 (2006.01)

(58) Field of Classification Search
CPC ......... C07C 59/42; C07C 33/03; C07C 49/24; G01N 33/92; A61K 31/336; A61K 31/201
USPC ....................................................... 514/475
See application file for complete search history.

(56) References Cited

FOREIGN PATENT DOCUMENTS

| | | |
|---|---|---|
| JP | 2015-51848 A | 7/2015 |
| WO | WO 1994/22848 A1 | 10/1994 |
| WO | WO 2004/067489 A2 | 8/2004 |
| WO | WO 2006/106438 A2 | 10/2006 |
| WO | WO 2008/104976 A1 | 9/2008 |
| WO | WO 2010/027762 A1 | 3/2010 |
| WO | WO 2013/157955 A1 | 10/2013 |

OTHER PUBLICATIONS

Burkey et al., "Isolation and Culture of Sensory Neurons from the Dorsal-Root Ganglia of Embryonic or Adult Rats," *Methods in Molecular Medicine* 99: 189-202, 2004.
Chiba et al., "The Precise Structures and Stereochemistry of Trihydroxy-linoleates Esterified in Human and Porcine Epidermis and Their Significance in Skin Barrier Function," *J of Bio Chem.* 291.28: 14540-14554, Jul. 2016.
Garssen et al., "The Formation of threo-11-Hydroxy-trans-12: 13-epoxy-9-cis-octadecenoic Acid by Enzymic Isomerisation of 13-L-Hydroperoxy-9-cis, 11-trans-octadecadienoic Acid by Soybean Lipoxygenase-1," *Eur J Biochem* 62.1: 33-36, Feb. 1976.
Goswami et al., "Itch-Associated Peptides: RNA-Seq and Bioinformatic Analysis of Natriuretic Precursor Peptide B and Gastrin Releasing Peptide in Dorsal Root and Trigeminal Ganglia, and the Spinal Cord," *Molecular Pain* 10.44: 1-8, Aug. 2014.
Han et al., "Intracellular Signaling and the Origins of the Sensations of Itch and Pain," *Sci Signal.* 4.187: er3, Aug. 2011.
ISA European Patent Office, International Search Report and Written Opinion for PCT/US2018/041086, dated Oct. 24, 2018, 12 pages.
Kato et al., "Structural Elucidation of 11-Hydroxy-12,13-epoxyoctadeca-(9Z, 15Z)-dienoic Acids from Rice Plants Suffering from Rice Blast Disease," *J Chem Soc, Chem Commun.* 70:743-744, Jan. 1986.
Kelley et al., "Role of the DNA Base Excision Repair Protein, APE1 in Cisplatin, Oxaliplatin, or Carboplatin Induced Sensory Neuropathy," *PLos One* 9.9: e106485, Sep. 2014.
Lin et al., "Synthesis of Six Epoxyketooctadecenoic Acid (EKODE) Isomers, Their Generation from Nonenzymatic Oxidation of Linoleic Acid, and Their Reactivity with Imidazole Nucleophiles," *J Org Chem.* 72: 9471-9480, Nov. 2007.
MacIntosh et al., "Low-n-6 and Low-n-6 Plus High-n-3 Diets for Use in Clinical Research," *Br J Nutr.* 110.3: 559-568, Aug. 2013.
Munoz-Garcia et al., "The Importance of the Lipoxygenase-Hepoxilin Pathway in the Mammalian Epidermal Barrier," *Biochim Biophys Acta* 1841.3: 401-408, Mar. 2014.
Oliw et al., "Payne Rearrangement During Analysis of Epoxyalcohols of Linoleic and α-Linolenic Acids by Normal Phase Liquid Chromatography with Tandem Mass Spectrometry," *Anal Biochem.* 354: 111-126, May 2006.
Patwardhan et al., "Activation of TRPV1 in the Spinal Cord by Oxidized Linoleic Acid Metabolites Contributes to Inflammatory Hyperalgesia," *PNAS* 106.44: 18820-18824, Nov. 2009.
Patwardhan et al., "Heat Generates Oxidized Linoleic Acid Metabolites that Activate TRPV1 and Produce Pain in Rodents," *J Clin Invest.* 120.5: 1617-1626, May 2010.

(56) References Cited

OTHER PUBLICATIONS

Ramsden et al., "Low Omega-6 vs. Low Omega-6 Plus High Omega-3 Dietary Intervention for Chronic Daily Headache: Protocol for a Randomized Clinical Trial," *Trials* 12.97: 1-11, Apr. 2011.
Ramsden et al., "Targeted Alteration of Dietary n-3 and n-6 Fatty Acids for the Treatment of Chronic Headaches: A Randomized Trial," *Pain* 154.11: 2441-2451, Nov. 2013.
Ramsden et al., "Targeted Alterations in Dietary n-3 and n-6 Fatty Acids Improve Life Functioning and Reduce Psychological Distress Among Chronic Headache Patients: Secondary Analysis of a Randomized Trial," *Pain* 156.4: 587-596, Apr. 2015.
Ramsden et al., "Dietary Linoleic Acid-Induced Alterations in Pro- and Anti-Nociceptive Liquid Autacoids: Implications for Idiopathic Pain Syndromes?" *Molecular Pain* 12: 1-14, Mar. 2016.
Ramsden et al., "A Systems Approach for Discovering Linoleic Acid Derivatives that Potentially Mediate Pain and Itch," *Sci Signal.* 10: eaa15241, Aug. 2017.
Spiteller et al., "Oxidation of Linoleic Acid in Low-Density Lipoprotein: An Important Event in Atherogenesis," *Angew Chem Int Ed.* 39.9: 585-589, 2000.
Swindell et al., "Proteogenomic Analysis of Psoriasis Reveals Discordant and Concordant Changes in mRNA and Protein Abundance," *Genome Medicine* 7.86: 1-22, Aug. 2015.
Sun et al., "Roles of Proton-Sensing Receptors in the Transition from Acute to Chronic Pain," *J Dent Res.* 95.2: 135-142, Feb. 2016.
Zheng et al., "Lipoxygenases Mediate the Effect of Essential Fatty Acid in Skin Barrier Formation," *J Bio Chem.* 286.27: 24046-24056, Jul. 2011.
Zhu et al., "Mass Spectrometric Characterization of Protein Modification by the Products of Nonenzymatic Oxidation of Linoleic Acid," *Chem Res Toxicol.* 22.8: 1386-1397, Jun. 2009.
Kodama, Mitsuaki et al., "Synthesis of Macrocyclic Terpenoids by Intramolecular Cyclization, XI. Total Synthesis of Zerumbone," *Chem. Pharm. Bull.* 1987, vol. 35, No. 10, pp. 4039-4042.
Official Action, dated Jul. 27, 201212, issued in corresponding Japan Patent Application No. 2019-572570, and machine-based English-language translation, 10 pages.

* cited by examiner

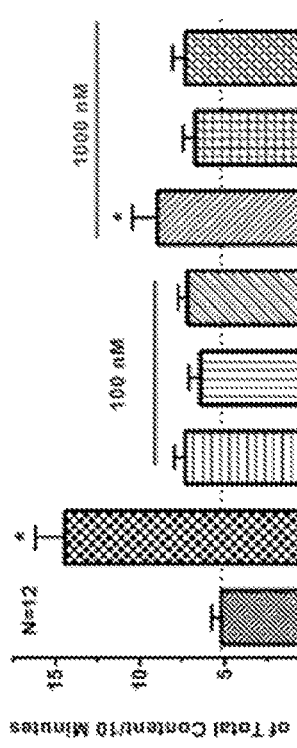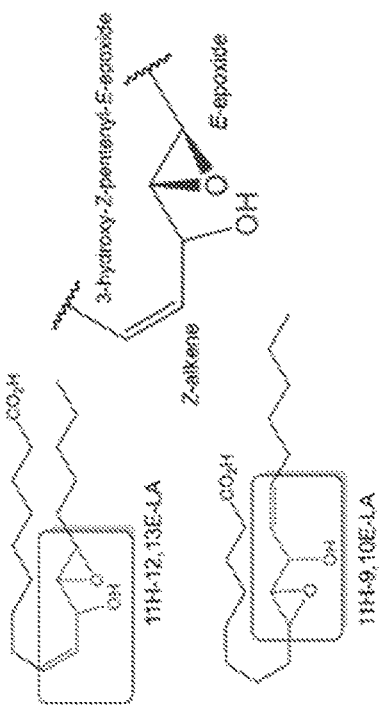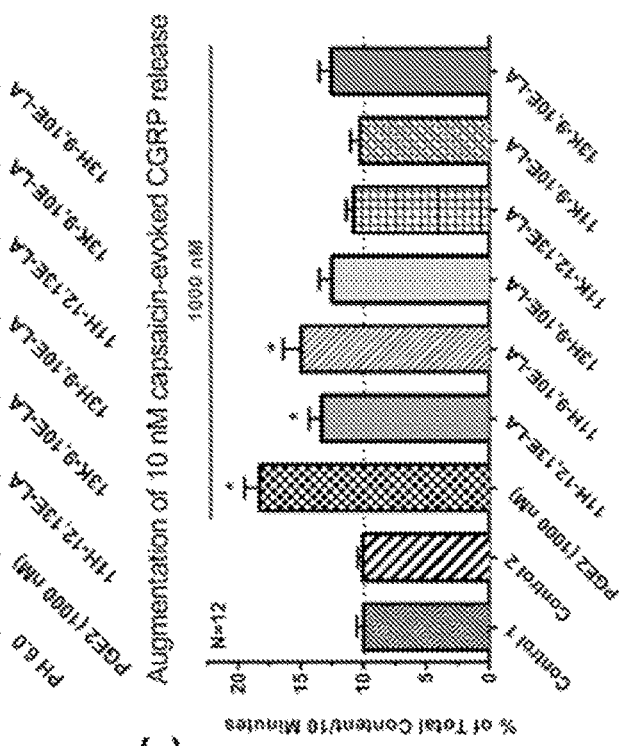

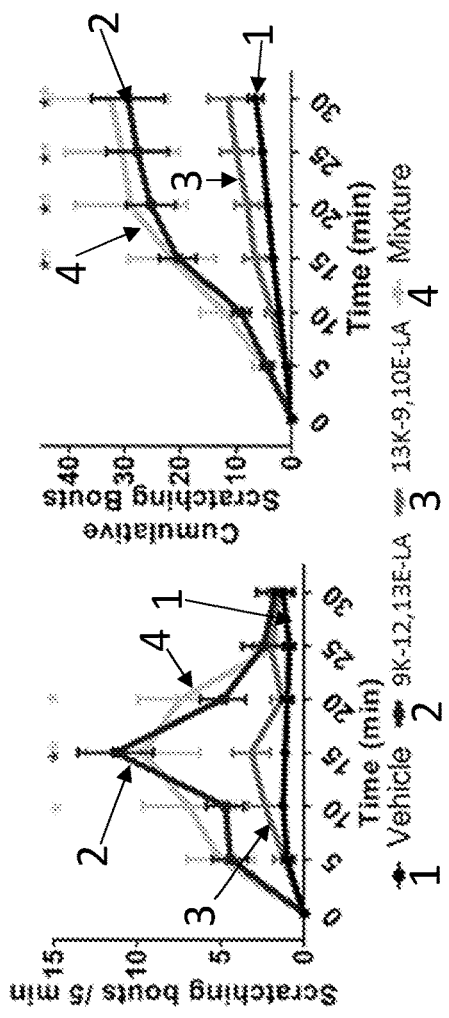
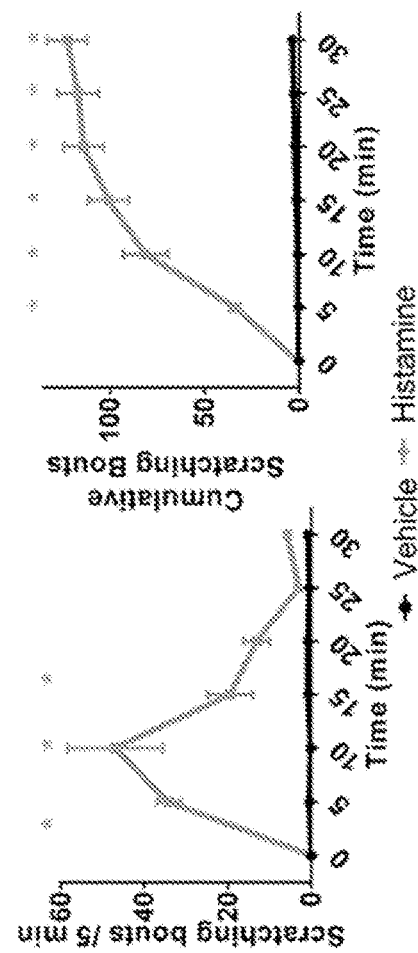
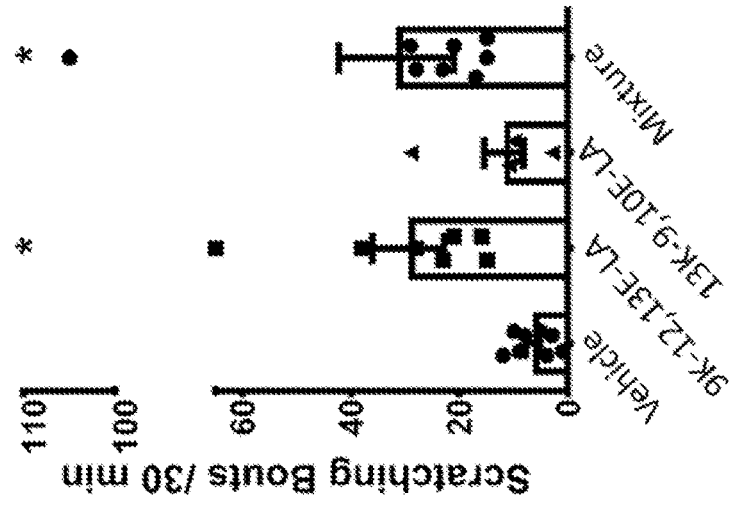
FIG. 4A
FIG. 4B
FIG. 4C

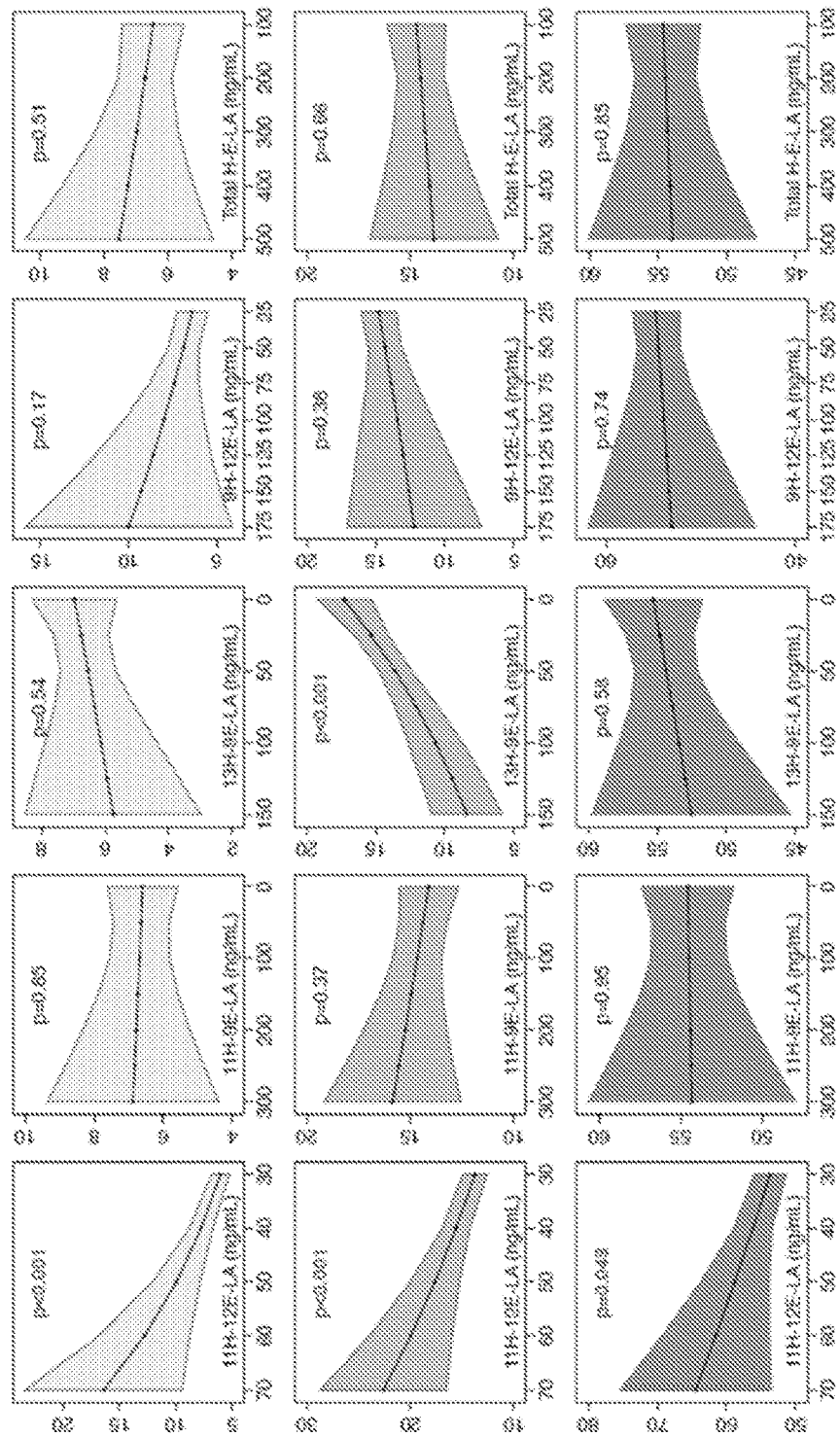
FIG. 5A
FIG. 5B
FIG. 5C
FIG. 5D

LC-MS of 13-hydroxy-9,10-*trans*-epoxy-(11*E*)-octadecenoic acid reacted under esterification conditions (positive LC-MS mode)

LC-MS of 13-hydroxy-9,10-*trans*-epoxy-(11*E*)-octadecenoic acid reacted under esterification conditions (negative LC-MS mode)

LC-MS of 9,10,13-trihydroxy-(11E)-octadecenoic acid reacted under esterification conditions (positive LC-MS mode)

LC-MS of 9,10,13-trihydroxy-(11E)-octadecenoic acid reacted under esterification conditions (negative LC-MS mode)

LC-MS of 2,2-dimethyl-13-hydroxy-9,10-*trans*-epoxy-(11*E*)-octadecenoic acid reacted under esterification conditions (positive LC-MS mode)

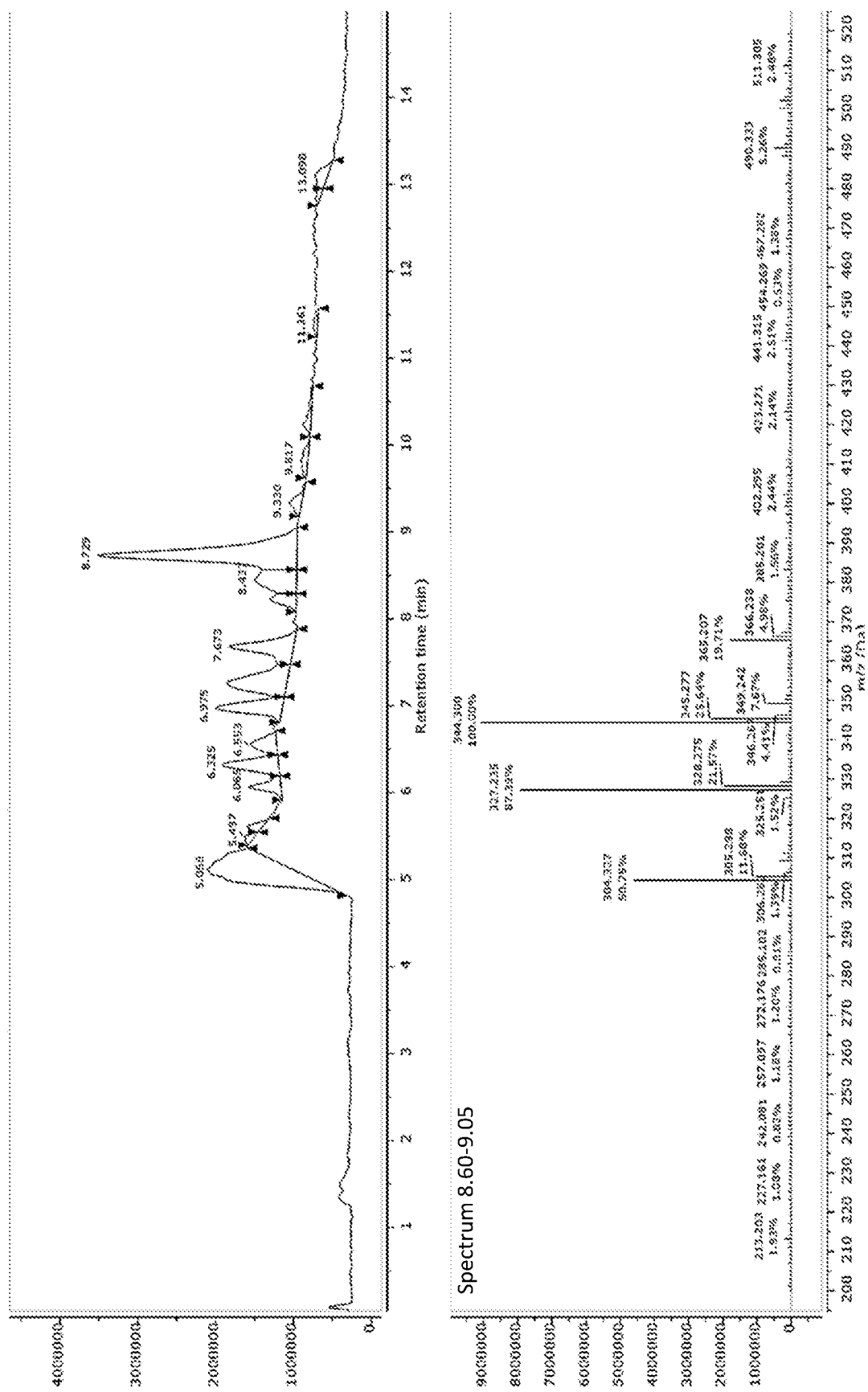

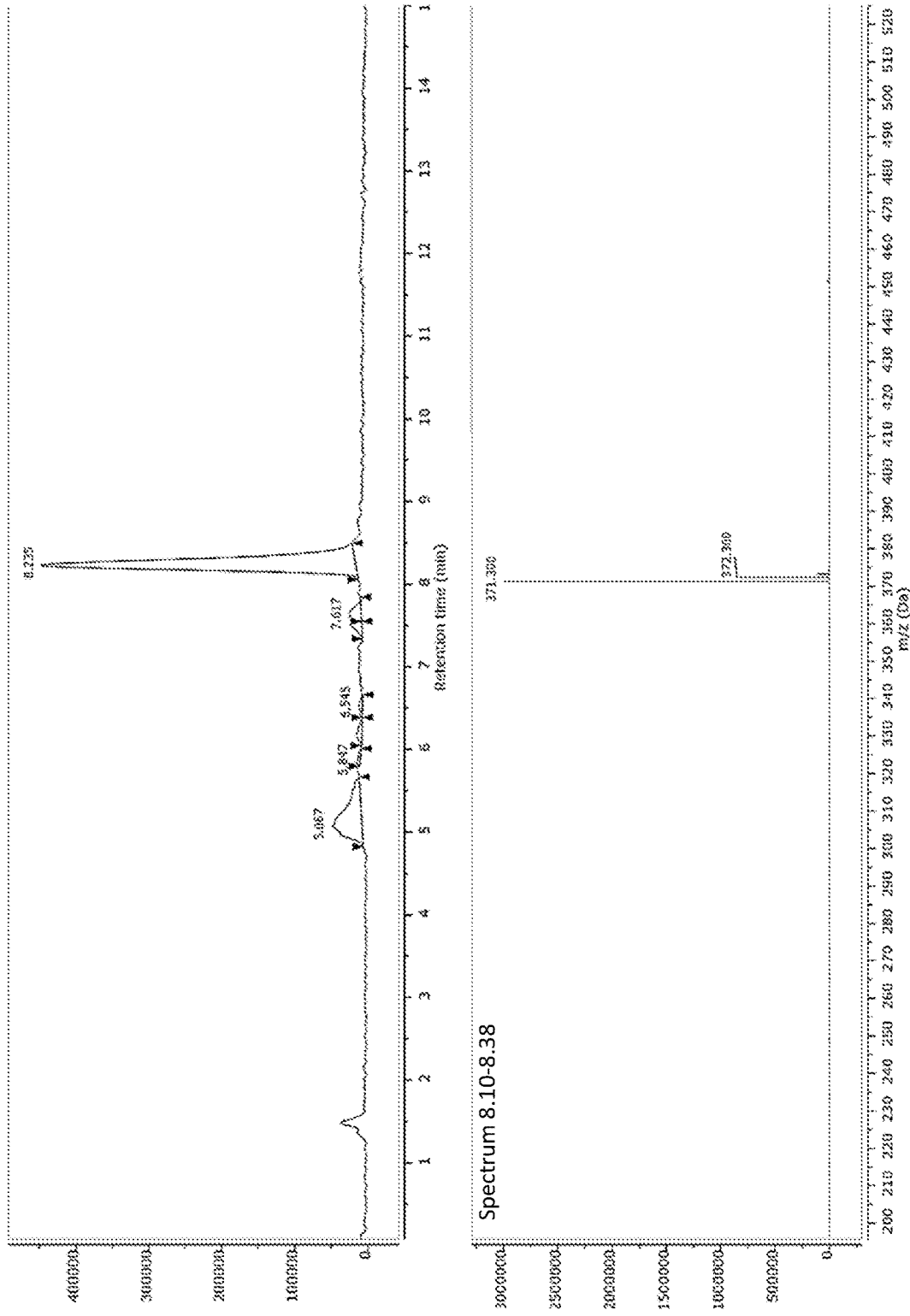
FIG. 17  LC-MS of 2,2-dimethyl-4-hydroxy-DHA reacted under esterification conditions (positive LC-MS mode)

FIG. 18

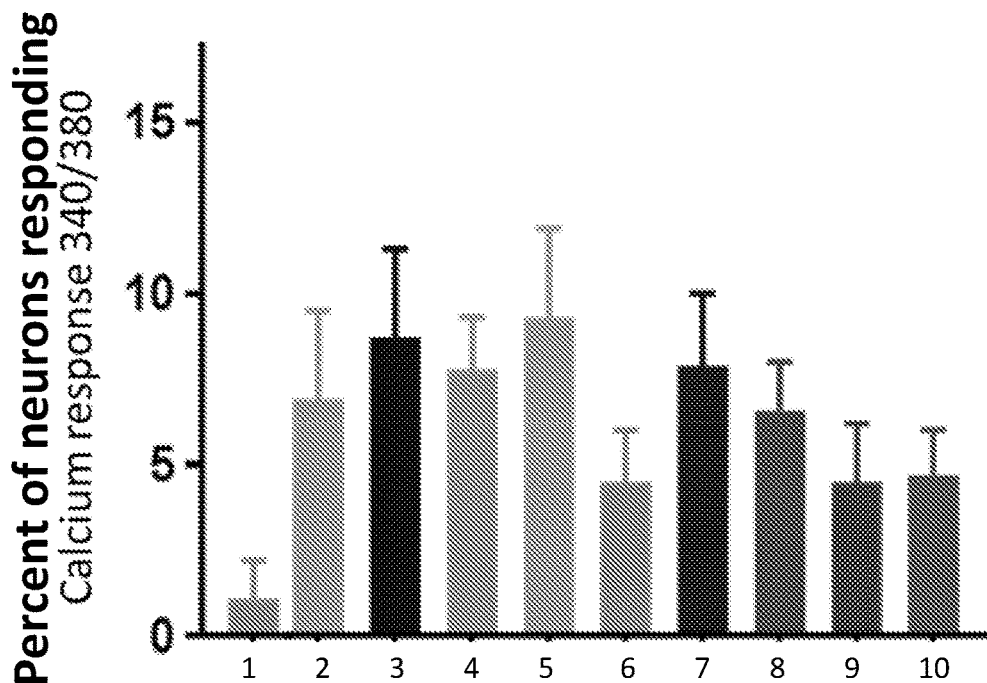

(1) Vehicle
(2) 13-hydroxy-9,10-epoxy-octadecenoate
(3) 13,9,10-trihydroxy-octadecenoate
(4) 2,2-dimethyl-13-hydroxy-9,10-epoxy-octadecenoate
(5) 13-methyl/hydroxyl-9,10-epoxy-octadecenoate
(6) 2,2-dimethyl-13-methyl/hydroxy-9,10-epoxy-octadecenoa
(7) Broad epoxyalcohol pharmacophore (1,5-epoxyalcohol)
(8) 2,2-dimethyl-13-methyl/hydroxy-9,10-diydroxy-octadecenoate
(9) Broad triol pharmacophore (1,5-triol)
(10) 2,2-dimethyl-13,9,10-trihydroxy-octadecenoate

FATTY ACID DERIVATIVES AND THEIR USE

CROSS REFERENCE TO RELATED APPLICATIONS

This is the U.S. National Stage of International Application No. PCT/US2018/041086 filed Jul. 6, 2018, which was published in English under PCT Article 21(2), which in turn claims the benefit of U.S. Provisional Application No. 62/529,846 filed Jul. 7, 2017. The provisional application is incorporated by reference herein in its entirety.

FIELD

This disclosure concerns fatty acid derivatives and methods of their use, for example, to treat inflammation, itch, pain, autoimmunity, and/or atherosclerosis in a subject.

BACKGROUND

Biological processes such as inflammation, itch, pain, autoimmunity, barrier dysfunction, degeneration, and atherosclerosis present ongoing problems for the medical field, partially in the context of patient treatment and evaluation. Although treatments for these diseases and conditions are available, they often fall short of demonstrated need. Accordingly, there is a need for new agents that can be used in a method of treating a subject having one or more of these diseases or conditions.

SUMMARY

This disclosure concerns fatty acid derivatives, pharmaceutical compositions comprising the fatty acid derivatives, and methods of using the fatty acid derivatives, for example, to treat inflammation, itch, pain, autoimmunity, atherosclerosis, and/or a skin disorder in a subject.

In some embodiments, the disclosed fatty acid derivatives are derivatives of labile endogenous bioactive compounds that are designed to maintain the effects of the corresponding endogenous bioactive compounds while maximizing stability, activity, and ease of delivery to a subject.

In some embodiments, the fatty acid derivative is a compound, or a stereoisomer, tautomer, or pharmaceutically acceptable salt thereof, having a structure according to:

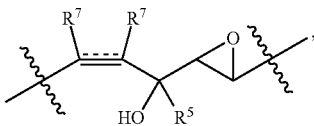

(I)

wherein X is aliphatic from 1-16 carbons in length, Z is aliphatic from 1-16 carbons in length, or is not present, Y is selected from any one of:

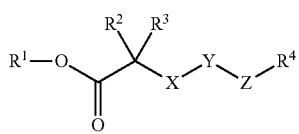

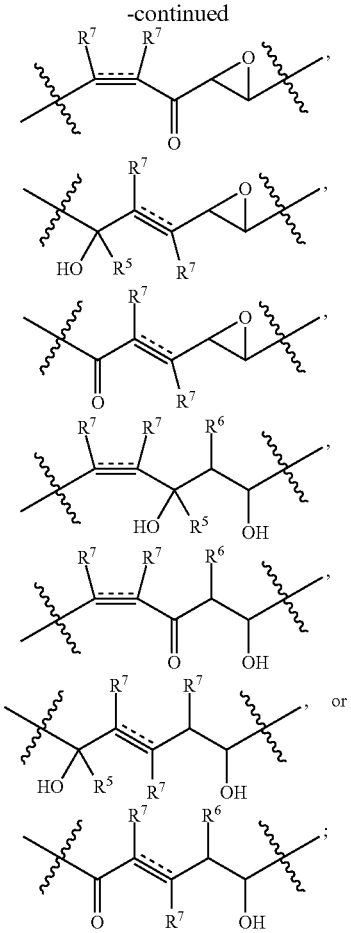

$R^1$, $R^2$, and $R^3$ are independently hydrogen or lower alkyl, $R^4$ is lower alkyl, hydroxyl, carboxyl, or amine, $R^5$ is hydrogen, lower alkyl, or halide, $R^6$ is hydroxyl or substituted thiol, and each $R^7$ is independently hydrogen or fluoride or is not present and the adjacent carbons form alkyne. In some embodiments, X and Z are independently alkynyl, or substituted or unsubstituted alkenyl. In some embodiments, X and Z independently are lower alkenyl and comprise one or more fluoroalkene or difluoroalkenle moieties.

In some embodiments, a method of treating a disease or condition in a subject using a disclosed fatty acid derivative is provided. The method comprises administering a therapeutically effective amount of a pharmaceutical composition comprising a disclosed fatty acid derivative to a subject having, or suspected of having, the disease or condition. Exemplary diseases or conditions for which the method can be applied include inflammation, chronic itch, chronic pain, an autoimmune disorder, atherosclerosis, a skin disorder, arthritis, a neurodegenerative disorder, or a psychiatric disorder.

In some embodiments, a method of diagnosing a disease or condition in a subject by measuring a level of a disclosed fatty acid derivative in a biological sample from the subject is provided. The method comprises obtaining a biological sample from the subject, measuring a level of any one of compounds 1-16 as provided herein in the biological sample; and diagnosing the subject as a subject with the disease or condition if an elevated level of the compound is detected in the biological sample compared to a normal control. Exemplary diseases or conditions for which the method can be applied include inflammation, chronic itch, chronic pain, an autoimmune disorder, and atherosclerosis.

Embodiments of a pharmaceutical composition are also provided, and include a fatty acid derivative as disclosed herein and a pharmaceutically acceptable carrier. The pharmaceutical composition may be formulated, for example, for topical, parenteral, or oral administration.

The foregoing and other features and advantages of this disclosure will become more apparent from the following detailed description of several embodiments which proceeds with reference to the accompanying figures.

BRIEF DESCRIPTION OF THE DRAWINGS

FIGS. 2A-2D. Regio-selective augmentation of calcitonin gene related peptide (CGRP) release from adult rat dorsal root ganglia (DRG) neurons (blinded analyses). Ex Vivo CGRP release measured from adult DRG neuronal cultures. Assayed compounds included: 11H-12,13E-LA (Compound 1), 11H-9,10E-LA (Compound 3), 11K-9,10E-LA (Compound 4), 9H-12,13E-LA (Compound 5), 9K-12,13E-LA (Compound 6), 13H-9,10E-LA (Compound 7), 11-keto(K)-12,13-trans-epoxy-(E)-octadecenoate (11K-12,13E-LA, Compound 2), and 13-keto(K)-9,10-trans-epoxy-(E)-octadecenoate (13K-9,10E-LA, Compound 8). At 1 µM concentrations, prostaglandin E2 (PGE2), 11H-12,13E-LA (FIGS. 2A and 2C) and 11H-9,10E-LA (FIGS. 2B and 2C) significantly augmented both low-pH-evoked and capsaicin-evoked CGRP release. 13H-9,10E-LA (FIGS. 2A and 2C) significantly augmented low pH-evoked CGRP release but had no effect on capsaicin-evoked release. (FIG. 2D) The shared 3-hydroxy-Z-pentenyl-E-epoxide moiety that is unique to these two lipids is the proposed pharmacophore mediating the effects of 11H-12,13E-LA and 11H-9,10E-LA. *indicates p<0.05 using ANOVA with Tukey's post hoc test. CGRP, calcitonin gene-related peptide.

(FIG. 3A) 11-hydroxy-12,13-epoxy-octadecenoate and PGE2 decreased C-fiber withdrawal latency responses compared to vehicle control. (FIG. 3B) PGE2 increased the proportion of withdrawal responses following Aδ fiber stimulation. N=12, 11, 10 for vehicle, 11-hydroxy-12,13-epoxy-octadecenoate, and PGE2, respectively.

FIGS. 4A-4C. Itch-related scratching responses after intradermal injection of disclosed fatty acid derivatives (blinded analyses). (FIG. 4A) Intradermal injection of disclosed fatty acid derivatives (100 µg) showed increased scratching responses to 9K-12,13E-LA, and to a mixture of 9K-12,13E-LA plus 13K-9,10E-LA (100 ug of each), but no response to 13K-9,10E-LA alone. N=8, 7, 6, 8 for vehicle, 9K-12,13E-LA, 13K-9,10E-LA and the mixture, respectively. (FIG. 4B) Scratching responses evoked by 9K-12,13E-LA became statistically greater than vehicle and reached a maximum at 10-15 minutes, and declined gradually thereafter. (FIG. 4C) Scratching responses evoked by histamine (50 µg) were significantly greater than vehicle within 5 minutes, reached a maximum at 5-10 minutes, and declined precipitously thereafter. N=6 for Histamine and control.

FIG. 5A-5D. Diet-induced decrease in plasma 11H-12,13E-LA correlated with clinical pain reduction. FIG. 5A shows that dietary LA lowering for 12 weeks decreased the plasma concentrations of 11H-12,13E-LA, 13H-9,10E-LA and total hydroxy-epoxy-octadecenoates in patients with chronic daily headache (n=44). FIGS. 5B-5D show that diet-induced reductions in 11H-12,13E-LA correlated with decreased headache hours per day (n=40), headache days per month (n=44), and headache impact (n=44). Graphs include the headache outcomes (y-axes) vs the fatty acid derivatives concentration at week 12 (x-axis) based on a Poisson regression model controlling for each outcome and fatty acid derivative concentration at baseline. The dashed lines in FIG. 5A indicate the limit of quantitation. 95% confidence intervals in FIGS. 5B-5D are shown with grey shading.

(FIG. 7A) 11-hydroxy epoxides and 11-keto-epoxides elicit concentration-dependent Ca2+ transients in mouse trigeminal sensory neurons in a blinded screen of 4 compounds. Concentration-response curves illustrate the increase in the number of cells responding to 11H-12,13E-LA and 11H-9,10E-LA (FIG. 7B).

FIG. 15. Retention time and mass spectrum obtained from LC-MS analysis of 4-hydroxy-DHA and 4-hydroxy-DHA lactone following incubation under esterification conditions.

FIG. 17. Retention time and mass spectrum obtained from LC-MS analysis of 2,2-dimethyl-4-hydroxy-DHA following incubation under esterification conditions.

FIG. 18. Endogenous lipids and novel compounds activate primary murine sensory neurons. The y-axis shows the percentage of murine dorsal root ganglia sensory neurons responding to endogenous mediators, stable analogs and small molecules containing their proposed pharmacophores. All compounds were tested at 1 µM with responses normalized to potassium chloride (KCL). Error bars represent standard error of the mean. ≥300 KCl-positive cells from ≥5 mice were tested for each compound.

DETAILED DESCRIPTION

Figure 1:
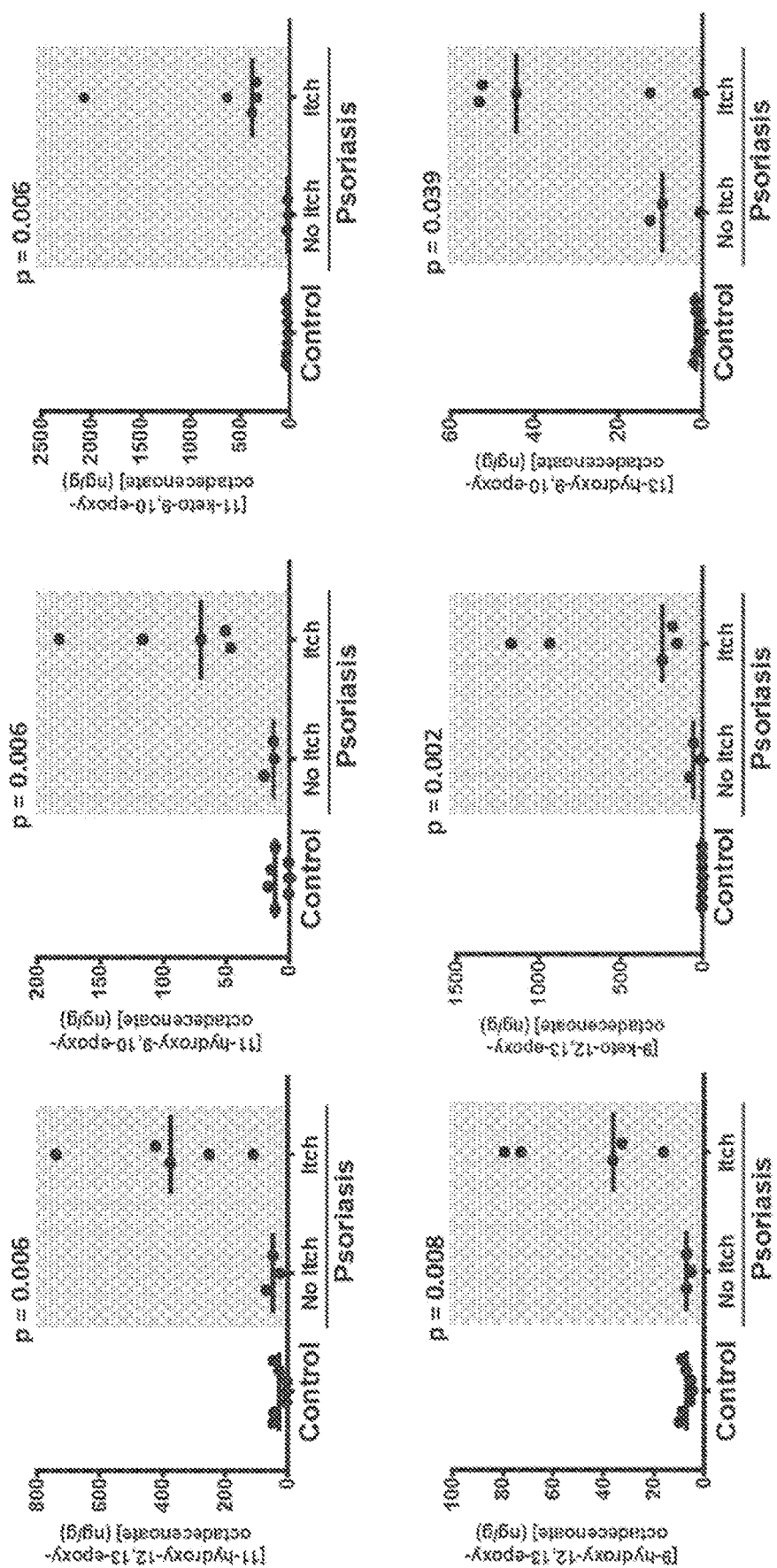
FIG. 1. Free hydroxy-epoxy- and keto-epoxy-octadecenoates are elevated in psoriatic skin lesions (especially itchy skin). Concentrations of free hydroxy-epoxy- and keto-epoxy-octadecenoates in psoriatic lesion and control human skin are shown. The compounds assayed are:
11-hydroxy(H)-12,13-trans-epoxy-(E)-octadecenoate (11H-12,13E-LA, Compound 1),
11-hydroxy(H)-9,10-trans-epoxy-(E)-octadecenoate (11H-9,10E-LA, Compound 3),
11-keto(K)-9,10-trans-epoxy-(E)-octadecenoate (11K-9,10E-LA, Compound 4),
9-hydroxy(H)-12,13-trans-epoxy-(E)-octadecenoate (9H-12,13E-LA, Compound 5),
9-keto(K)-12,13-trans-epoxy-(E)-octadecenoate (9K-12,13E-LA, Compound 6), and
13-hydroxy(H)-9,10-trans-epoxy-(E)-octadecenoate (13H-9,10E-LA, Compound 7). Statistical analysis was performed using the Kruskal-Wallis test. N=7, 3, and 5 for control skin, psoriasis lesion (no itch), and psoriasis lesion (itch), respectively.

This disclosure concerns a family of fatty acid derivatives that are shown to be active in in vitro and in vivo models of inflammation, nociceptive/pruriceptive sensitization, epithelial barrier integrity, lipoprotein function and atherosclerosis. Accordingly, the disclosed compounds regulate multiple highly leveraged cellular processes. Several of the identified fatty acid derivatives are present endogenously. Additional derivatives are also provided that share a functional moiety of an identified endogenous compound, and are modified to maintain or antagonize the effects of the corresponding endogenous bioactive compounds while maximizing stability, activity, and ease of delivery to a subject.

I. TERMS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Although the steps of some of the disclosed methods are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" and "provide" to describe the disclosed methods. These terms are high-level abstractions of the actual steps that are performed. The actual steps that correspond to these terms will vary depending on the particular implementation and are readily discernible by one of ordinary skill in the art.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Compound embodiments disclosed herein may contain one or more asymmetric elements such as stereogenic centers, stereogenic axes and the like, e.g., asymmetric carbon atoms, so that the chemical conjugates can exist in different stereoisomeric forms. These compound embodiments can be, for example, racemates or optically active forms. For compound embodiments with two or more asymmetric elements, these compound embodiments can additionally be mixtures of diastereomers. For compound embodiments having asymmetric centers, all optical isomers in pure form and mixtures thereof are encompassed by corresponding generic formulas unless context clearly indicates otherwise or an express statement excluding an isomer is provided. In these situations, the single enantiomers, i.e., optically active forms can be obtained by method known to a person of ordinary skill in the art, such as asymmetric synthesis, synthesis from optically pure precursors, or by resolution of the racemates. Resolution of the racemates can also be accomplished, for example, by conventional methods, such as crystallization in the presence of a resolving agent, or chromatography, using, for example a chiral HPLC column. All isomeric forms are contemplated herein regardless of the methods used to obtain them.

Administration: To provide or give to a subject an agent, for example, a disclosed fatty acid derivative, by any effective route. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

Alkyl: A hydrocarbon group having a saturated carbon chain. The chain may be cyclic, branched or unbranched. Examples, without limitation, of alkyl groups include methyl, ethyl, propyl, butyl, pentyl, hexyl, heptyl, octyl, nonyl and decyl. The term lower alkyl means the chain includes 1-10 carbon atoms. The terms alkenyl and alkynyl refer to hydrocarbon groups having carbon chains containing one or more double or triple bonds, respectively.

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Exemplary substituents include, but are not limited to, alkyl, alkenyl, alkynyl, halogenated alkenyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, or other functionality.

Amine or Amino: A group of the formula —NRR', where R and R' can be, independently, hydrogen or an alkyl, alkenyl, alkynyl, aryl, aralkyl, cycloalkyl, halogenated alkyl, halogenated alkenyl, or heterocycloalkyl group. For example, an "alkylamino" or "alkylated amino" refers to —NRR', wherein at least one of R or R' is an alkyl.

Aminoalkyl: An alkyl group as defined above where at least one hydrogen atom is replaced with an amino group (e.g, —$CH_2$—$NH_2$).

Aryl: A monovalent unsaturated aromatic carbocyclic group having a single ring (e.g., phenyl) or multiple condensed rings (e.g., naphthyl or anthryl), which can optionally be unsubstituted or substituted. A heteroaryl group is an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

Atherosclerosis: The progressive narrowing and hardening of a blood vessel over time. Atherosclerosis is a common form of arteriosclerosis in which deposits of yellowish plaques (atheromas) containing cholesterol, lipoid material and lipophages are formed within the intima and inner media of large and medium-sized arteries. Treatment of atherosclerosis includes reversing or slowing the progression of atherosclerosis, for example as measured by the presence of atherosclerotic lesions and/or functional signs of the disease, such as improvement in cardiovascular function as measured by signs (such as peripheral capillary refill), symptoms (such as chest pain and intermittent claudication), or laboratory evidence (such as that obtained by EKG, angiography, or other imaging techniques). "Diagnosing atherosclerosis" indicates determining if a subject has atherosclerosis, determining the prognosis of atherosclerosis in the subject, and/or determining if a therapeutic regimen administered to the subject is effective in treating or preventing atherosclerosis in the subject.

In several embodiments, the fatty acid derivatives disclosed herein can be used to treat or prevent atherosclerosis in a subject.

Autoimmune disorder: A disorder in which the immune system produces an immune response (for example, a B cell or a T cell response) against an endogenous antigen, with consequent injury to tissues. For example, rheumatoid arthritis is an autoimmune disorder, as are Hashimoto's thyroiditis, pernicious anemia, Addison's disease, type I diabetes, systemic lupus erythematosus, dermatomyositis, Sjogren's syndrome, dermatomyositis, lupus erythematosus, multiple sclerosis, myasthenia gravis, Reiter's syndrome, and Grave's disease, among others.

In several embodiments, the fatty acid derivatives disclosed herein can be used to treat or prevent an auto-immune disorder in a subject.

Carboxyl: The group —COO— or —COOH. The carboxyl group can form a carboxylic acid.

Control: A sample or standard used for comparison with an experimental sample. In some embodiments, the control is a sample obtained from a healthy patient. In other embodiments, the control is a sample obtained from a patient diagnosed with a disease or condition, such as inflammation, itch, pain, autoimmunity, and/or atherosclerosis. In some embodiments, the control is a sample obtained from a patient diagnosed with a disease or condition (such as inflammation, itch, pain, autoimmunity, and/or atherosclerosis), where the patient has not received treatment with a fatty acid derivative as disclosed herein. In still other embodiments, the control is a historical control or standard reference value or range of values (such as a previously tested control sample, such as a group of patients with known prognosis or outcome, or group of samples that represent baseline or normal values).

Decrease or Reduce: To reduce the quality, amount, or strength of something; for example a reduction in signs or symptoms of a disease or condition. In one example, a therapy reduces a sign or symptom of a disease or condition as compared to the response in the absence of the therapy. In a particular example, a therapy reduces a sign or symptom of a disease or condition, such as a reduction of at least 10%, at least 20%, at least 30%, at least 40%, at least 50%, at least 60%, at least 70%, at least 80%, or at least 90% as compared to the absence of the therapy.

Derivative: A derivative is a molecule that differs in chemical structure from a parent compound, for example a homolog (differing by an increment in the chemical structure, such as a difference in the length of an alkyl chain), a molecular fragment, a structure that differs by one or more functional groups, a change in ionization. In some examples, a derivative is structurally similar or related to an endogenous compound (for example, sharing a functional group) that contains unnatural (or non-biologically derived) modifications meant to confer a desired property, such as stability, solubility, and/or suitability for delivery in biological systems. Derivatives are not necessarily synthesized from the parent compound. Structural derivatives are often found using quantitative structure activity relationships (QSAR), with techniques such as those disclosed in Remington (*The Science and Practice of Pharmacology,* 19th Edition (1995), chapter 28).

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Hydroxyl: A group represented by the formula —OH.

Inflammation: When damage to tissue occurs, the body's response to the damage is usually inflammation. For example, the damage may be due to trauma, lack of blood supply, hemorrhage, autoimmune attack, transplanted exogenous tissue or infection. This generalized response by the body includes the release of many components of the immune system (for instance, IL-1 and TNF), attraction of cells to the site of the damage, swelling of tissue due to the release of fluid and other processes. Inflammation may be measured by many methods well known in the art, such as the number of leukocytes, the number of polymorphonuclear neutrophils (PMN), a measure of the degree of PMN activation, such as luminal enhanced-chemiluminescence, or a measure of the amount of cytokines present.

Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process. An example of chronic inflammation is inflammatory arthritis.

In several embodiments, the fatty acid derivatives disclosed herein can be used to treat or prevent inflammation in a subject.

Itch: Also known as pruritus, an itch is a tingling or irritation of the skin that induces a subject to scratch the affected area. Itching may occur all over the whole body or only in one location. Itch may be histamine dependent, or independent.

Itch can be classified as itch affecting primary diseased, inflamed skin (such as skin affected with inflammatory, infectious, autoimmune disorders, lymphomas or drug reactions), itch affecting primary non-diseased, non-inflamed skin (such as itch associated with a neurologic or psychiatric origin), or itch associated with secondary scratch lesions, which are scratch lesions caused by a patient in response to an initial itch, and include excoriations, crusts, papules, nodules and chronic secondary scratch lesions like prurigo nodularis.

Itch is the most common symptom of most inflammatory skin disorders (e.g. atopic dermatitis, psoriasis, contact dermatitis, urticaria, drug reactions, pemphigoid, dermatitis herpetiformis), parasitic or infectious diseases (e.g. scabies, mycoses, chickenpox), insect bites, as well as cutaneous T-cell lymphoma.

Chronic itch is an itch sensation that is present for at least 6 weeks, and is particularly prevalent under conditions such as atopic dermatitis, psoriasis, and kidney or liver disease.

In several embodiments, the fatty acid derivatives disclosed herein can be used to treat or prevent itch (such as chronic itch) in a subject.

Moiety: A moiety is a fragment of a molecule, or a portion of a conjugate.

Pain: An unpleasant sensory and emotional experience associated with actual or potential tissue damage, or described in terms of such damage. Pain experienced by mammals can be divided into two main categories: acute pain (or nociceptive) and chronic pain which can be subdivided into chronic inflammatory pain and chronic neuropathic pain. Acute pain is a response to stimulus that causes tissue injury and is a signal to move away from the stimulus to minimize tissue damage. Chronic pain, on the other hand, serves no biological function and develops as a result of inflammation caused by tissue damage (inflammatory pain) or by damage to the nervous system such as demyelination (neuropathic pain). Chronic pain is generally characterized by stimulus-independent, persistent pain or by abnormal pain perception triggered by innocuous stimuli. Non-limiting examples of pain include postsurgical pain, pain associated with tissue damage, pain from inflammation, pain from infection (shingles), pain from neuropathic conditions, and pain from skeletal muscular conditions.

In several embodiments, the fatty acid derivatives disclosed herein can be used to treat or prevent pain (such as chronic pain) in a subject.

Pharmaceutically acceptable: A substance that can be taken into a subject without significant adverse toxicological effects on the subject. The term "pharmaceutically acceptable form" means any pharmaceutically acceptable derivative or variation, such as stereoisomers, stereoisomer mixtures, enantiomers, solvates, hydrates, isomorphs, polymorphs, pseudomorphs, neutral forms, salt forms, and prodrug agents.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21st Edition (2005), describes compositions and formulations suitable for pharmaceutical delivery of one or more therapeutic compositions and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some examples, the pharmaceutically acceptable carrier is a non-naturally occurring or synthetic carrier. The carrier also can be formulated in a unit-dosage form that carries a preselected therapeutic dosage of the active agent, for example in a pill, vial, bottle, or syringe.

Pharmaceutically acceptable salt: A biologically compatible salt of a compound that can be used as a drug, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, benzene sulfonic acid (besylate), cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.).

Skin disorder: A disease or condition of the skin such as an inflammatory, proliferative, sensation, skin barrier dysfunction disease or condition. Non-limiting examples of skin disorders include atopic dermatitis, seborrheic dermatitis, acne, rosacea, ichthyosis, erythroderma, alopecia, wrinkles, dry skin/water barrier function, essential fatty acid deficiency, vitiligo, sebaceous cyst, pilonidal cyst, hypertrophic scar/keloid, seborrheic keratosis, and actinic keratosis.

Stereoisomers: Isomers that have the same molecular formula and sequence of bonded atoms, but which differ only in the three-dimensional orientation of the atoms in space. Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture." E/Z isomers are isomers that differ in the stereochemistry of a double bond. An E isomer (from entgegen, the German word for "opposite") has a trans-configuration at the double bond, in which the two groups of highest priority are on opposite sides of the double bond. A Z isomer (from zusammen, the German word for "together") has a cis-configuration at the double bond, in which the two groups of highest priority are on the same side of the double bond.

Subject: Living multi-cellular vertebrate organism, a category that includes human and non-human mammals.

Substituted or Substitution: Replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$fluoroalkenyl, $C_{2-6}$difluoroalkenyl, $C_{2-6}$alkynyl, $C_{3-6}$ cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

Tautomers: Constitutional isomers of organic compounds that differ only in the position of the protons and electrons, and are interconvertible by migration of a hydrogen atom. Tautomers ordinarily exist together in equilibrium.

Therapeutically effective amount: An amount sufficient to provide a beneficial, or therapeutic, effect to a subject or a given percentage of subjects. Therapeutically effective amounts of a therapeutic agent can be determined in many different ways, such as assaying for a reduction in a disease or condition (such as atherosclerosis). Therapeutically effective amounts also can be determined through various in vitro, in vivo or in situ assays. Therapeutic agents can be administered in a single dose, or in several doses, for example daily, during a course of treatment. However, the effective amount of can be dependent on the source applied, the subject being treated, the severity and type of the condition being treated, and the manner of administration.

Thiol: The group —SH. A substituted thiol is a thiol group having the hydrogen replaced with, for example a $C_{1-6}$alkyl group ("—S($C_{1-6}$alkyl)"), an aryl ("—S(aryl)"), or an aralkyl ("—S(alkyl)(aryl)") and so on.

Treating or treatment: With respect to disease or condition, either term includes (1) preventing the disease or condition, e.g., causing the clinical symptoms of the disease or condition not to develop in a subject that may be exposed to or predisposed to the disease or condition but does not yet experience or display symptoms of the disease or condition, (2) inhibiting the disease or condition, e.g., arresting the development of the disease or condition or its clinical symptoms, or (3) relieving the disease or condition, e.g., causing regression of the disease or condition or its clinical symptoms.

II. FATTY ACID DERIVATIVES

Embodiments of fatty acid derivatives are disclosed. As discussed in herein, the disclosed fatty acid derivatives have utility for treating multiple diseases and conditions, including inflammation, itch, pain, autoimmune disorders, and atherosclerosis. In several embodiments, the disclosed fatty acid derivatives have increased activity, lower toxicity, few side effects, greater stability, longer half-life in human patients, or a combination thereof, than prior agents utilized for treating inflammation, itch, pain, autoimmune disorders, and/or atherosclerosis. Advantageously, certain embodiments of the disclosed fatty acid derivatives are capable of crossing the blood-brain barrier.

In certain embodiments, the fatty acid derivative is a compound having a structure according to formula I or a stereoisomer, tautomer, or pharmaceutically acceptable salt thereof:

(I)

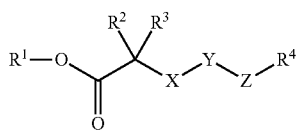

In formula I, X is aliphatic from 1-16 carbons in length (such as any one of 1, 2, 3, 4, 5, 6, 7, 8, 9, 10, 11, 12, 13, 14, 15, or 16), Z is aliphatic from 1-16 carbons in length (such as any one of 1, 2, 3, 4, 5, 6, 7, 8, 9, 10, 11, 12, 13, 14, 15, or 16), or is not present, Y is selected from any one of:

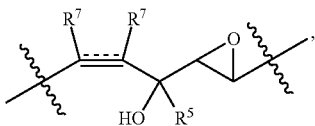

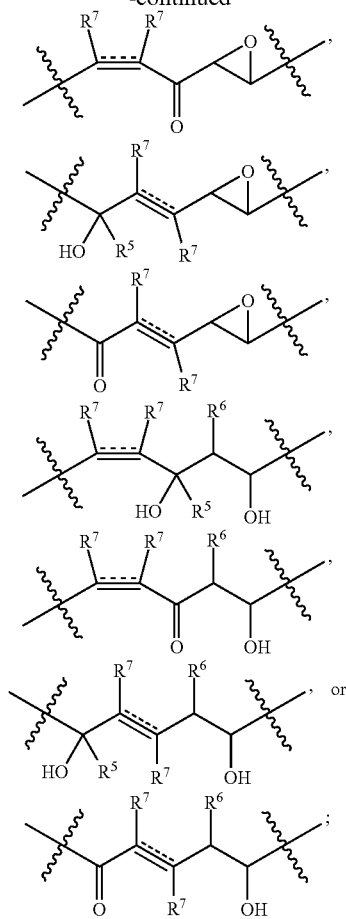

$R^1$ is hydrogen or lower alkyl (such as methyl, ethyl, propyl, or butyl); $R^2$ is hydrogen or lower alkyl (such as methyl, ethyl, propyl, or butyl); $R^3$ is hydrogen or lower alkyl (such as methyl, ethyl, propyl, or butyl); $R^4$ is lower alkyl (such as methyl, ethyl, propyl, or butyl), hydroxyl, carboxyl, or amine; $R^5$ is hydrogen, lower alkyl, or halide, $R^6$ is hydroxyl or substituted thiol, and each $R^7$ is independently hydrogen or fluoride or is not present and the adjacent carbons form alkyne. Y can be inserted into formula I in the orientation depicted above, or in the opposite orientation, to generate a compound of formula I.

In some embodiments of formula I, Y is selected from any one of

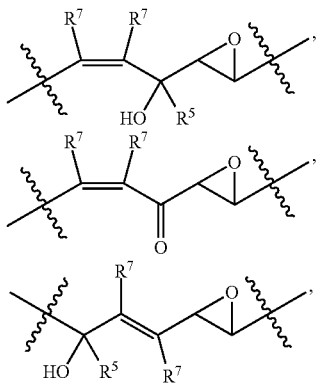

-continued

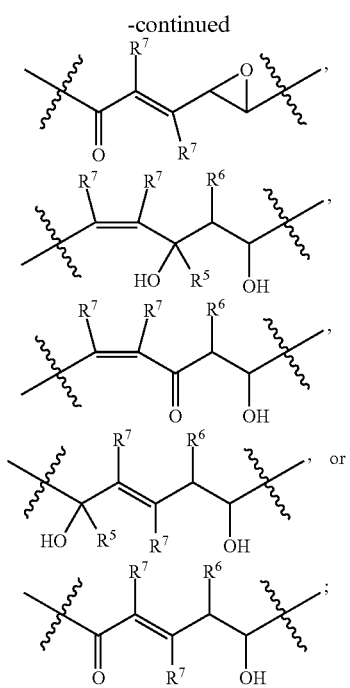

R[1] is hydrogen or lower alkyl (such as methyl, ethyl, propyl, or butyl); R[2] is hydrogen or lower alkyl (such as methyl, ethyl, propyl, or butyl); R[3] is hydrogen or lower alkyl (such as methyl, ethyl, propyl, or butyl); R[4] is lower alkyl (such as methyl, ethyl, propyl, or butyl), hydroxyl, carboxyl, or amine; R[5] is hydrogen, lower alkyl, or halide, R[6] is hydroxyl or substituted thiol, and each R[7] is independently hydrogen or fluoride. Y can be inserted into formula I in the orientation depicted above, or in the opposite orientation, to generate a compound of formula I.

In some embodiments of formula I, X and Z are independently selected from one of 1-10, 4-8, 2-6, 5-10, 4-12, or 10-16 carbons in length. In some embodiments, Z is from 1-10 carbons in length, and X is from 1-10 carbons in length. In some embodiments, Z is not present. In some embodiments of formula I, X is selected from 4-8 carbons in length and Z is selected from 1-6 carbons in length. In some embodiments of formula I, X is 6 carbons in length and/or Z is 4 carbons in length. In some embodiments of formula I, X and Z together are from 8-14 carbons in length. In some embodiments of formula I, X and Z together are from 7-12 carbons in length. In some embodiments of formula I, X and Z together are 10 carbons in length. In several embodiments, X and Z independently are alkyl or alkenyl, or halogenated alkenyl, particularly fluoroalkenyl or difluoroalkenyl. In some embodiments, X and Z independently comprise one or more fluoroalkene or difluoroalklene moieties.

In some embodiments of formula I, R[1], R[2], R[3], and/or R[4] are methyl. In some embodiments of formula I, R[1], R[2], R[3], and R[4] are methyl. In some embodiments of formula I, R[5] is hydrogen. In some embodiments of formula I, R[6] is hydroxyl. In some embodiments of formula I, R[6] is cysteine or glutathione. In some embodiments of formula (I), R[1] is hydrogen, R[2], R[3], and Rare methyl, R[5] is hydrogen, and R[6] is hydroxyl. In some embodiments of formula (I), R[1], R[2], R[3], and R[4] methyl, R[5] is hydrogen, and R[6] is hydroxyl.

In certain embodiments, the fatty acid derivative is a compound having a structure according to any one of formulas II-XVII, or a stereoisomer, tautomer, or pharmaceutically acceptable salt thereof:

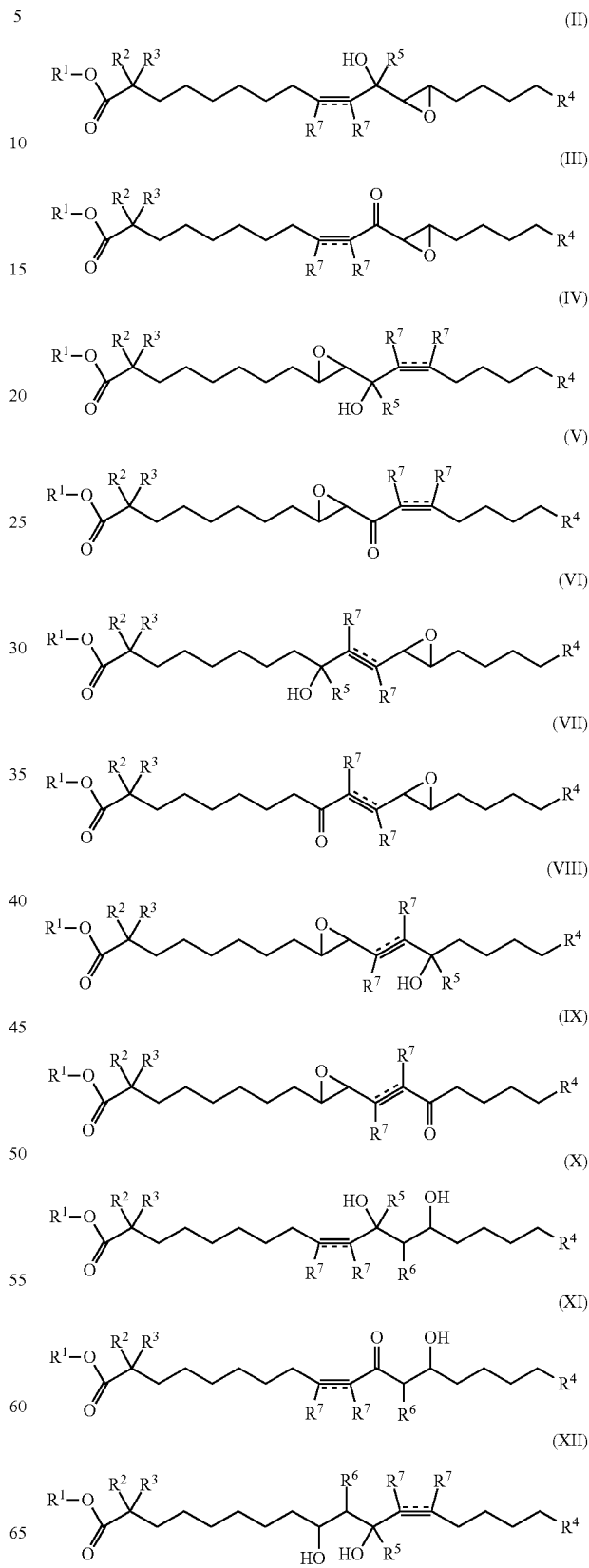

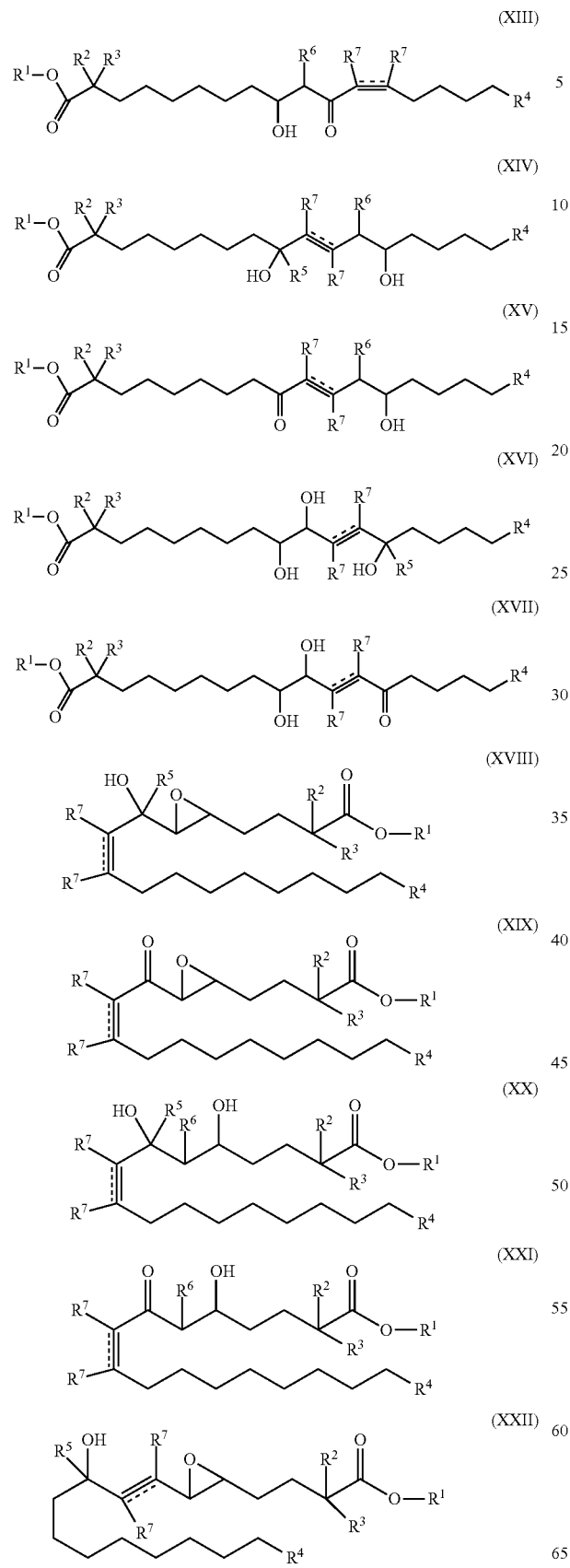
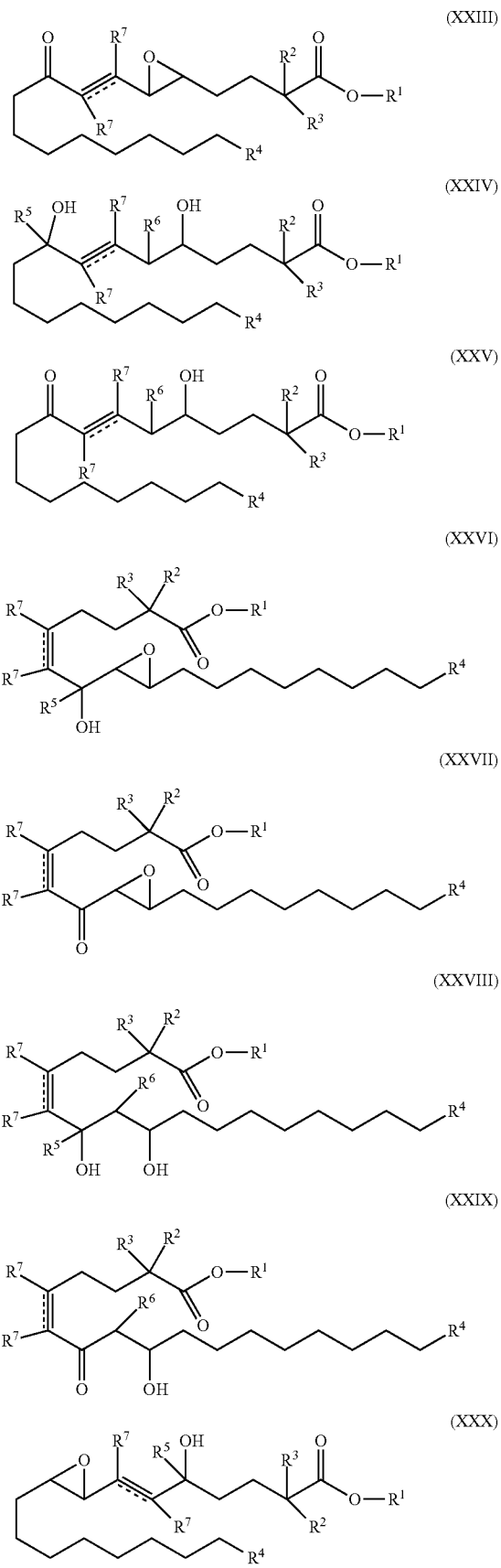

-continued
(XXXI)
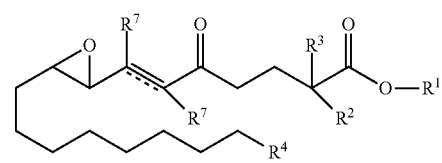
(XXXII)
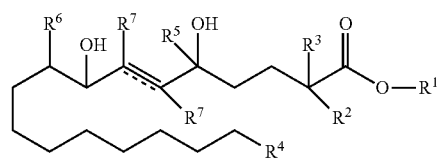
(XXXIII)
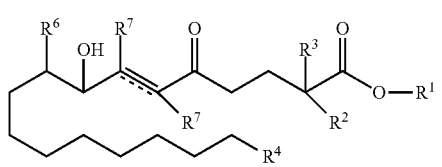
(XXXIV)
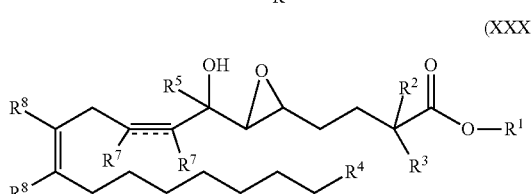
(XXXV)
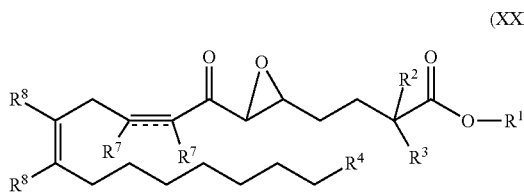
(XXXVI)
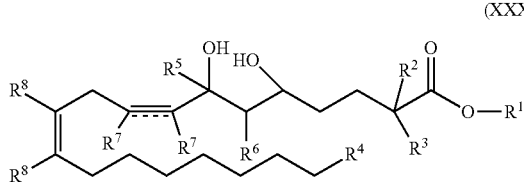
(XXXVII)
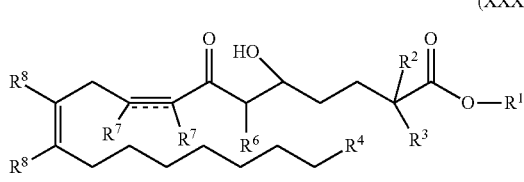
(XXXVIII)
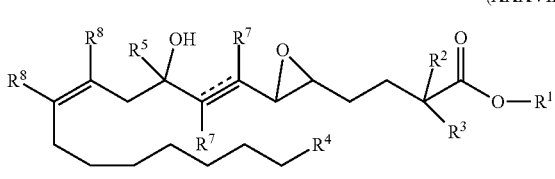
(XXXIX)
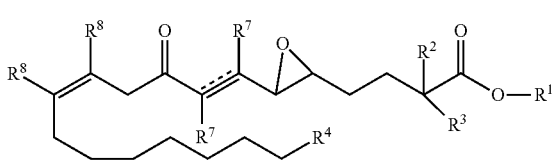
-continued
(XL)
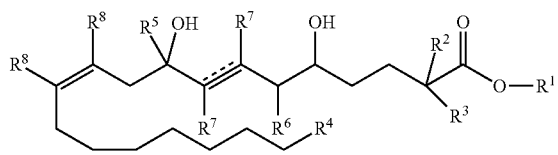
(XLI)
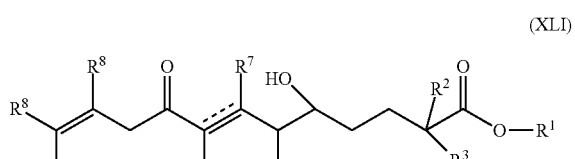
(XLII)
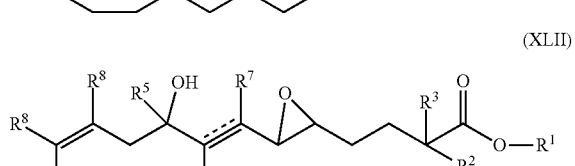
(XLIII)
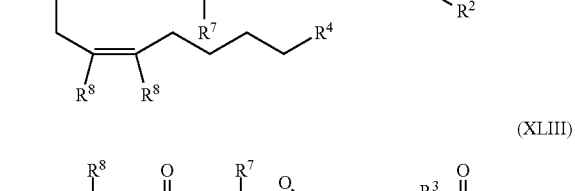
(XLIV)
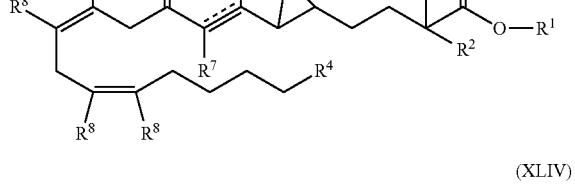
(XLV)
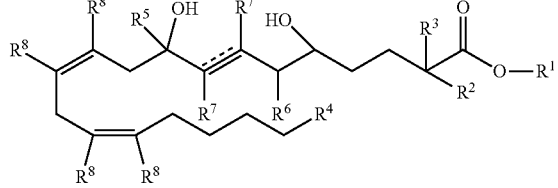
(XLVI)
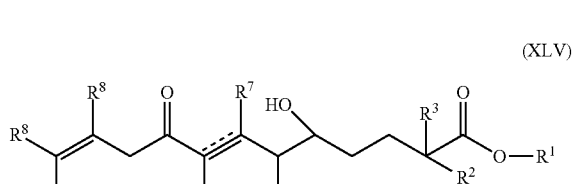

-continued
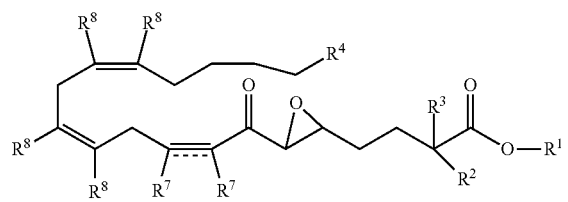
(XLVII)
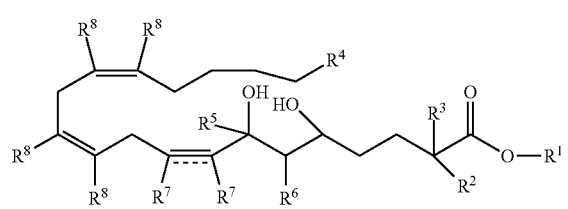
(XLVIII)
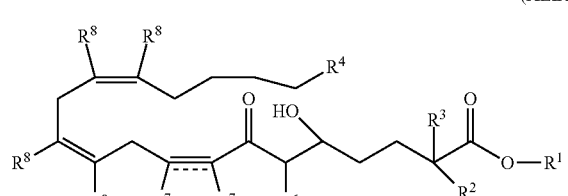
(XLIX)
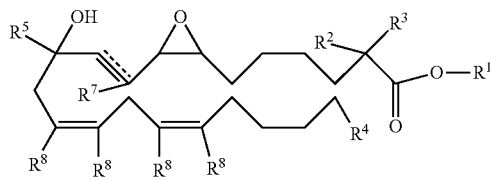
(L)
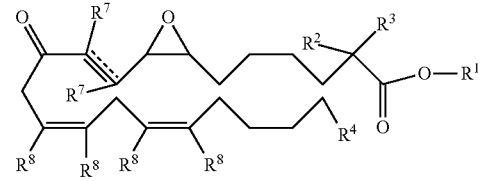
(LI)
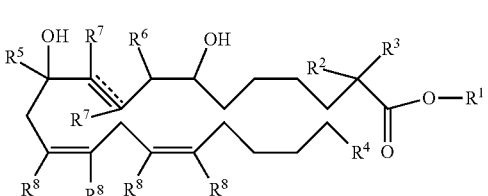
(LII)
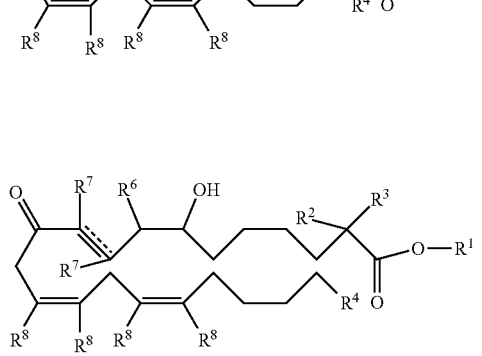
(LIII)
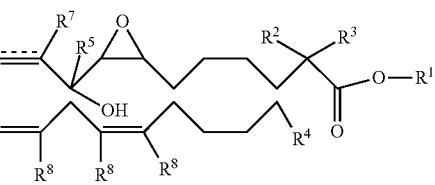
(LIV)
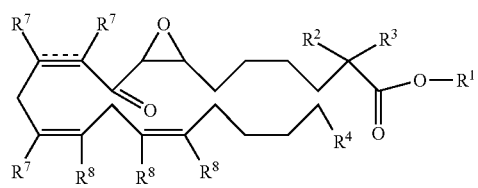
(LV)
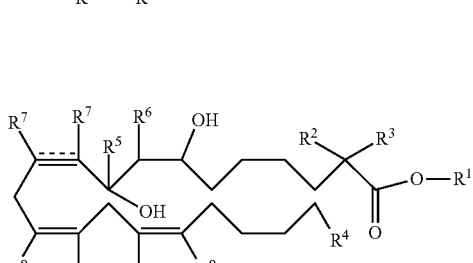
(LVI)
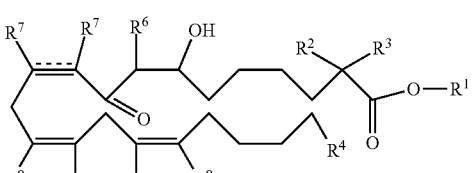
(LVII)
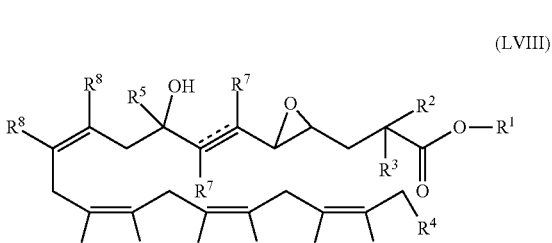
(LVIII)
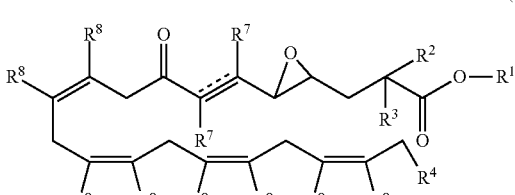
(LIX)
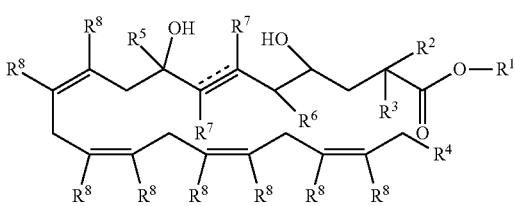
(LX)

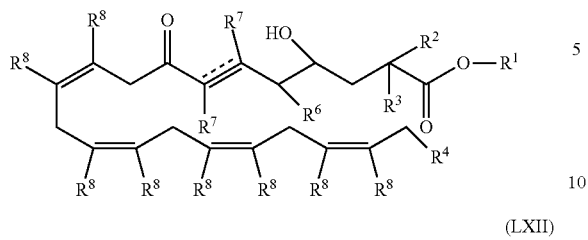
(LXI)
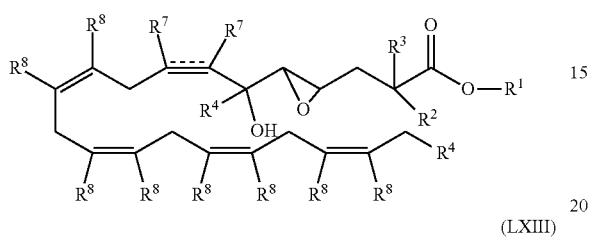
(LXII)
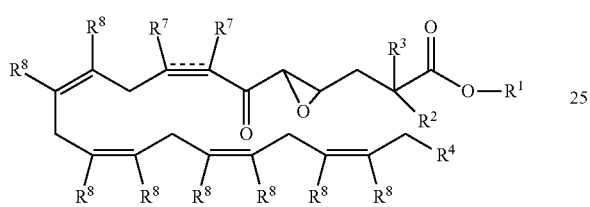
(LXIII)
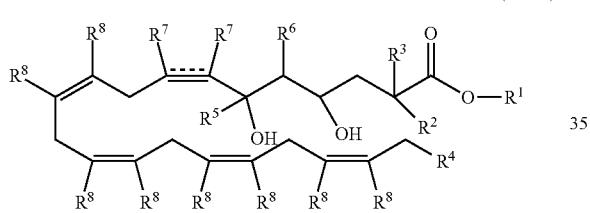
(LXIV)
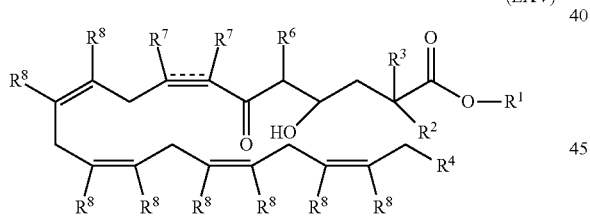
(LXV)
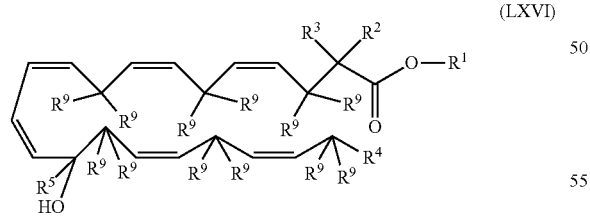
(LXVI)
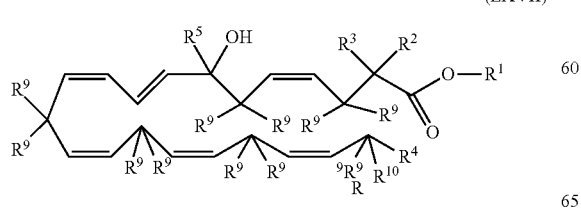
(LXVII)
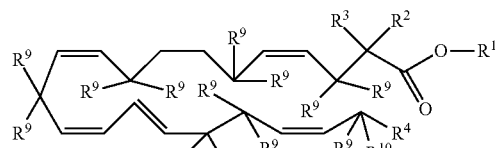
(LXVIII)
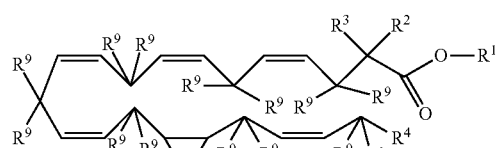
(LXIX)
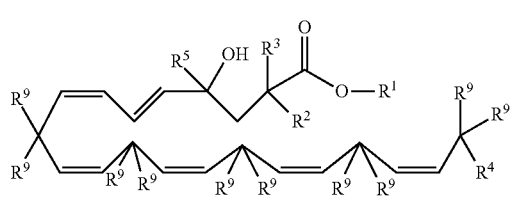
(LXX)
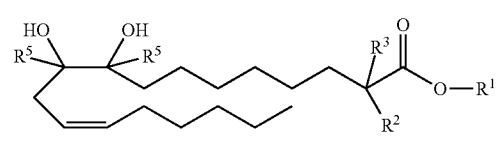
(LXXI)
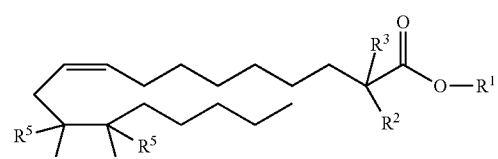
(LXXII)
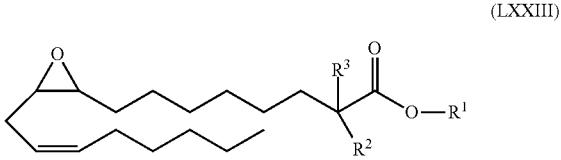
(LXXIII)
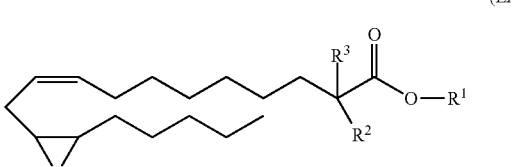
(LXXIV)
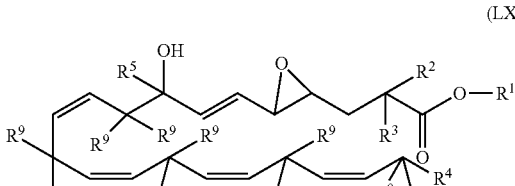
(LXXV)

(LXXVI)
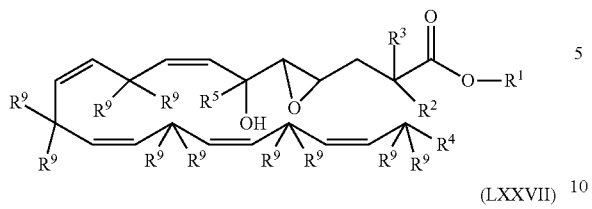
(LXXVII)
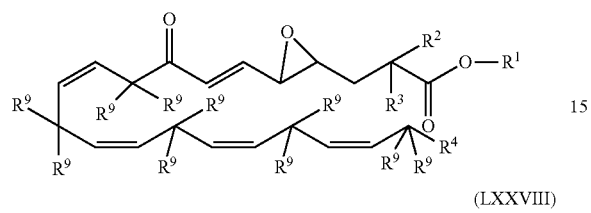
(LXXVIII)
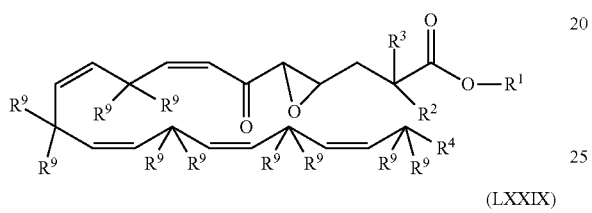
(LXXIX)
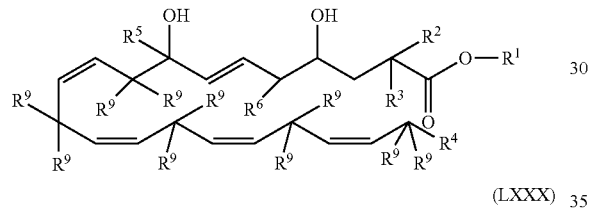
(LXXX)
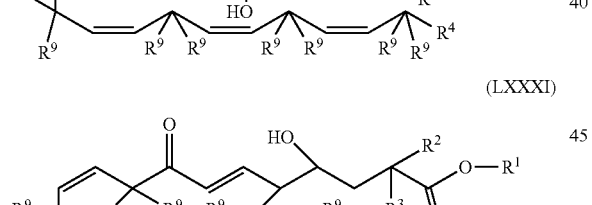
(LXXXI)
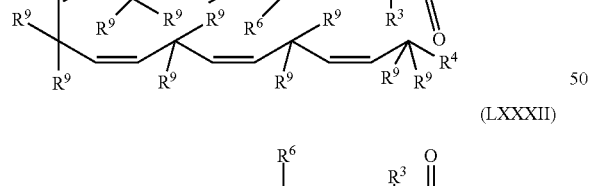
(LXXXII)
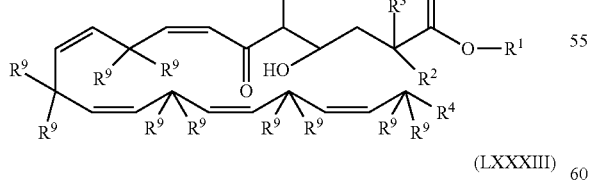
(LXXXIII)
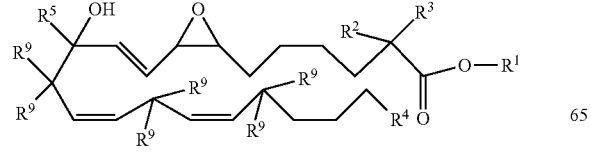
(LXXXIV)
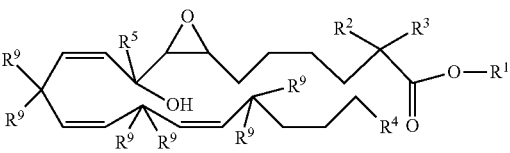
(LXXXV)
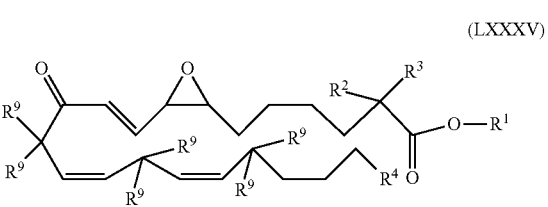
(LXXXVI)
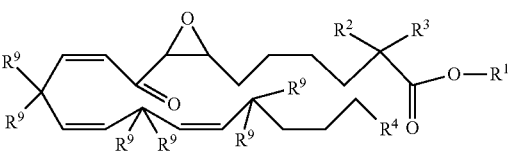
(LXXXVII)
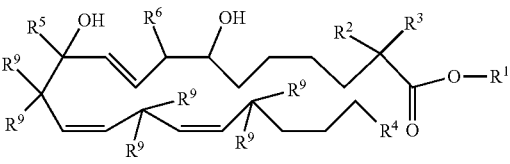
(LXXXVIII)
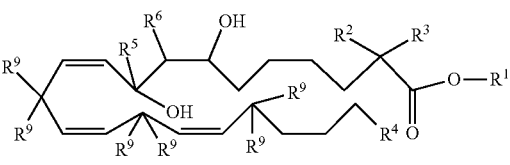
(LXXXIX)
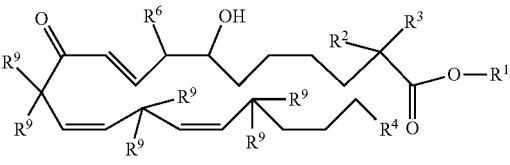
(XC)
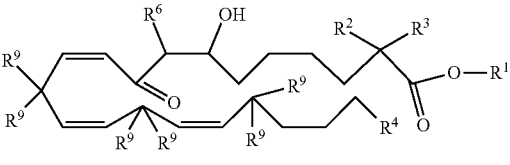
(XCI)
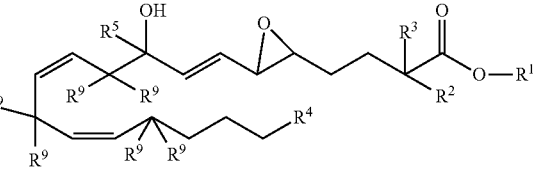

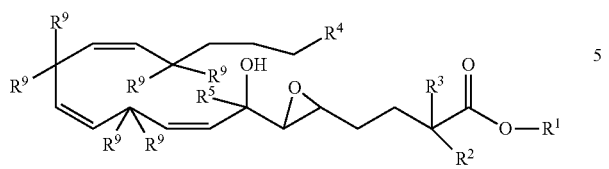
(XCII)

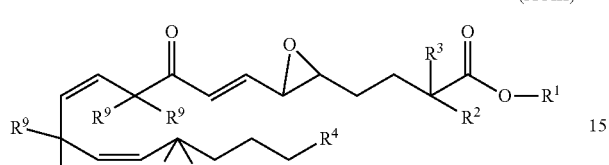
(XCIII)

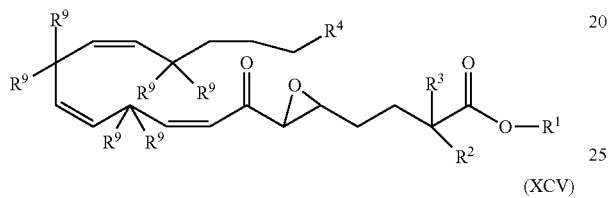
(XCIV)

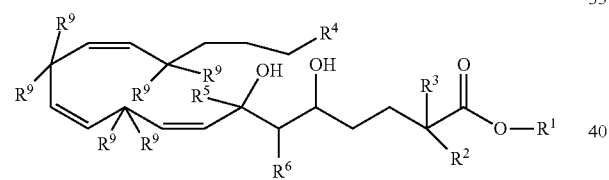
(XCV)

(XCVI)

(XCVII)

(XCVIII)

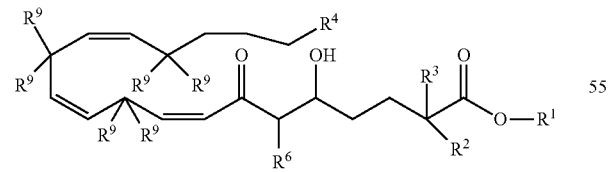
(XCIX)

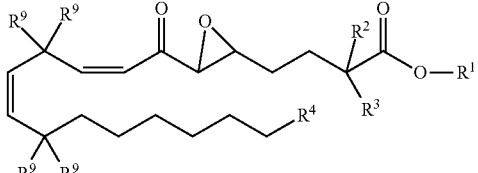
(C)

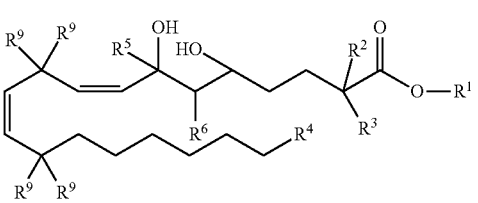
(CI)

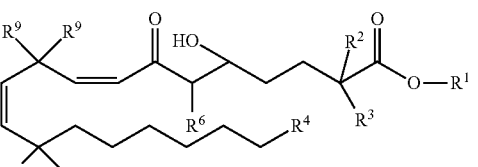
(CII)

In formulas (II)-(CII), if present, $R^1$ is hydrogen or lower alkyl (such as methyl, ethyl, propyl, or butyl), $R^2$ is hydrogen or lower alkyl (such as methyl, ethyl, propyl, or butyl), $R^3$ is hydrogen or lower alkyl (such as methyl, ethyl, propyl, or butyl), $R^4$ is lower alkyl (such as methyl, ethyl, propyl, or butyl), hydroxyl, carboxyl, or amine, $R^5$ is hydrogen, lower alkyl, or halide, $R^6$ is hydroxyl or substituted thiol, each $R^7$ is independently hydrogen or fluoride or not present and the adjacent carbons form alkyne, each $R^8$ is independently hydrogen or fluoride, and each $R^9$ is independently hydrogen or deuterium. The substitution of fluoride or deuterium for hydrogen in part of a 1,4 cis, cis-pentadiene makes these poor substrates for further enzymatic oxidation, thereby enhancing stability.

In some embodiments of any one of formulas (II)-(CII), if present, $R^1$ is hydrogen or lower alkyl (such as methyl, ethyl, propyl, or butyl), $R^2$ is hydrogen or lower alkyl (such as methyl, ethyl, propyl, or butyl), $R^3$ is hydrogen or lower alkyl (such as methyl, ethyl, propyl, or butyl), $R^4$ is lower alkyl (such as methyl, ethyl, propyl, or butyl), hydroxyl, carboxyl, or amine, $R^5$ is hydrogen, lower alkyl, or halide, $R^6$ is hydroxyl or substituted thiol, each $R^7$ is independently hydrogen or fluoride and the adjacent carbons form alkene, each $R^8$ is independently hydrogen or fluoride, and each $R^9$ is independently hydrogen or deuterium.. The substitution of fluoride or deuterium for hydrogen in part of a 1,4 cis, cis-pentadiene makes these poor substrates for further enzymatic oxidation, thereby enhancing stability.

In some embodiments of any one of formulas (II)-(CII), $R^1$, $R^2$, $R^3$, and/or $R^4$ are methyl. In some embodiments of any one of formulas (II)-(CII), $R^1$, $R^2$, $R^3$, and $R^4$ are methyl. In some embodiments of any one of formulas (II)-(CII), $R^5$ is hydrogen. In some embodiments of formulas (II)-(XVII), $R^6$ is hydroxyl. In some embodiments of any one of formulas (II)-(XVII), $R^6$ is cysteine or glutathione. In some embodiments of any one of formulas (II)-(CII), $R^1$ is hydrogen, $R^2$, $R^3$, and $R^4$ are methyl, $R^5$ is hydrogen, and $R^6$ is hydroxyl. In some embodiments of any one of formulas (II)-(CII), $R^1$, $R^2$, $R^3$, and $R^4$ are methyl, $R^5$ is hydrogen, and $R^6$ is hydroxyl.

Exemplary compound structures of this disclosure that fall within the scope of formula (I) include, but are not limited to:
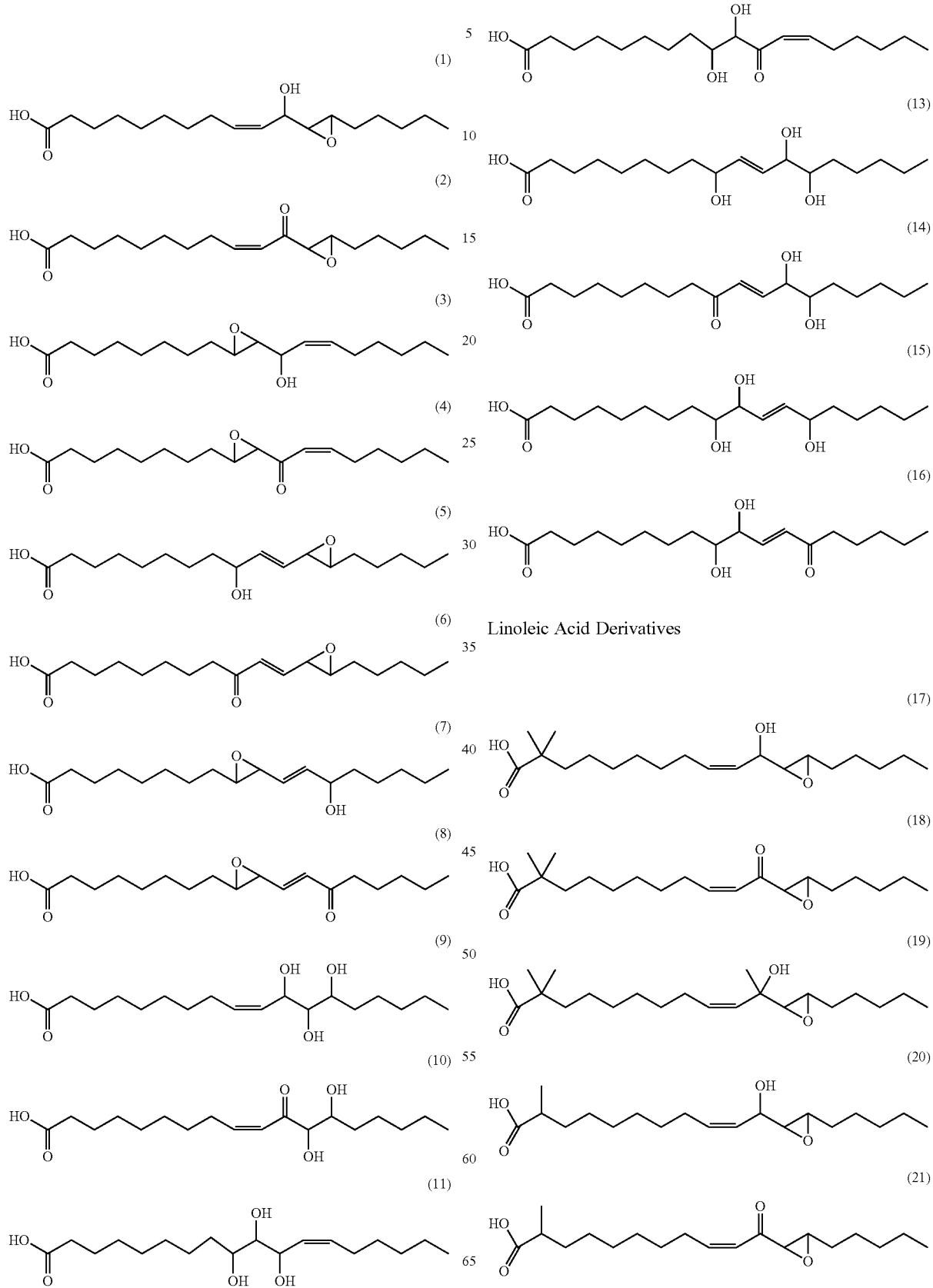
Linoleic Acid Derivatives

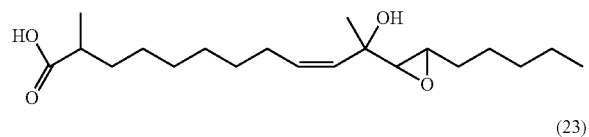
(22)
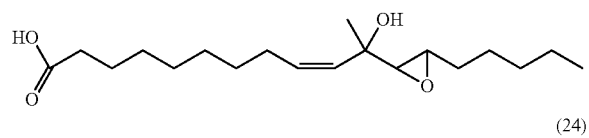
(23)
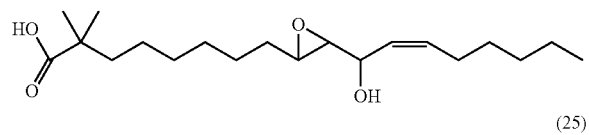
(24)
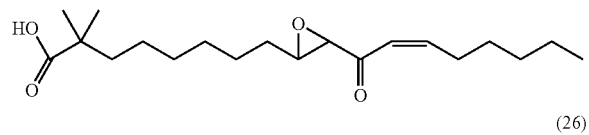
(25)
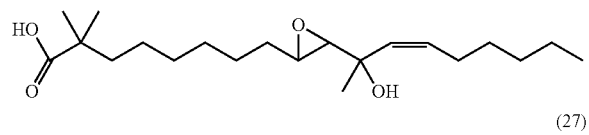
(26)
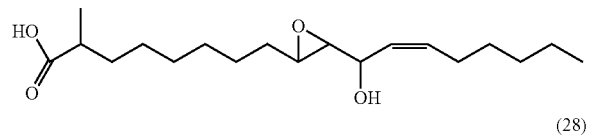
(27)
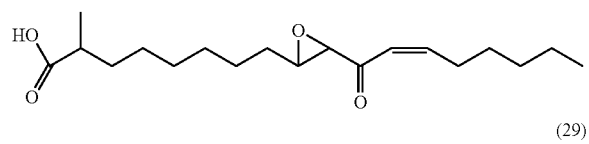
(28)
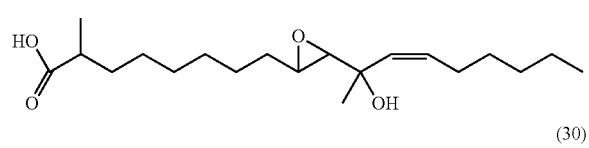
(29)
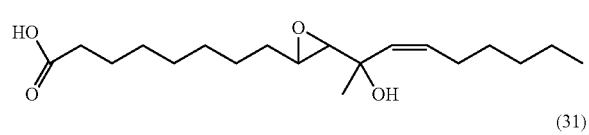
(30)
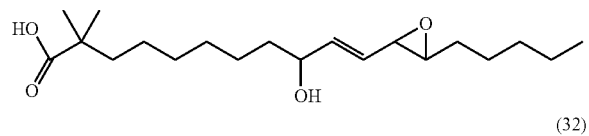
(31)
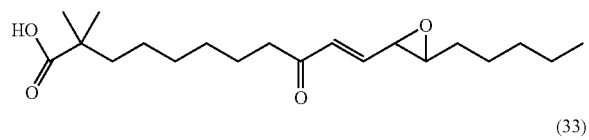
(32)
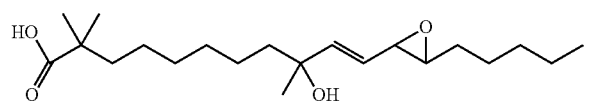
(33)
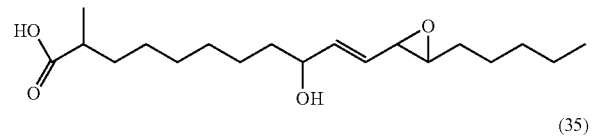
(34)
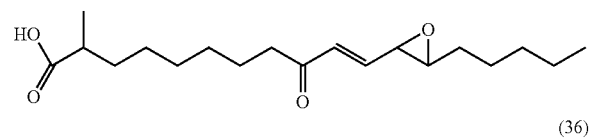
(35)
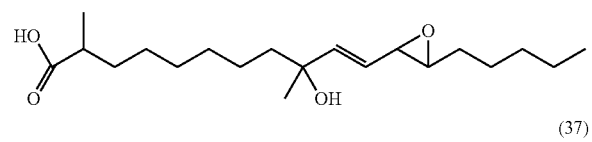
(36)
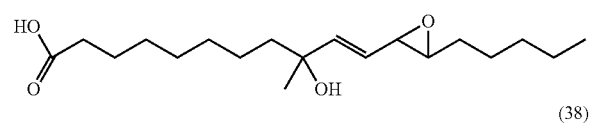
(37)
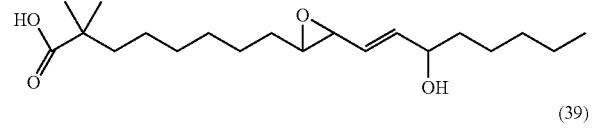
(38)
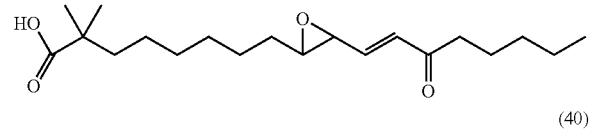
(39)
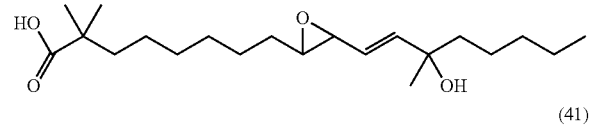
(40)
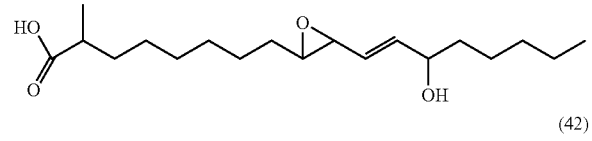
(41)
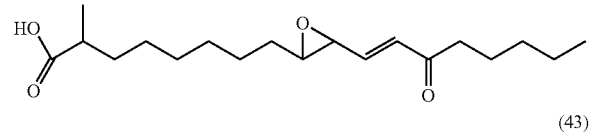
(42)
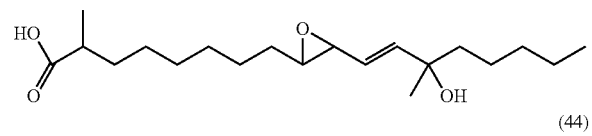
(43)
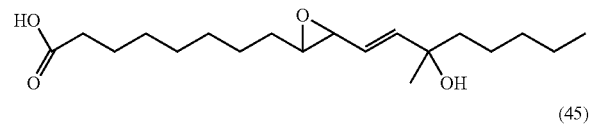
(44)
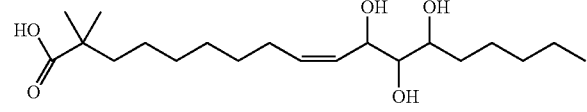
(45)

-continued
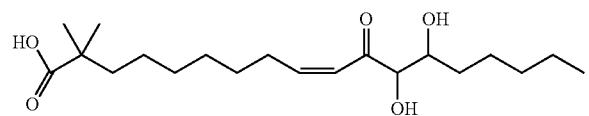
(46)
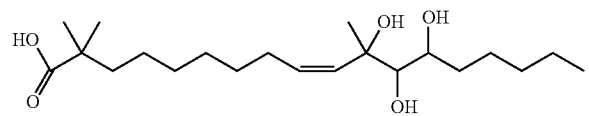
(47)
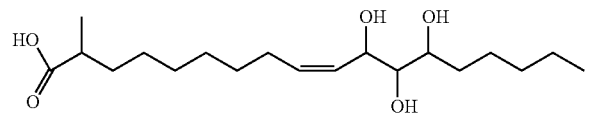
(48)
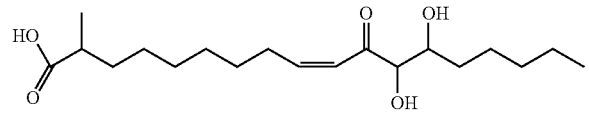
(49)
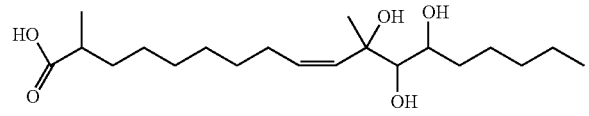
(50)
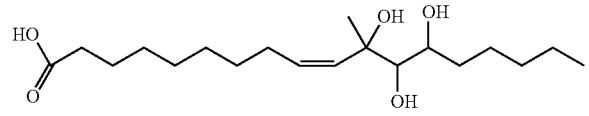
(51)
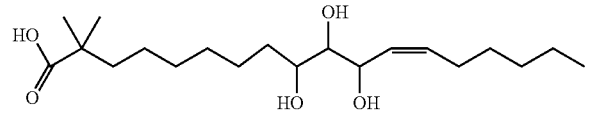
(52)
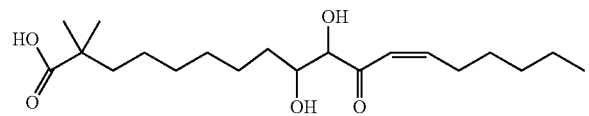
(53)
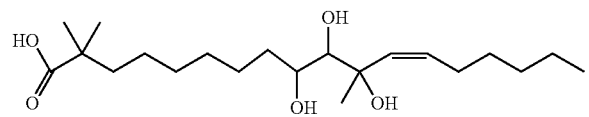
(54)
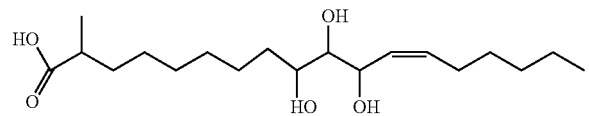
(55)
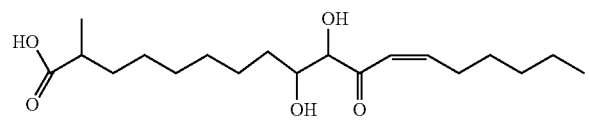
(56)
-continued
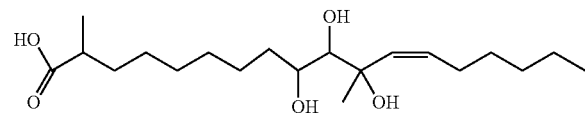
(57)
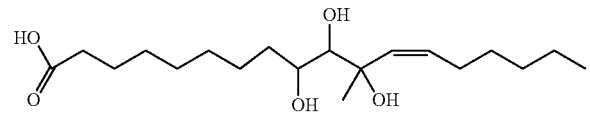
(58)
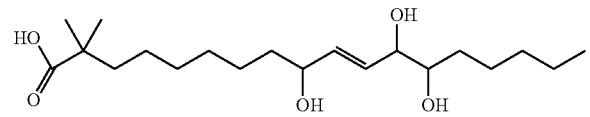
(59)
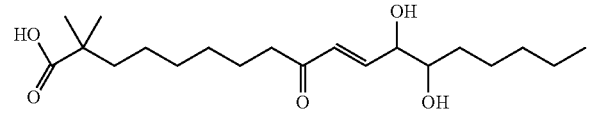
(60)
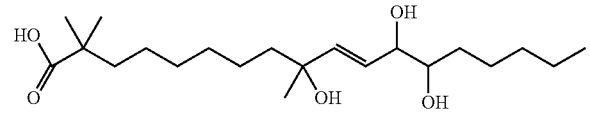
(61)
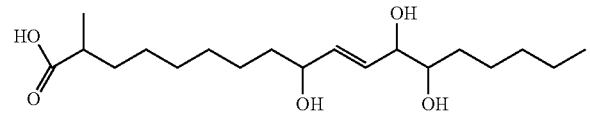
(62)
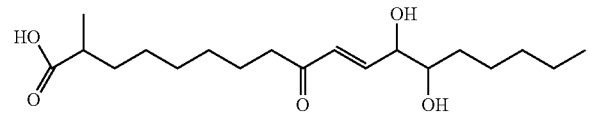
(63)
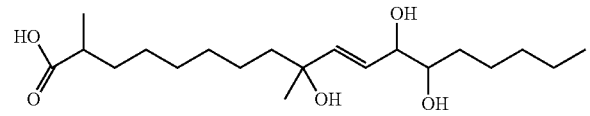
(64)
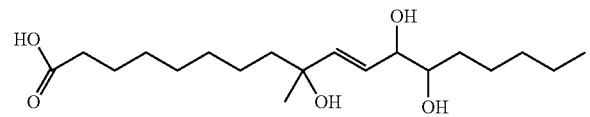
(65)
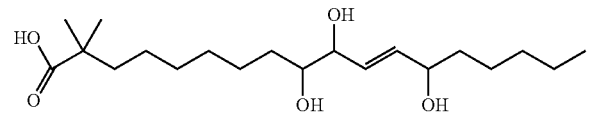
(66)
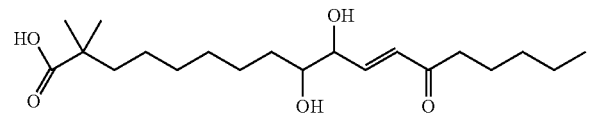
(67)

(68)
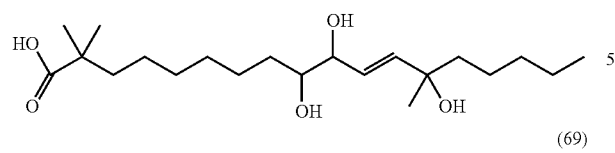
(69)
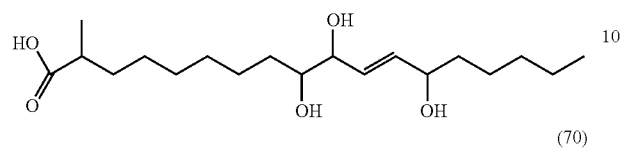
(70)
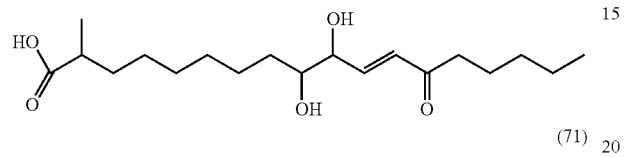
(71)
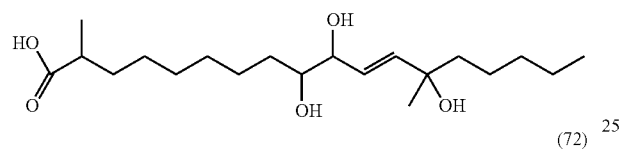
(72)
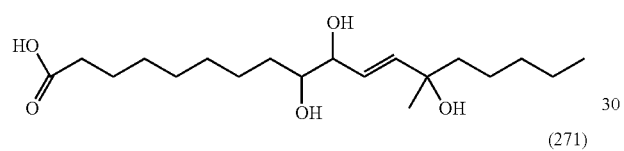
(271)
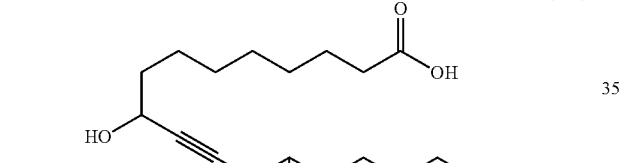
(272)
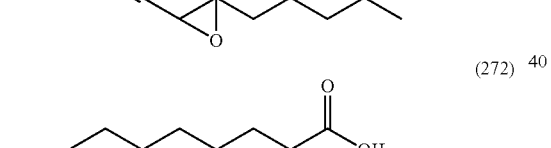
(273)
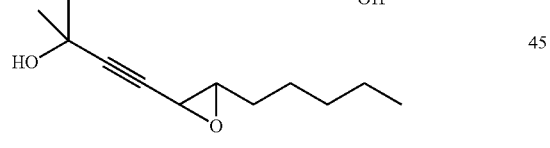
(274)
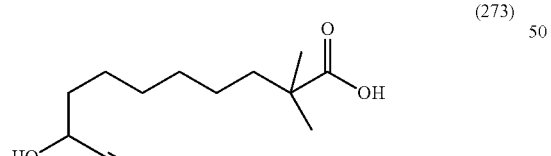
(275)
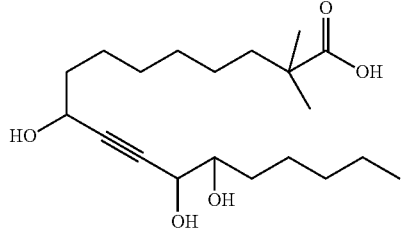
(276)
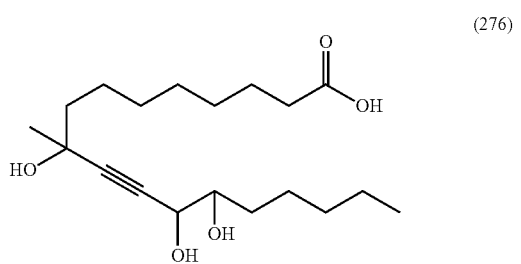
(277)
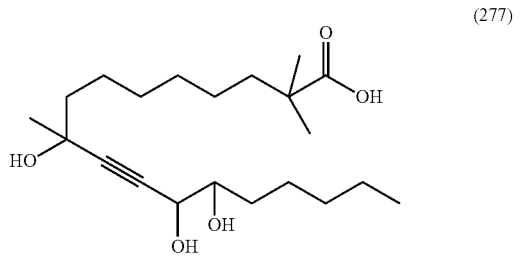
(278)
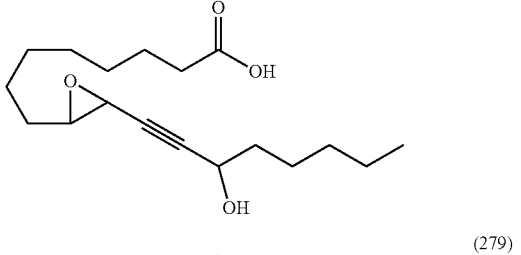
(279)
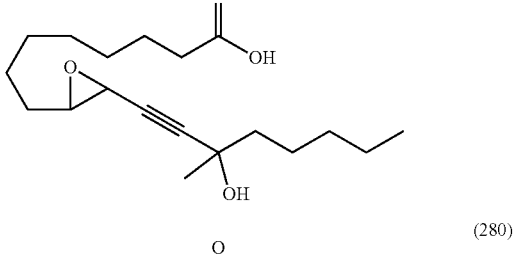
(280)
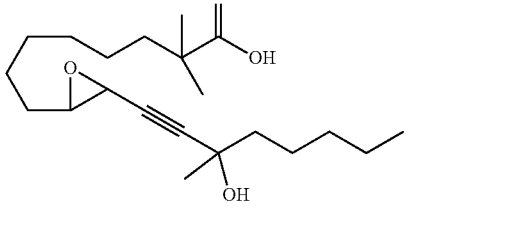

(281)
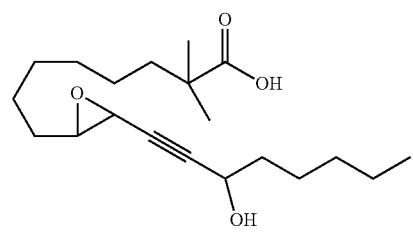
(282)
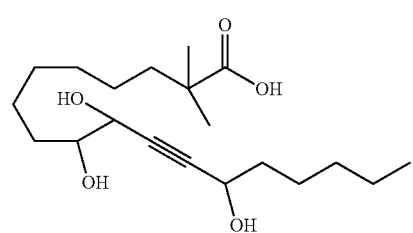
(283)
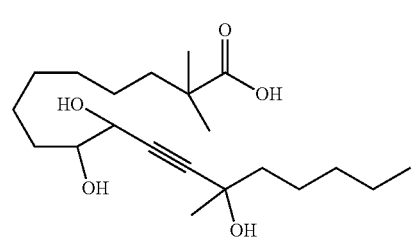
(284)
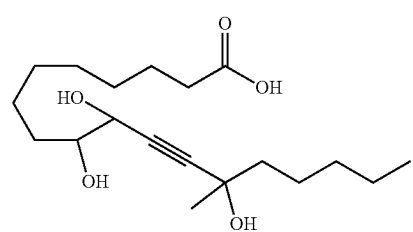
(285)
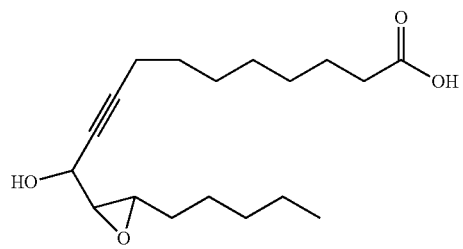
(286)
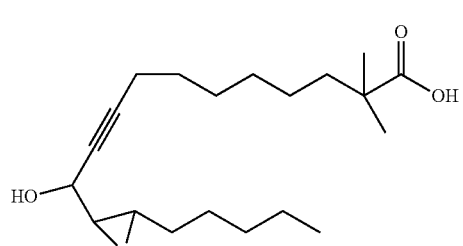
(287)
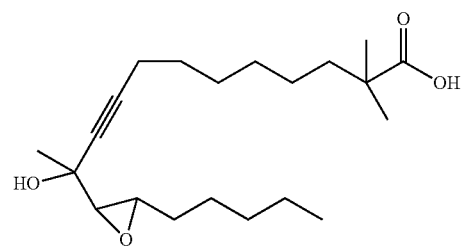
(288)
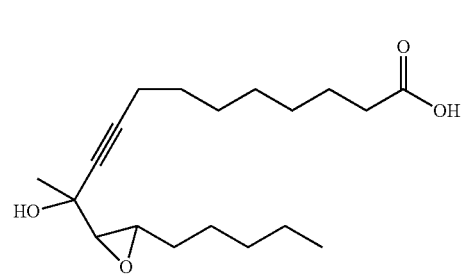
(289)
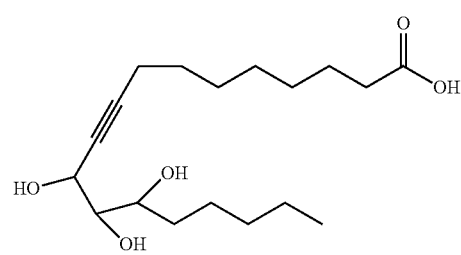
(290)
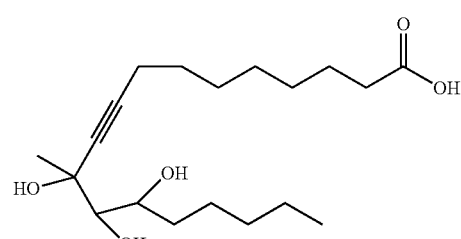
(291)
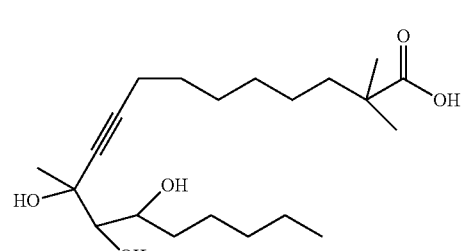
(292)
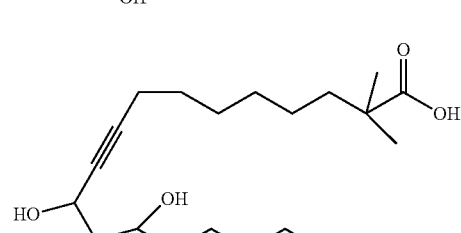

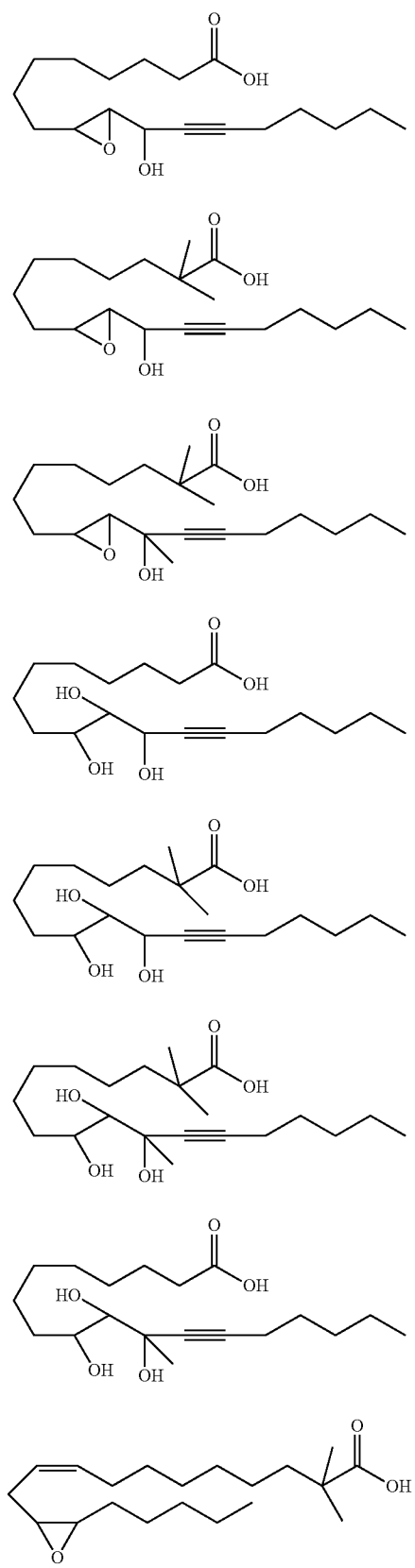
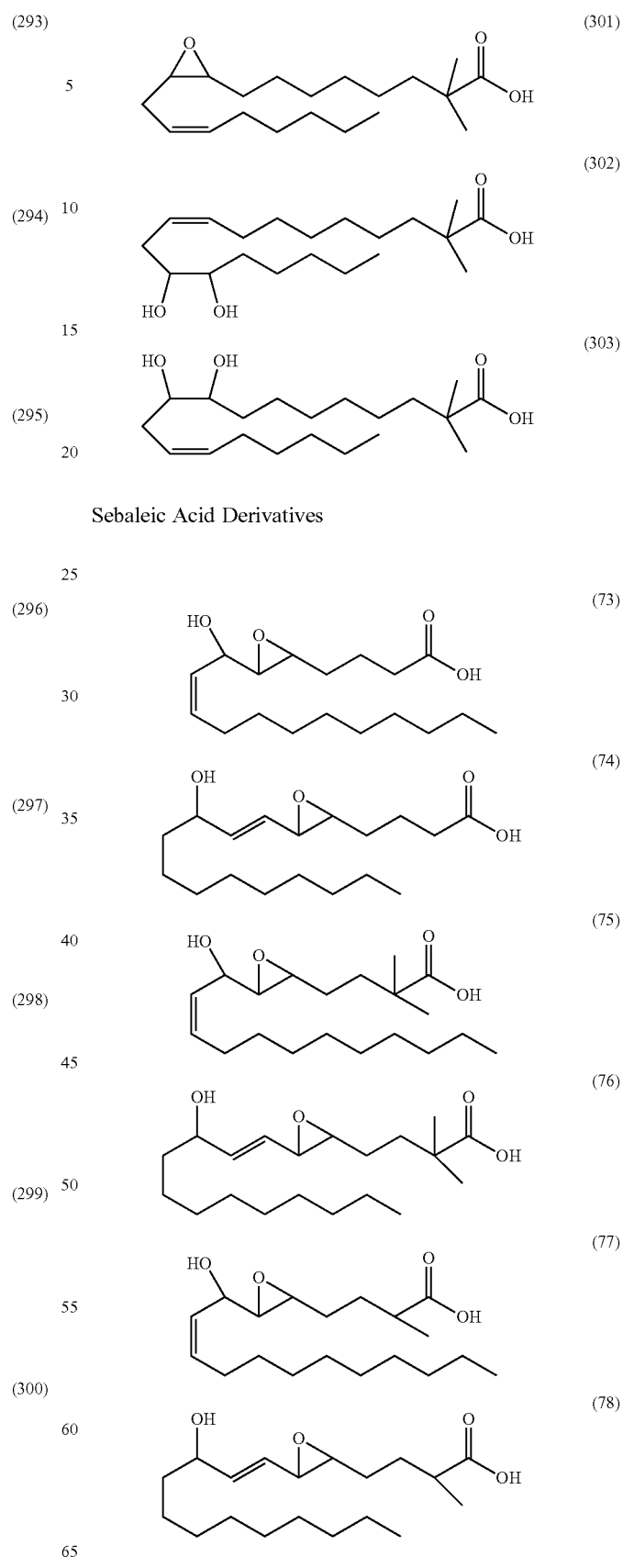
Sebaleic Acid Derivatives

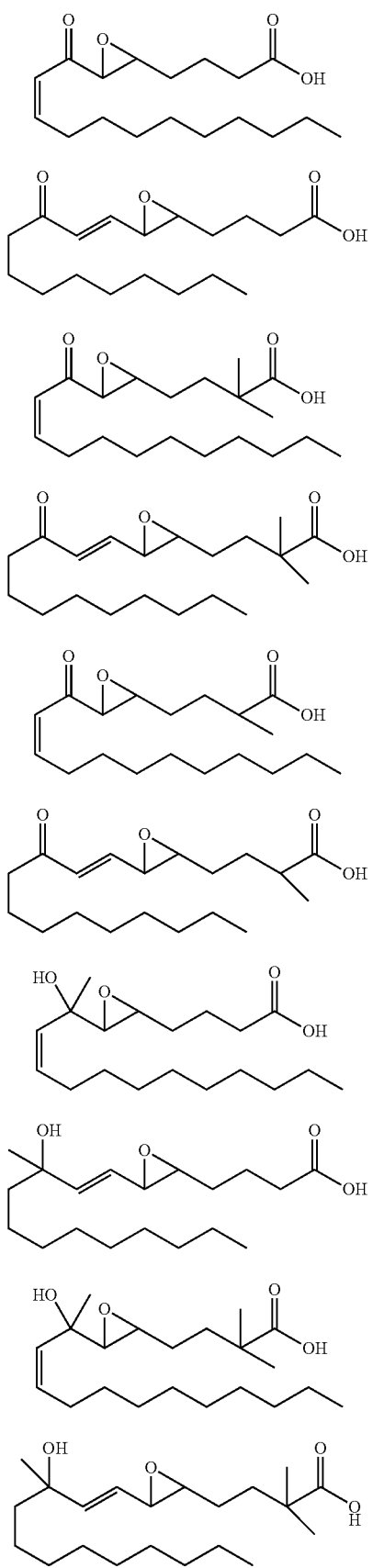
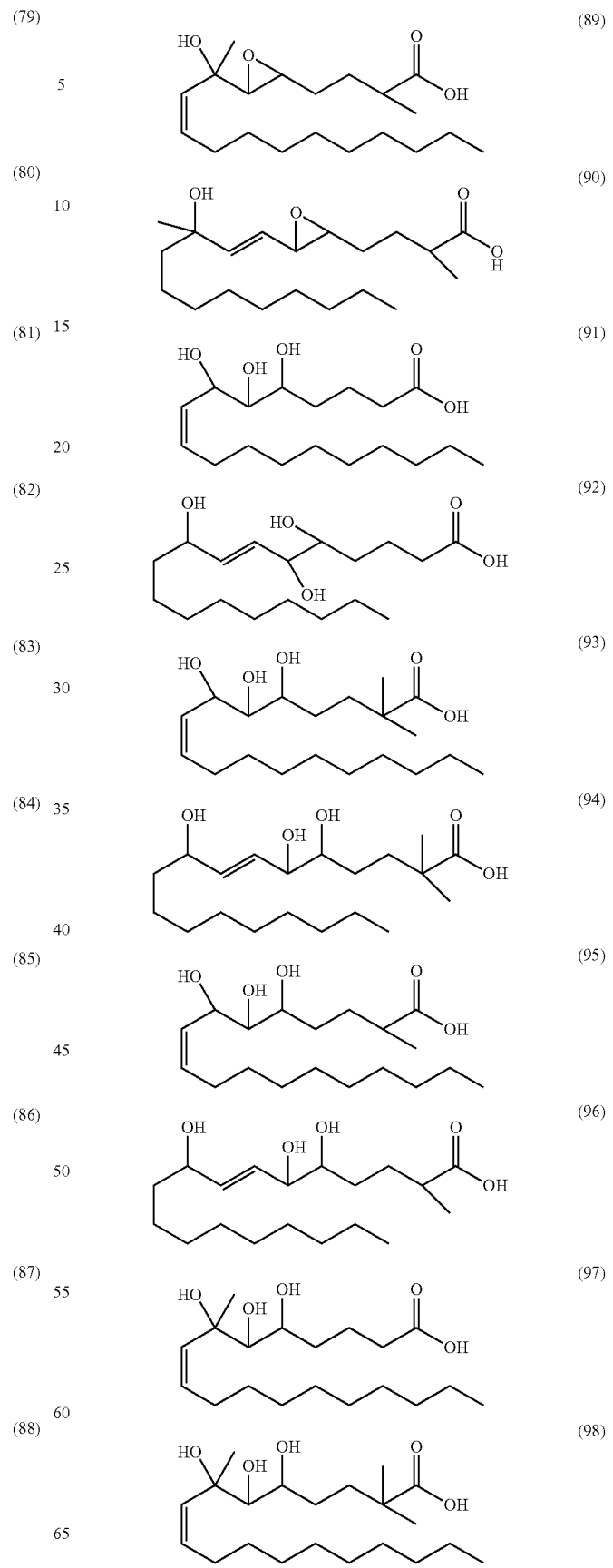

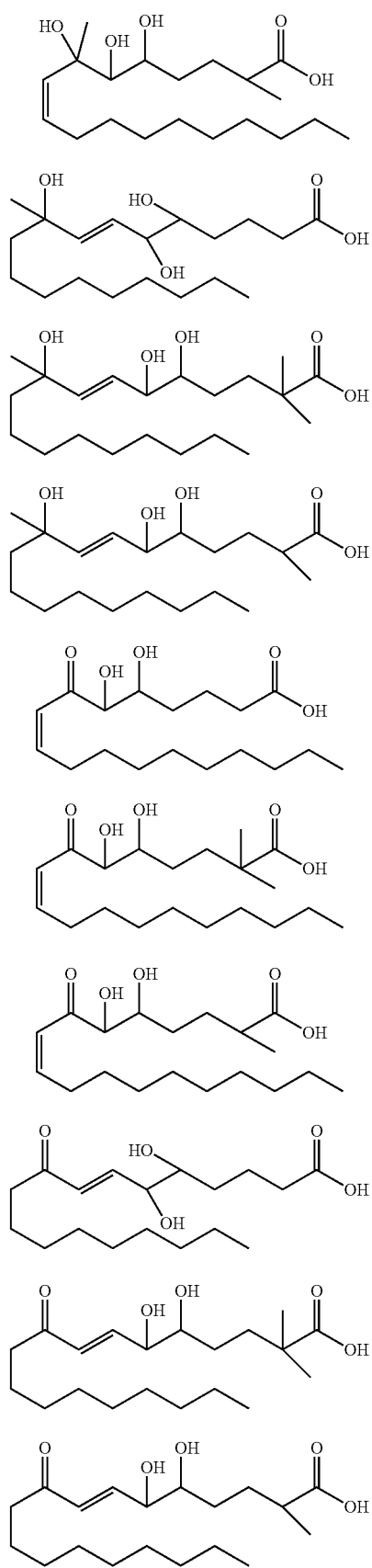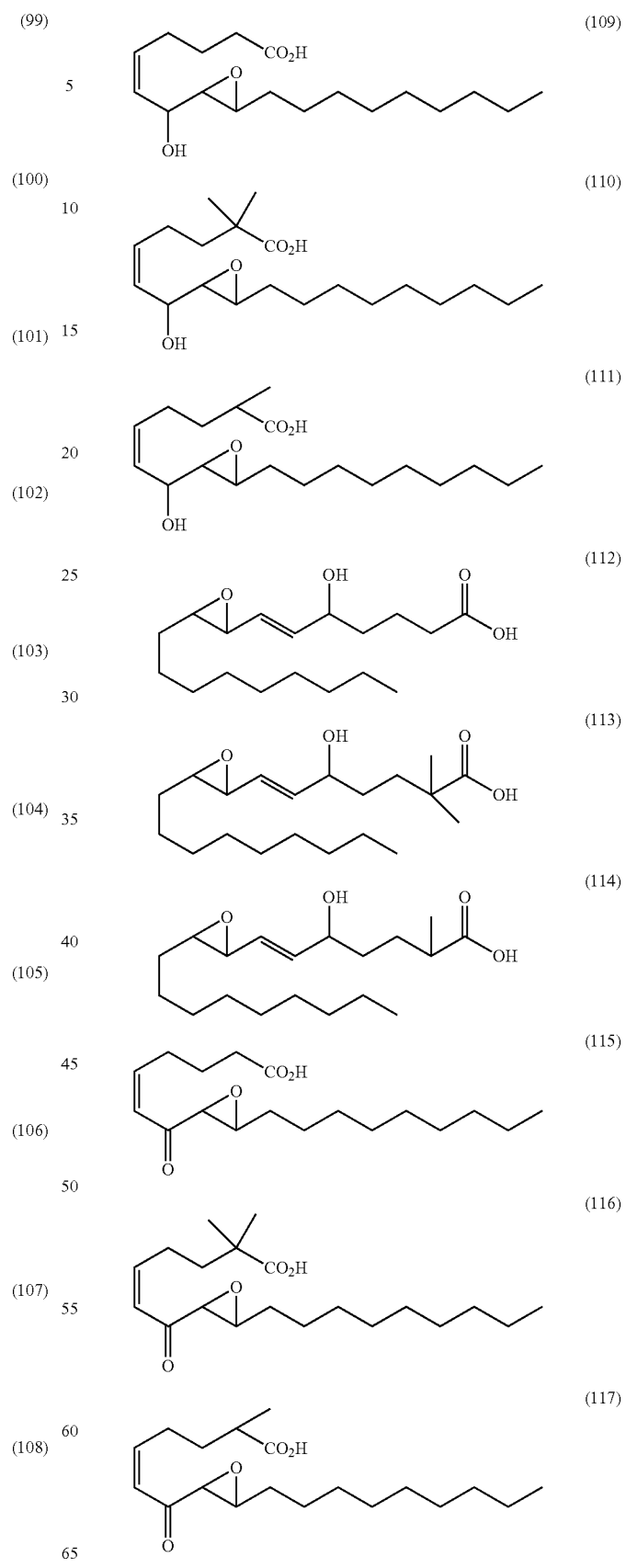

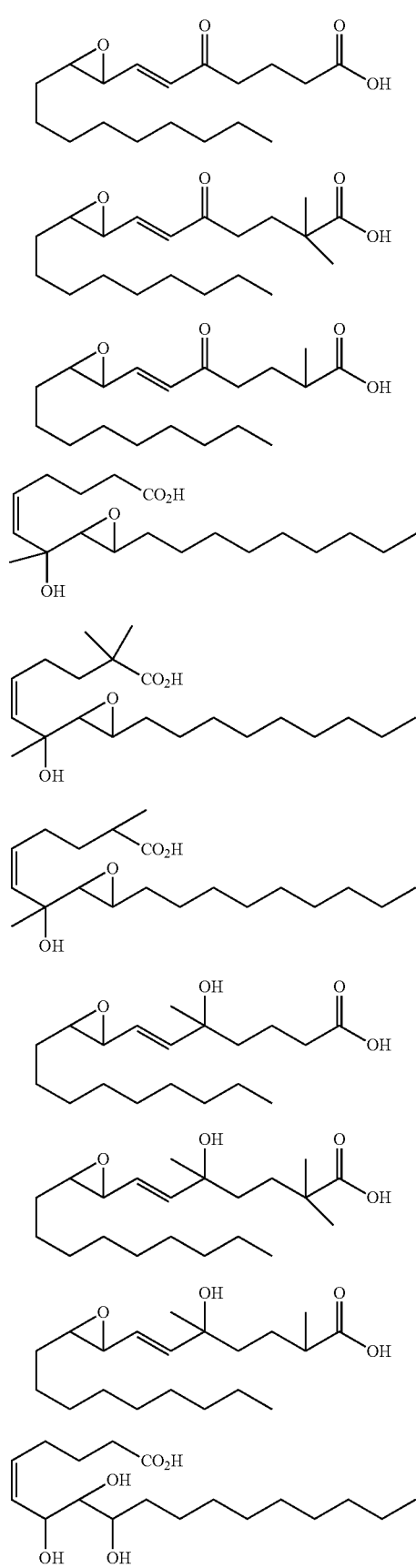
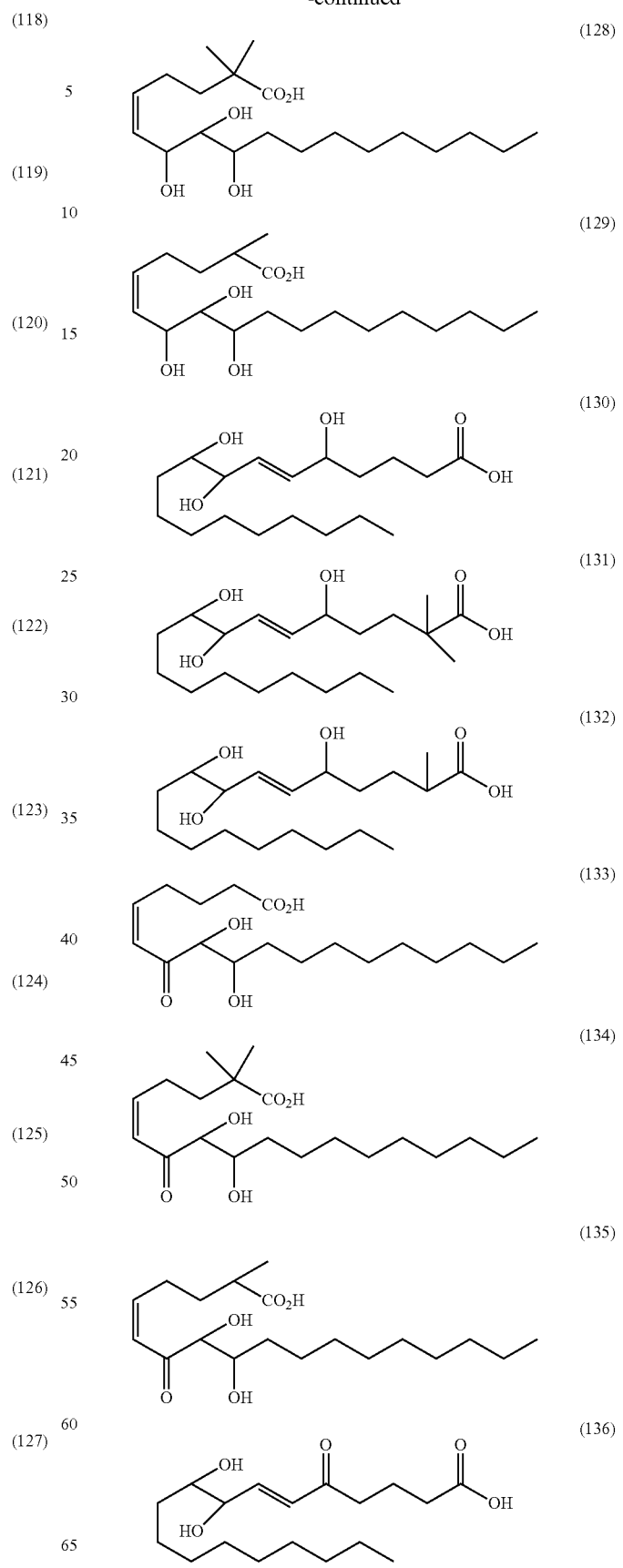

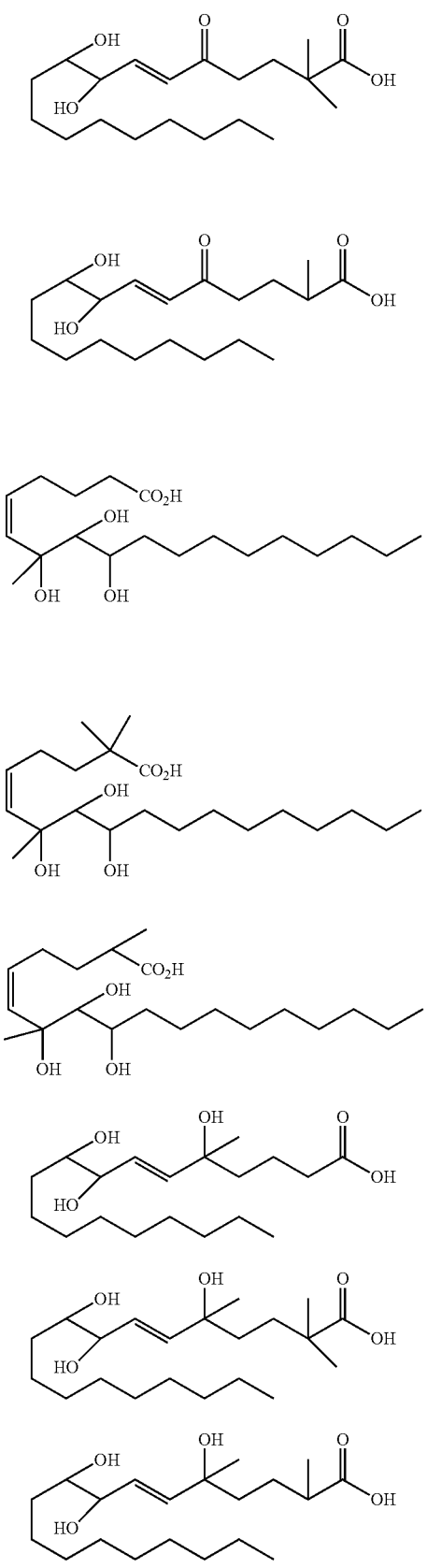
Mead [(5Z,8Z,11Z)-Eicosa-5,8,11-trienoic] Acid Derivatives
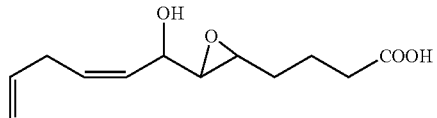
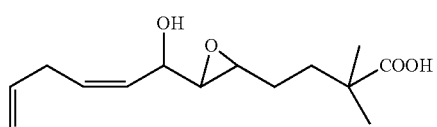
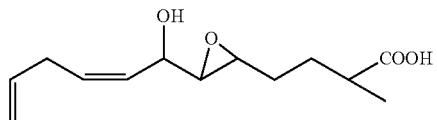
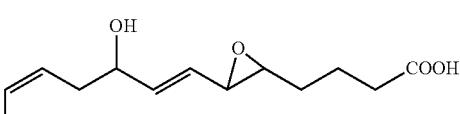
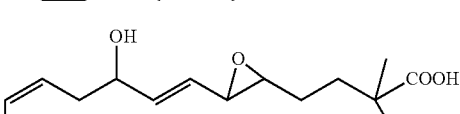
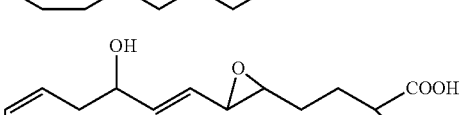
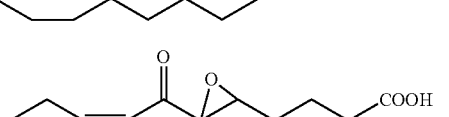
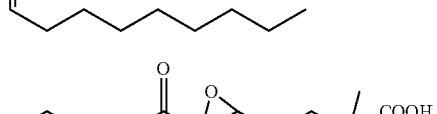
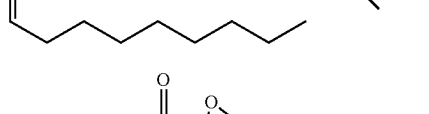
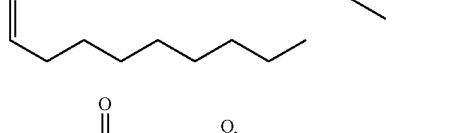

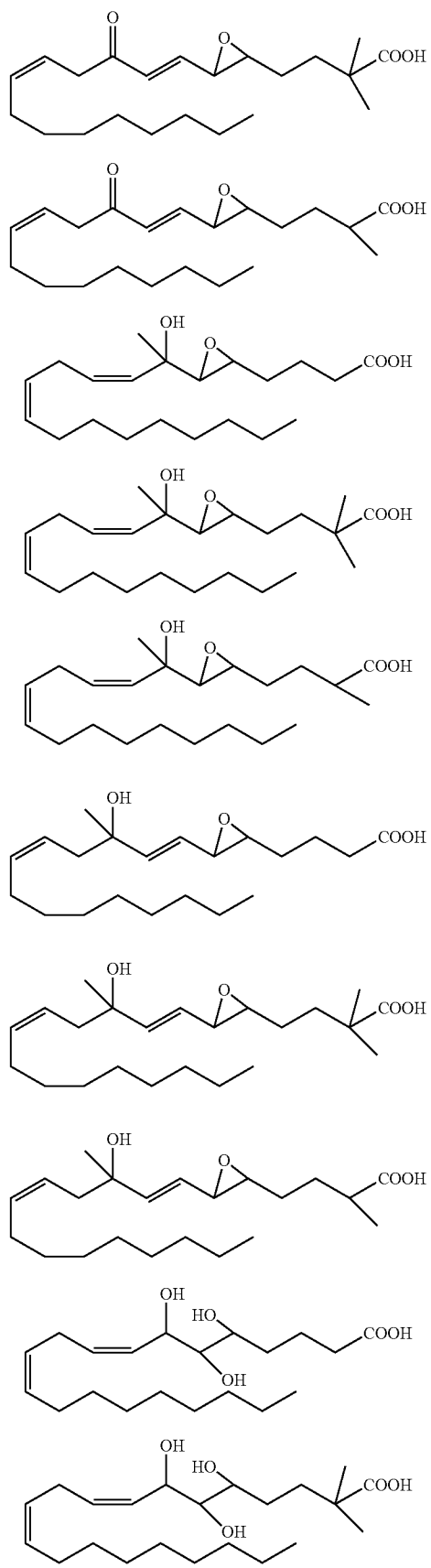
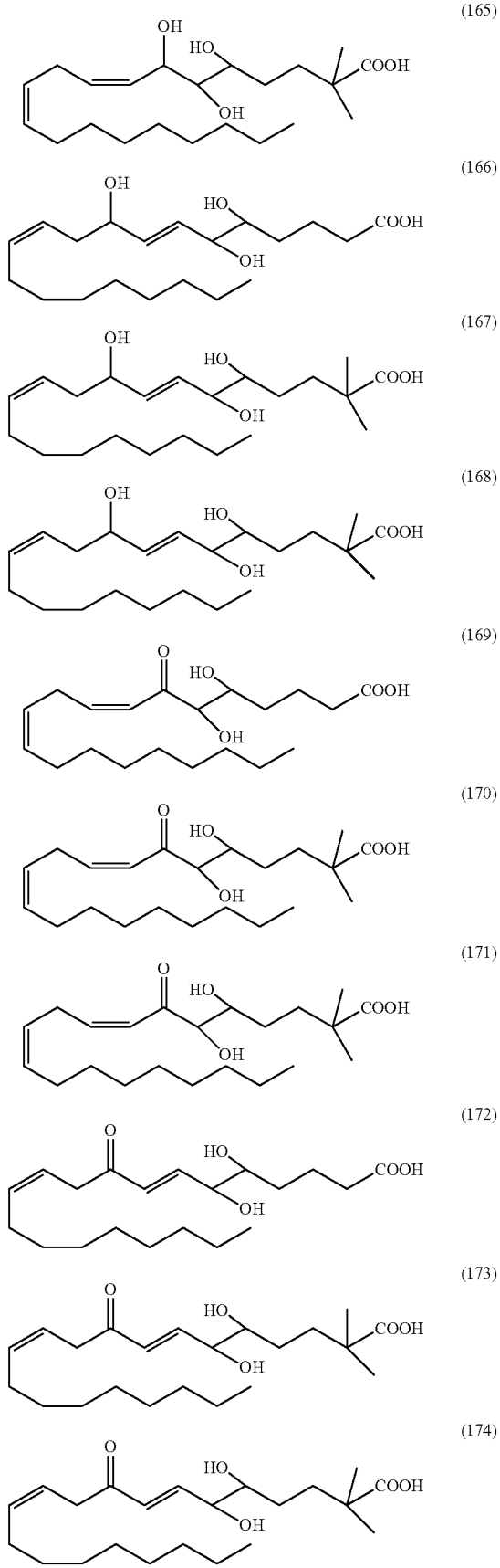

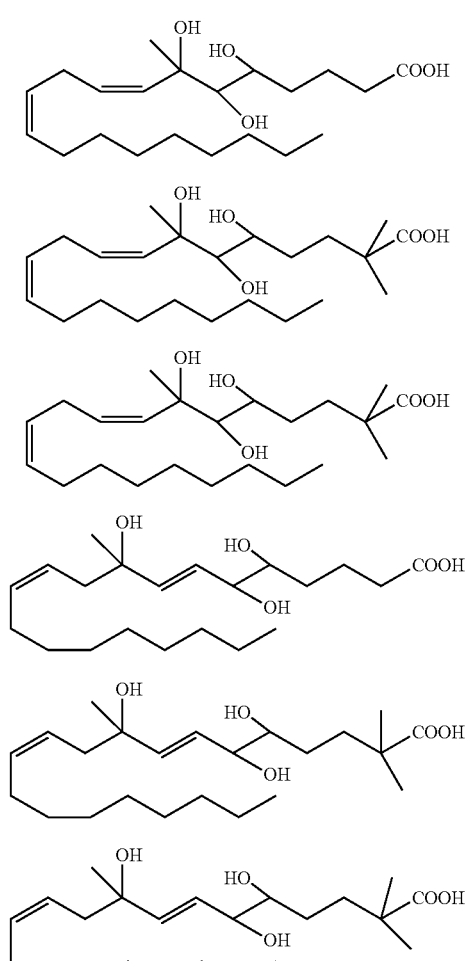
Arachidonic Acid Derivatives
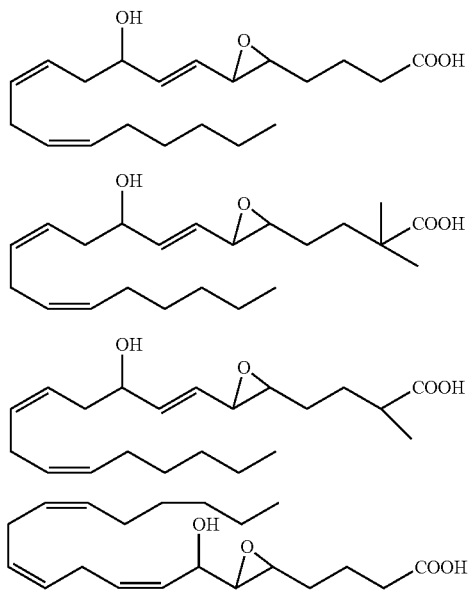
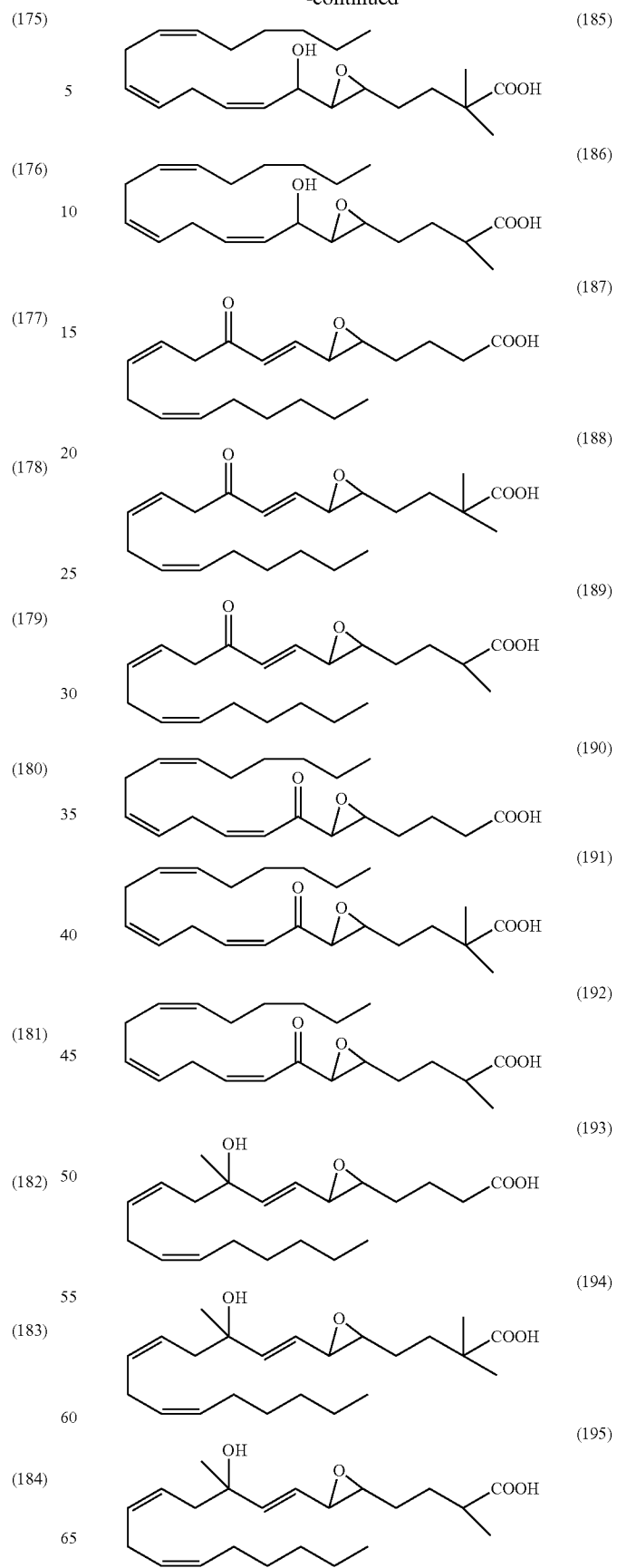

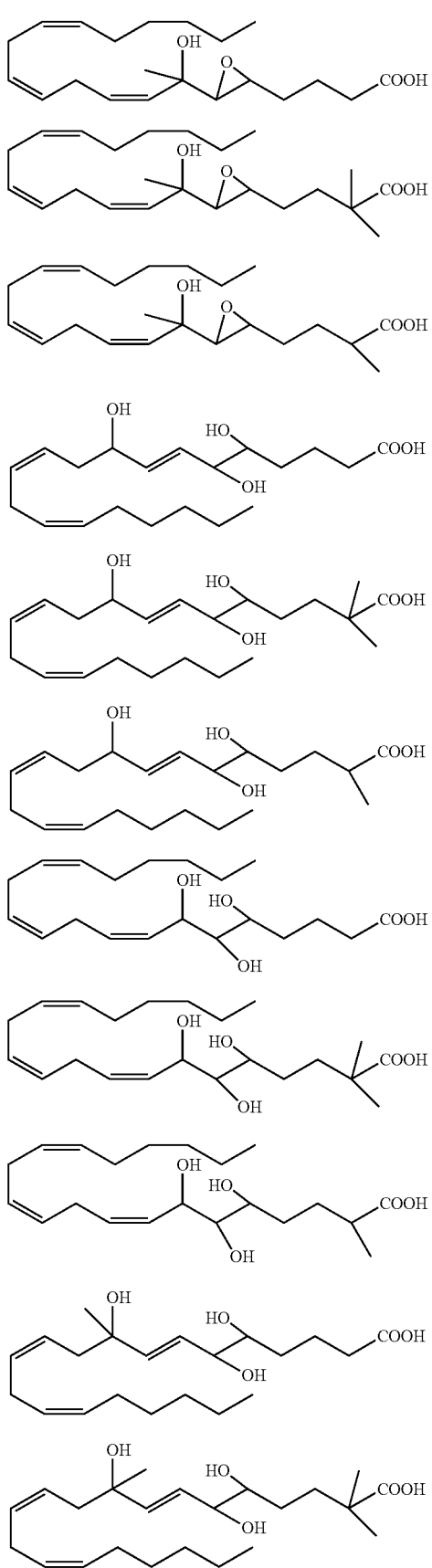
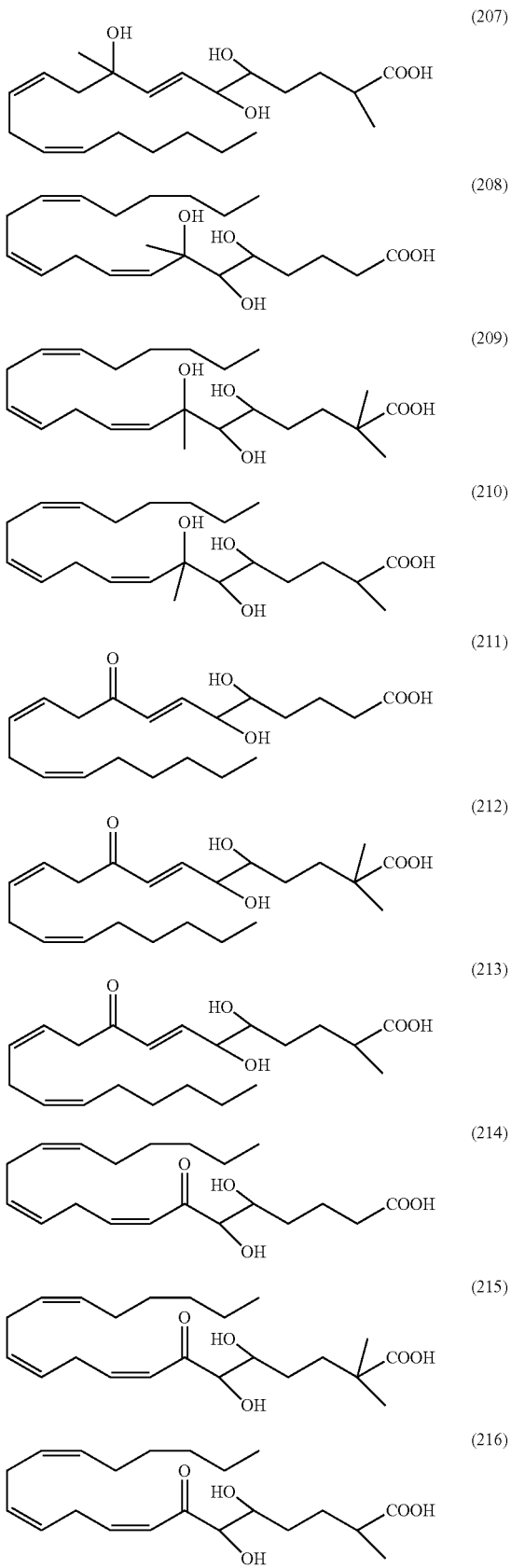

Docosatetraenic (Adrenic) Acid Derivatives
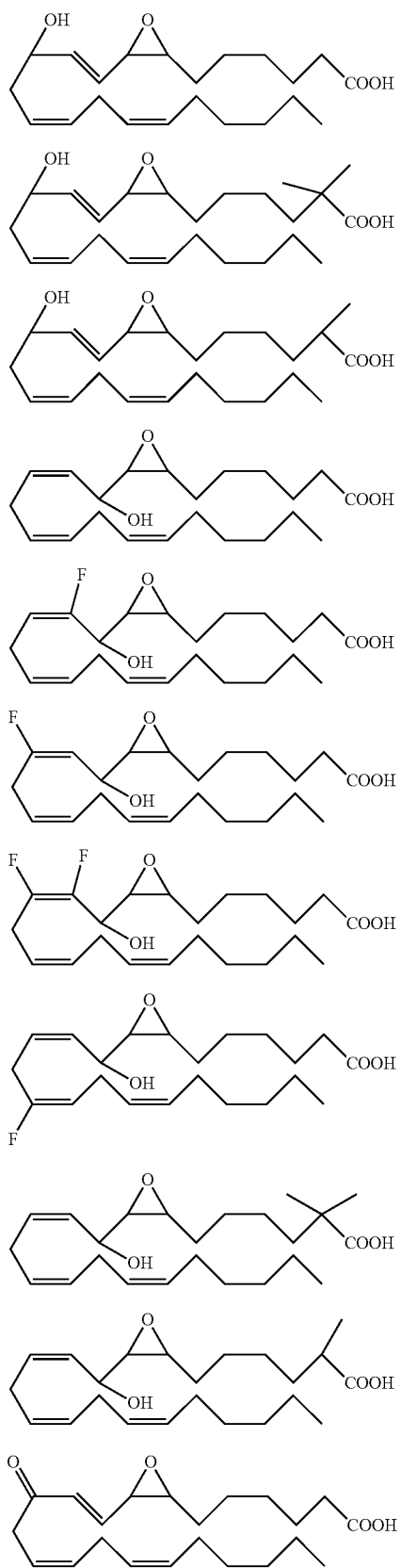
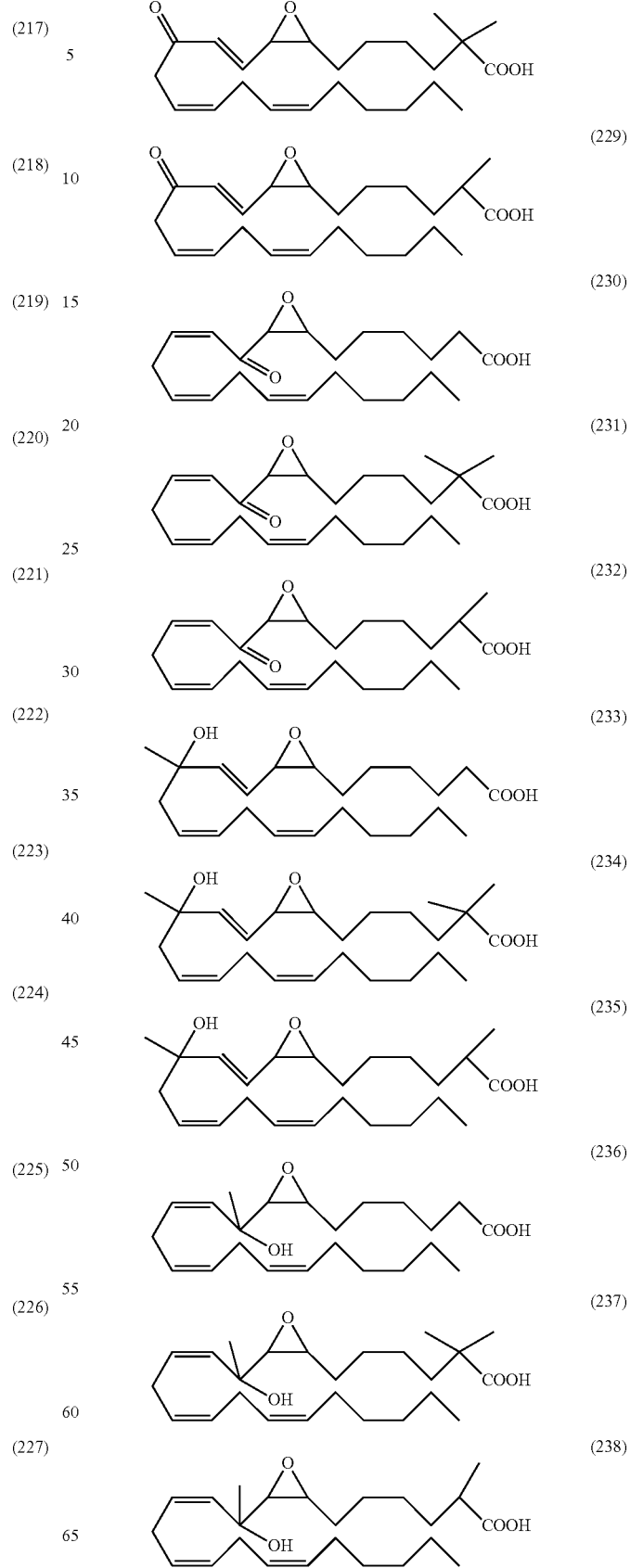

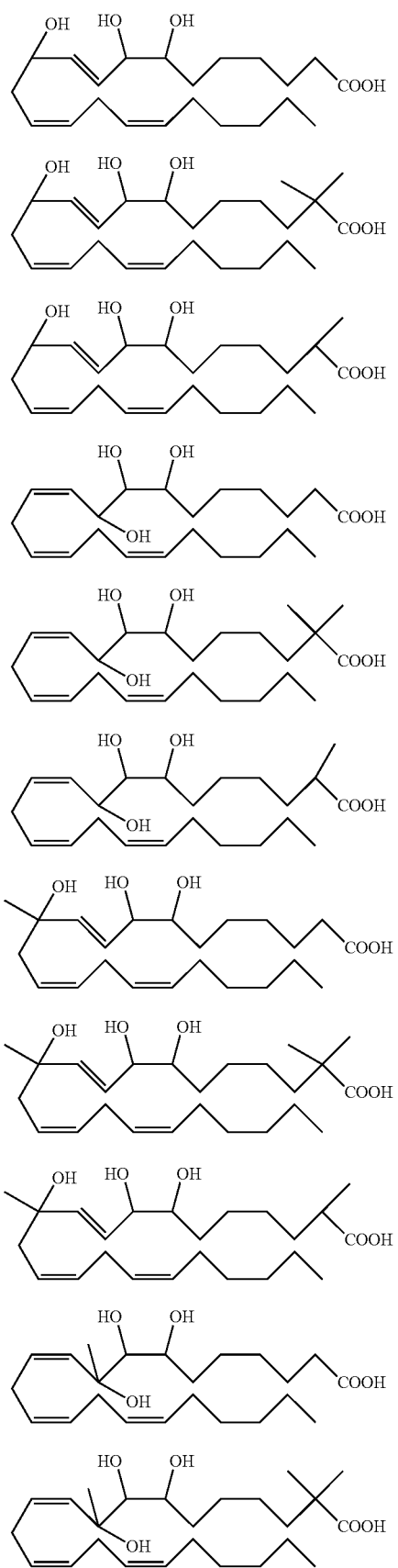
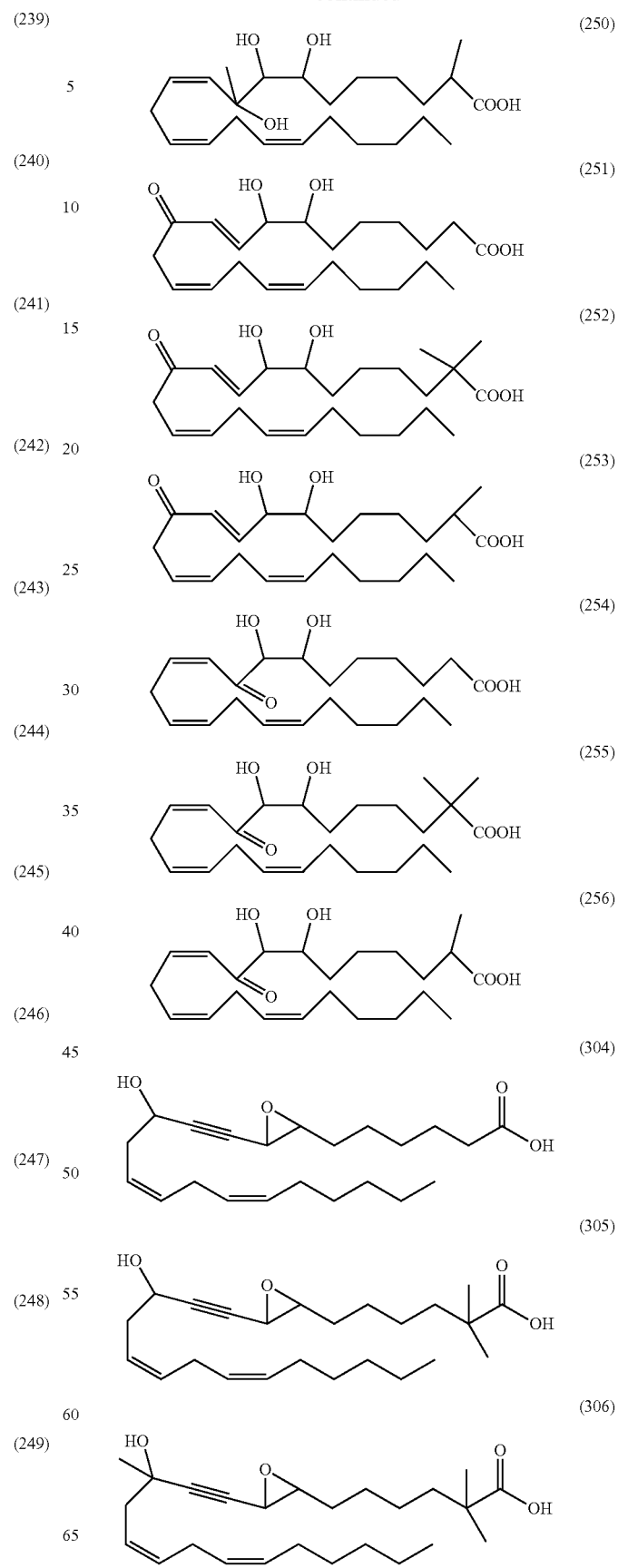

(307) 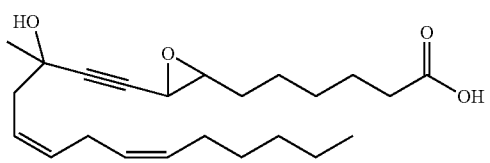
(308) 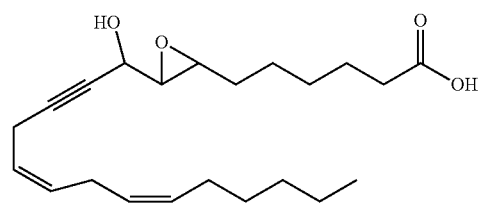
(309) 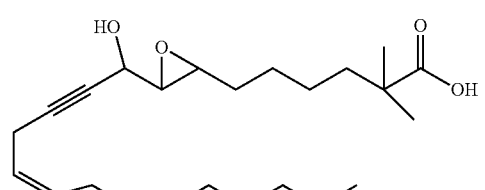
(310) 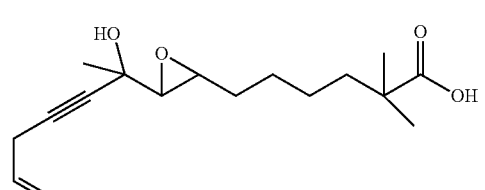
(311) 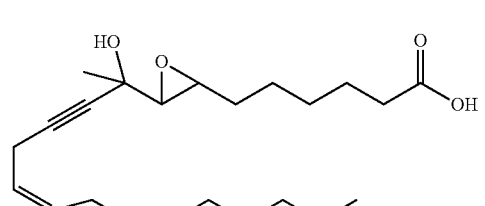
Docosahexaenoic Acid Derivatives
(257) 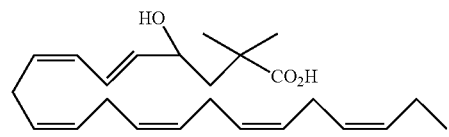
(258) 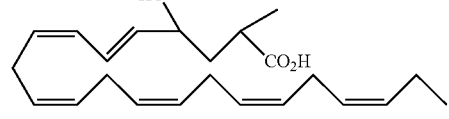
(259) 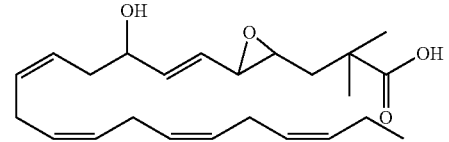
(260) 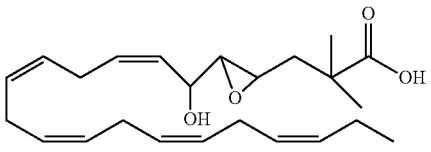
(261) 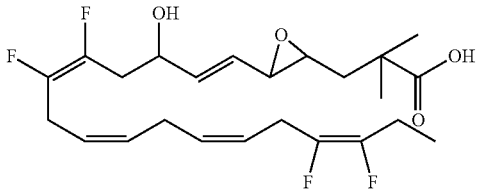
(262) 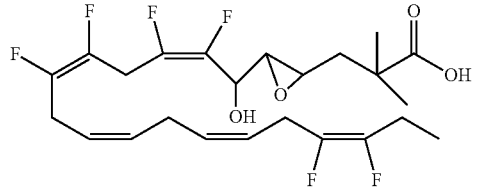
(312) 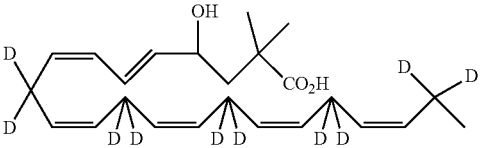
(313) 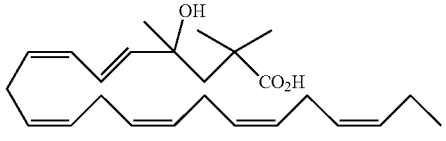
(314) 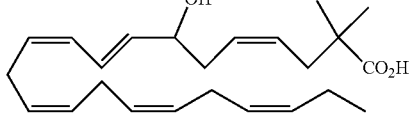
(315) 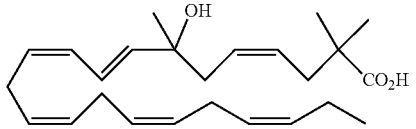
(316) 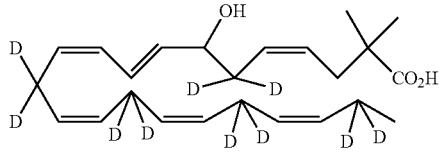
(317) 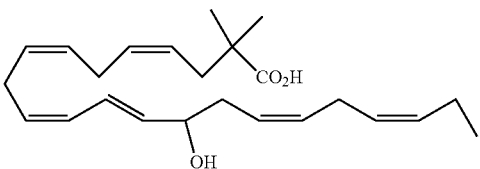

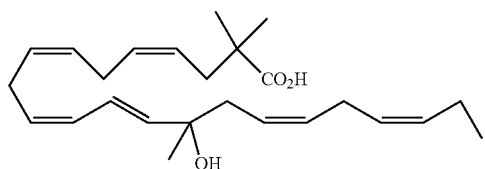
(318)

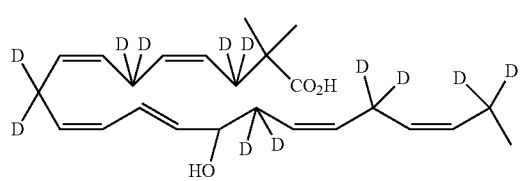
(319)

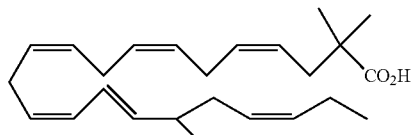
(320)

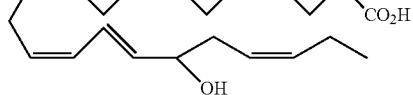
(321)

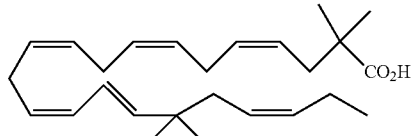
(322)

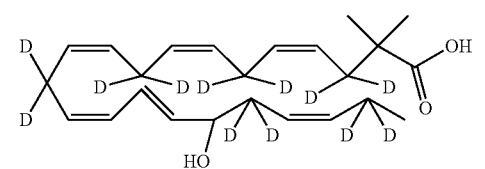
(323)

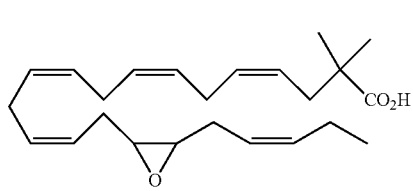
(324)

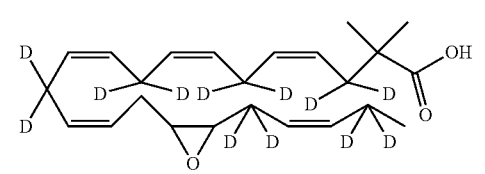
(325)

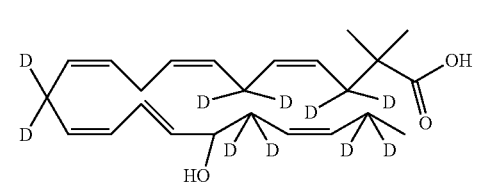
(326)

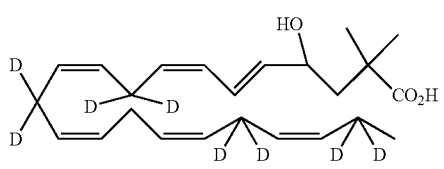
(327)

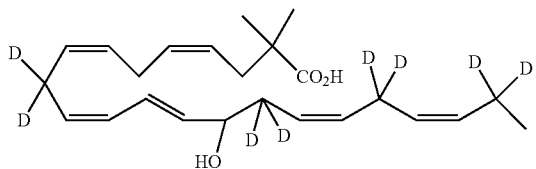
(328)

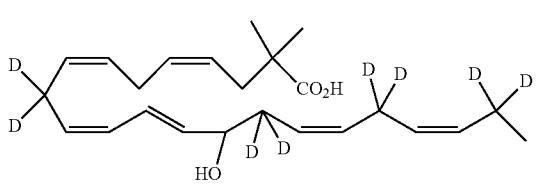
(329)

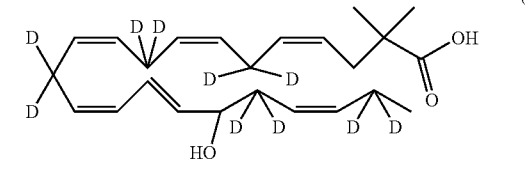
(330)

Any of the compounds disclosed herein that contain a carboxyl group (for example, Compounds 1-330) can be prepared with a methyl ester group in place of the carboxyl group. Further, any of the compounds disclosed herein that contain an alkenyl group can be prepared with a fluoride substituted in place of hydrogen on the carbon of any carbon-carbon double bond.

In certain embodiments, the fatty acid derivative is a compound having a structure according to any one of formulas (CIII)-(CX) or a stereoisomer, tautomer, or pharmaceutically acceptable salt thereof:

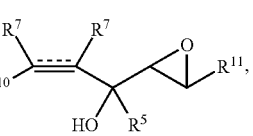
(CIII)

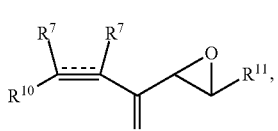
(CIV)

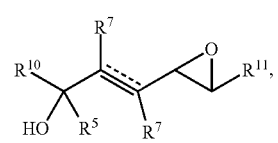
(CV)

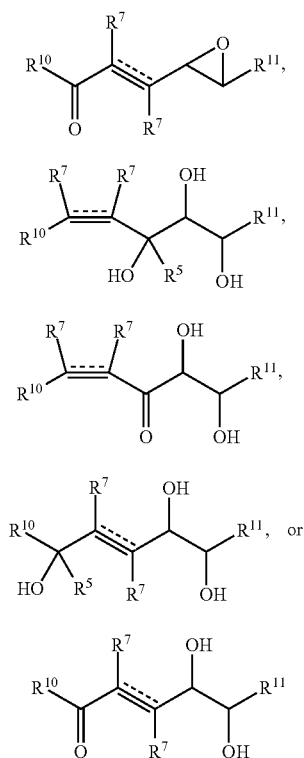

(CVI)
(CVII)
(CVIII)
(CIX)
(CX)

Formulas (CIII)-(CX) encompass the putative active site of compounds 1-16, and therefore are believed to modulate the activity of the endogenous targets of compounds 1-16. In formulas (CIII)-(CX), $R^5$ is hydrogen, lower alkyl, or halide, each $R^7$ is independently hydrogen or fluoride or is not present and the adjacent carbons form alkyne, and $R^{10}$ and $R^{11}$ are independently aliphatic.

In some embodiments of formulas (CIII)-(CX), $R^{10}$ and $R^{11}$ are independently substituted or unsubstituted lower alkyl, substituted or unsubstituted lower heteroalkyl, substituted or unsubstituted lower alkenyl (such as halogenated alkenyl, for example fluoroalkenyl or difluoroalkenyl), substituted or unsubstituted lower heteroalkenyl, substituted or unsubstituted lower alkynyl, substituted or unsubstituted lower heteroalkynyl, substituted or unsubstituted aryl, or substituted or unsubstituted heteroaryl.

In some embodiments of any one of formulas (CIII)-(CX), $R^5$ is hydrogen. In some embodiments of any one of formulas (CIII)-(CX), $R^{10}$ is methyl. In some embodiments of any one of formulas (CIII)-(CX), $R^{11}$ is methyl. In some embodiments of any one of formulas (CIII)-(CX), $R^5$ is hydrogen, $R^{10}$ is methyl, and $R^{11}$ is methyl.

Exemplary compound structures of this disclosure that fall within the scope of formulas (CIII)-(CX) include, but are not limited to:

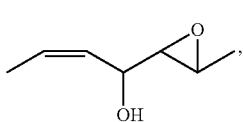

(263)

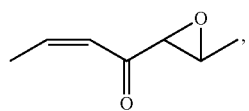

(264)

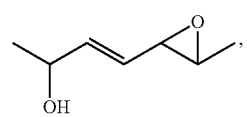

(265)

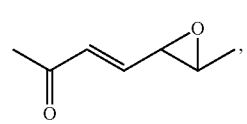

(266)

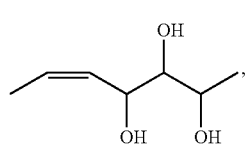

(267)

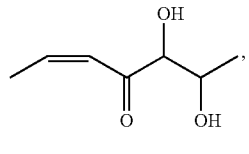

(268)

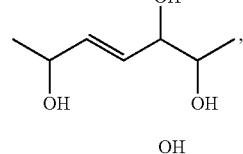

(269)

(270)

Compounds according to formulas (I)-(CX) (such as compounds 1-330) can be synthesized by conventional methods optionally supplemented with the synthesis methods provided herein (see the Examples). A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diastereomers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the disclosed compounds encompass any tautomeric, conformational isomeric, optical isomeric, and/or geometric isomeric forms of the compounds described herein, as well as mixtures of these various different isomeric forms.

Additional Compound Embodiments

In certain embodiments, the fatty acid derivative is an oxidized fatty acid having a 2,2-dimethyl, which as described herein, reduces esterification of the oxidized fatty acid. In several embodiments, 2,2-dimethyl modified oxidized fatty acid embodiments have increased half-life under physiological conditions (such as in blood, or in phosphate buffered saline) compared to corresponding unmodified oxidized fatty acid compounds. In some embodiments, the 2,2-dimethyl modified oxidized fatty acid compound has a structure according to formula CXI or a stereoisomer, tautomer, or pharmaceutically acceptable salt thereof.

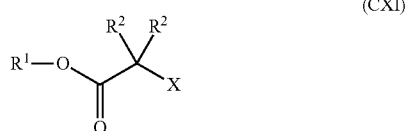

(CXI)

In formula CXI, X is aliphatic from 10-25 carbons in length (such as any one of 10, 11, 12, 13, 14, 15, 16, 17, 18, 19, 20, 21, 22, 23, 24, or 25 carbons in length) and comprises one or more epoxy, hydroxyl, or carbonyl substitutions or combination thereof, $R^1$ is hydrogen or lower alkyl (such as methyl, ethyl, propyl, or butyl), and each $R^2$ is independently methyl or hydrogen. In some embodiments of formula CXI, X is substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, or substituted or unsubstituted heteroaryl. In several embodiments, X is alkyl or alkenyl, or halogenated alkenyl, particularly fluoroalkenyl or difluoroalkenyl. In some embodiments, X comprises one or more fluoroalkene or difluoroalkenle moieties. In some embodiments, X is alkyl or alkenyl. In some embodiments, X comprises one or more bis-allylic deuterium substitutions, for example, X is deuteriobisallylalkenyl or dideuteriobisallyl alkenyl. In some embodiments, each $R^2$ is methyl. In some embodiments, each $R^2$ is hydrogen. In some embodiments, each $R^2$ is methyl and the compound is an oxidized derivative of linoleic acid. In some embodiments, the compound of formula CXI comprises one or more deuterium substitutions of hydrogen at an oxidation-sensitive site of the fatty acid or at a site that becomes oxygen sensitive upon further transformations, for example at bis-allylic positions.

III. PHARMACEUTICAL COMPOSITIONS

This disclosure also includes pharmaceutical compositions comprising at least one fatty acid derivative as disclosed herein, or a stereoisomer, tautomer, or pharmaceutically acceptable salt thereof. In some embodiments, the fatty acid derivative is a compound according to any one of structures 1-330. Some embodiments of the pharmaceutical compositions include at least one fatty acid derivative and at least one further pharmaceutically acceptable additive such as pharmaceutically acceptable carriers, thickeners, diluents, buffers, preservatives, surface active agents and the like in addition to the molecule of choice. Useful pharmaceutically acceptable carriers and excipients are known in the art.

The pharmaceutical compositions comprising one or more fatty acid derivatives may be formulated in a variety of ways depending, for example, on the mode of administration and/or on the location to be imaged. Parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as Cremophor® polyethyoxylated detergent, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The form of the pharmaceutical composition will be determined by the mode of administration chosen. Embodiments of the disclosed pharmaceutical compositions may take a form suitable for virtually any mode of administration, including, for example, oral, buccal, systemic, nasal, injection, transdermal, rectal, vaginal, etc., or a form suitable for administration by inhalation or insufflation. Generally, embodiments of the disclosed pharmaceutical compositions will be administered parenterally (e.g., by intravenous, intra-arterial, subcutaneous, intramuscular, or intraperitoneal injection), intrathecally, or orally.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. The composition may take such forms as suspension, solutions or emulsions in oily or aqueous vehicles, and may contain formulatory agents such as suspending, stabilizing and/or dispersing agents. For example, parenteral administration may be done by bolus injection or continuous infusion. Alternatively, the fatty acid derivative may be in powder form for reconstitution with a suitable vehicle, e.g. sterile water, before use.

Systemic formulations include those designed for administration by injection, e.g., subcutaneous, intravenous, intramuscular, intrathecal or intraperitoneal injection, as well as those designed for transdermal, transmucosal, oral or pulmonary administration.

Oral formulations may be liquid (e.g., syrups, solutions or suspensions), or solid (e.g., powder, tablets, or capsules). Oral formulations may be coupled with targeting ligands for crossing the endothelial barrier. Some fatty acid derivative formulations may be dried, e.g., by spray-drying with a disaccharide, to form fatty acid derivative powders. Solid compositions prepared by conventional means with pharmaceutically acceptable excipients such as binding agents (e.g., pregelatinised maize starch, polyvinylpyrrolidone or hydroxypropyl methylcellulose); fillers (e.g., lactose, mannitol, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Actual methods of preparing such dosage forms are known, or will be apparent, to those skilled in the art.

Liquid preparations for oral administration may take the form of, for example, elixirs, solutions, syrups or suspensions. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophor® detergent, or fractionated vegetable oils); and preservatives (e.g., methyl or propyl-p-hydroxybenzoates or sorbic acid). The preparations may also contain buffer salts, preservatives, flavoring, coloring and sweetening agents as appropriate. Preparations for oral administration may be suitably formulated to give controlled release of the fluorophore, as is well known.

Certain embodiments of the pharmaceutical compositions comprising fatty acid derivatives as described herein may be formulated in unit dosage form suitable for individual administration of precise dosages. The pharmaceutical compositions may, if desired, be presented in a pack or dispenser device which may contain one or more unit dosage forms containing the fatty acid derivative. The pack may, for example, comprise metal or plastic foil, such as a blister pack. The pack or dispenser device may be accompanied by instructions for administration. The amount of fatty acid derivative administered will depend at least in part on the subject being treated, the target (e.g., the size, location, and characteristics of a tumor), and the manner of administration, and is known to those skilled in the art. Within these bounds, the formulation to be administered will contain a quantity of the fatty acid derivative disclosed herein in an amount effective to provide a therapeutically effective dose of the drug to the subject being treated.

IV. METHODS

In additional embodiments, a method of treating a disease or condition in a subject using a disclosed fatty acid derivative is provided. The method comprises administering a therapeutically effective amount of a pharmaceutical composition comprising a disclosed fatty acid derivative to a subject having, or suspected of having, the disease or condition. Exemplary diseases or conditions for which the method can be applied include inflammation, chronic itch, chronic pain, an autoimmune disorder, atherosclerosis, a skin disorder, a neurodegenerative disorder, a psychiatric disorder, and arthritis. In additional embodiments, a disclosed fatty acid derivative can be used in any composition applied to the skin, such as a composition for cosmetic or personal care purposes, or insect repellant.

The pharmaceutical composition may be administered by any suitable route such as topically, parenterally, or orally. The subject may be a mammal such as a human or a non-human mammal. In certain examples, the subject is a human.

The fatty acid derivative can be administered to the subject in a single bolus delivery, via continuous delivery (for example, continuous intravenous delivery) over an extended time period, or in a repeated administration protocol (for example, by an hourly, daily, weekly, or biweekly, repeated administration protocol). The therapeutically effective amount of the fatty acid derivative can be provided as repeated doses within a prolonged treatment regimen that will yield clinically significant results to alleviate one or more symptoms or detectable conditions associated with the disease or condition. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the fatty acid derivative may simply inhibit or enhance one or more selected biological activities correlated with the disease or condition being treated, as set forth herein, for either therapeutic or diagnostic purposes.

The actual dosage of the fatty acid derivative will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the fatty acid derivative for eliciting the desired activity or biological response in the subject. Dosage regimens can be adjusted to provide an optimum therapeutic response. A therapeutically effective amount is also one in which any toxic or detrimental side effects of the fatty acid derivative is outweighed in clinical terms by therapeutically beneficial effects. A non-limiting range for a therapeutically effective amount of a fatty acid derivative within the methods and formulations of the disclosure may be within a range of from 0.01 mg/kg body weight to 5 g/kg body weight, such as 10 mg/kg to 5 g/kg body weight, or 1 g/kg to 5 g/kg body weight. In some embodiments, the fatty acid derivative may be administered in amount effective to provide a serum fatty acid derivative concentration of from 0.1-100 µM or from 1-5000 µg/mL.

Dosage can be varied by the attending clinician to maintain a desired concentration at a target site (for example, systemic circulation). Higher or lower concentrations can be selected based on the mode of delivery, for example, oral, intravenous, or topical delivery. Dosage can also be adjusted based on the release rate of the administered formulation, for example, of an intrapulmonary spray versus powder, sustained release oral versus injected particulate or transdermal delivery formulations, and so forth.

In some embodiments, the disclosed fatty acid derivatives have utility for treating itch (such as chronic itch) in a subject. In such embodiments, administering a therapeutically effective amount of the fatty acid derivative ameliorates at least one sign or symptom associated with the itch (such as chronic itch) in a subject. For example, the fatty acid derivative can be used to reduce itch (such as chronic itch) associated with inflamed skin, such as skin affected with inflammatory skin disorders (e.g. atopic dermatitis, psoriasis, contact dermatitis, urticaria, drug reactions, pemphigoid, dermatitis herpetiformis), parasitic or infectious diseases (e.g. scabies, mycoses, chickenpox), autoimmune disorders, lymphomas (e.g., cutaneous T-cell lymphoma)), as well as itch affecting primary non-diseased, non-inflamed skin (such as itch associated with a neurologic or psychiatric origin), or itch associated with secondary scratch lesions, which are scratch lesions caused by a patient in response to an initial itch, and include excoriations, crusts, papules, nodules and chronic secondary scratch lesions like prurigo nodularis. In some embodiments, administration of a therapeutically effective amount of a disclosed fatty acid derivative to a subject for treatment of itch can reduce the itch in the subject by at least 10%, at least 20%, at least 30%, at least 40%, at least 50%, at least 60%, at least 70%, at least 80%, at least 90%, or even at 100% compared to the absence of the treatment. Activity of the disclosed fatty acid derivatives for treating itch can be confirmed in an animal model, for example, by assessing itch activity of mice in response to histamine injections in combination with the relevant fatty acid derivative or a control (see, e.g., Example 1 below).

In some embodiments, the disclosed fatty acid derivatives have utility for treating pain (such as chronic pain) in a subject. In such embodiments, administering a therapeutically effective amount of the fatty acid derivative ameliorates at least one sign or symptom associated with the pain (such as chronic pain) in a subject. For example, the fatty acid derivative can be used to reduce pain associated with inflammation (including inflammation caused by tissue damage, inflammatory pain), or by damage to the nervous system such as demyelination (neuropathic pain), postsurgical pain, pain associated with tissue damage, pain from infection (shingles), pain from neuropathic conditions, and pain from skeletal muscular conditions. In some embodiments, administration of a therapeutically effective amount of a disclosed fatty acid derivative to a subject for treatment of pain can reduce the pain in the subject by at least 10%, at least 20%, at least 30%, at least 40%, at least 50%, at least 60%, at least 70%, at least 80%, at least 90%, or even at 100% compared to the absence of the treatment. Activity of a disclosed fatty acid derivatives for treating pain can be confirmed in an animal model, for example, by assessing pain responses of mice in response to PGE2 injections in combination with the relevant fatty acid derivative or a control (see, e.g., Example 1 below).

In some embodiments, the disclosed fatty acid derivatives have utility for treating atherosclerosis in a subject. In such embodiments, administering a therapeutically effective amount of the fatty acid derivative ameliorates at least one sign or symptom associated with atherosclerosis in a subject. For example, administration of a therapeutically effective amount of the fatty acid derivative to a subject can be used to reverse or slow the progression of atherosclerosis, for example as measured by the presence of atherosclerotic lesions and/or functional signs of the disease, such as improvement in cardiovascular function as measured by signs (such as peripheral capillary refill), symptoms (such as chest pain and intermittent claudication), or laboratory evidence (such as that obtained by EKG, angiography, or other imaging techniques). In some embodiments, administration of a therapeutically effective amount of the fatty acid derivative increases cholesterol flux in the subject. In some embodiments, administration of a therapeutically effective amount of the fatty acid derivative reduces a level of LDL cholesterol in the subject, for example, as compared to abase line level of LDL cholesterol. In some embodiments, administration of a therapeutically effective amount of a disclosed fatty acid derivative to a subject for treatment of atherosclerosis can reduce the atherosclerosis in the subject by at least 10%, at least 20%, at least 30%, at least 40%, at least 50%, at least 60%, at least 70%, at least 80%, at least 90%, or even at 100% compared to the absence of the treatment. In one example, activity of the disclosed fatty acid derivatives for treating atherosclerosis can be indicated by detecting an increase in cholesterol flux induced by ApoA1 in combination with the fatty acid derivative compared to a relevant control (see, e.g., Example 14 below).

In some embodiments, the disclosed fatty acid derivatives have utility for treating an autoimmune disorder in a subject. In such embodiments, administering a therapeutically effective amount of the fatty acid derivative ameliorates at least one sign or symptom associated with the autoimmune disorder in a subject. For example, administration of a therapeutically effective amount of the fatty acid derivative to a subject can be used to treat, prevent, and/or ameliorate symptoms of rheumatoid arthritis, Hashimoto's thyroiditis, pernicious anemia, Addison's disease, type I diabetes, systemic lupus erythematosus, dermatomyositis, Sjogren's syndrome, dermatomyositis, lupus erythematosus, multiple sclerosis, myasthenia gravis, Reiter's syndrome, or Grave's disease, among others. In some embodiments, administration of a therapeutically effective amount of a disclosed fatty acid derivative to a subject for treatment of an autoimmune disorder can reduce the autoimmune disorder in the subject by at least 10%, at least 20%, at least 30%, at least 40%, at least 50%, at least 60%, at least 70%, at least 80%, at least 90%, or even at 100% compared to the absence of the treatment.

In some embodiments, the disclosed fatty acid derivatives have utility for treating arthritis (such as degenerative arthritis) in a subject. In such embodiments, administering a therapeutically effective amount of the fatty acid derivative ameliorates at least one sign or symptom associated with the arthritis in a subject, such as a reduction in pain and/or swelling in the hips, knees, lower lumbar and cervical vertebrae, proximal and distal interphalangeal joints of the fingers, first carpometacarpal joints, and/or first tarsometatarsal joints of the feet. For example, administration of a therapeutically effective amount of the fatty acid derivative to a subject can be used to treat, prevent, and/or ameliorate symptoms of arthritis. In some embodiments, administration of a therapeutically effective amount of a disclosed fatty acid derivative to a subject for treatment of the arthritis can reduce the arthritis in the subject by at least 10%, at least 20%, at least 30%, at least 40%, at least 50%, at least 60%, at least 70%, at least 80%, at least 90%, or even at 100% compared to the absence of the treatment.

In some embodiments, the disclosed fatty acid derivatives have utility for treating a neurodegenerative disorder in a subject. In such embodiments, administering a therapeutically effective amount of the fatty acid derivative ameliorates at least one sign or symptom associated with the neurodegenerative disorder in a subject. For example, administration of a therapeutically effective amount of the fatty acid derivative to a subject can be used to treat, prevent, and/or ameliorate symptoms of Alzheimer's disease, vascular dementia, Parkinson's disease, Huntington's disease, multiple sclerosis, or amyotrophic lateral sclerosis (ALS). In some embodiments, administration of a therapeutically effective amount of a disclosed fatty acid derivative to a subject for treatment of the neurodegenerative disorder can reduce the neurodegenerative disorder in the subject by at least 10%, at least 20%, at least 30%, at least 40%, at least 50%, at least 60%, at least 70%, at least 80%, at least 90%, or even at 100% compared to the absence of the treatment.

In some embodiments, the disclosed fatty acid derivatives have utility for treating a psychiatric disorder in a subject. In such embodiments, administering a therapeutically effective amount of the fatty acid derivative ameliorates at least one sign or symptom associated with the psychiatric disorder in a subject. For example, administration of a therapeutically effective amount of the fatty acid derivative to a subject can be used to treat, prevent, and/or ameliorate symptoms of depression, anxiety, and/or psychosis. In some embodiments, administration of a therapeutically effective amount of a disclosed fatty acid derivative to a subject for treatment of the psychiatric disorder can reduce the neurodegenerative disorder in the subject by at least 10%, at least 20%, at least 30%, at least 40%, at least 50%, at least 60%, at least 70%, at least 80%, at least 90%, or even at 100% compared to the absence of the treatment.

In some embodiments, the disclosed fatty acid derivatives have utility for treating a skin disorder in a subject. In such embodiments, administering a therapeutically effective amount of the fatty acid derivative ameliorates at least one sign or symptom associated with the skin disorder in a subject. For example, administration of a therapeutically effective amount of the fatty acid derivative to a subject can be used to treat, prevent, and/or ameliorate symptoms of atopic dermatitis, seborrheic dermatitis, acne, rosacea, ichthyosis, erythroderma, alopecia, wrinkles, dry skin/water barrier function, essential fatty acid deficiency, vitiligo, sebaceous cyst, pilonidal cyst, hypertrophic scar/keloid, seborrheic keratosis, and actinic keratosis. In some embodiments, administration of a therapeutically effective amount of the fatty acid derivative to a subject can be used to treat, prevent, and/or ameliorate symptoms of a condition with water barrier dysfunction or increased epidermal water loss, such as ichthyosis, eczema/atopic dermatitis, psoriasis, and/or dry skin. For example, a pharmaceutical composition comprising a disclosed compound that is an oxidized derivative of linoleic acid and has 2-methyl or 2,2-dimethyl and is an oxidized derivative of linoleic acid (such as any one of compounds 31-36, 38-43, or 66-72) can be applied topically to the subject to treat, prevent, and/or ameliorate the condition with water barrier dysfunctionor increased epidermal water loss. In some embodiments, administration of a therapeutically effective amount of a disclosed fatty acid derivative to a subject for treatment of the skin disorder can reduce the neurodegenerative disorder in the subject by at least 10%, at least 20%, at least 30%, at least 40%, at least 50%, at least 60%, at least 70%, at least 80%, at least 90%, or even at 100% compared to the absence of the treatment.

In additional embodiments, methods are provided for diagnosing a disease or condition in a subject, for example for determining the likelihood that the subject, such as an otherwise healthy subject, or a subject suspected or at risk of having the disease or condition, has the disease or condition, or will likely develop the disease or condition in the future. The method comprises measuring a level of any one of compounds 1-16 in a biological sample from the subject, and diagnosing the subject as a subject with the disease or condition, or at risk of developing the disease or condition if an altered level (such as an elevated level, for example at least a 2-fold increase) of the compound is detected in the biological sample compared to a corresponding control (such as a level of the compound in a subject without the disease or condition or a subject not at risk of developing the disease or condition). In several embodiments, the disease or condition is selected from one of inflammation, chronic itch, chronic pain, an autoimmune disorder, a skin disorder, and atherosclerosis. In some embodiments, the measured levels of any one of compounds 1-16 in a biological sample from the subject can be used to guide targeted interventions or advice for preventing or managing the disease or condition. For example, a subject with an identified increase in any one of Compounds 1-16 can be placed on a diet intervention to reduce the level of the compounds, for example, a reduced polyunsaturated fatty acid diet.

In some embodiments, methods are provided herein for evaluating inflammation, for example for determining the likelihood that a subject, such as an otherwise healthy subject, or a subject suspected or at risk of having an inflammation disorder, has an inflammation disorder or will likely develop an inflammation disorder in the future. The method includes measuring a level of any one of compounds 1-16 in a biological sample from the subject, and diagnosing the subject as a subject with an inflammation disorder or at risk of an inflammation disorder if an elevated level (such as an elevated level, for example at least a 2-fold increase) of the compound is detected in the biological sample compared to a corresponding control (for example, a corresponding level of the compound in a healthy subject).

In some embodiments, methods are provided herein for evaluating chronic itch, for example for determining the likelihood that a subject, such as an otherwise healthy subject, or a subject suspected or at risk of having chronic itch, has chronic itch or will likely develop chronic itch in the future. The method includes measuring a level of any one of compounds 1-16 in a biological sample from the subject, and diagnosing the subject as a subject with chronic itch or at risk of chronic itch if an elevated level (such as an elevated level, for example at least a 2-fold increase) of the compound is detected in the biological sample compared to a corresponding control (for example, a corresponding level of the compound in a healthy subject).

In some embodiments, methods are provided herein for evaluating chronic pain, for example for determining the likelihood that a subject, such as an otherwise healthy subject, or a subject suspected or at risk of having chronic pain, has chronic pain or will likely develop chronic pain in the future. The method includes measuring a level of any one of compounds 1-16 in a biological sample from the subject, and diagnosing the subject as a subject with chronic pain or at risk of chronic pain if an elevated level (such as an elevated level, for example at least a 2-fold increase) of the compound is detected in the biological sample compared to a corresponding control (for example, a corresponding level of the compound in a healthy subject).

In some embodiments, methods are provided herein for evaluating autoimmunity, for example for determining the likelihood that a subject, such as an otherwise healthy subject, or a subject suspected or at risk of having an autoimmune disorder, has an autoimmune disorder or will likely develop an autoimmune disorder in the future. The method includes measuring a level of any one of compounds 1-16 in a biological sample from the subject, and diagnosing the subject as a subject with an autoimmune disorder or at risk of an autoimmune disorder if an elevated level (such as an elevated level, for example at least a 2-fold increase) of the compound is detected in the biological sample compared to a corresponding control (for example, a corresponding level of the compound in a healthy subject).

In some embodiments, methods are provided herein for evaluating atherosclerosis, for example for determining the likelihood that a subject, such as an otherwise healthy subject, or a subject suspected or at risk of having atherosclerosis, has atherosclerosis or will likely develop atherosclerosis in the future. The method includes measuring a level of any one of compounds 1-16 in a biological sample from the subject, and diagnosing the subject as a subject with atherosclerosis or at risk of atherosclerosis if an elevated level (such as an elevated level, for example at least a 2-fold increase) of the compound is detected in the biological sample compared to a corresponding control (for example, a corresponding level of the compound in a healthy subject). In some examples, the subject may have elevated cholesterol or tri-glyceride levels, elevated C-reactive protein levels, diabetes, or high blood pressure. Thus, the methods disclosed herein can be used to confirm a prior clinical suspicion of disease.

In some examples, a biological sample is obtained from the subject for evaluation. The biological sample can be any relevant biological sample, such as, but not limited to, serum, blood, plasma, urine, purified cells (for example, blood cells, such as white blood cells, B cells, T cells, or mononuclear cells), saliva, a biopsy or tissue (such as skin) sample, such as a sample including blood vessels, adipose cells, heart tissue, neural tissue obtained from the subject are used to predict the subject's risk of the disease or condition (such as inflammation, chronic itch, chronic pain, an autoimmune disorder, and atherosclerosis).

V. EXAMPLES

The following examples are provided to illustrate particular features of certain embodiments, but the scope of the claims should not be limited to those features exemplified.

Example 1

Systems Approach Used to Discover New Mediators of Pain and Itch

Chronic pain and itch are common sources of personal suffering, disability and societal expense. Current treatments often provide only partial or transient relief and have substantial side effects. The discovery of new endogenous mediators and mechanisms underlying pain and itch is needed to facilitate development of targeted, effective, safer interventions.

As the largest sensory organ, skin is richly innervated by cutaneous nerve endings that can sense the microenvironment. Linoleic acid (LA, 18:2n-6)—by far the most abundant polyunsaturated fatty acid in skin—is known as an 'essential fatty acid' because a small amount (about 0.5% of energy) is needed in diet to form the outer waxy epidermal barrier that prevents transepidermal water loss. Since itch and pain are common manifestations of cutaneous inflammatory conditions, and LA is an endogenous substrate for conversion to bioactive lipid mediators, LA-derived mediators may be uniquely positioned to modulate cutaneous itch and pain.

It was previously shown in rats that increasing dietary LA increases well-known LA derivatives in a dose-dependent manner in many tissues including skin. In humans, a low LA dietary intervention decreased headache pain, and reductions in circulating LA correlated with pain relief, suggesting that LA-derived lipid mediators might contribute to sensory signaling. However, the specific derivatives of LA that mediate or modulate sensation and the molecular pathways involved in their biosynthesis and signaling are incompletely understood.

It was hypothesized that novel LA-derived autacoids that are abundant in skin may play a role in the genesis of pain and itch. This hypothesis was investigated by applying a systems-based, translational approach in rats and humans to:

(1) predict novel lipid mediators based on tissue-specific precursor abundance and gene expression profiles of biosynthetic genes;

(2) synthesize predicted compounds by total chemical synthesis;

(3) identify and quantitate these mediators in rat and human tissues using authentic standards and liquid chromatography tandem mass spectrometry (LC-MS/MS);

(4) determine whether levels of these compounds can be altered by diet and by a chronic inflammatory state; and (5) examine the algesic and pruritogenic activities of these novel lipids using blinded ex vivo sensory neuronal cultures and in vivo behavioral testing. This approach and systematic review of the literature to identify biosynthetic genes and their expression identified new LA-derived lipid mediators that can regulate inflammatory skin disorders, pruritus and nociception.

Results

Predicting Mediators Based on Precursor Abundance and Biosynthetic Gene Expression Profiles Precursor fatty acid compositions and gene expression profiles of tissues were used to guide prediction of novel lipid mediators. LA was observed to be the most abundant polyunsaturated fatty acid in rat skin and sciatic nerve, accounting for 27.4% and 24.6% of total fatty acids, respectively. LA was much less abundant in sensory ganglia and in dorsal spinal cord.

ALOX12B and ALOX15B genes—which code for enzymes capable of peroxidation of polyunsaturated fatty acids containing a 1,4-cis,cis-pentadiene system were well expressed in human skin; ALOX12B, but not ALOX15B, was also well expressed in rat skin. ALOX15B was fairly well expressed in human tibial nerve and dorsal root ganglia (DRG), but less expressed or absent in rat neural tissues comprising the nociceptive circuit (i.e., sciatic nerve, DRG and spinal cord dorsal horn). The ALOXE3 gene—which codes an enzyme capable of isomerization of fatty acid hydroperoxides to form specific hydroxy- and keto-epoxide derivatives was also well expressed in rat and human skin, but less expressed or absent in peripheral nerves, sensory ganglia and dorsal cord. The CYP2S1 gene—which codes for another enzyme capable of isomerization of fatty acid hydroperoxides was well expressed in rat skin and especially sciatic nerve, but less expressed or absent in human pain circuit tissues. Together, these gene expression and precursor fatty acid data formed a template for predicting novel lipid mediators.

Tissue-specific distributions of hydroxy-epoxy- and keto-epoxy-octadecenoates

Based on high levels of LA and moderate-to-high expression of genes encoding the biosynthetic enzymes noted above, it was predicted that two novel 11-hydroxy-trans-epoxy-octadecenoates:

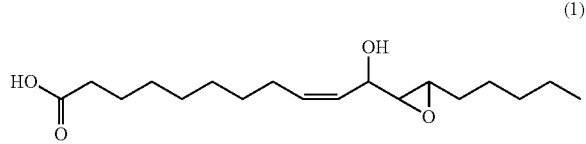

(1)

11-hydroxy(H)-12,13-trans-epoxy-(E)-octadecenoate (11H-12,13E-LA)

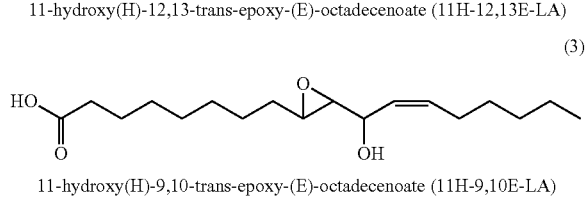

(3)

11-hydroxy(H)-9,10-trans-epoxy-(E)-octadecenoate (11H-9,10E-LA)

and two novel 11-keto-trans-epoxy-octadecenoates:

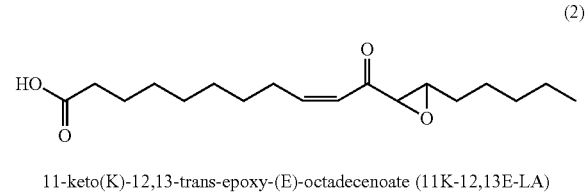

(2)

11-keto(K)-12,13-trans-epoxy-(E)-octadecenoate (11K-12,13E-LA)

-continued (4)

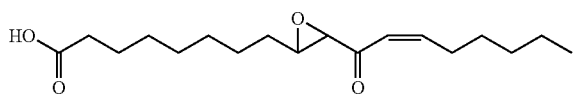

11-keto(K)-9,10-trans-epoxy-(E)-octadecenoate (11K-9,10E-LA)

and four previously identified 9- or 13-hydroxy- or keto-trans-epoxy-octadecenoates:

(5)

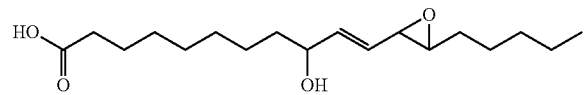

9-hydroxy(H)-12,13-trans-epoxy-(E)-octadecenoate (9H-12,13E-LA)

(7)

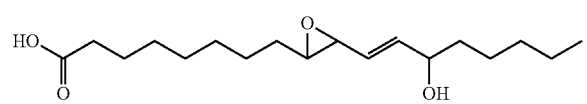

13-hydroxy(H)-9,10-trans-epoxy-(E)-octadecenoate (13H-9,10E-LA)

(6)

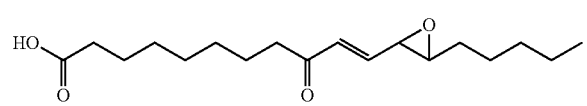

9-keto(K)-12,13-trans-epoxy-(E)-octadecenoate (9K-12,13E-LA)

(8)

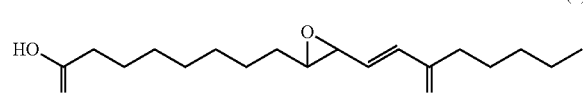

13-keto(K)-9,10-trans-epoxy-(E)-octadecenoate (13K-9,10E-LA)

would be abundant in human and rat skin. These compounds are as follows:

After total chemical synthesis of these eight LA derivatives for use as authentic standards (see Materials and Methods and following Examples), ultra-performance liquid chromatography tandem mass spectrometry (UPLC-MS/MS) was used to quantify these mediators in rat and human tissues. Five of the eight mediators were found to be present in rat skin, but none were detected in rat dorsal horn, indicating tissue-specificity in accordance with the predictive model. All eight mediators were detected in human skin; seven of these eight mediators were confirmed by matching the ion spectra of authentic standards and human skin extracts at characteristic retention times.

Elevated Levels of Free Mediators in Inflamed Psoriatic Human Skin

Psoriatic lesions exhibited higher expression of genes coding for lipase-mediated release (PLA2G2A, PLA2G2F), enzymatic peroxidation (ALOX12B), and hydroperoxide isomerization (CYP2S1), compared to non-lesional psoriatic skin. Thus, increases in both local biosynthesis and release of esterified, preformed lipids could potentially contribute to the higher concentrations of hydroxy-epoxy- and keto-epoxy-octadecenoates observed in psoriatic lesions.

In human psoriatic skin lesions and non-psoriatic control skin, these mediators were measured in both the non-esterified (free) and total (sum of free plus esterified) lipid fractions. There were no significant differences between psoriatic skin lesions and control skin in the total lipid fraction. However, six of the mediators (11H-12,13E-LA, 11H-9,10E-LA, 11K-9,10E-LA, 9H-12,13E-LA, 9K-12,13E-LA and 13H-9,10E-LA) were markedly elevated as free acids (the bioactive pool) in psoriatic skin lesions compared to control skin. Concentrations of free 11H-12,13E-LA and 9K-12,13E-LA were >6-fold and >30-fold higher in psoriatic lesions compared to control skin, respectively. The highest concentrations were observed in lesions of psoriasis patients who reported itch (FIG. 1).

To gain further insight into the biochemical state of each mediator, the free acid concentration was divided by the total mediator concentration to determine the percent of each mediator that was present as a bioavailable free acid. The percent as free acid differed markedly according to mediator. In control human skin, the percent as free acid ranged from 0.05% for 13H-9,10E-LA to 44.4% for 11H-12,13E-LA. In psoriatic skin lesions, the percent as free acid was significantly higher than control skin for 11H-12,13E-LA, 11K-12,13E-LA; 9K-12,13E-LA; and 13H-9,10E-LA. These findings support the hypothesis that there is increased enzymatic synthesis and/or release of free acids from esterified lipids in chronic epidermal inflammation.

Mediator Concentrations in Serum Did not Correlate with Skin or Psoriasis Status To determine whether measurements obtained from the circulating blood can provide surrogate markers of skin inflammation, we next quantified these mediators in serum from psoriatic patients and non-psoriatic controls. Unlike skin, serum concentrations of these eight mediators did not differ by disease status.

Novel LA Derivatives Stimulate Rat Sensory Neurons in a Regio-Selective Manner

To determine whether these mediators sensitize DRG neurons, we tested each mediator in an adult rat DRG ex vivo calcitonin gene related peptide (CGRP) release assay, with PGE2 serving as a positive control. At 1 µM concentrations at neutral pH, neither PGE2 nor any of the other tested compounds directly stimulated CGRP release. However, 11H-12,13E-LA and 11H-9,10E-LA significantly augmented both low-pH-evoked and capsaicin-evoked CGRP release. 13H-9,10E-LA significantly augmented low pH-evoked CGRP release but had no effect on capsaicin-evoked release. Neither 9H-12,13E-LA, nor any of the tested keto-epoxy-octadecenoates, augmented low pH-evoked or capsaicin-evoked CGRP release (FIGS. 2A-2C). These observations indicate that octadecenoate-induced sensitization was regio-selective, with the most robust effects observed for compounds containing both a hydroxyl group at carbon 11 and an adjacent epoxide group. These two compounds share a 3-hydroxy-Z-pentenyl-E-epoxide moiety, identifying this sub-structure as a possible pharmacophore mediating nociceptor sensitization (FIG. 2D).

Intradermal Injection of Novel Mediators Elicits Pain and Itch-Related Behaviors in Rodents Next, behavioral responses to intradermal injections of mediators that produced sensitization as measured by an augmentation of evoked CGRP release from isolated sensory neurons were assayed. 11H-12,13E-LA was selected as the first mediator to test for pain responses because it was abundant as a free acid in inflamed human skin and it augmented capsaicin and pH-stimulated CGRP release in rat sensory neurons.

Figure 3A:
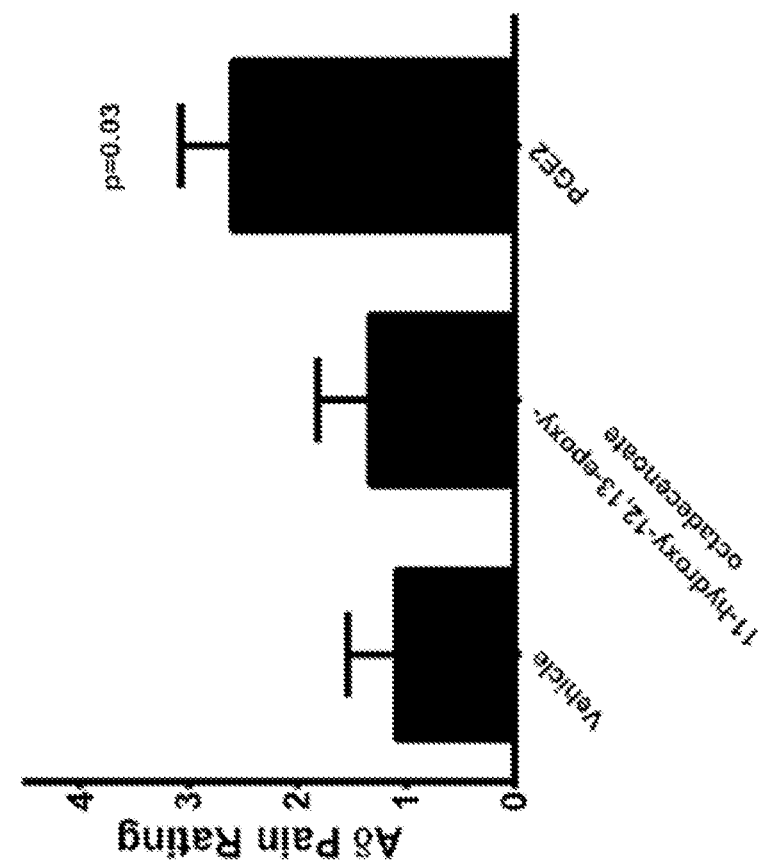
FIGS. 3A and 3B. Pain-related behavior responses after intradermal hind paw injection of disclosed fatty acid derivatives (blinded analyses).
Figure 3B:
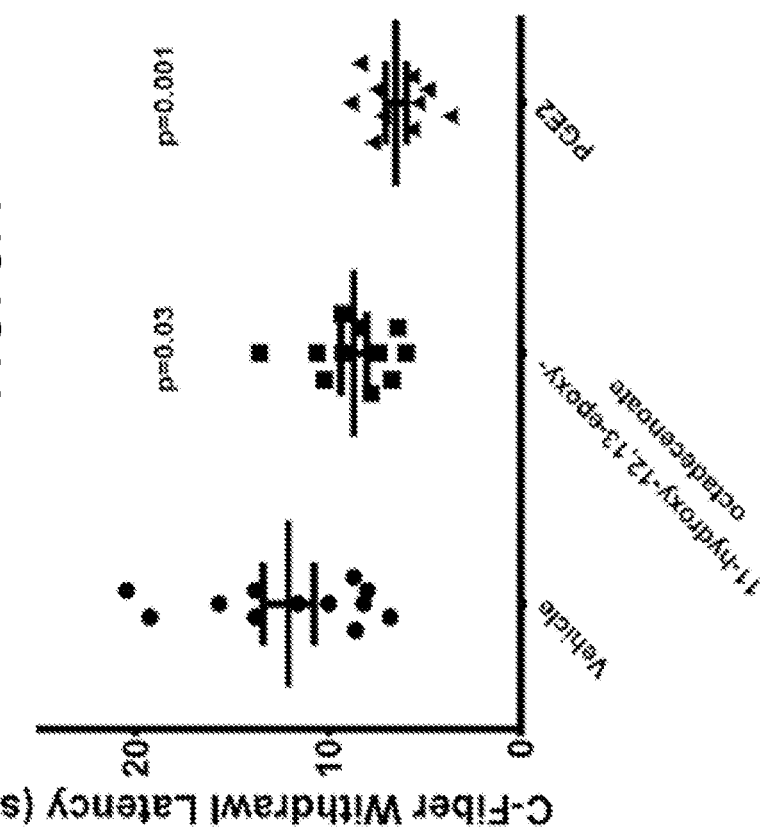

For these experiments, the effects of the LA derivatives were compared to vehicle and to the classic inflammatory mediator, PGE2, which served as a positive control. It was observed that after injection, C-fiber withdrawal latencies were decreased by 28% (p=0.03) and 46% (p=0.001) for 11H-12,13E-LA and PGE2, respectively, indicating nociceptive hypersensitivity (FIG. 3). Intradermal injection of PGE2, but not 11H-12,13E-LA, also significantly enhanced the proportion of withdrawal responses following stimulation with a laser tuned to excite Aδ fibers.

Next, to examine the effects of these eight mediators on itch, a mouse model was employed for quantifying itch-related scratching bouts over the first 30 minutes following intradermal injection into the nape of the neck. In pilot testing of all 8 mediators with n=3 per group, two mediators—9K-12,13E-LA and 13K-9,10E-LA—appeared to increase scratching bouts compared to vehicle. With a larger sample size of n=6-8 per group, we observed that 9K-12, 13E-LA, but not 13K-9,10E-LA, induced itch-related scratching behavior (p=0.001) (FIG. 4A). In combination, 9K-12,13E-LA plus 13K-9,10E-LA also significantly increased scratching behavior compared to vehicle (p=0.002), but to the same degree as observed with 9K-12, 13E-LA alone. Scratching responses evoked by 9K-12,13E-LA had a slower onset and more gradual tapering than those observed for histamine.

Together with the results showing that 9K-12,13E-LA was exclusively elevated in psoriatic lesional skin of those with itch (FIG. 2B), these behavioral findings suggest that 9K-12,13E-LA may represent a novel itch mediator.

Novel Mediators are Regulated by Dietary LA and Decreases in Plasma Levels Correlate with Clinical Pain Reduction Next, to determine whether these mediators can be decreased by lowering the amount of their precursor LA in the diet, plasma samples were used from a completed randomized human clinical trial testing a 12-week LA lowering diet in patients with severe Chronic Daily Headache. It was observed that five of these eight mediators were present in plasma (FIG. 5). Two mediators—11H-12,13E-LA and 13H-9,10E-LA—were significantly decreased by the LA lowering dietary intervention; the sum of the four hydroxy-epoxide-octadecenoates was reduced by 41% (p<0.001)(FIG. 5A). Moreover, it was observed that diet-induced reductions in one of these mediators (11H-12,13E-LA), but not the others, was closely correlated with decreases in headache hours per day and headache days per month (FIGS. 5B and 5C). Each standard deviation decrease in 11H-12,13E-LA was associated with 25% and 11% decreases in headache hours per day and headache days per month (both p's<0.001), respectively; reduction in 11H-12, 13E-LA also tended to correlate with improvements in overall headache impact (FIG. 5D) and physical function but was not related to psychological distress.

Discussion

This example provides an interdisciplinary, translational approach in rodents and humans to discover and characterize a new family of endogenous lipid mediators of pain and itch. As predicted, significant concentrations of 11H-12,13E-LA, 11H-9,10E-LA, 11K-12,13E-LA, and 11K-9,10E-LA were measured in human skin. It is believed that this is the first demonstration of any of these four compounds in any species. Notably, 11H-12,13E-LA was elevated in inflamed psoriatic human skin, sensitized primary afferent dorsal root ganglia neurons in ex vivo CGRP release assays, and induced C-fiber mediated pain-related hypersensitivity in rats. Moreover, plasma 11H-12,13E-LA correlated with headache frequency and impact in humans, and was reduced by lowering the amount of its dietary precursor (LA) in diet.

In aggregate, these findings suggest that 11H-12,13E-LA may be a mediator of pain modulated by diet and inflammation. 11H-9,10E-LA—which shares a 3-hydroxy-Z-pentenyl-E-epoxide moiety with 11H-12,13E-LA —was also elevated in inflamed human skin and sensitized rat sensory neurons, suggesting that it might also contribute to inflammation-related primary afferent sensitization.

In addition to identifying novel endogenous LA-derivatives, the findings confirm the presence of previously identified hydroxy- and keto-epoxy-octadecenoates in human skin, and provide novel insights into their potential bioactions. The genes coding for 12-R-lipoxygenase (ALOX12B), 15-lipoxygenase-2 (ALOX15B), and the hydroperoxide-isomerase e-lipoxygnease-3 (ALOXE3), were highly expressed in skin. It was previously suggested that the consecutive actions of two specific enzymes, 12-R-lipoxygenase and e-lipoxygenase-3, oxidized the LA esterified in acyl-ceramides to form a specific stereoisomer of 13H-9,10E-LA (13-(R)hydroxy-9(R),10(R)-trans-epoxy-(11E)-octadecenoate and/or its trihydroxy LA derivatives, which in turn are proposed to play a critical role in formation of the corneocyte lipid envelope. This proposed need for these specific LA derivatives to form a functional water barrier may explain the mechanism whereby small amounts of dietary LA are required to prevent the clinical manifestations of "essential fatty acid deficiency", including skin dryness, thickening and desquamation. Consistent with the previous findings, relatively high concentrations of 13H-9-E-LA in rodent and human skin were observed herein. In human skin, 13H-9-E-LA was found almost exclusively (median >99.5%) in the esterified lipid pool, which is consistent with its proposed role in epidermal corneocyte lipid envelope formation. In addition, it is reported here for the first time that concentrations of free 13H-9-E-LA were 9-fold higher in psoriatic skin lesions as compared to control human skin. Together with the finding that free 13H-9-E-LA augmented sensory neuron CGRP release in a low pH environment, higher levels of this free acid in psoriatic skin suggests that it could potentially contribute to the hypersensitivity accompanying cutaneous inflammation.

Identification of 9-keto-12,13-epoxy-octadecenoate as a Novel Endogenous Pruritogen Another finding of the present example is the identification of 9K-12,13E-LA as an endogenous pruritogen that was elevated in the inflamed human skin of psoriatic patients who reported chronic itch, but was not elevated in lesions that were not characterized by itch sensations. 9K-12,13E-LA has previously been detected in human plasma and has been reported to stimulate adrenal steroidogenesis, indicating that it is biologically active. Similar to 13H-9,10E-LA, in control human skin it was observed that the vast majority (>99%) of 9K-12,13E-LA was found in the esterified lipid fraction. The markedly higher (>30-fold) concentration of this mediator in the free fatty acid lipid pool of psoriatic skin lesions compared to control skin suggests that 9K-12,13E-LA may act as a signaling molecule in cutaneous inflammation. Consistent with this, it was observed that injection of free 9K-12,13E-LA into mouse dermis caused itch-related scratching behavior. It is believed that 9K-12,13E-LA is only the fourth lipid mediator reported to induce scratching behavior in a rodent itch model. Unlike the other known lipid pruritogens (leukotriene B4, thromboxane A2, hydroperoxy-eicosatetraenoic acid), which are believed to be present exclusively as free acids, the majority of 9K-12,13E-LA is stored preformed in esterified skin lipids. This accumulation in esterified lipids suggests that preformed 9K-12, 13E-LA can be released by lipases to directly stimulate pruritus, obviating the need for de novo biosynthesis. In this regard, high expression of PLAG2A and PLAG2F were detected in rat skin and especially inflamed human skin that could serve the relevant lipase function.

Regulation of Hydroxy-Epoxy-Octadecenoates and Chronic Headaches by Diet

It was previously demonstrated in rats that increasing dietary LA as a controlled variable markedly increased the abundance of LA and its well-known oxidized LA derivatives (e.g. hydroxy-octadecadienoates (HODEs), epoxy-octadecenoates, dihydroxy-octadecenoates) in tissues associated with idiopathic pain syndromes, including skin. Moreover, in patients with severe chronic headaches, an LA lowering dietary intervention decreased headache pain, and decreases in circulating LA were associated with clinical pain reduction, suggesting that LA or its autacoid derivatives could potentially contribute to pain in humans. In the present study, the finding that diet-induced reduction in circulating 11H-12,13E-LA was closely correlated with clinical pain reduction raises the possibility that high LA intakes could contribute to a biochemical susceptibility to develop chronic pain or itch, in part by increasing tissue levels of hydroxy- and keto-epoxy-octadecenoates.

The current report introduces new mediators to the growing field of lipid mediators of pain and itch. The vast majority of the work in this field has focused on mediators derived from longer chain (≥20 carbons) polyunsaturated fatty acids, especially those derived from arachidonic acid (AA). Since LA is much more abundant than AA and other polyunsaturated fatty acids in skin and certain epithelial tissues, and is also a substrate for enzymatic conversion to oxidized mediators, LA-derived mediators are uniquely positioned to regulate nociceptive and pruriceptive responses in these tissues. Hargreaves and coworkers (Patwardhan et al., *The Journal of clinical investigation* 120, 1617, 2010; Patwardhan et al., *P.N.A.S.*, 106, 18820, 2009) have previously implicated 9-HODE, 13-HODE and other well-known LA-derivatives in both peripheral and central nervous system nociceptive responses. In vivo cutaneous inflammatory responses are characterized by low pH and concurrent elevations in numerous lipid and non-lipid mediators, which together are implicated in inflammation-associated hypersensitivity (Han and Simon, Science signaling 4, er3, 2011; Sun and Chen, *J dental research*, 95, 135, 2016). In these conditions, 9-HODE and 13-HODE could potentially be converted by cytochrome p450 epoxygenases or lipoxygenases to form 9H-12,13E-LA, 13H-9,10E-LA and other bioactive LA-derived mediators.

Materials and Methods

Clinical sample preparation, rodent behavioral testing, ex vivo CGRP release assays, and all laboratory analyses were performed by investigators who were blinded to clinical data and treatment groups.

Data Analysis

Normally distributed data were expressed as mean standard error and compared using the Student's t-test (two groups) or one-way ANOVA (multiple groups) with corrections for multiple comparisons as described in figure legends. Data that were not normally distributed were expressed as median and interquartile ranges, and compared using Wilcoxon rank-sum test (two groups) and Kruskal-Wallis test (multiple groups), with corrections for multiple comparisons as described in figure legends. $p<0.05$ when adjusted for multiple comparisons was considered significant.

Rat Tissue Collection

The rat tissues analyzed in this study were obtained under protocols approved by the institutional Animal Care and Use Committees of the National Institute of Dental and Craniofacial Research and the Clinical Center, NIH. Male Sprague-Dawley rats were housed in pairs and given access to Rodent NIH-31M modified formula chow (Ziegler) and water ad libitum. To obtain hind paw, sciatic nerve, DRG, TG and dorsal horn tissue, rats were anesthetized with isoflurane, decapitated and tissues were dissected immediately. Sections of the plantar surface of the hind paw were collected using a scalpel. Sciatic nerves were dissected starting from just distal to the sciatic notch and extending to just above the sciatic trifurcation. L4 and L5 DRGs were removed after laminectomy. Spinal cord was ejected from the vertebral column by hydraulic force using a syringe and saline, and the left and right dorsal quadrants were isolated. Tissues were frozen immediately on dry ice and stored at −80° C. until processed. Rat DRG and sciatic nerve RNA-Seq data are available under project PRJNA313202 in the SRA database.

Precursor Fatty Acid Analysis of Rat Pain Circuit Tissues

Tissue fatty acids were analyzed as previously described (11). Briefly, samples were thawed, weighed, and homogenized in butylated hydroxytoluene (BHT)/methanol for fatty acid extraction according to the method of Folch et. al (Ramsden et al., *Molecular pain* 12, 2016). BHT was added in the methanol to reduce lipid oxidation during the procedures. The internal standard methyl tricosanoate (23:0) was added to each sample. This was followed by methylation with 14% BF3/methanol. The hexane extracts were concentrated to a small volume with a stream of nitrogen and transferred to microvials for GC analysis. Fatty acid methyl esters were analyzed with an HP-7890A gas chromatograph equipped with a flame ionization detector (Hewlett-Packard, Palo Alto, Calif.) and a fused silica capillary column (DB-FFAP, 15 m×0.100 mm i.d.×0.10 μm film thickness, J & W Scientific, Folsom, Calif.). The detector and injector temperatures were set to 250° C. The oven temperature program began at 150° C. for 0.25 min and increased to 200° C. at the rate of 10° C./min, then at the rate of 3.5° C./min to 225° C. for 0.5 min, and finally increased at the rate of 40° C./min to 245° C., with a final hold for 15 min. Hydrogen was used as carrier gas at a linear velocity of 50 cm/s. A custom mixed, 30-component, quantitative methyl ester standard containing 10-24 carbons and 0-6 double bonds was used for assignment of retention times and to ensure accurate quantification (Nu Chek Prep 462, Elysian, MN). Fatty acid data were expressed as % of total peak area, which corresponded to weight % to within 5%, as demonstrated by quantitative standard mixtures. Internal standards were used to calculate tissue fatty acid concentrations.

Gene Expression of Human Pain Circuit Tissues

Collection of Tissue and RNA Purification for RNA-Seq Analyses

Four human L3 DRGs were purchased from Anabios (San Diego, Calif.) from four different normal organ donors of mixed sex. Three human medullary dorsal horn samples were collected at the level of the pyramidal decussation, and gray matter of the dorsal horn was isolated from fresh tissue by dissection as part of the collection procedure from the NIMH Human Brain Collection Core as described in Goswami et al. (*Molecular pain* 10, 44, 2014). Rat and human samples were homogenized in Qiazol reagent (Qiagen Inc, Valencia Calif.) using a Fastprep 24 homogenizer (MP Biomedicals, Santa Ana, Calif.) or using a Polytron homogenizer (IKA, Wilmington, N.C.) and purified using the RNeasy Mini kit (Qiagen Inc, Valencia Calif.) with DNase digestion. RNA integrity number (RIN) was assessed after gel electrophoresis using an Agilent Bioanalyzer (Agilent Technologies, Santa Clara, Calif.). For rat tissues, samples with a RIN above 8.5 were sequenced. For human DRGs, samples with a RIN above 7 were sequenced. For other human samples, the highest possible RIN was obtained. The lowest sample included in this study was 5.5.

Alignment and Quantification of RNA-Seq Count Data

Rat data were aligned by STAR (version 2.4.2a) (Dobin et al. (*Bioinformatics* 29, 15, 2013) and the rn6 genome build (Ensembl). Bam files resulting from this analysis were quantified using QoRTs (version 0.3.18) (Hartley and Mullikin, BMC bioinformatics 16, 224, 2015) and converted to raw read counts and FPKM (Fragments Per Kilobase of transcript per Million mapped reads). Data from human skin (lower leg) and tibial nerve were accessed by selecting 8 samples of high quality (based on RIN) from the GTEx repository. RPKM values were directly mined from data files available through the consortium (Consortium, *Nature genetics* 45, 580, 2013). Psoriatic skin samples were accessed from the SRA database (PRJNA236547) (Swindell et al., *Genome medicine* 7, 86, 2015). Data from SRA, and other human data were aligned and quantified using the MAGIC pipeline (Zhang et al., *Genome biology* 16, 133, 2015) and a genome target built in March 2016 based on Refseq and Aceview annotations (Thierry-Mieg and Thierry-Mieg, *Genome biology* 7 Suppl 1, S12 1, 2006). Genomic target files for MAGIC alignment are available upon request. Quantification and normalization of gene counts was performed by MAGIC and is reported in sFPKM.

Total Chemical Synthesis of Hydroxy-Epoxy- and Keto-Epoxy-Octadecenoates

Each compound was performed by total chemical synthesis. Synthesized compounds were purified via flash chromatography and/or normal phase HPLC. NMR analysis indicated chemical shifts and coupling constants consistent with each chemical structure. Hydroxy-epoxy- or keto-epoxy-octadecenoates were analyzed by proton NMR in deuterated chloroform as their free acids or methyl esters as indicated.

Identification and Quantitation of Hydroxy- and Keto-Epoxide-Octadecenoates with LC-MS/MS Authentic standards prepared by total synthesis were used to identify and quantitate these eight endogenous compounds in human and rat tissues using UPLC-MS/MS. Briefly, solid-phase extraction (SPE) of oxylipins from biological matrices was performed using Strata X cartridges (33 u, 200 mg/6 mL, Phenomenex, PA). The cartridges were conditioned with 6 mL of methanol, followed by 6 mL of water before samples were extracted. Samples were washed with 6 mL of 10% methanol. The oxylipins were eluted with 6 mL of methanol into a glass tube containing 10 µL of 30% glycerol in methanol. The eluate was evaporated to dryness under a stream of nitrogen and reconstituted with 40 µL of methanol, and an aliquot (10 µL) was injected into the LC/MS/MS system. A UPLC (Shimadzu Scientific Instruments, Columbia, Md.) coupled with a Qtrap 5500 (AB SCIEX, USA) was used for qualitative and quantitative analysis. Briefly, separation was performed on a ZorBAX RRHD Eclipse Plus C18 column (100 mm×4 mm; 1.8 µm) (Agilent Corporation, Palo Alto, Calif.) consisted of (A) 12 mM ammonium acetate solution and acetic acid (100:0.02 v/v) and (B) 12 mM ammonium acetate and was composed of acetonitrile/water/acetic acid (90:10:0.02, v/v/v). The flow rate was 0.5 mL/min. The column oven temperature was set at 30° C. The elution gradient conditions were as follows: 25-40% B from 0-2.0 min, 40-46% B from 2 to 8 min, 46-57% B from 8 to 9 min, 57-66% B from 9 to 20 min, 66-76% B from 20 to 22 min, 76-100% B from 22 to 27 min, held at 100% B from 27 to 33 min, 100-25% B from 33.1 to 35 min. The mass spectrometer was operated in electrospray negative ionization using scheduled multiple reaction monitoring (sMRM) acquiring MRM data for each analyte with the retention time window of 90 s. The source parameters were set as follows: ion spray voltage, −4500V; nebulizer gas (GS1), 65 psi; turbo-gas (GS2), 70 psi; and the turbo ion spray source temperature (TEM), 500° C. The analytes were quantified using MRM. For hydroxy-epoxy-octadecenoates and keto-epoxy-octadecenoates with two or three isomeric peaks in the synthesized standards, quantitation was performed by sum peak area ratios of its related peak area component/peak area IS generated from Analyst 1.6.2 and plotting the best fit of total peak-area ratios of analyte/peak area IS vs concentration in Microsoft Excel, and fitted to the equation $y=ax+b$. The MS/MS spectra were obtained by using enhanced product ion scan mode at a scan speed of 1000 Da/s. Collision-induced dissociation (CID) was performed using the collision energy of 35 V with collision energy spread of 10. Data processing was performed using analyst software (version 1.6.2, AB Sciex). The identification of seven of the eight predicted endogenous compounds was confirmed by matching of the MS/MS spectra and retention times of endogenous LA derivatives from psoriatic skin samples with synthetic material using total ion mode.

Human Studies with Sample Collection

Skin biopsies and serum collection from psoriatic and control participants

Eight consecutive psoriasis participants and 7 non-psoriatic controls were included in the study (age range 26-82 years) enrolled in an ongoing NIH observational study of psoriasis and cardiometabolic diseases (NCT01778569). Study procedures were approved by the National Heart, Lung and Blood Institute Institutional Review Board. All participants submitted written informed consent prior to enrollment. Briefly, a diagnosis of psoriasis was confirmed and quantified by a dermatologist using the Psoriasis Area Severity Index (PASI). The presence or absence of substantial itch was documented using a self-reported questionnaire. Corresponding controls were consecutively recruited to undergo the same testing as the psoriasis participants. All participants were free of any systemic anti-psoriatic treatments or topical therapy within 2 weeks before biopsy. At baseline, 4 mm punch biopsies were obtained under local anesthesia from psoriatic plaque and unaffected skin. Biopsy sites were selected based on active plaques and varied between subjects. However, biopsies of unaffected and control skin were predominantly from buttocks. Whole blood from the same participants was collected in serum separator tubes, centrifuged and immediately stored at −20° C. until analysis.

The Chronic Daily Headache (CDH) Trial

The CDH trial was a randomized, 12-week trial designed to test the clinical and biochemical effects of a diets low in linoleic acid (L6 intervention) with or without a concurrent increase in n-3 fatty acids (H3-L6 intervention) in a population with CDH. The trial was conducted at the University of North Carolina at Chapel Hill (UNC) from April 2009 to November 2011. Trial procedures were approved by the UNC Institutional Review Board, and the trial protocol, dietary compositions, and primary clinical and some biochemical findings were previously described (Ramsden et al., *Trials* 12, 97, 2011; MacIntosh et al., *The British journal of nutrition* 110, 559, 28, 2013). Briefly, adults meeting the CDH criteria of headaches >4 hours per day and >15 days per month for at least 3 months and a headache history of >2 years were recruited to participate. During the 4-week pre-intervention phase, participants continued usual care and habitual diets and recorded headache characteristics in a daily headache diary. On completion of the run-in phase, participants were randomized to one of the two study diets, which lasted 12 weeks. LA was reduced in study diets by restricting consumption of vegetable oils and other rich sources of LA, and replacing them with vegetable oils and foods rich in monounsaturated and saturated fats. Plasma was collected at baseline and at the conclusion of the 12-week diet phase. It was previously reported that the H3-L6 intervention produced marked reductions in headache frequency and severity and enhanced quality of life and function while reducing the use of acute pain medications (Ramsden et al., *Pain* 154, 2441, 2013; Ramsden et al., *Pain* 156, 587, 2015). Diet-induced changes in one or more families of n-6 or n-3-derived lipid autacoids likely contributed to these clinical benefits; however, the specific mechanisms responsible for these effects are unknown. In the present study, pre- and post-intervention plasma samples were used to investigate: (1) whether the study diets altered plasma levels of hydroxy- and keto-epoxide derivatives of LA using the Wilcoxon matched-pairs signed-ranks test; and (2) whether changes in mediator concentrations correlated with clinical pain reduction using regression models adjusted for the baseline values of each outcome and mediator.

Preparation of Solid Tissues for LC-MS/MS Analysis

Solid tissues (human skin, rat hind paw, rat dorsal horn) were transferred into FastPrep Lysing Matrix tubes on ice (MP Biomedicals, USA; Lysing Matrix A for skin and hindpaw, Lysing Matrix D for dorsal horn) and at least 8 times greater volume ice-cold methanol with 0.02% of BHT and 0.02% of EDTA was immediately added to each tube (v/v). A known amount of internal standards were added to each sample and samples were homogenized using a FastPrep-24 homogenizer (MP Bio). Tissue homogenates were transferred to −80° C. for 1 hour to precipitate proteins. Homogenates were centrifuged at 17000 g in 4° C. for 10 min and supernatant was transferred to a new test tube. Half the supernatant was stored in −80° C. until SPE purification and LC-MS/MS analysis. To allow for analysis of total lipid pools the other half of the supernatant was saponified with 2.6% sodium carbonate (by weight) at 60° C. for 30 min under gentle shaking. The solution was then neutralized (pH 5-7) using acetic acid and stored in −80° C. overnight. Immediately before purification by SPE and LC-MS-MS analysis, lipid extracts (free and saponified total) were added to 9-fold greater volume of ice cold water.

Preparation of Plasma and Serum for LC-MS-MS Analysis

200 μL of plasma or serum were transferred to 500 μL of ice-cold methanol with 0.02% of BHT and 0.02% of EDTA and transferred to −80° C. to precipitate proteins (as described above). A known amount of internal standards were then added, samples were centrifuged and supernatant collected as described above. The supernatant was then added to 9-fold greater volume of ice cold water and purified with SPE and analyzed by LC-MS/MS, as described above.

Ex Vivo Sensory Neuron Sensitization Assays (CGRP Release Assays)

For release experiments, the work was approved by the Animal Care and Use Committee at Indiana University School of Medicine, Indianapolis, Ind. Adult rat sensory neuronal cultures were prepared as previously described (Burkey, Hingtgen, and Vasko, *Methods in molecular medicine* 99, 189, 2004; Kelley et al., *PloS one* 9, e106485, 2014). Cells were maintained for 10-12 days in F-12 media (Invitrogen, Carlsbad, Calif.) supplemented with 10% horse serum, 2 mM glutamine, 100 μg/ml Normocin™, 50 μg/ml penicillin, 50 μg/ml streptomycin, 50 μM 5-fluoro-2'-deoxyuridine (Invitrogen), 150 μM uridine, and 30 ng/ml of NGF (Harlan Bioproducts for Science, Inc. Indianapolis, Ind.) in 3% $CO_2$ at 37° C. On the day of the release experiments, cultures were washed with HEPES buffer (25 mM HEPES, 135 mM NaCl, 3.5 mM KCl, 2.5 mM $CaCl_2$), 1 mM $MgCl_2$, 3.3 mM D-glucose, and 0.1% bovine serum albumin, pH 7.4 and maintained at 37° C. Cultures were then incubated with 0.4 ml of the same buffer in the absence or presence of drugs. Basal release was determined by exposing the cells to HEPES buffer alone for 10 min, then to buffer in the presence of mediators for 10 min to ascertain if the compounds stimulated release. Cultures were then exposed to buffer containing 30 nM capsaicin or buffer with the pH adjusted to 6.0 in the absence or presence of mediators. Cells then were re-exposed to HEPES buffer without drugs for a 10 min incubation to reestablish basal release. After each incubation, the buffer was removed to measure the amount of CGRP using radioimmunoassay as previously described (Chen et al., *Peptides* 17, 31, 1996). At the end of each release experiment, cells were hypotonically lysed by exposing the cultures to 0.1 M HCl for 10 min and an aliquot taken to measure total CGRP content in the cultures using radioimmunoassay. Total content of CGRP was not significantly altered by exposure to inflammatory mediators. Release data are presented in fmol/well of cell/10 min from three independent experiments from separate harvests. Statistical analysis was performed using ANOVA with Tukey's post hoc test.

Rodent Behavioral Assays

Pruriceptive (Itch) Behavior

Hydroxy- and keto-epoxide derivatives of LA (100 μg) or histamine (50 μg) were injected intra-dermally into the nape of neck of the female mice (C57BL/6J from Jackson Laboratory). LA derivatives (9-keto-12,13-epoxy-(10E)-octadecenoate or 13-keto-9,10-epoxy-(11E)-octadecenoate) were injected independently, and in combination (9-keto-12,13-epoxy-(10E)-octadecenoate plus 13-keto-9,10-epoxy-(11E)-octadecenoate (100 μg of each)). Pruriceptive behavior was quantified as the number of scratching bouts assessed over 30 minutes, as previously described (Mishra and Hoon, *Science* 340, 968, 2013).

Nociceptive (Pain) Behavior 11-hydroxy-12,13-trans-epoxy-(9Z)-octadecenoate (30 μg) was injected intradermally into the hindpaw of male Sprague-Dawley rats. Baseline measurements were taken for all tests prior to injection. A-delta and C-fiber mediated hindpaw withdrawal responses were measured as previously described (Mitchell et al., *Pain* 155, 733, 2014). Briefly, by stimulation of the plantar surface of the paw with a 100 ms laser pulse, producing a rapid withdrawal response. Laser pulses were delivered by an infrared diode laser (LASS-10 M; Lasmed, Mountain View, Calif., USA) and calibrated to 3500 mA at 0.5 mm diameter, and delivered from 1 cm distance, C-fiber mediated responses were measured by delivery of a slow temperature ramp to the plantar surface of the hindpaw, with stimulus termination by voluntary withdrawal of the paw. The laser stimulus was adjusted to result in an approximately 10 second withdrawal latency (1000 mA, 13 cm distance).

Example 2

11-hydroxy- and 11-keto-trans-epoxy-octadecenoates

This example illustrates production of exemplary 11-hydroxy and 11-keto-trans-epoxy-octadecenoate compounds. The following illustrates an exemplary reaction process:

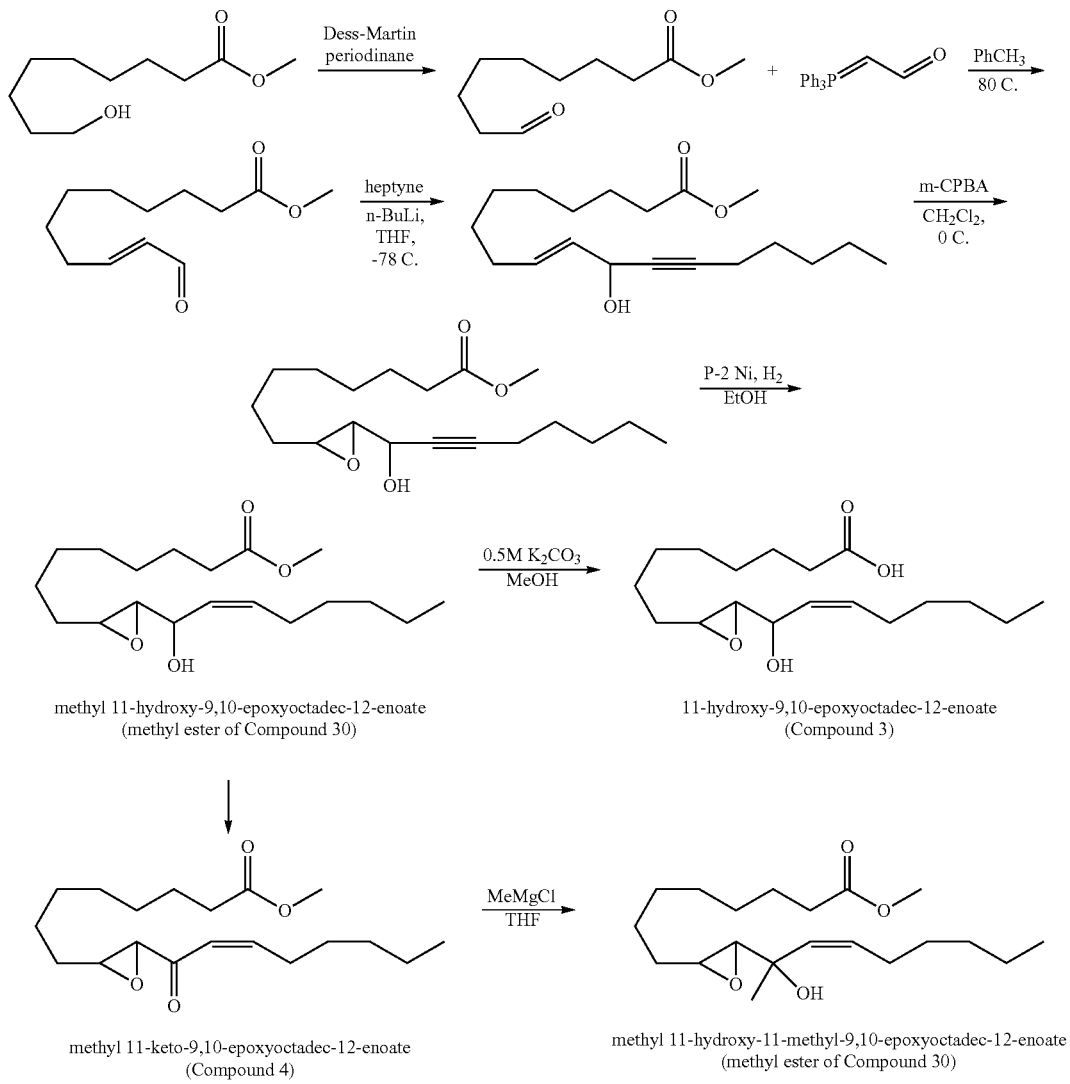

methyl 11-hydroxy-9,10-epoxyoctadec-12-enoate
(methyl ester of Compound 30)

11-hydroxy-9,10-epoxyoctadec-12-enoate
(Compound 3)

methyl 11-keto-9,10-epoxyoctadec-12-enoate
(Compound 4)

methyl 11-hydroxy-11-methyl-9,10-epoxyoctadec-12-enoate
(methyl ester of Compound 30)

To a solution of methyl 9-hydroxy nonanoate (1 g) in dichloromethane (8 ml) at 0° C. was added Dess-Martin periodinane (1.7 equiv; 3.83 g). The ice bath was removed after 10 minutes, and the reaction was allowed to proceed for up to 2 hours (until no starting material remained by TLC). The reaction was diluted with 200 ml of 10% ethyl acetate/hexane, and it was immediately poured onto silica gel. Elution with the same solvent produced the product aldehyde in 90% yield (890 mg).

A solution of 2.44 g of (formylmethyl)triphenylphosphonium chloride in 12 ml of toluene was treated with triethylamine (1.1 equiv; 1.11 ml) and stirred for one hour, then a solution of the aldehyde (890 mg; 4.78 mmol) in toluene was added and the reaction was stirred at 80° C. for 2 hours. The mixture was then filtered through Celite and purified on silica gel (15% ethyl acetate/hexane) to yield 608 mg of the en-al product.

To a cooled (−78° C.) solution of heptyne (1.5 equiv; 0.562 ml) in 5 ml THF was added a solution of the en-al (608 mg; 2.87 mmol) in 2 ml THF dropwise. After stirring at −78° C. for 1-2 hours, TLC indicated reaction completion so it was diluted with ether and washed with 1M HCl until pH 7, then water and then brine. The organic layer was dried over sodium sulfate, and then the product was purified on silica gel (eluted with 20 to 30% ethyl acetate/hexane) to yield 503 mg (57% yield) of the hydroxy en-yne.

To a cooled solution of the hydroxy en-yne (250 mg; 0.812 mmol) in dichloromethane was added 77% m-CPBA (1.5 equiv; 272 mg). After 10 minutes the ice bath was removed and the reaction proceeded until TLC indicated completion (approximately 3 hours). The reaction was poured into saturated sodium thiosulfate, layers separated, and the organic layer was then washed with 10% sodium bicarbonate, then it was dried over sodium sulfate. Purification on silica gel (15-20% ether/hexane elution) produced 166 mg (63%) of the epoxy alkyne.

In a 2-neck 100 ml RBF equipped with a gas balloon apparatus containing 5 ml of ethanol was added Ni(OAc)$_2$ tetrahydrate (12.5% mol; 15.9 mg). The atmosphere purged with vacuum and backfilled with hydrogen 3×, then allowed to stir under hydrogen atmosphere until fully dissolved. Solid sodium borohydride (12.5% mol; 2.42 mg) was added, the atmosphere again vacuum/hydrogen purged, and the black mixture stirred under hydrogen atmosphere for 45 minutes. Then, ethylene diamine (25% mol; 8.5 µl) was added, the atmosphere once more vacuum/hydrogen purged, and the reaction stirred for 45 minutes. The epoxy alkyne (166 mg) was dissolved in 1 ml of ethanol and added via syringe to the mixture. The atmosphere was vacuum/hydrogen purged and the reaction proceeded overnight. Then the reaction was diluted with ether and poured into water. The layers were separated, the aqueous re-extracted 4× with ether, then the organic layers combined and washed with brine, then dried over sodium sulfate. Evaporation and purification on silica gel (15-20% ether/hexane) yielded 155 mg of the epoxy alkene product. Hydrolysis of the ester in methanol with 0.5M (aqueous) K$_2$CO$_3$ provided the free acid: 11-hydroxy-9,10-trans-epoxy-(12Z)-octadecenoic acid (11H-9,10E-LA): 1H NMR (400 MHz, CDCl13) δ 5.63 (tt, J=7.46, 11.39 Hz, 1H), 5.26-5.52 (m, 1H), 4.66 (dd, J=2.84, 8.69 Hz) and 4.28 (ddd, J=0.91, 5.35, 8.74 Hz, 1H), 3.01 (dt, J=2.38, 5.58 Hz, 1H), 2.92 (dt, J=2.38, 5.67 Hz, 1H), 2.74-2.82 (m, 1H), 2.34 (t, J=7.41 Hz, 2H), 1.97-2.24 (m, 2H), 1.46-1.69 (m, 5H), 1.22-1.46 (m, 16H), 0.88 (t, J=6.77 Hz, 3H)

To a solution of methyl-1-hydroxy-9,10-trans-epoxy-(12Z)-octadecenoate (75 mg) in 7 ml of dichloromethane at 0° C. was added Dess-Martin periodinane (1.7 equiv; 166 mg). After 20 min, TLC showed reaction completion so the reaction was diluted with 5% ether/hexane and immediately purified on silica gel to yield 70 mg of the enone. 1H NMR (400 MHz, CDCl3) δ 6.26 (td, J=7.30, 11.57 Hz, 1H), 6.13-6.18 (m, 1H), 3.66 (s, 3H), 3.20 (d, J=1.65 Hz, 1H), 2.99-3.04 (m, 1H), 2.64 (q, J=7.44 Hz, 2H), 2.20-2.34 (m, 2H), 1.53-1.67 (m, 5H), 1.22-1.49 (m, 16H), 0.87 (br t, J=6.86 Hz, 3H).

To a solution of 20 mg of the enone in 3 ml of THF at 0° C. was added MeMgCl (3.0M, 1.3 equiv; 27 µl). The reaction was allowed to reach room temperature and stirred until the starting material was mostly consumed. It was diluted with ether and washed rapidly with 1M HCl (to pH 6-7) followed by water and then brine. Dried over sodium sulfate and purified on silica gel (20-30% ether/hexane) to yield 15 mg of the hydroxy methyl epoxide: 1H NMR (400 MHz, METHANOL-d4) ä5.31-5.48 (m, 2H), 3.64 (s, 3H), 3.02 (dt, J=2.20, 5.58 Hz, 1H), 2.72-2.80 (m, 1H), 2.76 (d, J=2.20 Hz, 1H), 2.30 (q, J=6.83 Hz, 4H), 1.50-1.62 (m, 4H), 1.27-1.48 (m, 18H), 1.18-1.27 (m, 1H), 0.90 (t, J=6.86 Hz, 3H).

Example 3

11-hydroxy- and 11-keto-trans-epoxy-octadecenoates

This example illustrates production of exemplary 11-hydroxy and 11-keto-trans-epoxy-octadecenoate compounds. The following illustrates an exemplary reaction process:

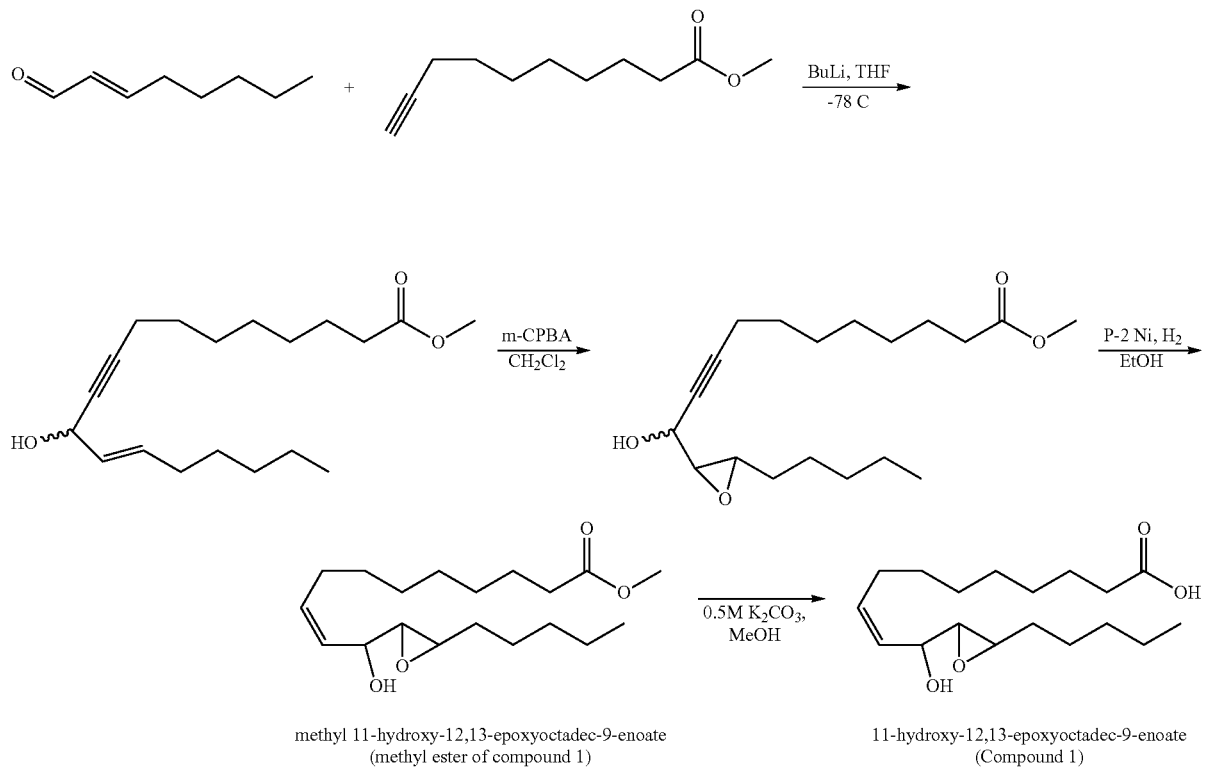

methyl 11-hydroxy-12,13-epoxyoctadec-9-enoate (methyl ester of compound 1)

11-hydroxy-12,13-epoxyoctadec-9-enoate (Compound 1)

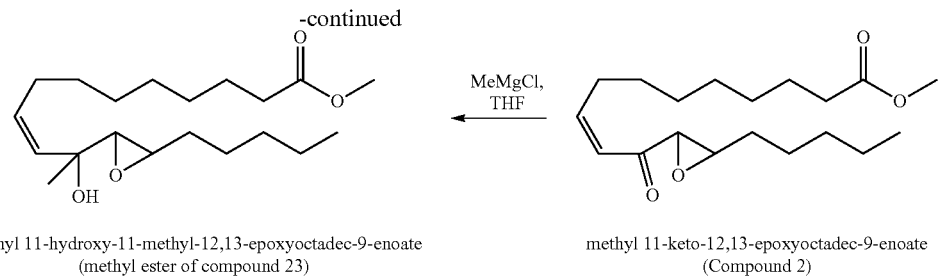

methyl 11-hydroxy-11-methyl-12,13-epoxyoctadec-9-enoate (methyl ester of compound 23) ← MeMgCl, THF — methyl 11-keto-12,13-epoxyoctadec-9-enoate (Compound 2)

To a solution of methyl 9-decynoate (1 g; 5.49 mmol) in 8 ml of THF was added n-BuLi (2.5M; 1.1 equiv; 2.41 ml) dropwise. The reaction was stirred at 0° C. for 45 min, then it was cooled back down to −78° C., and a solution of 2-E-octenal (0.9 equiv; 735 μl) in 1.5 ml THF was added. The reaction proceeded for 2-3 hours (until TLC showed completion) as it warmed to room temperature. Then it was diluted with ether and washed with 1M HCl (to pH 6-7), then water followed by brine. It was dried over sodium sulfate and purified on silica gel (eluted with 5-10% ethyl acetate/hexane) to yield 1.16 g (68%).

To a solution of the hydroxy en-yne (650 mg) in 10 ml dichloromethane at 0° C. was added 77% m-CPBA (1.5 equiv; 699 mg). After 10 min the ice bath was removed and the reaction proceeded until completion. Workup as before followed by purification (15-30% ether/hexane) produced the epoxy-alkyne product, 627 mg (59%).

The semi-hydrogenation and ester hydrolysis were carried as for example 1, producing 123 mg of 11-hydroxy-12,13-trans-epoxy-(9Z)-octadecenoic acid (11H-12,13E-LA). 1H NMR (400 MHz, CDCl3) δ 5.59 (td, J=7.48, 11.02 Hz, 1H), 5.26-5.50 (m, 1H), 4.62-4.67 and 4.25 (tdd, J=1.37, 5.51, 8.58 Hz, 1H), 4.12-4.19 (m, 1H), 3.02 (dt, J=2.20, 5.49 Hz, 1H), 2.88-2.95 (m, 1H), 2.76-2.81 (m, 1H), 2.32 (dt, J=1.37, 7.46 Hz, 2H), 1.98-2.21 (m, 2H), 1.22-1.68 (m, 18H), 0.82-0.93 (m, 3H).

The keto-epoxide was derived from the alcohol as for example 1. Methyl 11-keto-12,13-trans-epoxy-(9Z)-octadecenoate (11K-12,13E-LA methyl ester): 1H NMR (400 MHz, CDCl3) δ 6.19-6.29 (m, 1H), 6.11-6.18 (m, 1H), 3.65 (s, 3H), 3.19 (d, J=1.83 Hz, 1H), 3.01 (dt, J=2.20, 5.49 Hz, 1H), 2.56-2.68 (m, 2H), 2.28 (t, J=7.51 Hz, 2H), 1.36-1.70 (m, 9H), 1.23-1.35 (m, 11H), 0.84-0.92 (m, 3H).

The hydroxy methyl derivative was prepared from the ketone as described in Example 1: 1H NMR (400 MHz, METHANOL-d4) δ 5.33-5.47 (m, 2H), 4.85 (s, 2H), 3.64 (s, 3H), 3.02 (dt, J=2.01, 5.49 Hz, 1H), 2.76 (d, J=1.65 Hz, 1H), 2.26-2.34 (m, 4H), 1.45-1.64 (m, 5H), 1.28-1.45 (m, 16H), 0.85-0.97 (m, 3H).

Example 4

13-hydroxy- and 13-keto-trans-epoxy-octadecenoates

This example illustrates production of exemplary 13-hydroxy- and 13-keto-trans-epoxy-octadecenoate compounds. The following illustrates an exemplary reaction process:

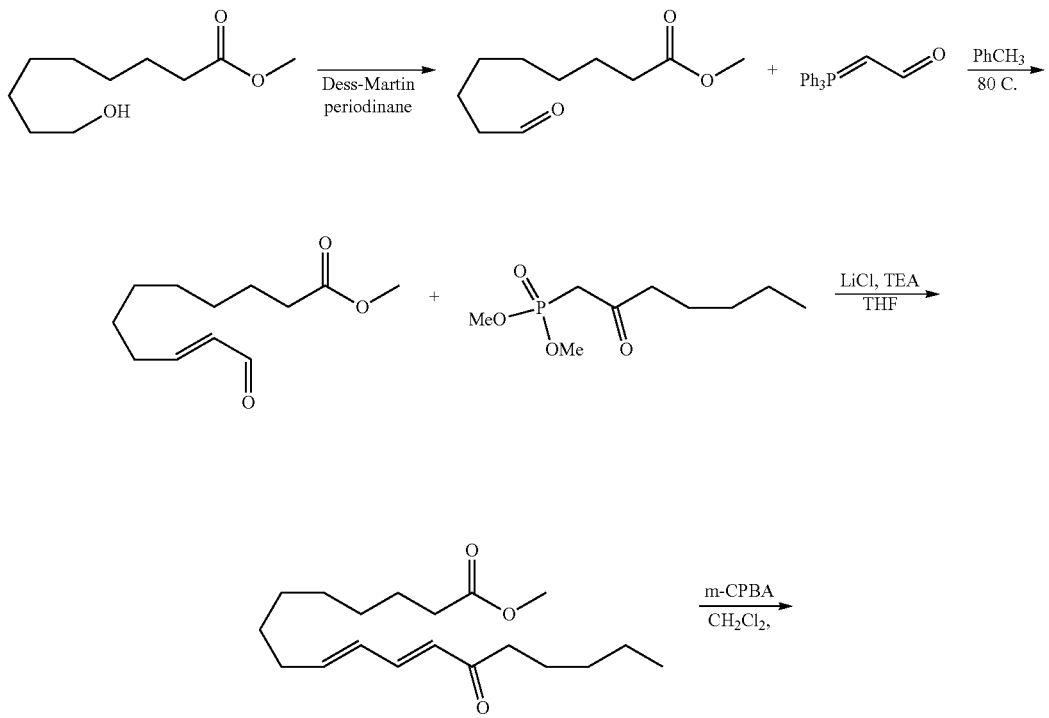

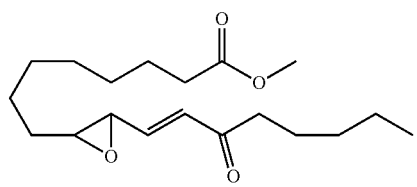

methyl 13-keto-9,10-epoxyoctadec-11-enoate
(methyl ester of compound 8)

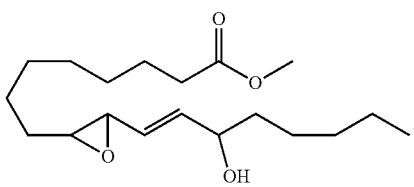

methyl 13-hydroxy-9,10-epoxyoctadec-11-enoate
(methyl ester of compound 7)

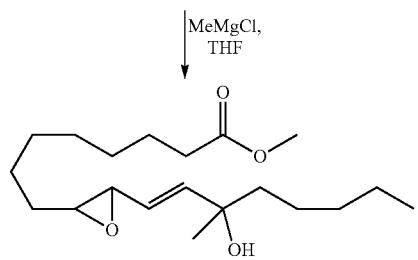

methyl 13-hydroxy-13-methyl-9,10-epoxyoctadec-11-enoate
(methyl ester of Compound 44)

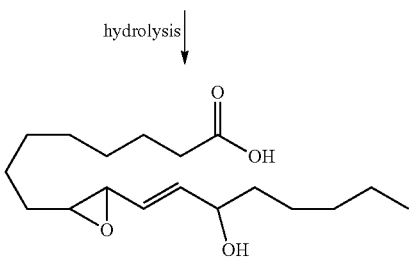

13-hydroxy-9,10-epoxyoctadec-11-enoate
(Compound 7)

Following the same procedures as described in Example 1, the en-al was prepared (400 mg). This was added slowly to a mixture of the phosphonate (3 equiv; 1.25 g) and anhydrous LiCl (3 equiv; 237 mg) in 12 ml THF. Then triethylamine (3.3 equiv; 876 µl) was added, and the reaction allowed to react for 3-4 hours (until TLC showed completion). The reaction was diluted with ether and washed with water then brine. Dried over sodium sulfate, purified on silica gel using 10-15% ether/hexane to elute. There were 371 mg (64%) of the dienone. This was further purified by normal phase HPLC (960/40 heptane/MTBE, 275 nm) to yield 348 mg of a white solid.

The dienone (348 mg) was dissolved in 13 ml of dichloromethane and cooled to 0° C., then 77% m-CPBA (1.5 equiv; 374 mg) was added. After 15 minutes the ice bath was removed and the reaction was allowed to proceed until completion (3 hours). It was diluted diluted with dichloromethane and washed with saturated sodium thiosulfate, then 10% sodium bicarbonate, then water. Dried over sodium sulfate and purified on silica gel (15-30% ether/hexane) to produce 226 mg (62%) of a white solid: 13-keto-9,10-trans-epoxy-(11E)-octadecenoic acid (13K-9,10E-LA): 1H NMR (400 MHz, CDCl3) δ 6.47-6.54 (m, 1H), 6.34-6.43 (m, 1H), 3.20 (dd, J=1.83, 6.86 Hz, 1H), 2.89 (dt, J=2.01, 5.58 Hz, 1H), 2.41-2.60 (m, 2H), 2.25-2.37 (m, 2H), 1.56-1.71 (m, 4H), 1.40-1.53 (m, 2H), 1.11-1.38 (m, 12H), 0.82-0.94 (m, 3H).

The hydroxy methyl derivative was prepared from the ketone as in Example 1: 1H NMR (400 MHz, METHANOL-d4) δ 5.98 (d, J=15.74 Hz, 1H), 5.35 (dd, J=7.96, 15.65 Hz, 1H), 3.64 (s, 2H), 3.14 (dd, J=2.20, 7.87 Hz, 2H), 2.83 (dt, J=2.20, 5.58 Hz, 2H), 2.31 (t, J=7.41 Hz, 2H), 1.42-1.62 (m, 7H), 1.25-1.39 (m, 12H), 1.22-1.25 (m, 3H), 0.89 (t, J=6.95 Hz, 3H).

The hydroxyl compound was produced from sodium borohydride reduction of the ketone in a 1:1 mixture of methanol and borate buffer (pH 8.5) at 0° C., followed by ester hydrolysis in methanol with dilute potassium carbonate to yield 13-hydroxy-9,10-trans-epoxy-(11E)-methyl-octadecenoate (13H-9,10E-LA methyl ester): 1H NMR (400 MHz, CDCl3) δ 5.91 (dd, J=6.40, 15.55 Hz, 1H), 5.40 (dd, J=7.87, 15.55 Hz, 1H), 3.90-4.17 (m, 1H), 3.65 (s, 3H), 3.08 (dd, J=2.10, 7.78 Hz, 1H), 2.80 (dt, J=2.01, 5.58 Hz, 1H), 2.29 (t, J=7.50 Hz, 2H), 1.69 (br. s., 1H), 1.48-1.63 (m, 6H), 1.24-1.45 (m, 13H), 0.87 (t, J=6.59 Hz, 3H)

Example 5

9-hydroxy- and 9-keto-trans-epoxy-octadecenoates

This example illustrates production of exemplary 9-hydroxy- and 9-keto-trans-epoxy-octadecenoate compounds. The following illustrates an exemplary reaction process:

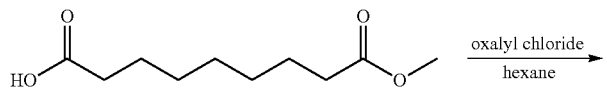 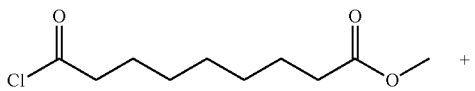

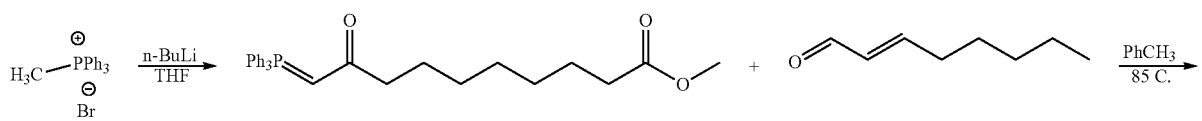

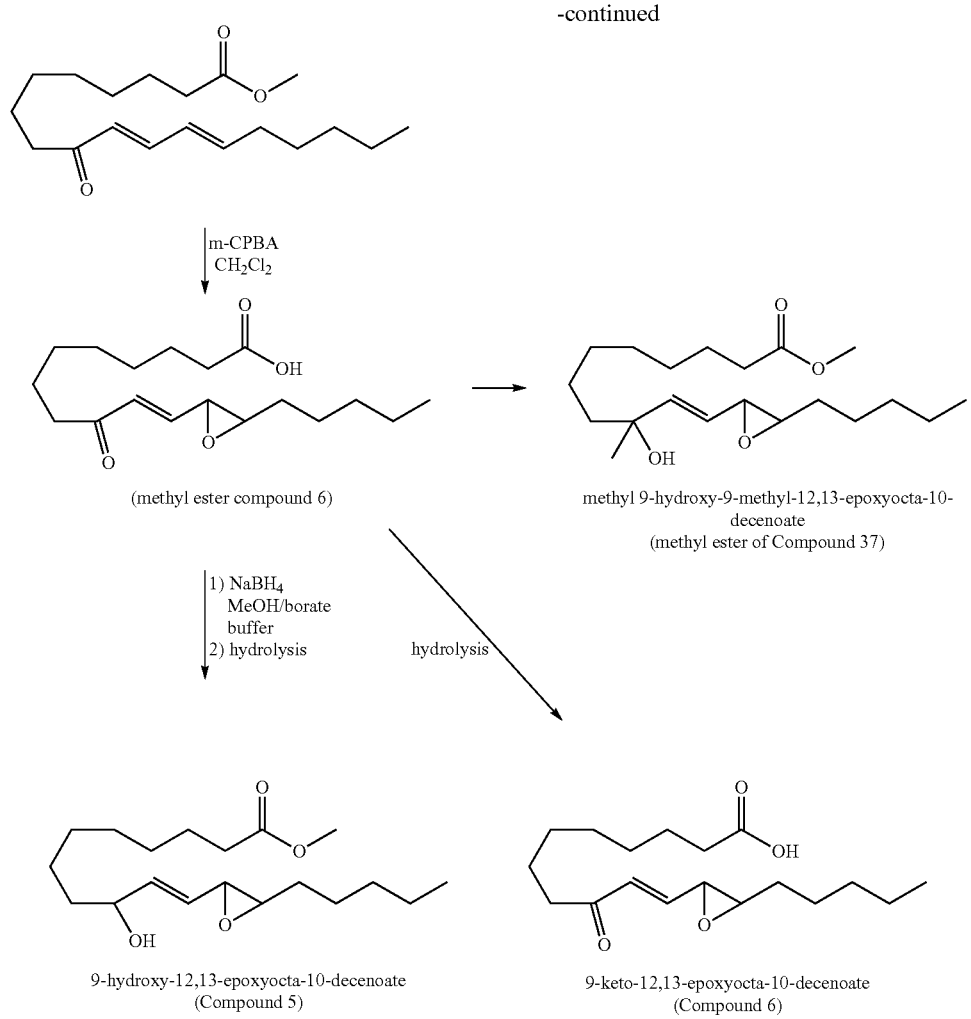

The 9-keto-12,13-trans-epoxy-(10E)-methyl-octadecenoate (9K-12,13E-LA methyl ester) was prepared following similar procedures as published by Sayre et. al. in *J. Org. Chem.* 2007, 72, 9471-9480, with the modification of installing the epoxide on the dienone produced by the Wittig reaction instead of on the en-al (prior to the Wittig reaction) as published by Sayre. The hydroxy compound was produced as in Example 3: 9-hydroxy-12,13-trans-epoxy-(10E)-octadecenoic acid (9H-12,13E-LA): 1H NMR (400 MHz, CDCl3) δ 5.91 (dd, J=6.22, 15.55 Hz, 1H), 5.41 (dd, J=7.87, 15.55 Hz, 1H), 4.12 (quin, J=5.95 Hz, 1H), 3.04-3.16 (m, 1H), 2.82 (dt, J=1.92, 5.54 Hz, 1H), 2.33 (t, J=7.50 Hz, 2H), 1.49-1.64 (m, 5H), 1.27-1.47 (m, 11H), 1.09-1.27 (m, 3H), 0.79-0.93 (m, 3H).

The hydroxy methyl derivative was prepared from the ketone as in Example 1: 1H NMR (400 MHz, METHANOL-d4) δ 5.97 (d, J=15.74 Hz, 1H), 5.35 (dd, J=8.05, 15.74 Hz, 1H), 3.64 (s, 3H), 3.14 (dd, J=2.01, 8.05 Hz, 1H), 2.84 (dt, J=2.01, 5.58 Hz, 1H), 2.30 (t, J=7.41 Hz, 2H), 1.38-1.63 (m, 9H), 1.28-1.37 (m, 13H), 1.18-1.27 (m, 4H), 0.86-0.96 (m, 3H).

Example 6

2,2-dimethyl-13-hydroxy- and 2,2-dimethyl-13-keto-trans-epoxy-octadecenoates

This example illustrates production of exemplary 2,2-dimethyl-13-hydroxy- and 2,2-dimethyl-13-keto-trans-epoxy-octadecenoate compounds. The following illustrates an exemplary reaction process:

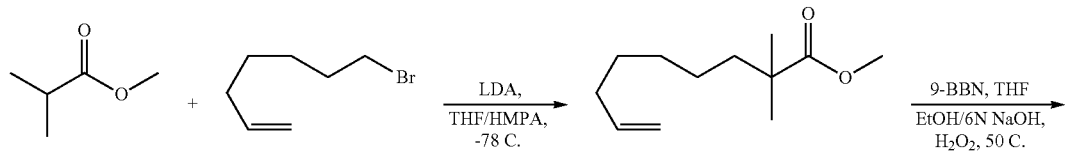

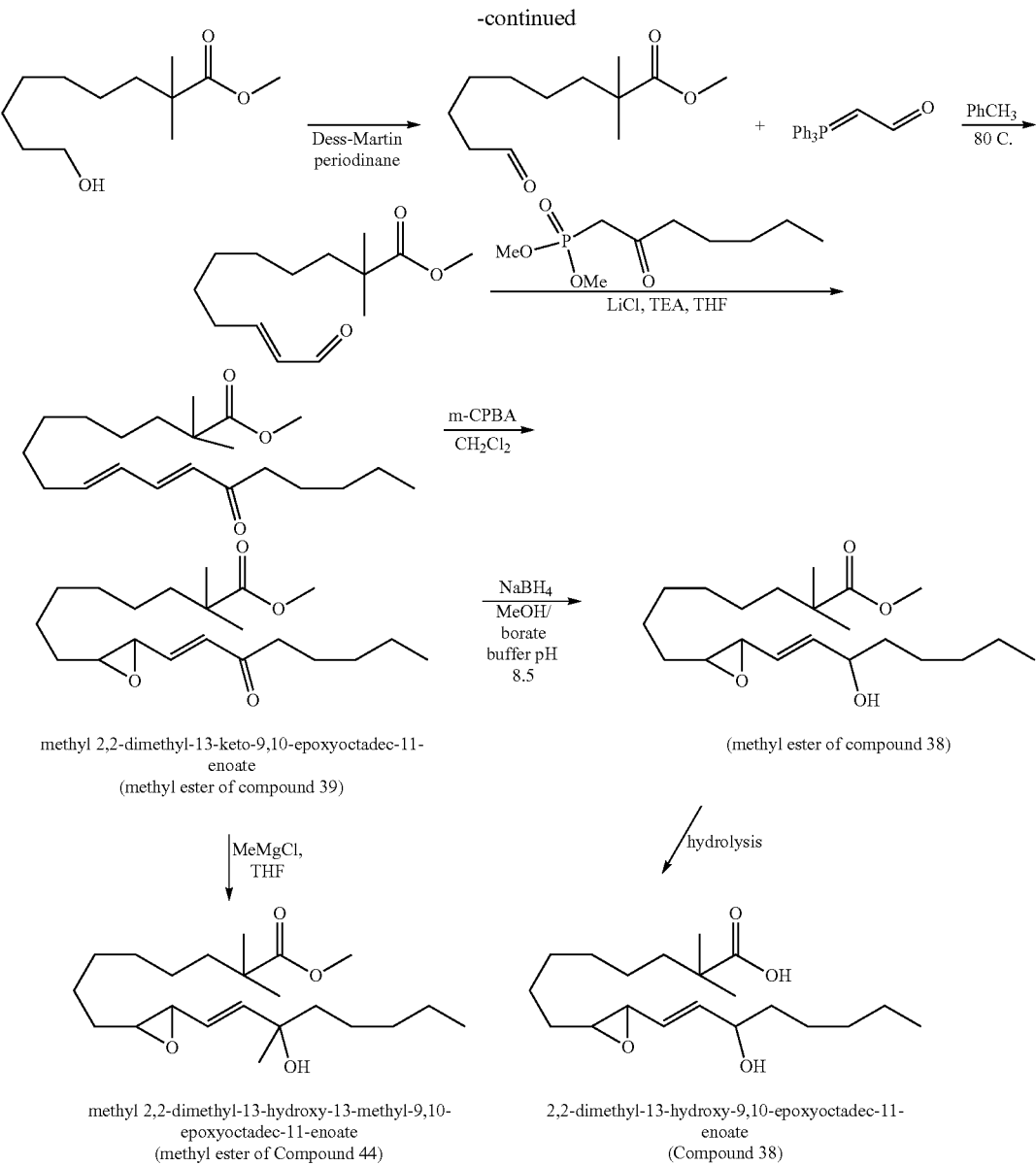

methyl 2,2-dimethyl-13-keto-9,10-epoxyoctadec-11-enoate
(methyl ester of compound 39)

(methyl ester of compound 38)

methyl 2,2-dimethyl-13-hydroxy-13-methyl-9,10-epoxyoctadec-11-enoate
(methyl ester of Compound 44)

2,2-dimethyl-13-hydroxy-9,10-epoxyoctadec-11-enoate
(Compound 38)

To a solution of methyl isobutyrate (2 g; 19.60 mmol) in 25 ml of THF at −78° C. was added lithium diisopropylamide (2.0M, 1.2 equiv; 11.77 ml) dropwise. After 30 minutes, a solution of 7-bromo-1-heptene (1.2 equiv; 4.14 g) in 5 ml of THF was added slowly. The reaction was stirred at room temperature for 1-2 hours (until TLC showed completion), then it was diluted with ether and washed with 1M HCl, then water and finally brine. It was dried over sodium sulfate and purified on silica gel (5% ethyl acetate/hexane) to yield 3.25 g (87%).

To a stirred solution of 0.5M 9-BBN in THF (1 equiv; 20 ml) was added a solution of 2,2-dimethyl methyl nonenoate (2 g; 10.10 mmol) in THF. The solution was stirred for 2 hours and then it was cooled to 0° C. and 6 ml of ethanol was added followed by 2.2 ml of 6N NaOH and 3.4 ml of 30% hydrogen peroxide. The reaction was heated to 50° C. and stirred for 1 hour, then cooled to room temperature and diluted with ethyl acetate and washed with water then brine. Dried over sodium sulfate and purified on silica gel to yield 1.61 g (76%).

The rest of the synthesis was carried out as in Example 3.

2,2-dimethyl-13-hydroxy-9,10-trans-epoxy-(11E)-octadecenoate: 1H NMR (400 MHz, CHLOROFORM-d) δ 5.88-5.97 ((m, 1H), 5.41 (dddd, J=1.01, 3.09, 7.88, 15.57 Hz, 1H), 4.05-4.20 (m, 1H), 3.06-3.13 (m, 1H), 2.79-2.86 (m, 1H), 2.04 (s, 1H), 1.33-1.61 (m, 10H), 1.20-1.32 (m, 9H), 1.18 (s, 5H), 0.81-0.96 (m, 3H).

2,2-dimethyl-13-keto-9,10-trans-epoxy-(11E)-methyl-octadecenoate: 1H NMR (400 MHz, CHLOROFORM-d) δ 6.63 (dd, J=6.59, 15.75 Hz, 1H), 6.50 (dd, J=6.96, 16.11 Hz, 1H), 6.34-6.41 (m, 1H), 3.64 (s, 3H), 3.37-3.46 (m, 1H), 3.18 (dd, J=1.83, 6.96 Hz, 1H), 2.84-2.92 (m, 1H), 2.51 (t, J=7.32 Hz, 2H), 2.38-2.45 (m, 1H), 2.22-2.33 (m, 1H), 1.53-1.63 (m, 4H), 1.38-1.50 (m, 4H), 1.16-1.37 (m, 11H), 1.14 (s, 6H), 0.87 (t, J=6.77 Hz, 3H)

2,2-dimethyl-13-hydroxy-13-methyl-9,10-trans-epoxy-(11E)-octadecenoate: 1H NMR (400 MHz, CHLOROFORM-d) δ 5.95 (d, J=15.74 Hz, 1H), 5.39 (br dd, J=7.78, 15.65 Hz, 1H), 3.64 (s, 3H), 3.39-3.63 (m, 1H), 3.09 (br d, J=7.78 Hz, 1H), 2.78-2.90 (m, 1H), 1.32-1.67 (m, 13H), 1.17-1.32 (m, 20H), 1.15 (s, 6H), 0.87 (br t, J=6.59 Hz, 5H)

Example 7

2,2-dimethyl-11-hydroxy-, methyl-2,2-dimethyl-11-keto-, and methyl-2,2-dimethyl-11-hydroxy-trans-epoxy-octadecenoates This example illustrates production of exemplary 2,2-dimethyl-11-hydroxy-, methyl-2,2-dimethyl-11-keto-, and methyl-2,2-dimethyl-11-hydroxy-trans-epoxy-octadecenoate compounds. The following illustrates an exemplary reaction process:

The indicated 2,2-dimethyl-11-hydroxy-, methyl-2,2-dimethyl-11-keto-, and methyl-2,2-dimethyl-11-hydroxy-trans-epoxy-octadecenoate compounds can be prepared as shown in Examples 6 and 2 with modifications in light of the reaction process shown above.

Example 8

2,2-dimethyl-11-hydroxy-, methyl-2,2-dimethyl-11-hydroxy-, methyl-2,2-dimethyl-11-keto-trans-epoxy-octadecenoates This example illustrates production of exemplary 2,2-dimethyl-11-hydroxy-, methyl-2,2-dimethyl-11-hydroxy-methyl-2,2-dimethyl-11-keto-trans-epoxy-octadecenoate compounds. The following illustrates an exemplary reaction process: ,

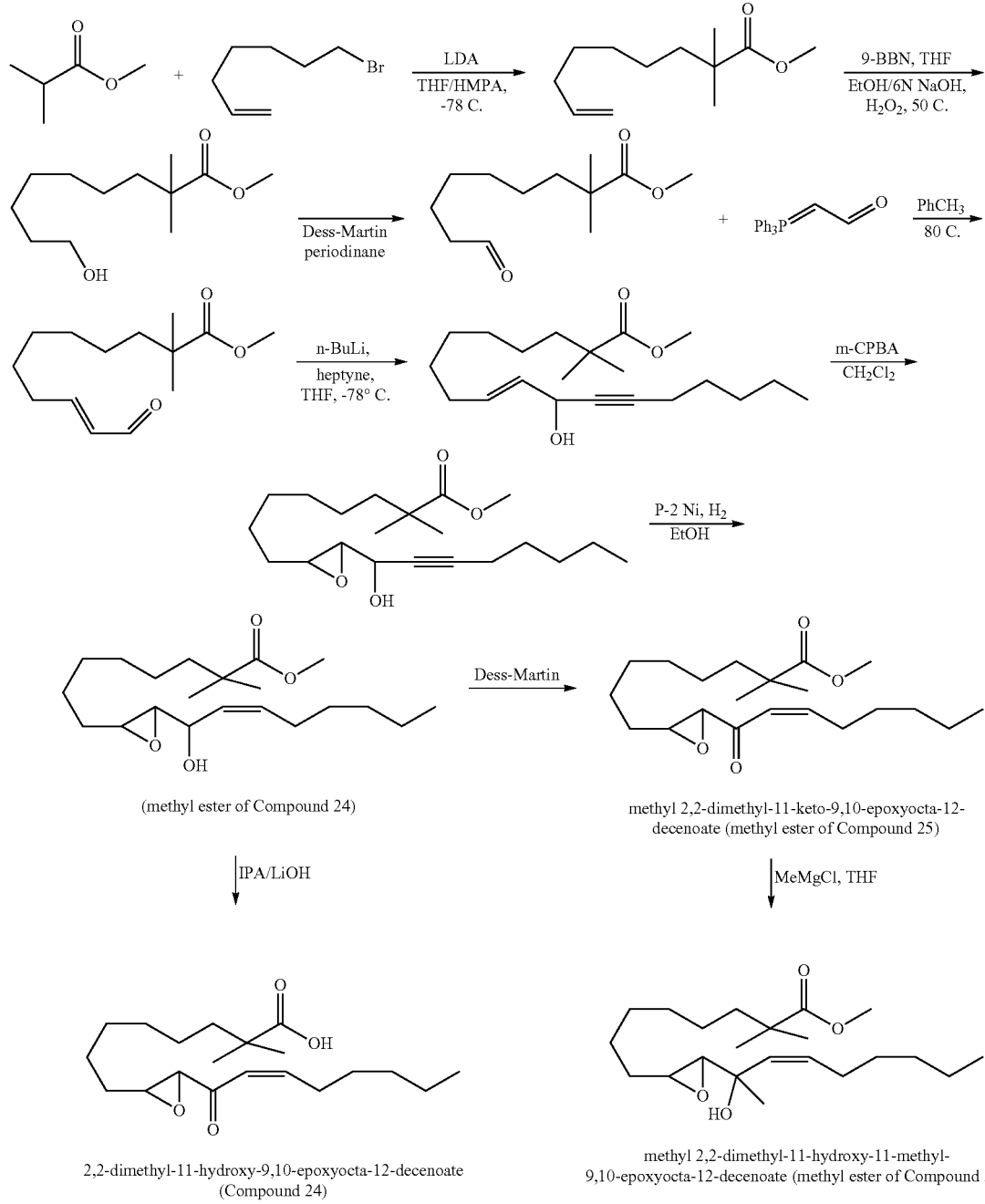

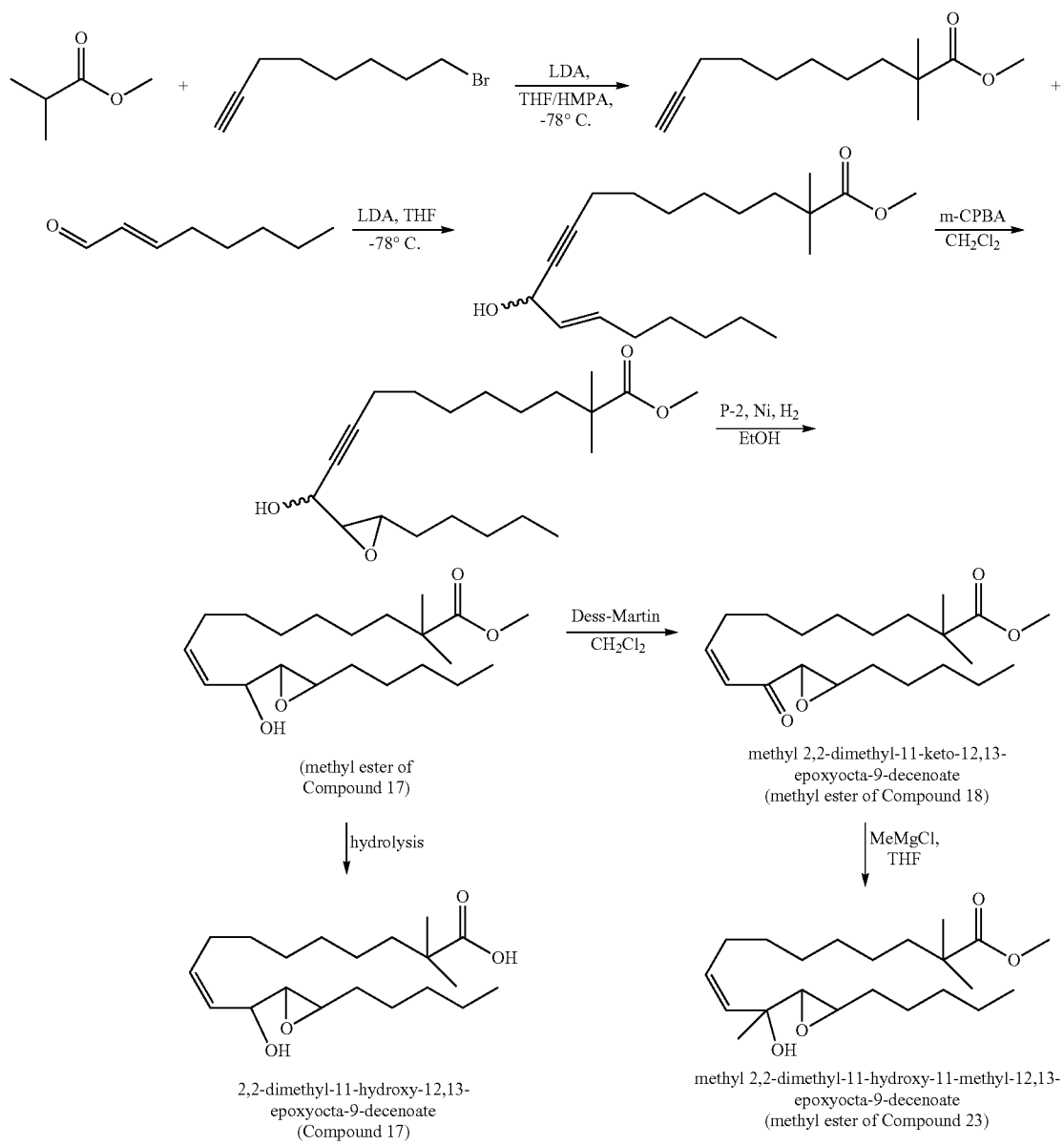

(methyl ester of Compound 17)

methyl 2,2-dimethyl-11-keto-12,13-epoxyocta-9-decenoate
(methyl ester of Compound 18)

2,2-dimethyl-11-hydroxy-12,13-epoxyocta-9-decenoate
(Compound 17)

methyl 2,2-dimethyl-11-hydroxy-11-methyl-12,13-epoxyocta-9-decenoate
(methyl ester of Compound 23)

The indicated 2,2-dimethyl-11-hydroxy-, methyl-2,2-dimethyl-11-hydroxy-, methyl-2,2-dimethyl-11-keto-trans-epoxy-octadecenoate compounds can be prepared as shown in Examples 6 and 3 with modifications in light of the reaction process shown above and the description below.

2,2-dimethyl-11-hydroxy-12,13-trans-epoxy-(9Z)-octadecenoate: 1H NMR (400 MHz, CHLOROFORM-d) δ 5.54-5.83 (m, 1H), 5.40-5.54 (m, 1H), 5.16-5.40 (m, 1H), 4.66 (br dd, J=2.06, 8.74 Hz, 1H), 4.26 (dd, J=5.67, 8.51 Hz, 1H), 3.03 (br dd, J=2.97, 8.46 Hz, 1H), 2.87-2.98 (m, 1H), 2.80 (dd, J=2.24, 5.44 Hz, 1H), 1.97-2.20 (m, 2H), 1.47-1.59 (m, 3H), 1.20-1.45 (m, 14H), 1.18 (s, 4H), 0.79-0.96 (m, 3H).

Methyl 2,2-dimethyl-11-keto-12,13-trans-epoxy-(9Z)-octadecenoate: 1H NMR (400 MHz, CHLOROFORM-d) δ 6.20-6.29 (m, 1H), 6.13-6.18 (m, 1H), 3.64 (s, 3H), 3.20 (d, J=1.83 Hz, 1H), 3.00-3.06 (m, 1H), 2.63 (q, J=7.32 Hz, 2H), 2.36-2.48 (m, 1H), 1.53-1.67 (m, 2H), 1.37-1.50 (m, 6H), 1.17-1.35 (m, 11H), 1.14 (s, 6H), 0.83-0.94 (m, 3H).

Methyl 2,2-dimethyl-11-hydroxy-11-methyl-12,13-trans-epoxy-(9Z)-octadecenoate: 1H NMR (400 MHz, CHLOROFORM-d) δ 5.60-5.76 (m, 1H), 5.44 (td, J=7.24, 12.05 Hz, 1H), 5.26-5.38 (m, 1H), 5.07-5.26 (m, 1H), 3.65 (s, 3H), 2.95-3.07 (m, 1H), 2.74-2.95 (m, 1H), 2.24-2.47 (m, 1H), 2.09-2.24 (m, 2H), 1.34-1.58 (m, 8H), 1.19-1.34 (m, 10H), 1.13-1.19 (m, 5H), 0.88 (br d, J=3.93 Hz, 3H).

Example 9

2,2-dimethyl-9-hydroxy-, methyl-2,2-dimethyl-9-keto-, methyl-2,2-dimethyl-9-hydroxy-trans-epoxy-octadecenoates This example illustrates production of exemplary 2,2-dimethyl-9-hydroxy-, methyl-2,2-dimethyl-9-keto-, methyl-2,2-dimethyl-9-hydroxy-trans-epoxy-octadecenoate compounds. The following illustrates an exemplary reaction process:

101

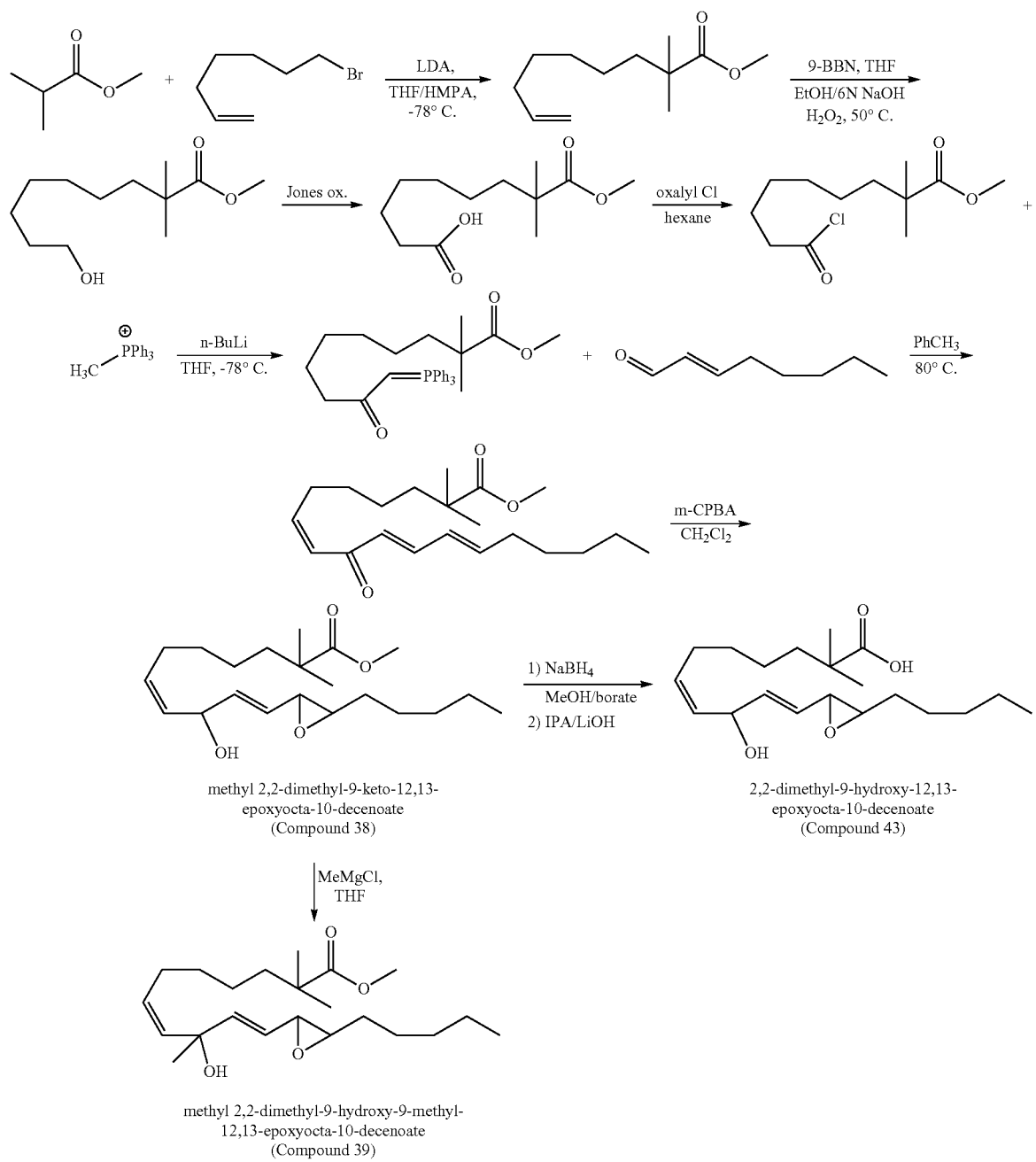

The indicated 2,2-dimethyl-9-hydroxy-, methyl-2,2-dimethyl-9-keto-, methyl-2,2-dimethyl-9-hydroxy-trans-epoxy-octadecenoate compounds can be prepared as shown in Examples 6 and 7 with modifications in light of the reaction process shown above.

102

Example 10

1,5-epoxy Pharmacophores

This example illustrates production of exemplary 1,5-epoxy pharmacophore compounds. The following illustrates an exemplary reaction process:

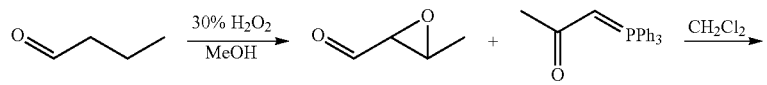

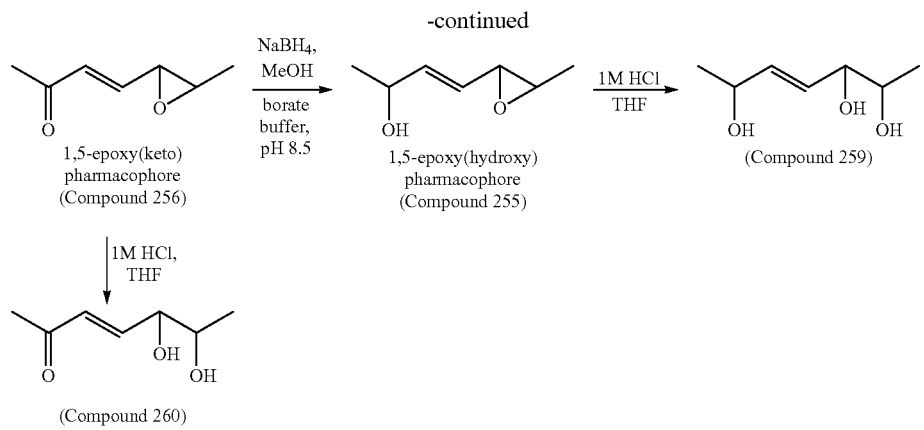

To a solution of crotonaldehyde (1 g) in 15 ml of methanol at 0° C. was added 30% hydrogen peroxide (>3 equiv; 6.5 ml) followed by NaHCO₃ (1.2 equiv; 1.44 g). After 15 minutes the ice bath was removed, and the reaction stirred for 2 hours. It was diluted with dichloromethane and washed with brine, then dried over sodium sulfate and concentrated to approximately 8 ml. It was then cooled to 0° C. and a solution of 1-(triphenylphosphoranylidene)-2-propanone (1.1 equiv; 4.85 g) in 15 ml of dichloromethane was added dropwise. The reaction was allowed to reach room temperature, stirring for 4-5 hours. Then it was washed with water and dried over sodium sulfate. Purified on silica gel (5-15% ethyl acetate/hexane) to yield 200 mg of the 1,5-epoxy(keto) pharmacophore: 1H NMR (82 MHz,) δ 6.20-5.66 (m, 1H), 2.94-2.41 (m, 1H), 1.82 (s, 3H), 1.10-0.9 (m, 3H).

At 0° C., sodium borohydride (1 equiv; 7.5 mg) was added to a solution of the ketone (25 mg) in 2 ml of 1:1 methanol: borate buffer (pH 8.5). After 20 minutes, the reaction was complete and it was diluted with ethyl acetate and washed with saturated ammonium chloride followed by brine. Dried over sodium sulfate. The yield of the 1,5-epoxy (hydroxy) pharmacophore was 25 mg.

To a solution of the ketone (55 mg) in 4 ml of THF was added 1M HCl (8-9 drops). It was left overnight and then it was diluted with ethyl acetate and washed with water followed by brine. Dried over sodium sulfate and purified on silica gel to yield 63 mg of the keto-dihydroxy compound: ¹H NMR (82 MHz,) δ 6.62 (dd, J=15.8, 7.8 Hz, 1H), 6.07 (d, J=15.9 Hz, 1H), 4.25 (dd, J=7.8, 4.4 Hz, 1H), 4.04-3.50 (m, 2H), 2.02 (d, J=11.3 Hz, 4H), 1.07 (d, J=6.1 Hz, 3H).

The trihydroxy compound was prepared using the same method as the keto diol.

Example 11

1,3-epoxy Pharmacophores

This example illustrates production of exemplary 1,3-epoxy pharmacophore compounds. The following illustrates an exemplary reaction process:

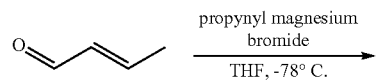

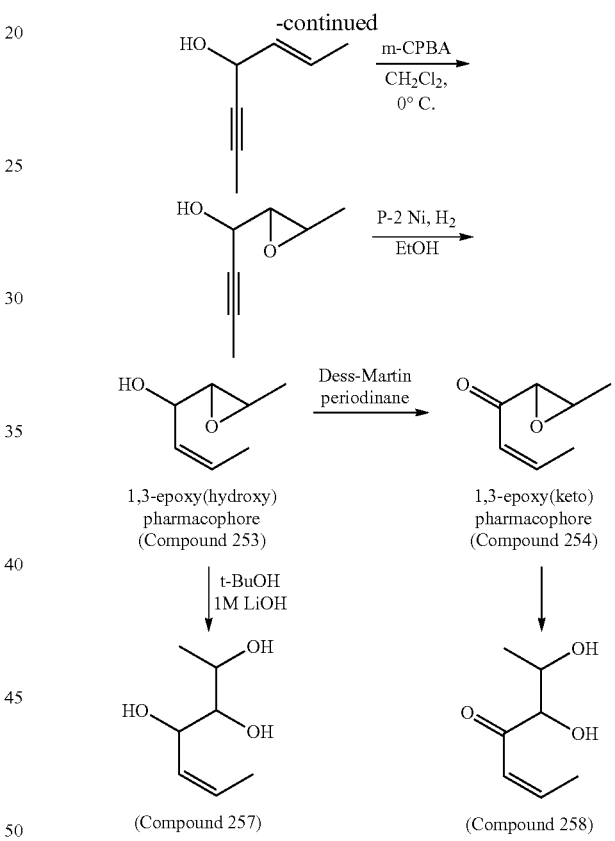

To a solution of 0.5M propynylmagnesium bromide (1.2 equiv; 68 ml) in THF at 0° C. was added a solution of crotonaldehyde (2 g) in 2 ml of THF slowly. The reaction was allowed to reach room temperature over 5 hours, then it was diluted with ether and washed with 1M HCl followed by water and then brine. Dried over sodium sulfate and purified on silica gel to yield 3.13 g (>99%).

At 0° C., 77% m-CPBA (1.3 equiv; 8.29 g) was added to a solution of the en-yne (3.13 g) in 25 ml of dichloromethane. The ice bath was removed after 20 minutes, and the reaction stirred for 5 hours. It was filtered through Celite, and then washed with saturated sodium thiosulfate followed by saturated sodium bicarbonate then dried over sodium sulfate. Purification on silica gel produced 3 g of an oil contaminated with inseparable impurities.

In a 2-neck 100 ml RBF equipped with a gas balloon apparatus containing 16 ml of ethanol was added Ni(OAc)2 tetrahydrate (12.5% mol; 385 mg). The atmosphere purged with vacuum and backfilled with hydrogen 3×, then allowed to stir under hydrogen atmosphere until fully dissolved. Solid sodium borohydride (12.5% mol; 61 mg) was added, the atmosphere again vacuum/hydrogen purged, and the black mixture stirred under hydrogen atmosphere for 45 minutes. Then, ethylene diamine (25% mol; 206 ml) was added, the atmosphere once more vacuum/hydrogen purged, and the reaction stirred for 45 minutes. The epoxy alkyne (1.56 g) was dissolved in 2 ml of ethanol and added via syringe to the mixture. The atmosphere was vacuum/hydrogen purged and the reaction proceeded overnight. Then the reaction was diluted with ether and poured into water. The layers were separated, the aqueous re-extracted 4× with ether, then the organic layers combined and washed with brine, then dried over sodium sulfate. Evaporation and purification on silica gel yielded 894 mg (56%) of the 1,3-epoxy(hydroxy) pharmacophore: $^1$H NMR (82 MHz) δ 5.07 (h, J=5.4 Hz, 2H), 4.00-3.67 (m, J=7.5, 3.8 Hz, 1H), 3.01 (s, 1H), 2.71-2.11 (m, 2H), 1.21 (d, J=5.7 Hz, 3H), 0.81 (d, J=5.2 Hz, 3H).

The hydroxy epoxide (142 mg) was dissolved in 4 ml of dichloromethane and then Dess-Martin periodinane (1.7 equiv; 787 mg) was added. After 3 hours, it was diluted with 5% ethyl acetate/hexane and filtered through silica gel and purified to yield 39 mg (28%) of the 1,3-epoxy(keto) pharmacophore: 1H NMR (82 MHz,) δ 6.27-5.62 (m, 2H), 2.77 (d, J=4.3 Hz, 2H), 1.76 (d, J=5.9 Hz, 3H), 1.20-0.81 (m, 3H).

The hydroxy epoxide (62 mg) was dissolved in 2 ml of t-butanol and then 1M LiOH (8 ml) was added. The reaction was stirred overnight, and then it was quenched with 1M HCl (pH 3-4), diluted with water, and then eluted through a 1 g C18 SPE (water followed by methanol). Evaporation of the methanol layer and purification of a portion of the crude on silica gel produced 3 mg of the triol pharmacophore.

The keto dihydroxy compound can be prepared from the keto epoxide using either basic or acidic hydrolysis.

Example 12

7-hydroxy-5,6-trans-epoxy-(8Z)-octadecenoic acid (7H-5E-SA)

This example illustrates production of exemplary 7-hydroxy-5,6-trans-epoxy-(8Z)-octadecenoic acid compounds. The following illustrates an exemplary reaction process:

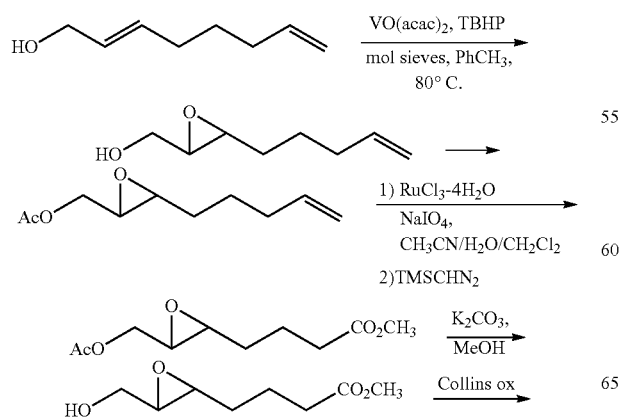

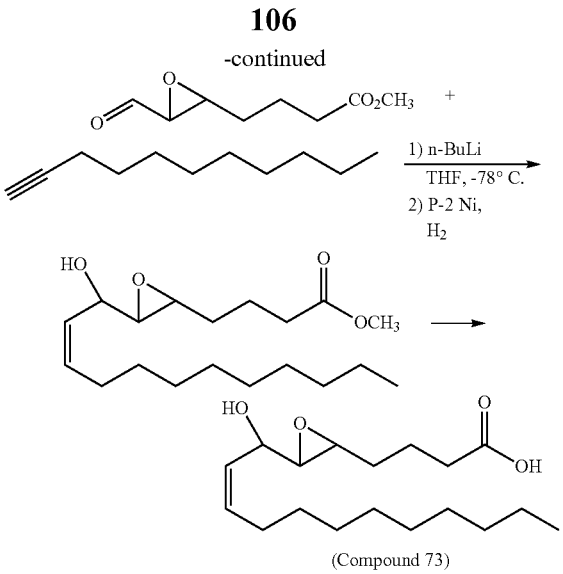

(Compound 73)

Example 13

9-hydroxy-5,6-trans-epoxy-(7E)-octadecenoic acid (9H-5E-SA)

This example illustrates production of exemplary 9-hydroxy-5,6-trans-epoxy-(7E)-octadecenoic acid compounds. The following illustrates an exemplary reaction process:

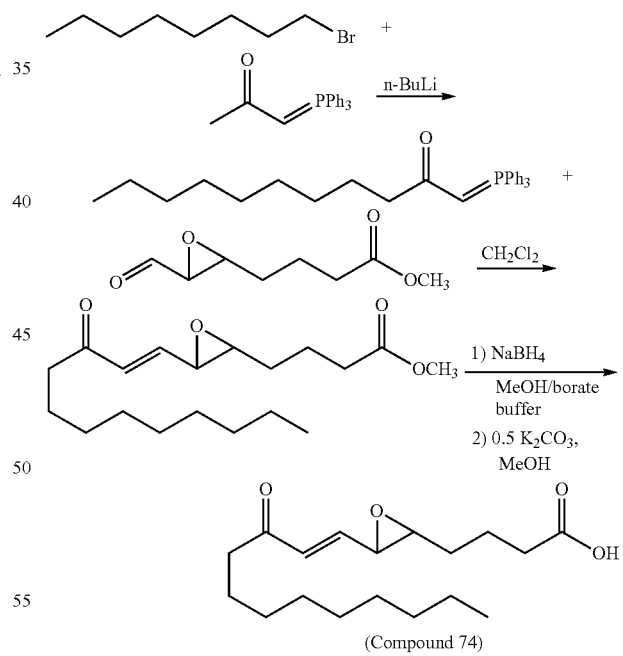

(Compound 74)

Example 14

5-hydroxy-8,9-trans-epoxy-(6E)-octadecenoic acid (5H-8E-SA)

This example illustrates production of exemplary 5-hydroxy-8,9-trans-epoxy-(6E)-octadecenoic acid compounds. The following illustrates an exemplary reaction process:

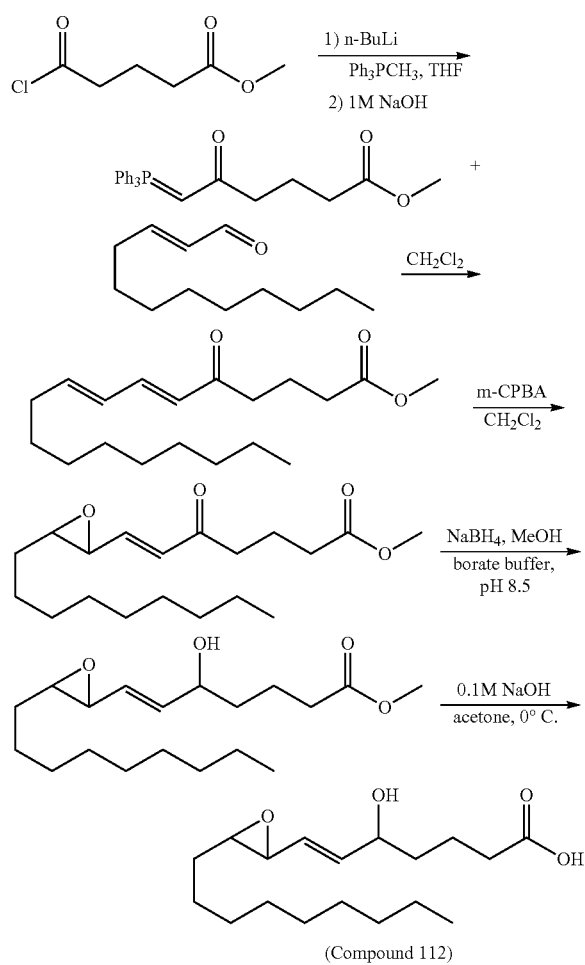

(Compound 112)

Example 15

5-hydroxy-8,9-trans-epoxy-(6E)-octadecenoic acid (5H-8E-SA)

This example illustrates production of exemplary 5-hydroxy-8,9-trans-epoxy-(6E)-octadecenoic acid compounds. The following illustrates an exemplary reaction process:

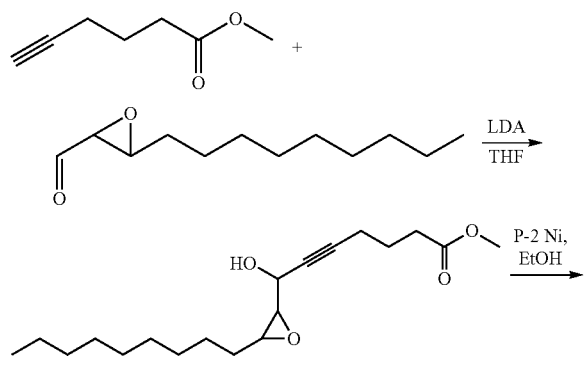

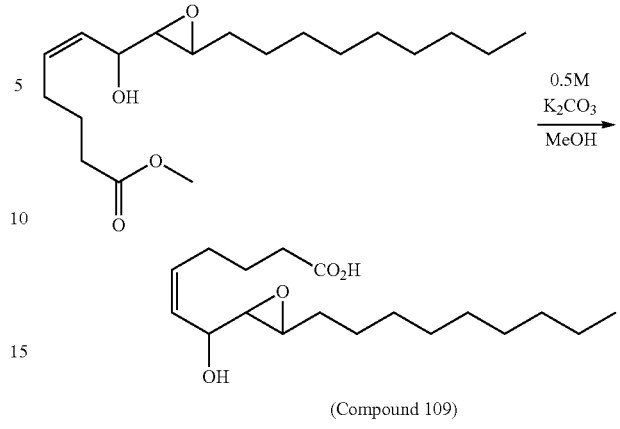

(Compound 109)

Example 16

9-hydroxy-5,6-trans-epoxy-(7E,11Z)-eicosadienoic acid (9H-5E-MA)

This example illustrates production of exemplary 9-hydroxy-5,6-trans-epoxy-(7E,11Z)-eicosadienoic acid compounds. The following illustrates an exemplary reaction process:

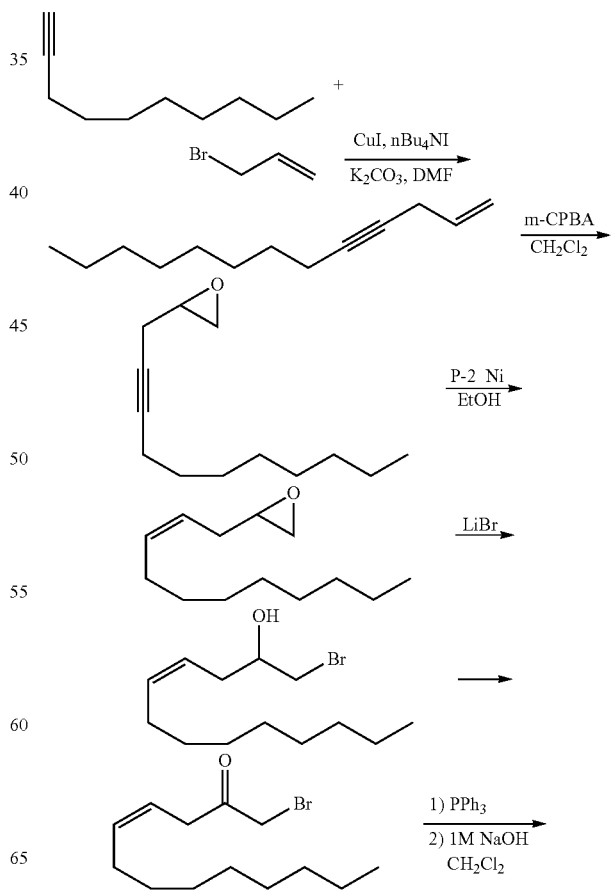

-continued

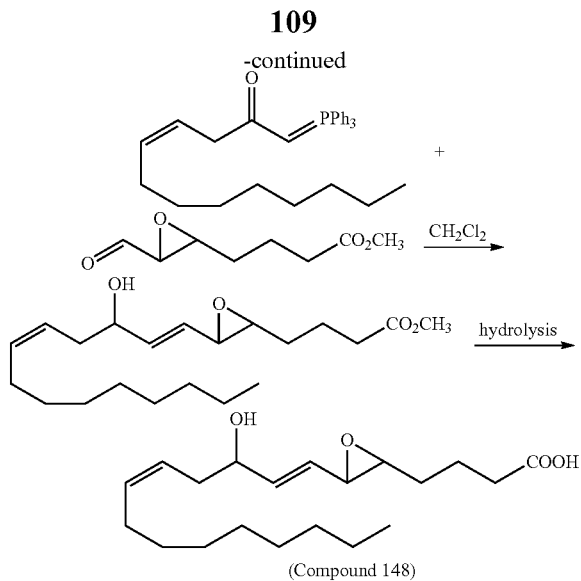

(Compound 148)

Example 17

7-hydroxy-5,6-trans-epoxy-(8Z,11Z)-eicosadienoic acid (7H-5E-MA)

This example illustrates production of exemplary 7-hydroxy-5,6-trans-epoxy-(8Z,11Z)-eicosadienoic acid compounds. The following illustrates an exemplary reaction process:

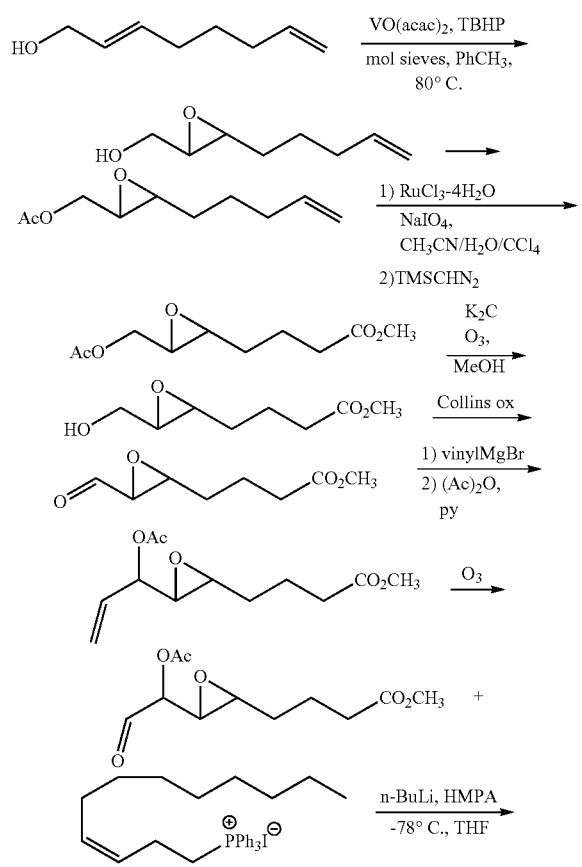

-continued

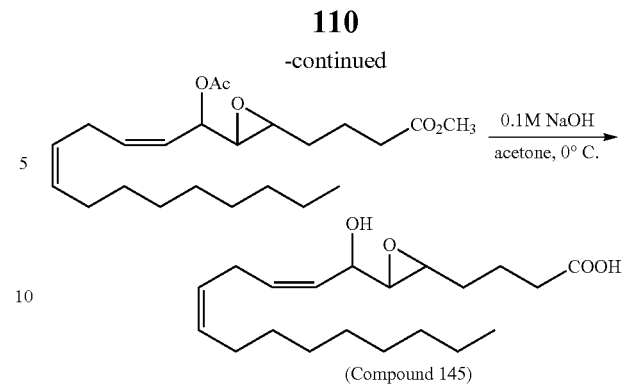

(Compound 145)

Example 18

9-hydroxy-5,6-trans-epoxy-(7E,11Z,14Z)-eicosatrienoic acid (9H-5E-AA)

This example illustrates production of exemplary 9-hydroxy-5,6-trans-epoxy-eicosatrienoic acid compounds. The following illustrates an exemplary reaction process:

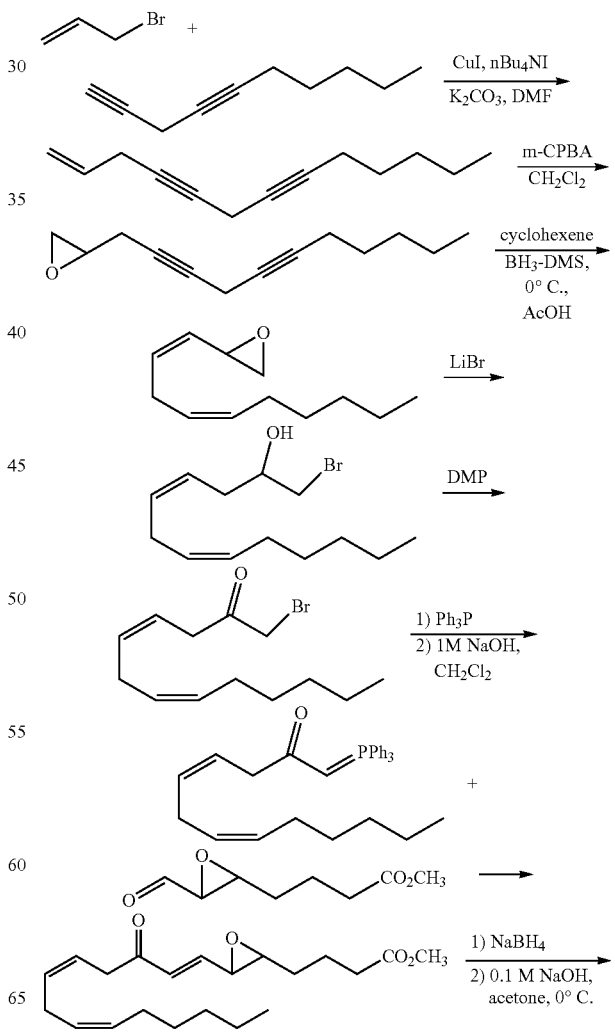

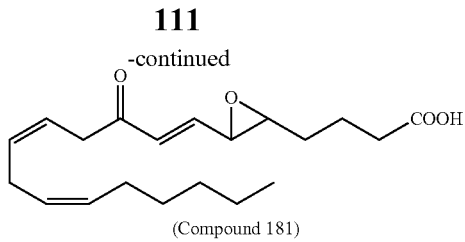

(Compound 181)

Example 19

7-hydroxy-5,6-trans-epoxy-(8Z,11Z,14Z)-eicosatrienoic acid (7H-5E-AA)

This example illustrates production of exemplary 7-hydroxy-5,6-trans-epoxy-eicosatrienoic acid compounds. The following illustrates an exemplary reaction process:

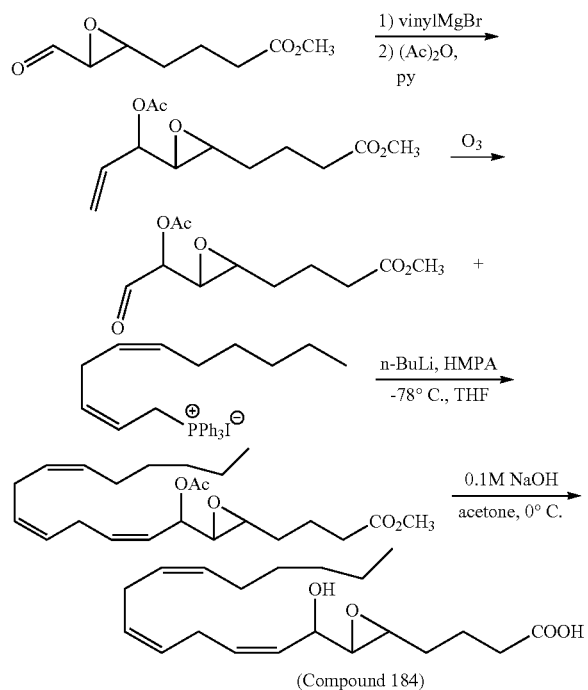

(Compound 184)

Example 20

2,2-dimethyl-5,6-epoxide intermediate synthesis

This example illustrates production of 2,2-dimethyl-5,6-epoxide intermediates. The following illustrates an exemplary reaction process:

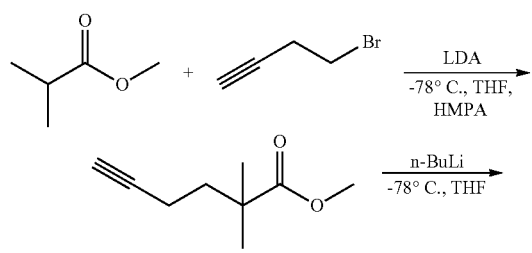

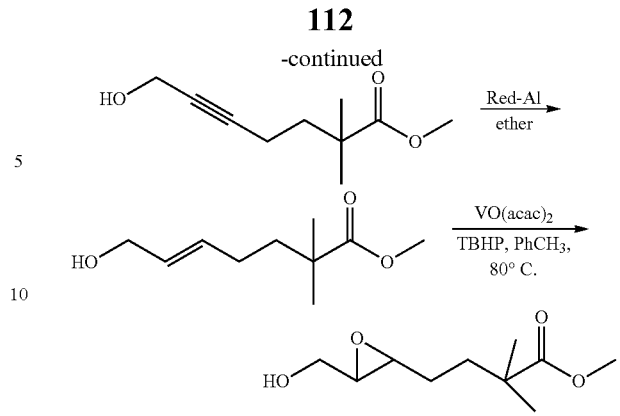

Intermediate is then used in synthesis of each PUFA derivative as described previously.

Example 21

2,2-dimethyl-4-hydroxy-DHA synthesis

This example illustrates production of 2,2-dimethyl-4-hydroxy-DHA. The following illustrates an exemplary reaction process:

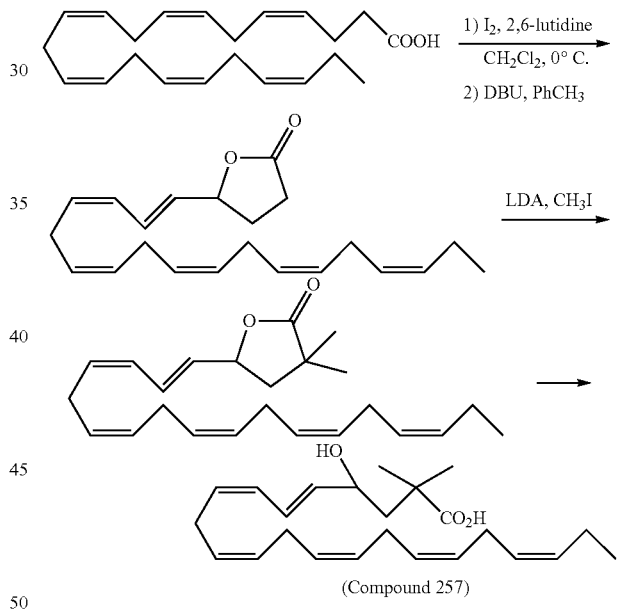

(Compound 257)

To a solution of 417 mg of docosahexaenoic acid in anhydrous dichloromethane (7 ml) at 0° C. was added 2,6-lutidine, followed by iodine. The reaction was stirred at room temperature under nitrogen overnight. It was diluted with ethyl acetate and washed with 10% sodium thiosulfate, followed by water and then brine. It was dried over sodium sulfate, and then it was purified by flash chromatography to yield 570 mg of the iodolactone.

The iodolactone was dissolved in anhydrous toluene (6 ml), and DBU was added, turning the mixture dark brown and viscous. It was stirred under nitrogen overnight. It was diluted with ethyl acetate, washed with 1M HCl, then water and then brine. Dried over sodium sulfate, and then purified by flash chromatography to yield 330 mg of a pale yellow oil that darkened gradually. This material was flushed with argon and stored at −80° C.

To prepare the dimethyl analog, 83 mg of the lactone was dissolved in 2 ml of anhydrous THF, and cooled to −78° C., then LDA (2 eq of 2M soln) was added. After 30 min, methyl iodide (2 eq) was added, and it was stirred for 45 minutes, then it was rapidly diluted with ether and washed with 1M HCl, then water and then brine. Dried over sodium sulfate and then purified by flash chromatography to yield 61 mg of the 2-methyl analog. A portion of this material (19 mg) was reacted as above to yield 17 mg after purification of the 2,2-dimethyl analog. LC-MS confirmed the identity of both analogs. LC-MS (2-methyl-4-HDHA lactone) (m/z) 341.2 $[M+H]^+$, 358.2 $[M+H2O]^+$, 379.2 $[M+K]^+$; LC-MS (2,2-dimethyl-4-HDHA lactone) (m/z) 355.2 $[M+H]^+$, 372.2 $[M+H2O]^+$, 393.2 $[M+K]^+$.

Example 22

Modulation of Neuronal Activity by Fatty Acid Derivatives

This example illustrates the modulation Ca+ response in neurons by embodiments of the disclosed fatty acid derivatives.

Figure 6:
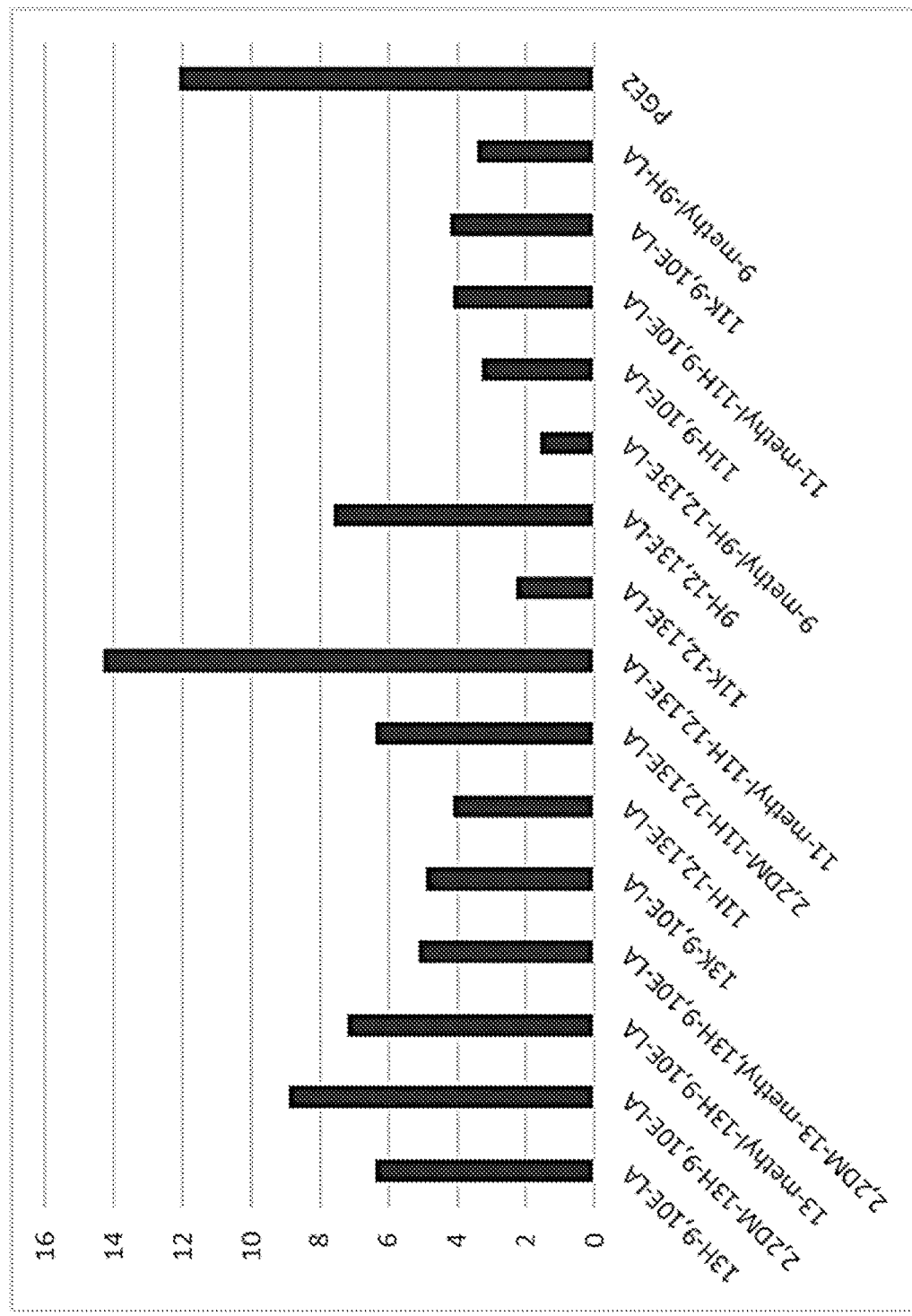
FIG. 6. $Ca^{2+}$ responses to disclosed endogenous fatty acid derivatives and their stable analogs in murine dorsal root ganglia sensory neurons (blinded analyses). Endogenous lipids and stable analogs thereof (1 µM) elicit Ca2+ transients in mouse dorsal root ganglia sensory neurons in a blinded screen of 15 compounds (72-273 cells/compound). The assayed compounds include: 13H-9,10E-LA (Compound 7), 2,2DM-13H-9,10E-LA (Compound 53), 13-methyl-13H-9,10E-LA (Compound 56), 2,2DM-13-methyl-13H-9,10E-LA (Compound 55), 13K-9,10E-LA (Compound 8), 11H-12,13E-LA (Compound 1), 2,2DM-11H-12,13E-LA (Compound 17), 11-methyl-11H-12,13E-LA (Compound 26), 11K-12,13E-LA (Compound 2), 9H-12,13E-LA (Compound 5), 9-methyl-9H-12,13E-LA (Compound 46), 11H-9,10E-LA (Compound 3), and 11-methyl-11H-9,10E-LA (Compound 36). PGE2, positive control (919 cells).

Murine dorsal root ganglia sensory neurons were isolated and cultured in vitro and the assays were performed as previously described (PMID: 25297838). Fatty acid derivatives (1 μM) were applied to the cultured neurons and any resulting $Ca^{2+}$ response was measured in a blinded manner. The assayed compounds include: 13H-9,10E-LA (Compound 7), 2,2DM-13H-9,10E-LA (Compound 53), 13-methyl-13H-9,10E-LA (Compound 56), 2,2DM-13-methyl-13H-9,10E-LA (Compound 55), 13K-9,10E-LA (Compound 8), 11H-12,13E-LA (Compound 1), 2,2DM-11H-12,13E-LA (Compound 17), 11-methyl-1H-12,13E-LA (Compound 26), 11K-12,13E-LA (Compound 2), 9H-12,13E-LA (Compound 5), 9-methyl-9H-12,13E-LA (Compound 46), 11H-9,10E-LA (Compound 3), and 11-methyl-11H-9,10E-LA (Compound 36). Results are shown in FIG. 6.

Figure 7A:
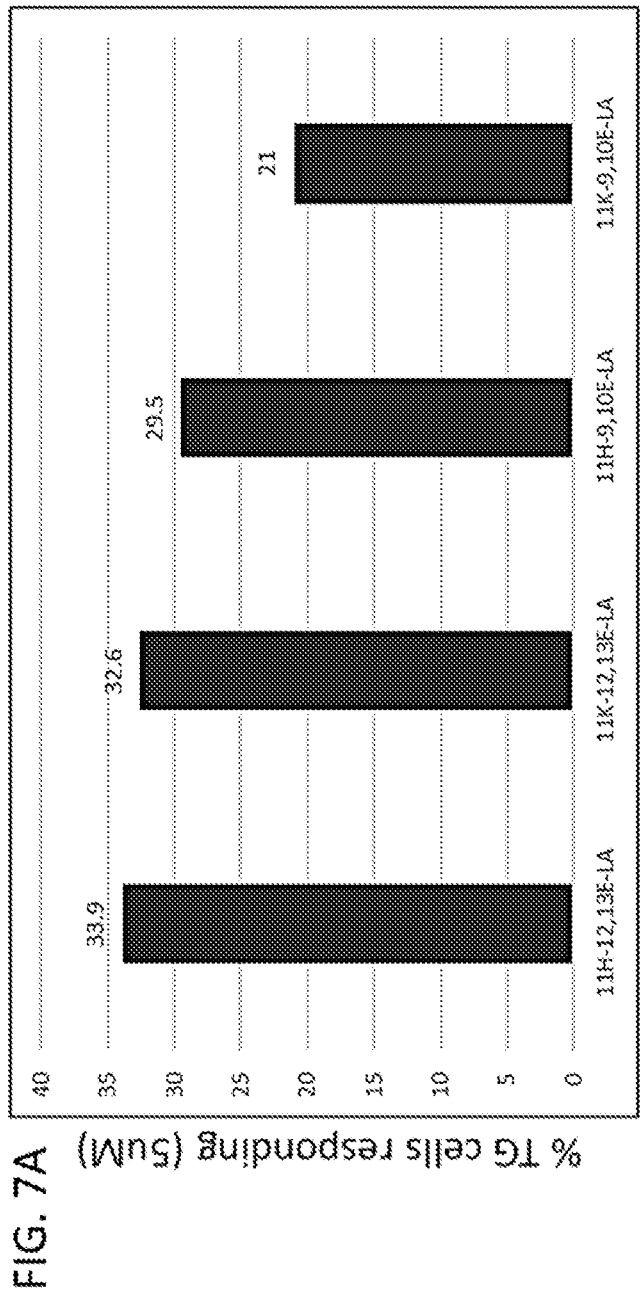
FIGS. 7A and 7B. $Ca^{2+}$ responses to disclosed endogenous fatty acid derivatives in trigeminal sensory neurons (blinded analyses).
Figure 7B:
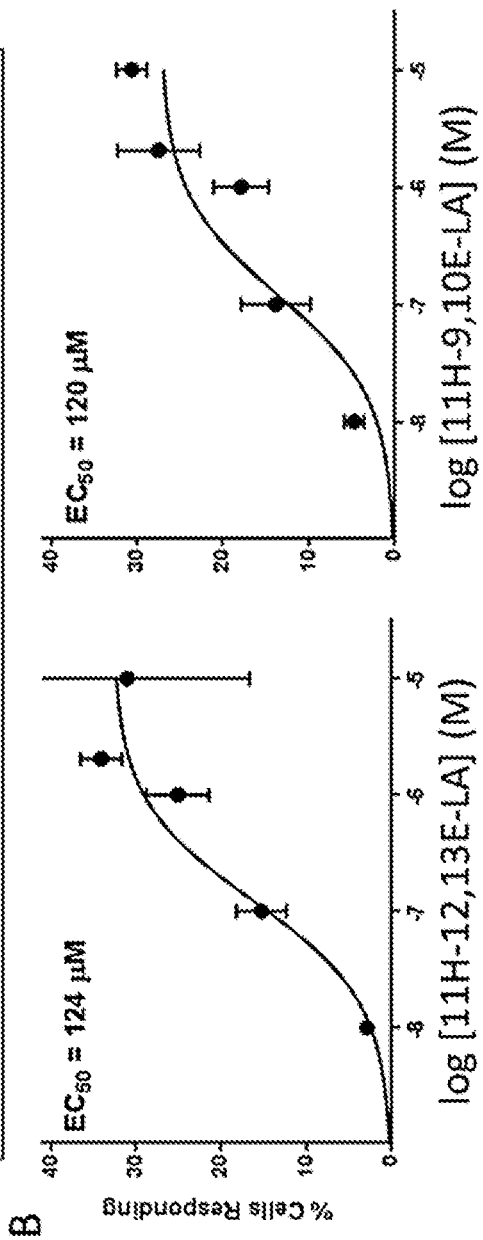

Additionally, murine trigeminal sensory neurons were isolated and cultured in vitro. Fatty acid derivatives were applied to the cultured neurons and any resulting $Ca^{2+}$ response was measured in a blinded manner. The assayed compounds include: 11H-12,13E-LA (Compound 1), 11K-12,13E-LA (Compound 2), 11H-9,10E-LA (Compound 3), and 11K-9,10E-LA (Compound 4). Results are shown in FIG. 7A. Concentration-response curves illustrating the increase in the number of cells responding to 11H-12,13E-LA and 11H-9,10E-LA (FIG. 7B).

Example 23

Modulation of Itch Response by Fatty Acid Derivatives

This example illustrates the modulation an itch response by embodiments of the disclosed fatty acid derivatives.

Figure 8:
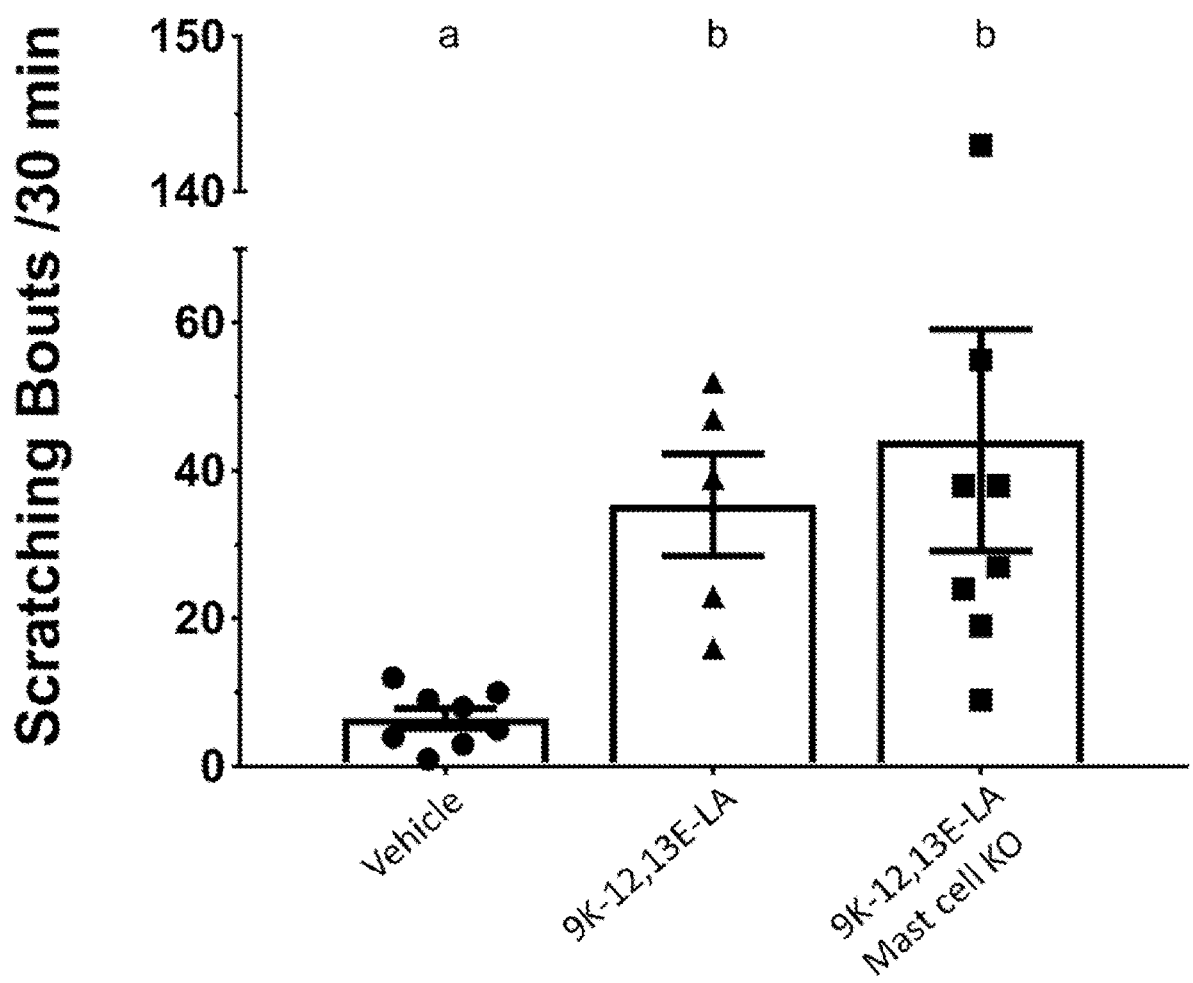
FIG. 8. Itch-related scratching responses after intradermal injection of disclosed fatty acid derivatives (blinded analyses). Intradermal injection of disclosed fatty acid derivatives (100 µg) showed increased scratching responses to 9K-12,13E-LA in both wild type and mast cell knockout mice. N=5 to 8 per group.

The fatty acid derivative 9K-12,13E-LA (100 μg) was injected intra-dermally into the nape of neck of normal mice or a mast cell knock-out mouse (FIG. 8) in a blinded manner. Pruriceptive behavior was quantified as the number of scratching bouts assessed over 30 minutes, as previously described (Mishra and Hoon, Science 340, 968, 2013).

Example 24

Modulation of Cholesterol Efflux by Fatty Acid Derivatives

This example illustrates the modulation of cholesterol efflux by embodiments of the disclosed fatty acid derivatives.

Figure 9:
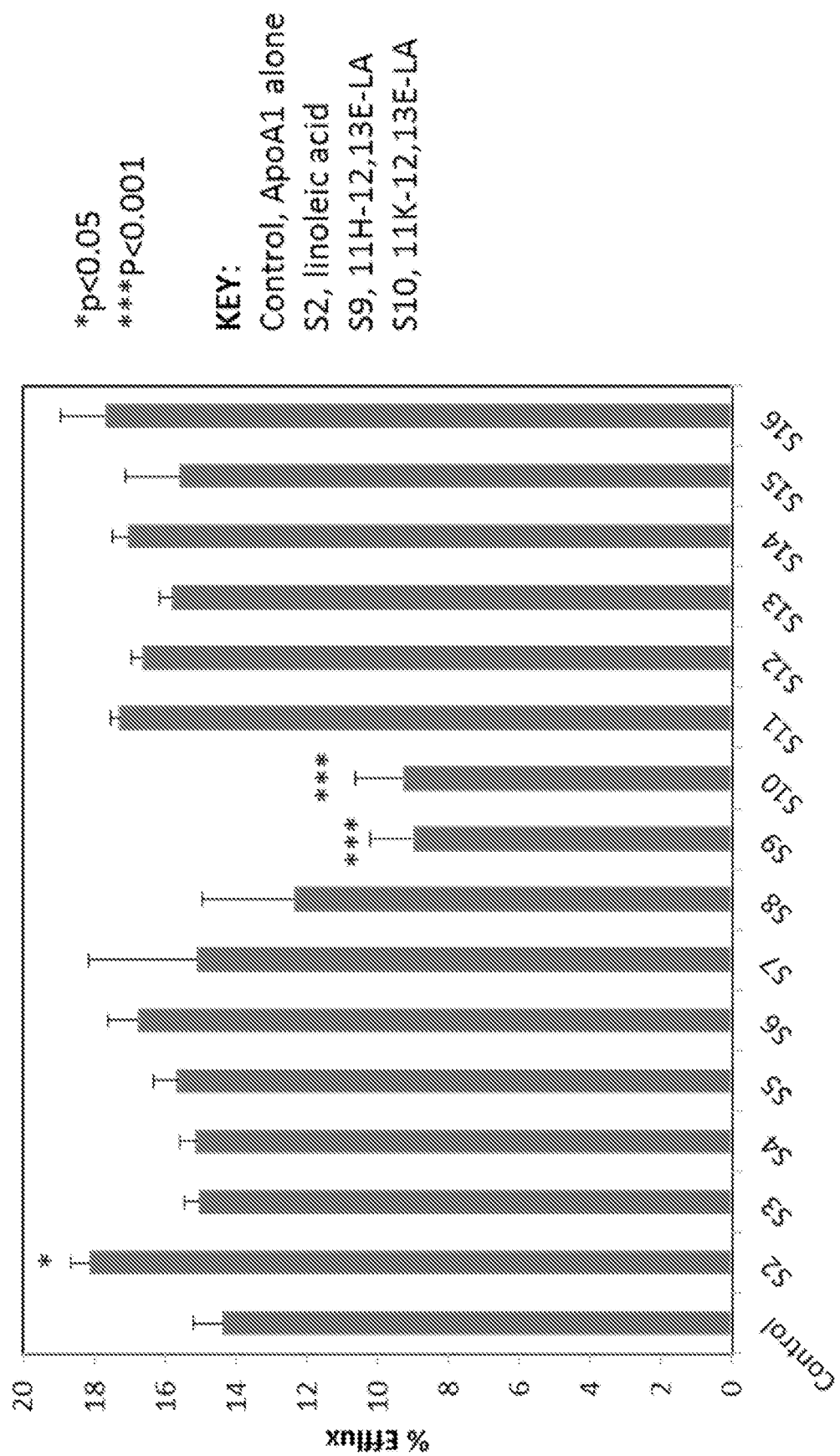
FIG. 9. Blinded ApoA1 Cholesterol efflux screen in human THP-1 cells. 9-hydroxy-octadecadienoic acid increased, and 11H-12,13E-LA and 11K-12,13E-LA (50 µM) inhibited Apolipoprotein A1 (ApoA1)-mediated monocyte cholesterol efflux.
Figure 10:
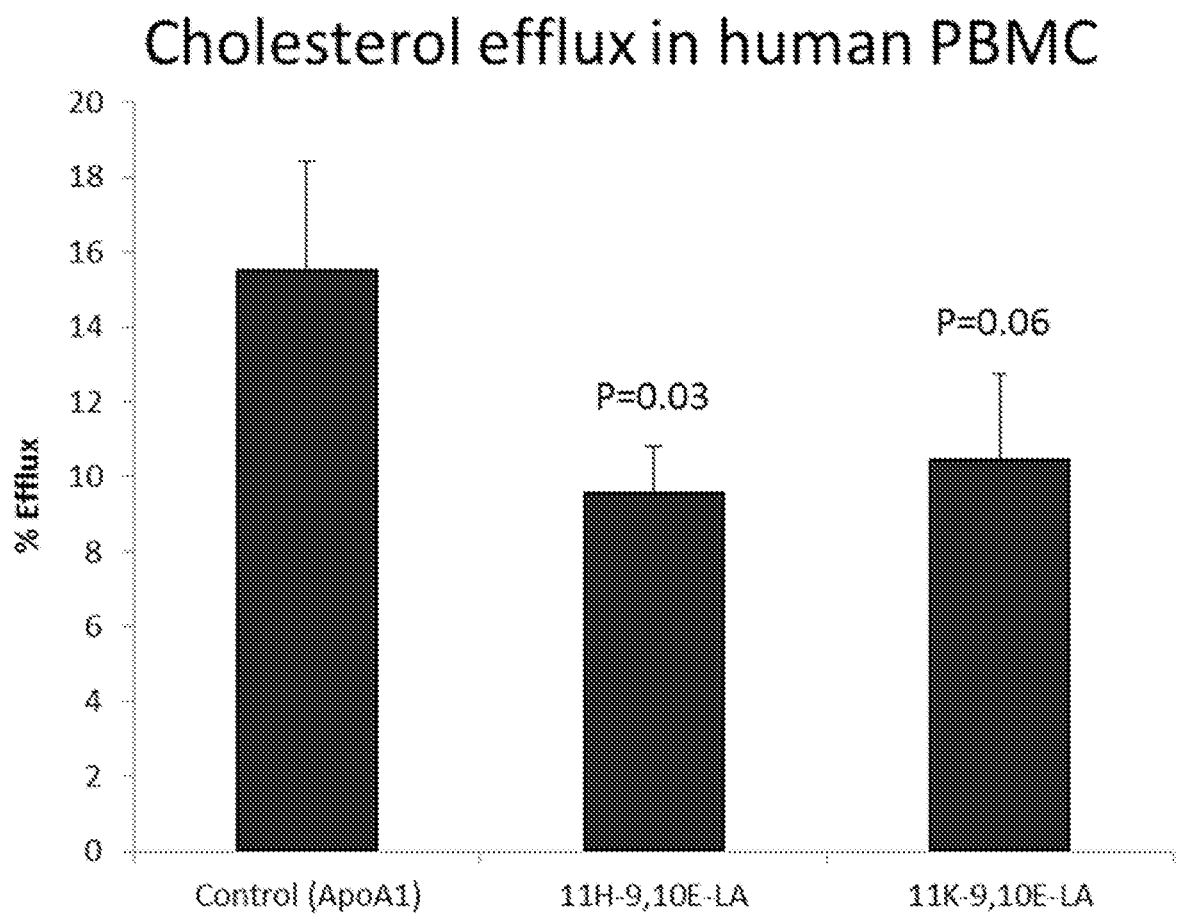
FIG. 10. Blinded ApoA1 Cholesterol efflux screen in freshly isolated human PBMCs. 11H-12,13E-LA and 11K-12,13E-LA (50 µM) inhibited ApoA1-mediated monocyte cholesterol efflux.

Human THP-1 cells were incubated with ApoA1 in the presence of linoleic acid or several different fatty acid derivatives (50 μM) in a blinded manner, and resulting cholesterol efflux was measured (FIG. 9) as previously described (PMID: 26879139). Linoleic acid acid increased cholesterol efflux, and the 11H-12,13E-LA and 11K-12,13E-LA derivatives (50 μM) inhibited ApoA1-mediated monocyte cholesterol efflux. Similar results were observed with the same cholesterol efflux assay using freshly isolated human PBMCs (FIG. 10).

Example 25

Modulation of PBMC Cytokine Secretion by Fatty Acid Derivatives

This example illustrates the modulation of PBMC cytokine secretion by embodiments of the disclosed fatty acid derivatives.

Figure 11A:
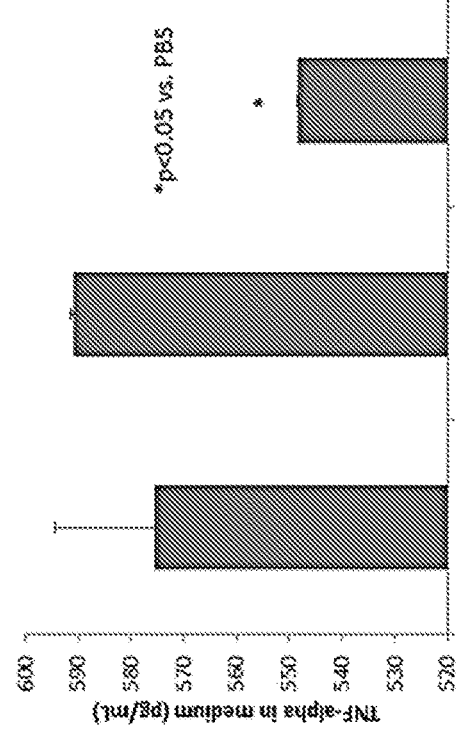
FIGS. 11A-11D. Effects of 11H-12,13E-LA and 11K-12, 13E-LA (100 µM) on human PBMCs cytokines secretion (measured by ELISA) (blinded analyses). Incubation with 11H-12,13E-LA and 11K-12,13E-LA inhibits native lipopolysaccharide (LPS)-induced (FIG. 11A) and native (FIG. 11B) tumor necrosis factor (TNF)-alpha secretion, but has no effect on interleukin (IL)-1 (FIGS. 11C and 11D).
Figure 11B:
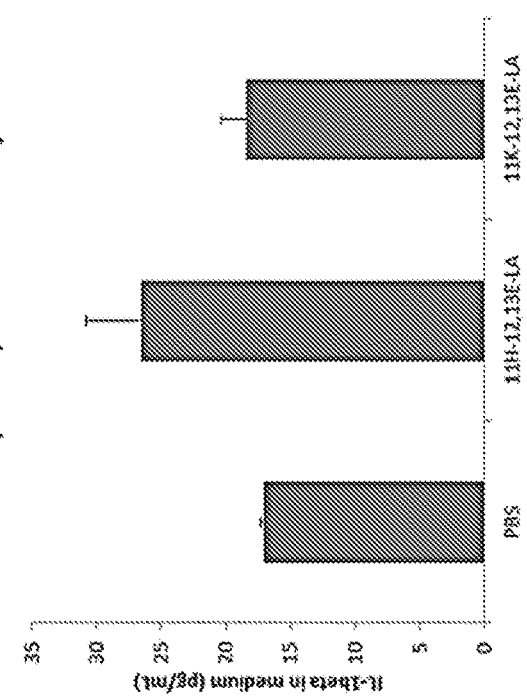
Figure 11C:
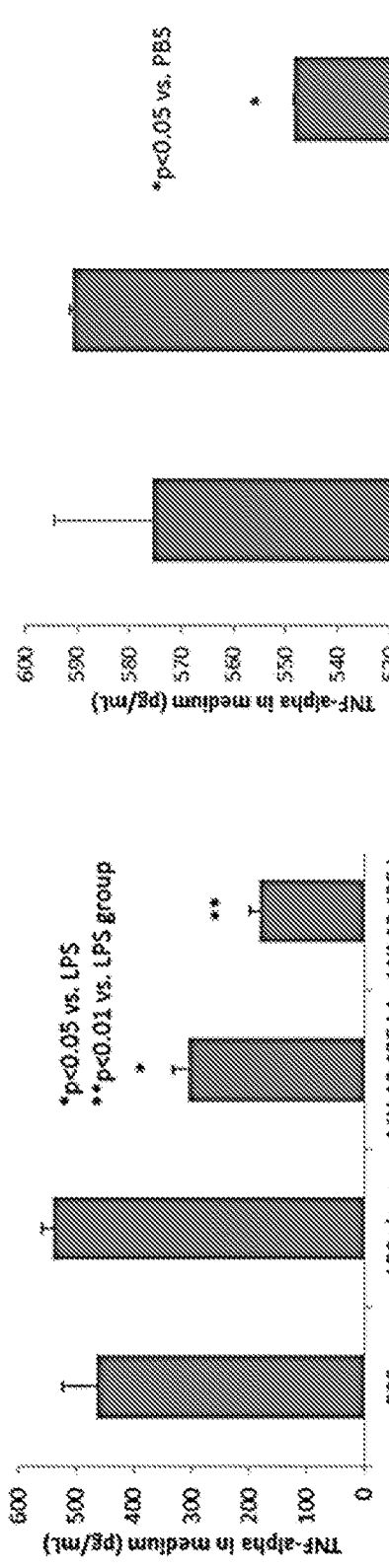
Figure 11D:
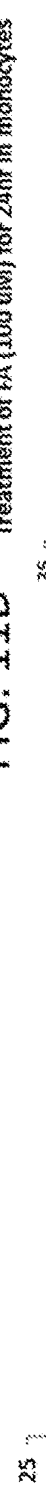

Freshly isolated human PBMCs were pre-incubated (FIGS. 11A and 11C) or not (FIGS. 11B and 11D) with LPS, and then incubated with ferulic acid ("FA," 100 μM) and 11H-12,13E-LA, 11K-12,13E-LA, PBS, or LPS alone for 24 hours (blinded). Then, the medium concentration of TNF-alpha (FIGS. 11A and 11B) or IL-beta (FIGS. 11C and 11D) was measured using enzyme-linked immunosorbent assay. The results show that 11H-12,13E-LA and 11K-12,13E-LA reduced TNF-alpha secretion with no significant change in IL-beta secretion.

Example 26

Synthesis of 2,2-dimethyl-4-HDHA-d10

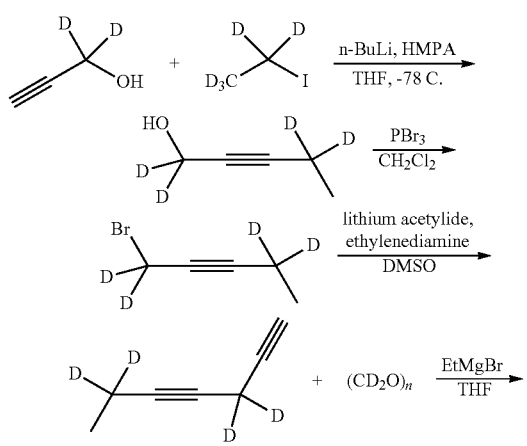

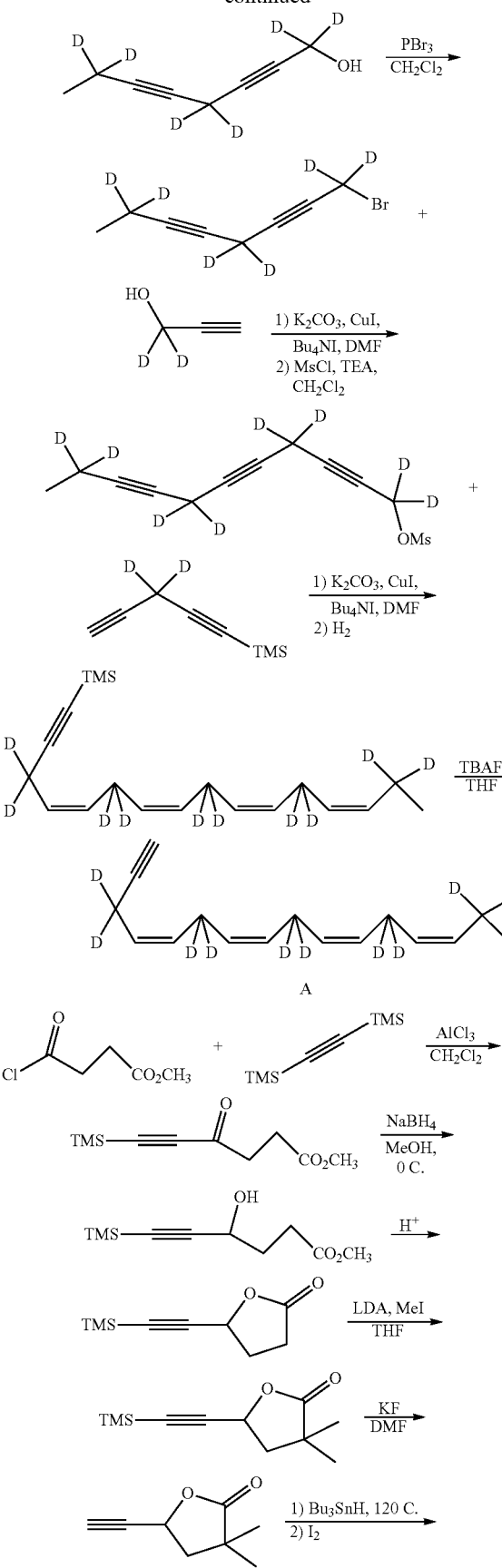
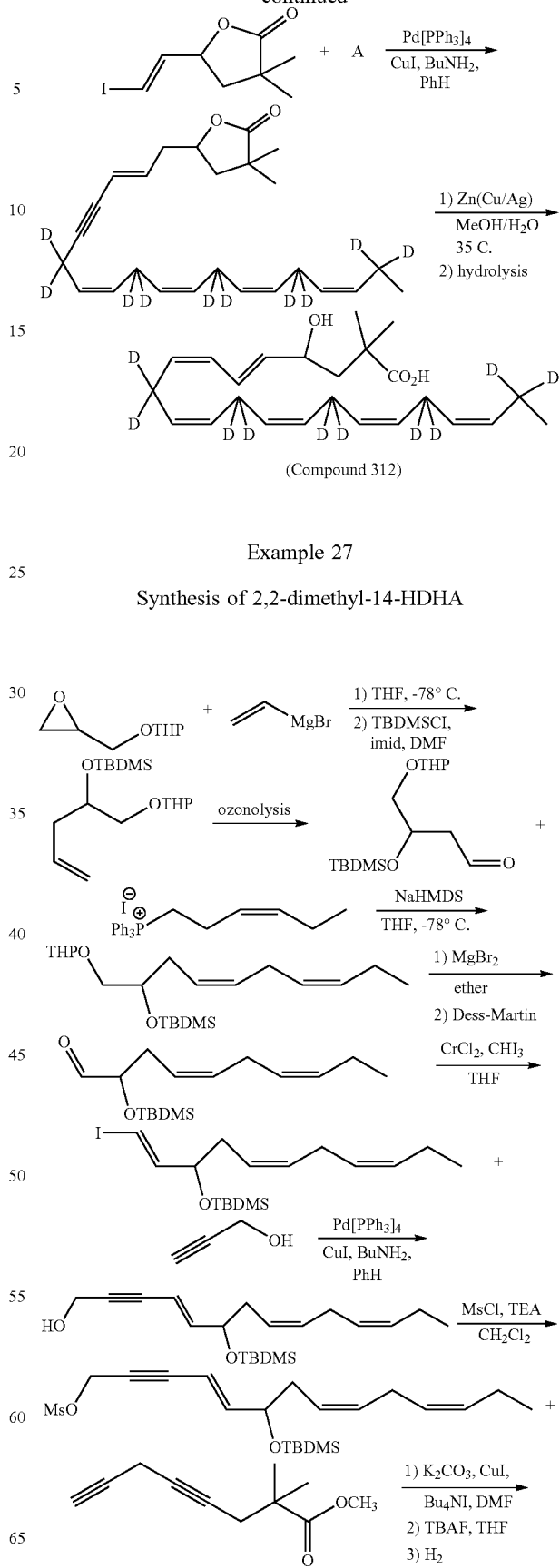
Example 27
Synthesis of 2,2-dimethyl-14-HDHA

117
-continued
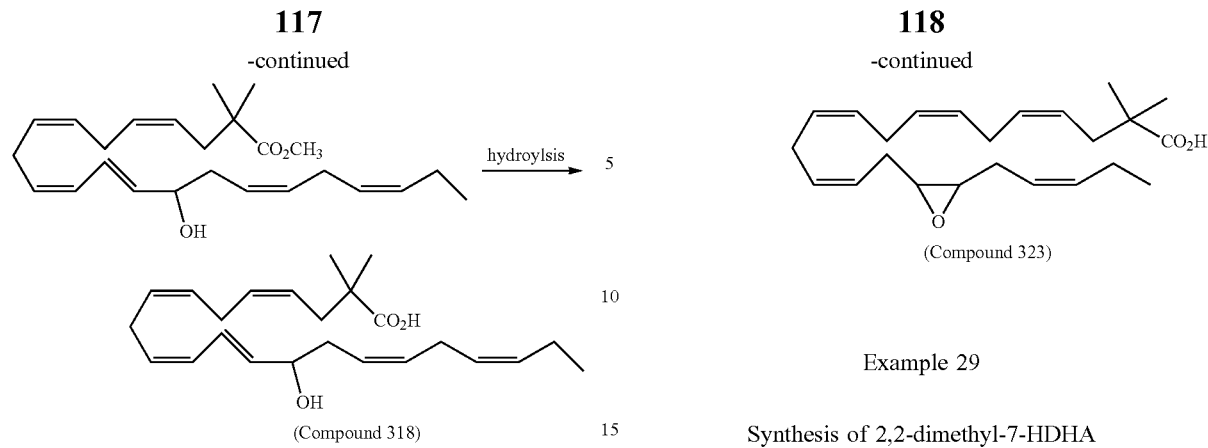
(Compound 318)
Example 28
Synthesis of 2,2-dimethyl-16,17-epoxy-DHA
118
-continued
(Compound 323)
Example 29
Synthesis of 2,2-dimethyl-7-HDHA
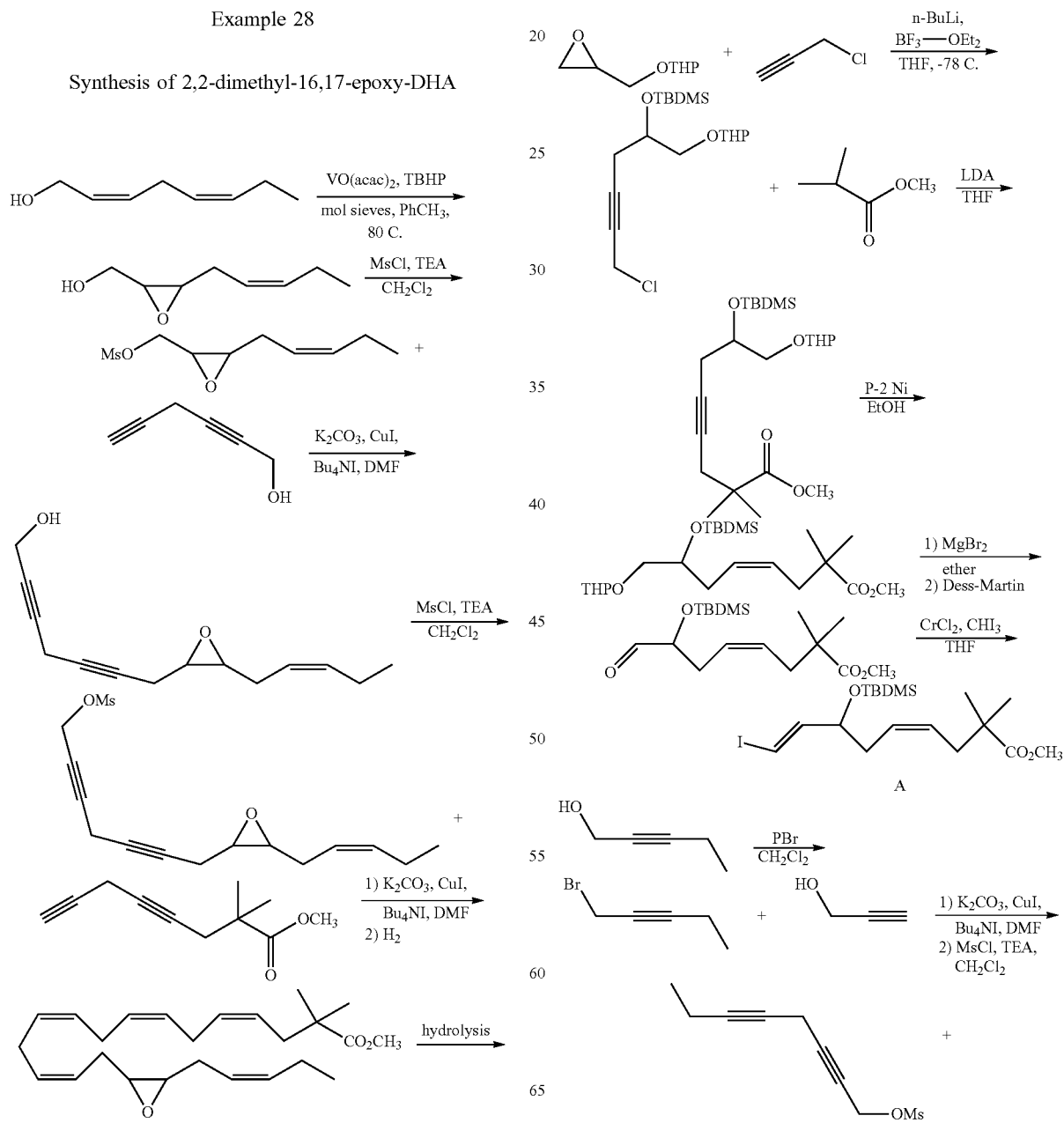

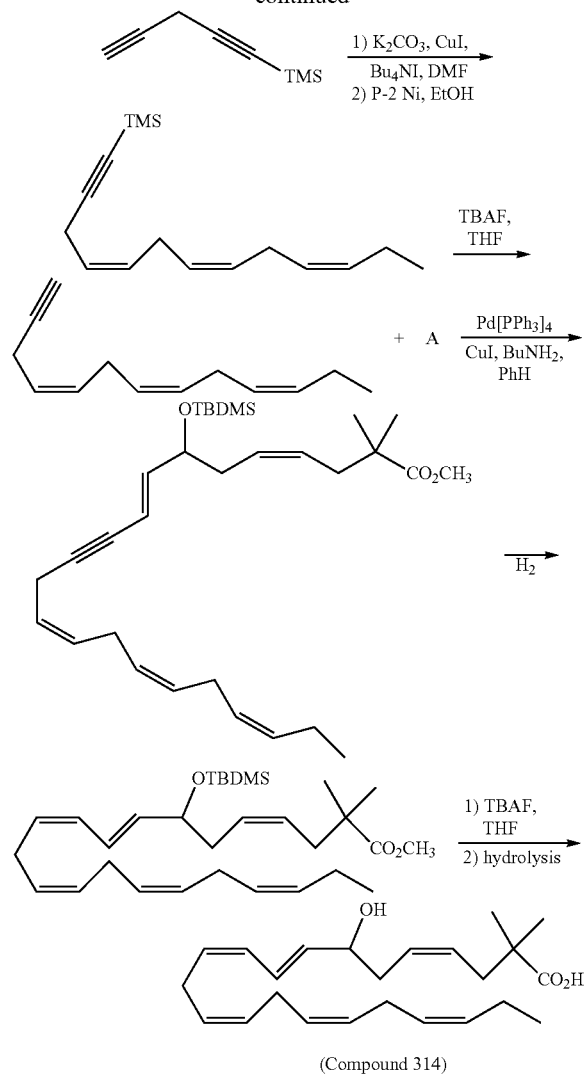
Example 30
Synthesis of 2,2-dimethyl-17-HDHA
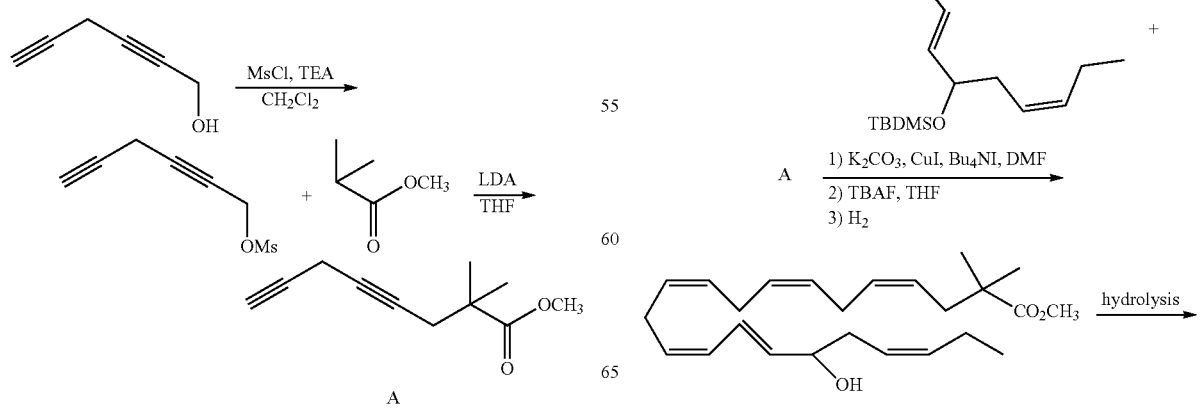

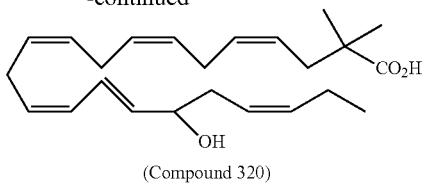

(Compound 320)

Example 31

Synthesis of 11-OH-7,8-epoxy-9,10-dehydro adrenic acid

This example illustrates production of exemplary 11-hydroxy and 11-keto-trans-epoxy-9,10-dehydrodocosadienoate compounds. The following illustrates an exemplary reaction process:

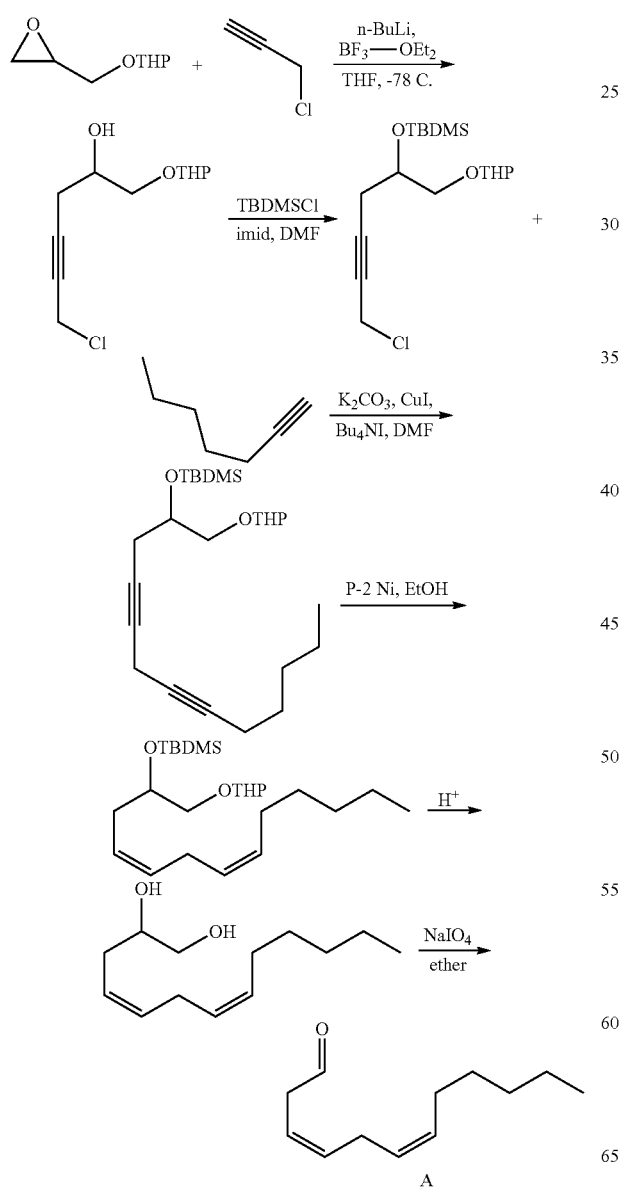

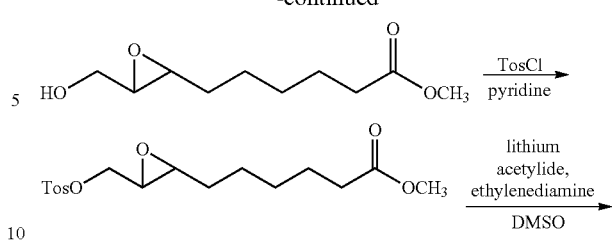

(compound 304)

Example 32

Synthesis of 9-OH-7,8-epoxy-10,11-dehydro adrenic acid

This example illustrates production of exemplary 9-hydroxy and 9-keto-trans-epoxy-10,11-dehydrodocosadienoate compounds. The following illustrates an exemplary reaction process:

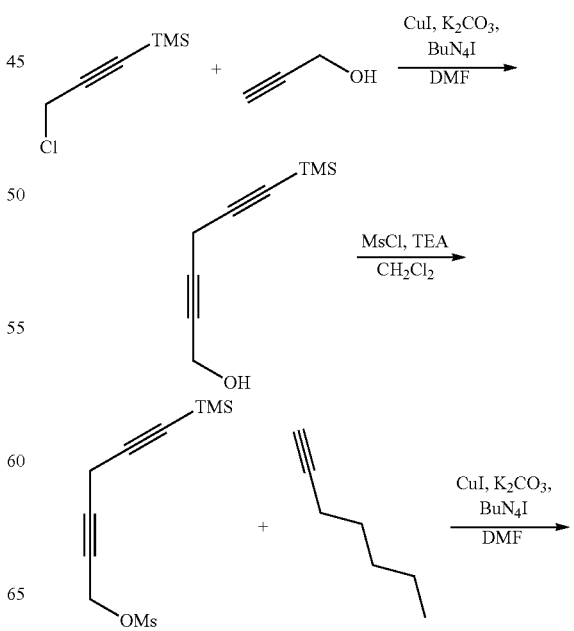

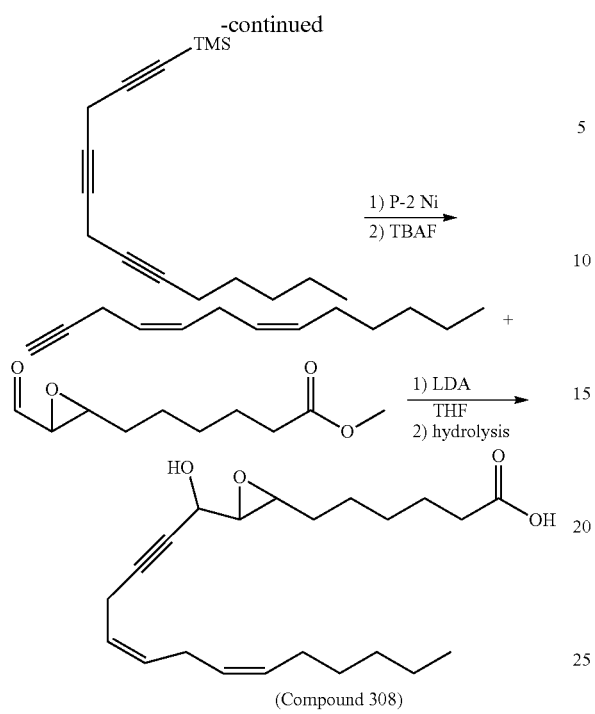
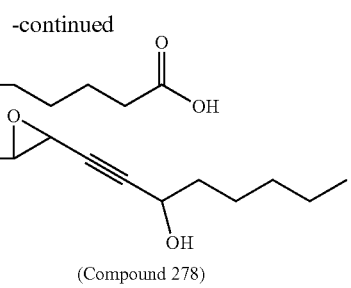
(Compound 278)
Example 34
Synthesis of 9-hydroxy-12,13-trans-epoxy-10,11-dehydro-octadecenoic acid
Example 33
Synthesis of 13-hydroxy-9,10-trans-epoxy-11,12-dehydro-octadecenoic acid
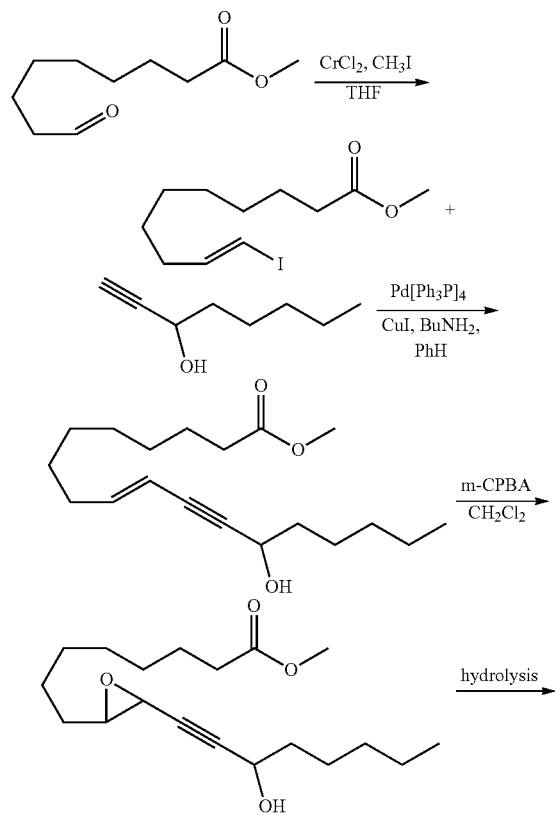
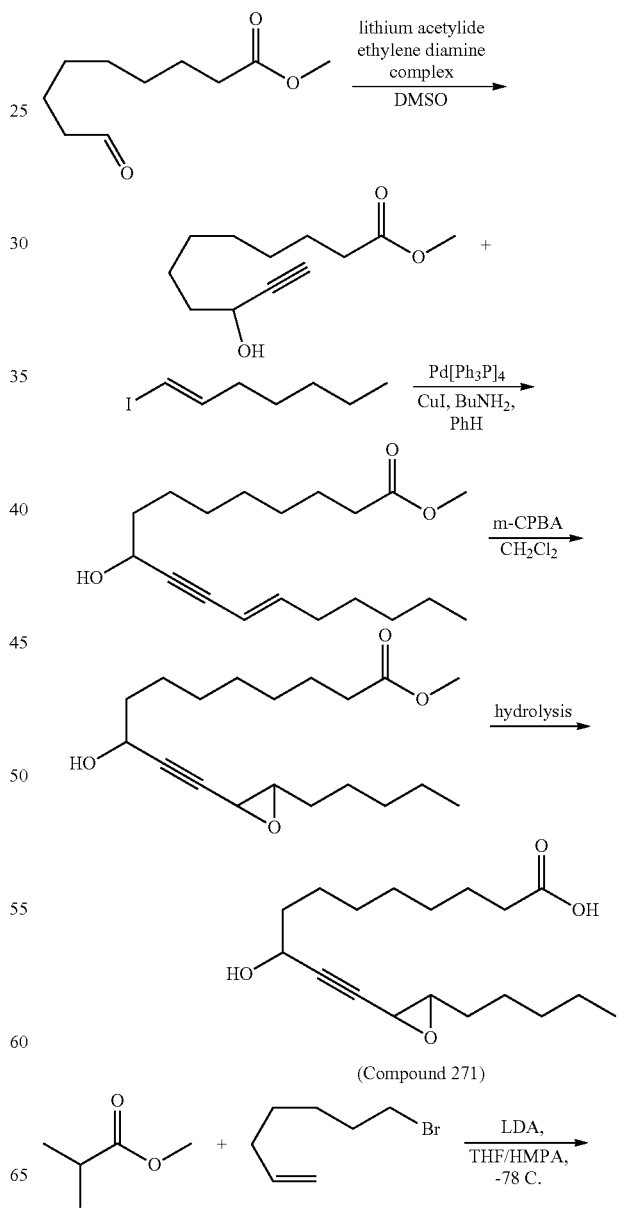

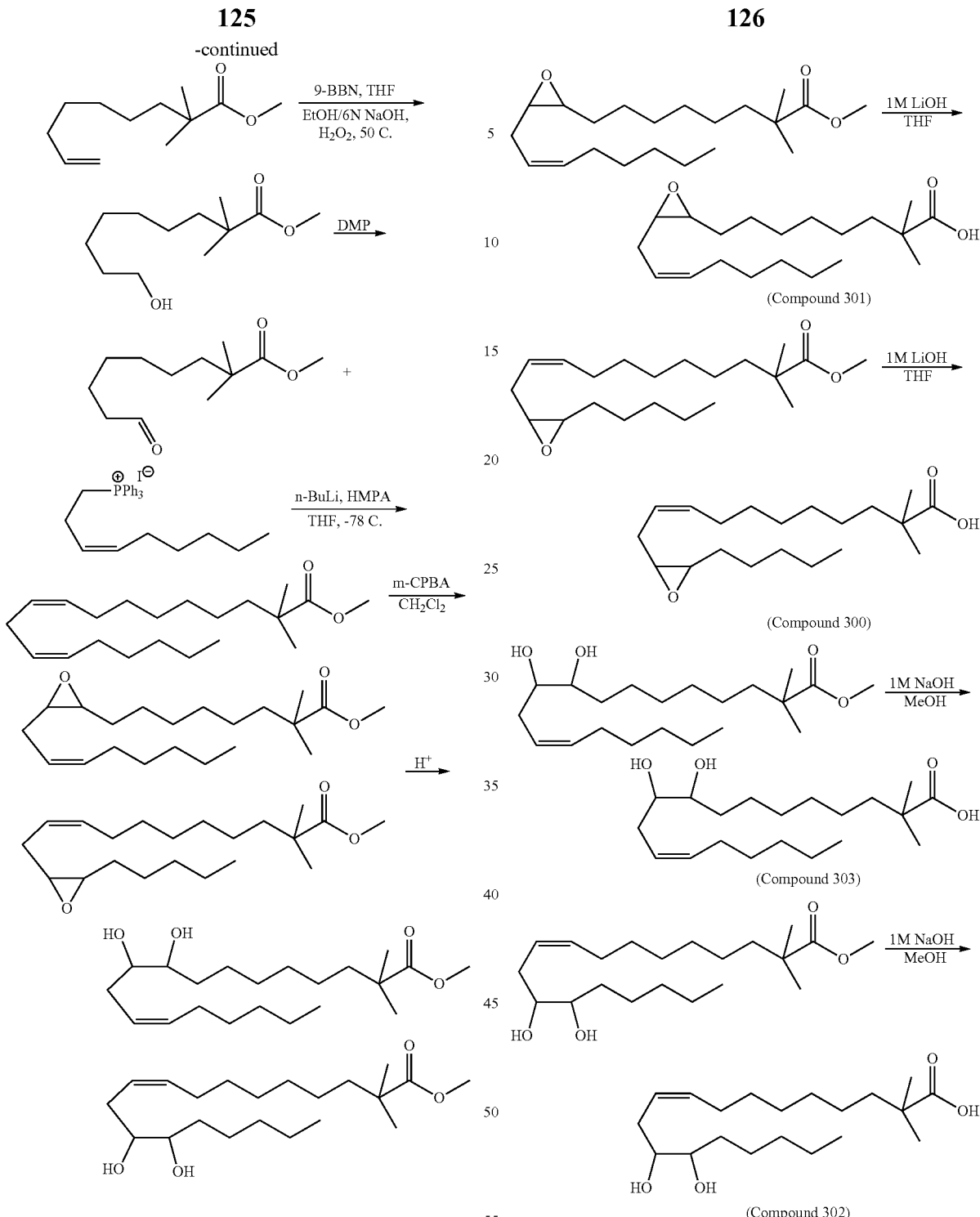

The 2,2-dimethyl 9-hydroxy methyl nonanoic acid is prepared as described above (Example 6), oxidized to the aldehyde, and then reacted under Wittig conditions to provide the methyl ester of 2,2-dimethyl linoleic acid. This is treated with m-CPBA, or other non-selective epoxidation reagent, to yield a mixture of 9,10 and 12,13 2,2-dimethyl-EpOMEs. These can be separated chromatographically, characterized by 1H NMR and mass spec, and the methyl ester hydrolyzed. Alternatively, these compounds can be hydrolyzed to their corresponding 2,2-dimethyl diHOME methyl esters. The methyl ester is hydrolyzed as before to produce the free acids.

Example 35

Synthesis of 13-hydroxy-9(R),10(R)-epoxy-octadec-11-enoate

This example illustrates an exemplary synthesis scheme for the preparation of individual diastereomers of compound 7 and related stable analogs.

127

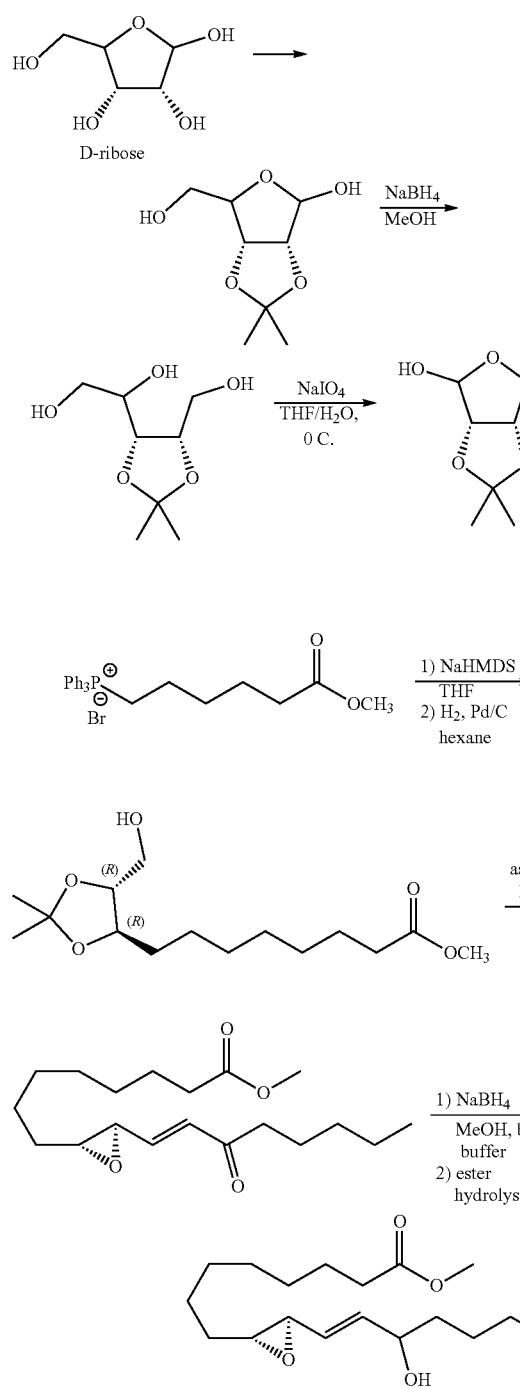

128

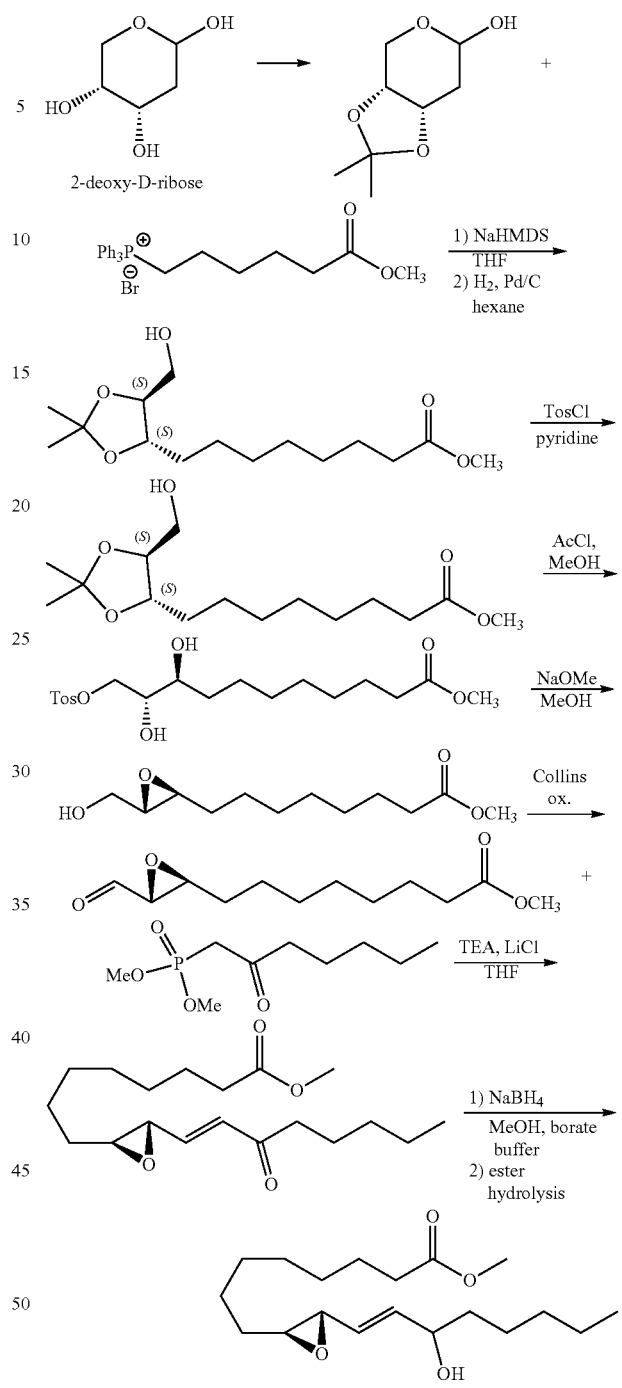

The diastereomers can then be separated chromatographically. Using appropriately modified starting materials, the 2,2-dimethyl analog can also be prepared.

Example 36

Synthesis of 13-hydroxy-9(S),10(S)-epoxy-octadec-11-enoate

This example illustrates an exemplary synthesis scheme for the preparation of individual diastereomers of compound 7 and related stable analogs.

The diastereomers can then be separated chromatographically. Using appropriately modified starting materials, the 2,2-dimethyl analog can also be prepared.

Example 37

Synthesis of 9,10,13-trihydroxy-octadec-11-enoate

This example provides an exemplary process for the preparation of individual diastereomers of compound 13 and related stable analogs.

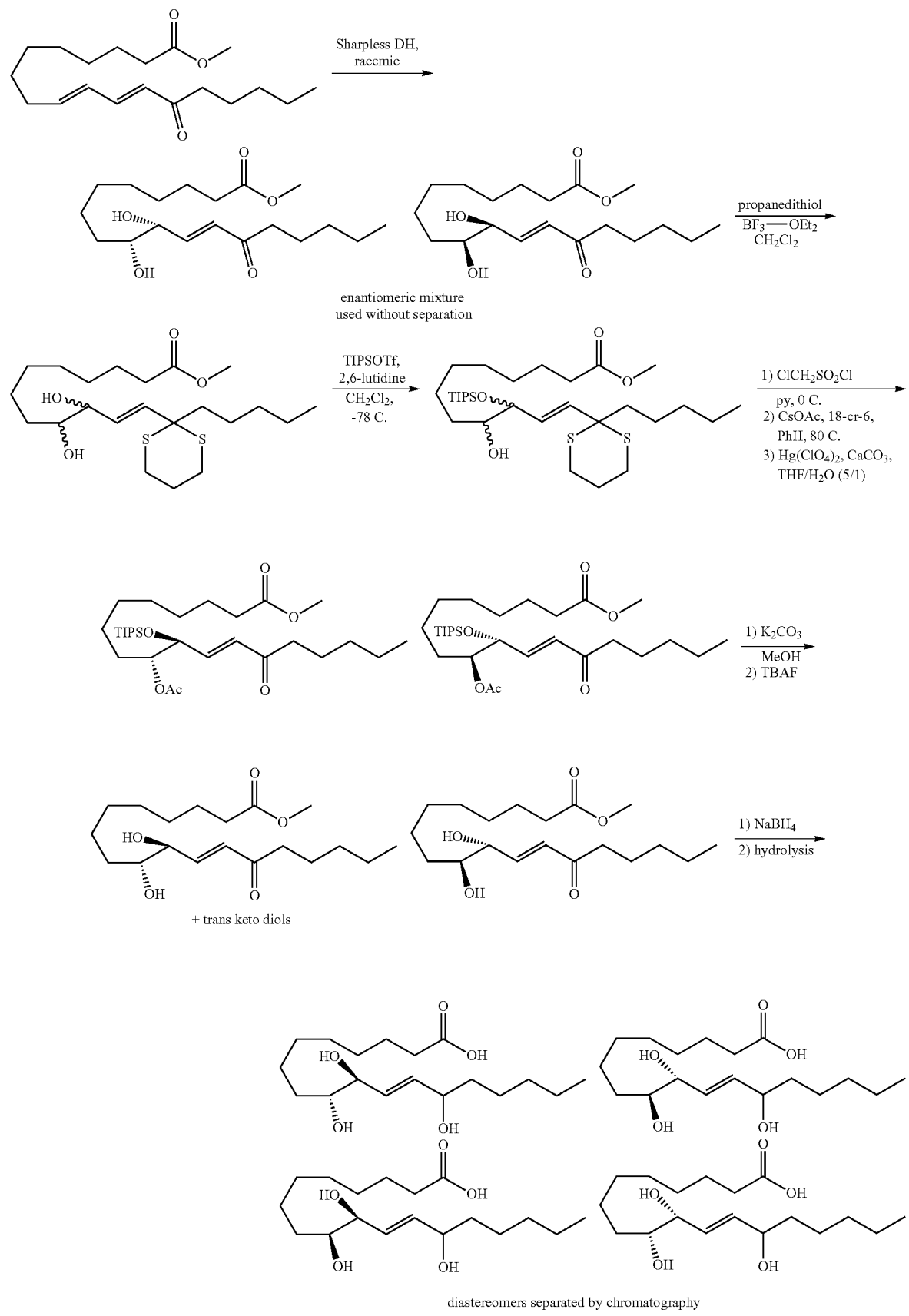

Adapted from Y. Kurashina et. al., *Tetrahedron* 62 (2006) 9483-9496. The 2,2-dimethyl derivative can also be prepared using this methodology using appropriately modified starting materials, as can the 13-methyl-13-hydroxy and the 2,2-dimethyl-13-methyl-13-hydroxy derivatives.

Example 38

2,2-dimethyl Moiety for Esterification Prevention

This example illustrates the resistance to esterification provided by addition of a 2,2-dimethyl modification to oxidized fatty acids.
LC-MS conditions: Agilent 1100 LC
A: 10 mM NH4OAc, pH 7.4
B: Acetonitrile+0.1% formic acid
0-1.50 min: 5% B
1.50-2 min: 5-90% B
2-10 min: 90% B
10.01-15 min: 5% B
DAD1 254 nm
DAD2 215 nm
Agilent Zorbax XDB-C18 5 µm C18 50×2.0 mm
0.4 ml/min
MS parameters: Agilent 6120 with electrospray ionization
Drying gas flow: 11.0 L/min
Nebulizer pressure: 40 psig
Drying gas temperature: 350 C
Positive capillary voltage: 4000 V
Negative capillary voltage: 3000 V Approximately 30 mg of silica gel was added to 25 mg of glycerol, and it was then vortexed to coat all of the silica with glycerol, until the admixture was free-flowing. Between 5-10 mg of this material was added to a solution of the free acid in ether, and it was vortexed briefly. The reaction was left for 3 days, then filtered and evaporated under nitrogen. The residue was redissolved in ethanol and analyzed by LC-MS, in both positive and negative modes. Results for several compounds reacted under these conditions are shown in FIGS. 12-17.

None of the 2,2-dimethyl analogs were esterified under these conditions as could be detected by LC-MS, while each of the endogenous compounds was esterified in high yield, with the exception of 4-HDHA, which was found to readily lactonize despite using the lithium salt of its carboxylate. The stable analog 2,2-dimethyl-4-HDHA did not lactonize and it was not esterified with lipase, thus further confirming the resistance to esterification from the 2,2-dimethyl groups.

13-hydroxy-9,10-trans-epoxy-(11E)-octadecenoic acid 2-glyceryl ester

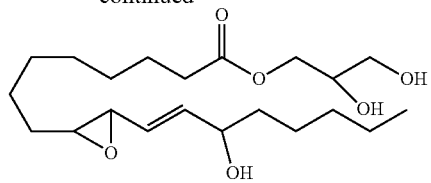

(Compound 7)
Chemical Formula: $C_{18}H_{32}O_4$
Exact Mass: 312.23
Molecular Weight: 312.45 glycerol/silica
Candida lipase
on acrylic resin
ether

-continued

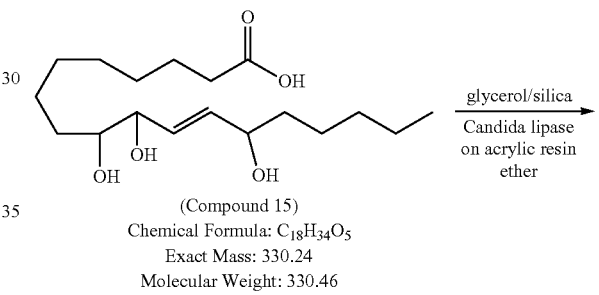

Chemical Formula: $C_{21}H_{38}O_6$
Exact Mass: 386.27
Molecular Weight: 386.53

Figure 12A:
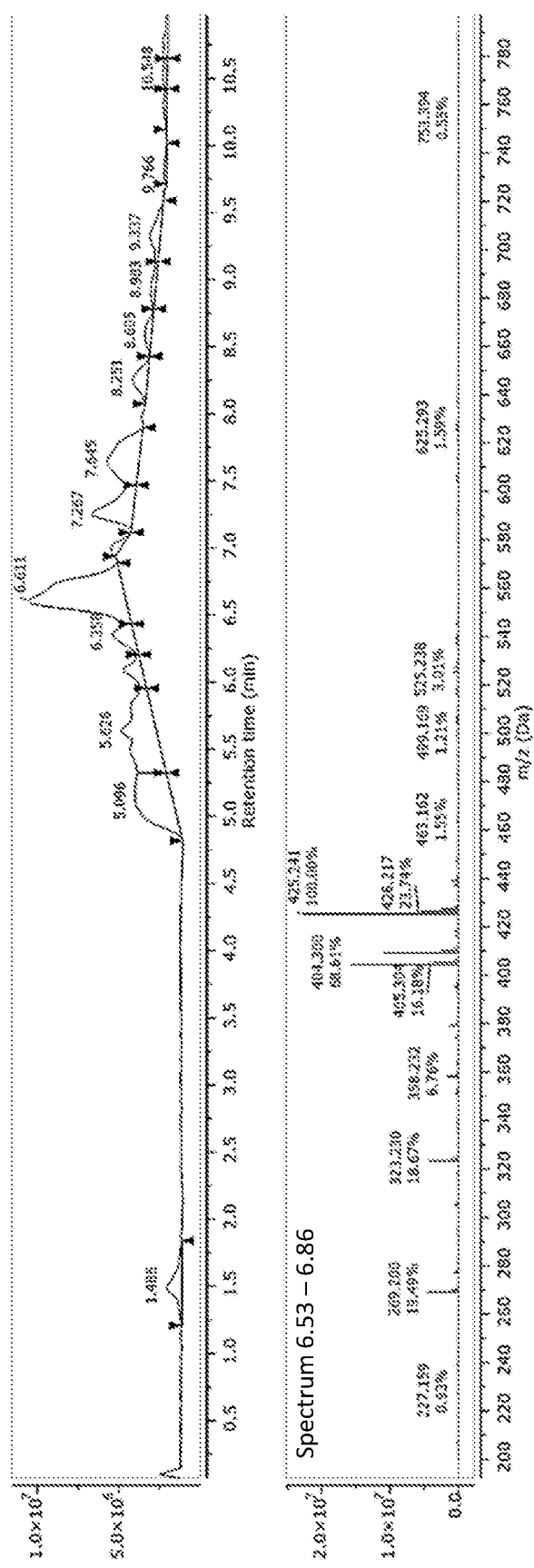
FIGS. 12A and 12B. Retention time and mass spectra obtained from LC-MS analysis of 13-hydroxy-9,10-trans-epoxy-(11E)-octadecenoic acid following incubation under esterification conditions.
Figure 12B:
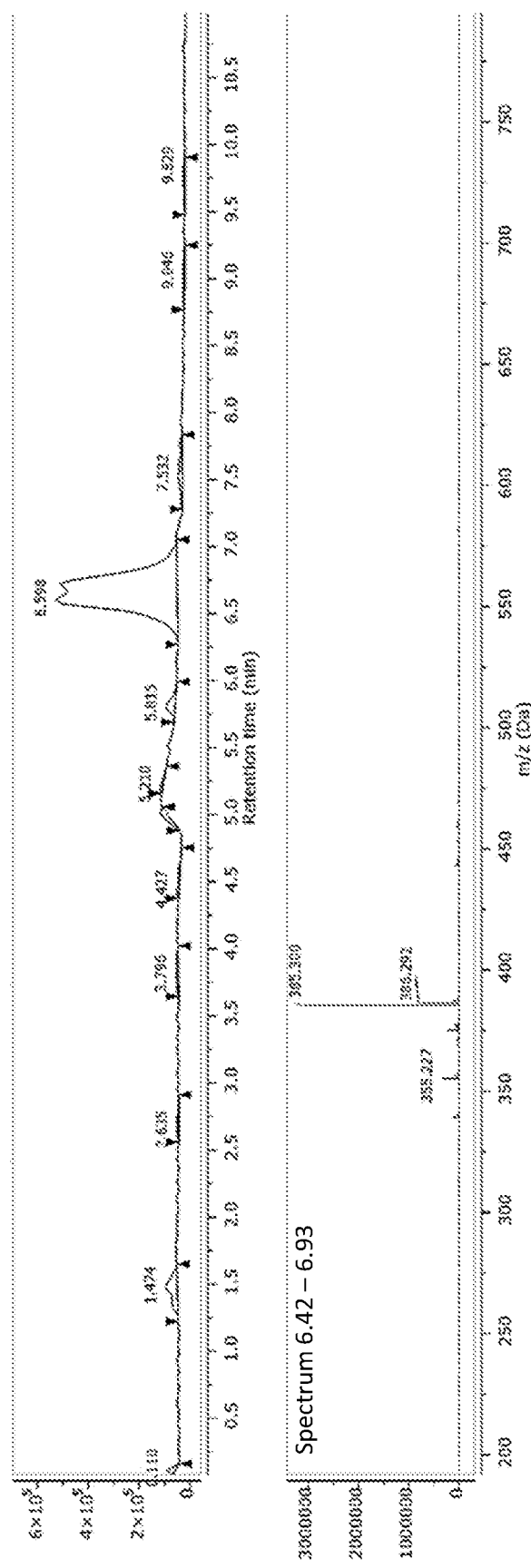

Glyceryl ester product RT=6.61 min, (m/z) 404.3 [M+H2O]$^+$, 425.24 [M+K]$^+$ 385.30 [M–H]$^-$ FIG. 12 shows retention time and mass spectrum for positive (FIG. 12A) and negative (FIG. 12B) LC-MS modes for 13-hydroxy-9,10-trans-epoxy-(11E)-octadecenoic acid reacted under esterification conditions. The results show that the endogenous oxidized fatty acid was esterified.

9,10,13-trihydroxy-(11E)-octadecenoic acid 2-glyceryl ester

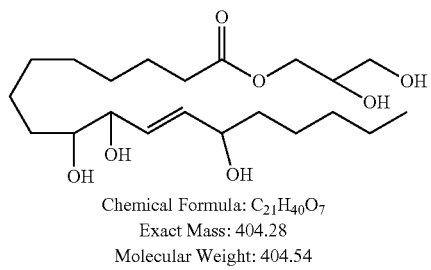

(Compound 15)
Chemical Formula: $C_{18}H_{34}O_5$
Exact Mass: 330.24
Molecular Weight: 330.46 glycerol/silica
Candida lipase
on acrylic resin
ether

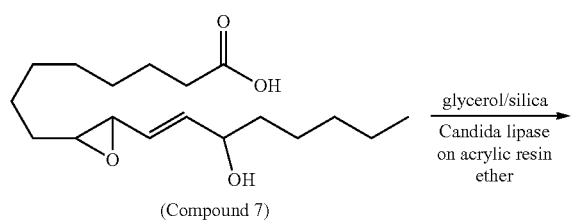

Chemical Formula: $C_{21}H_{40}O_7$
Exact Mass: 404.28
Molecular Weight: 404.54

Figure 13A:
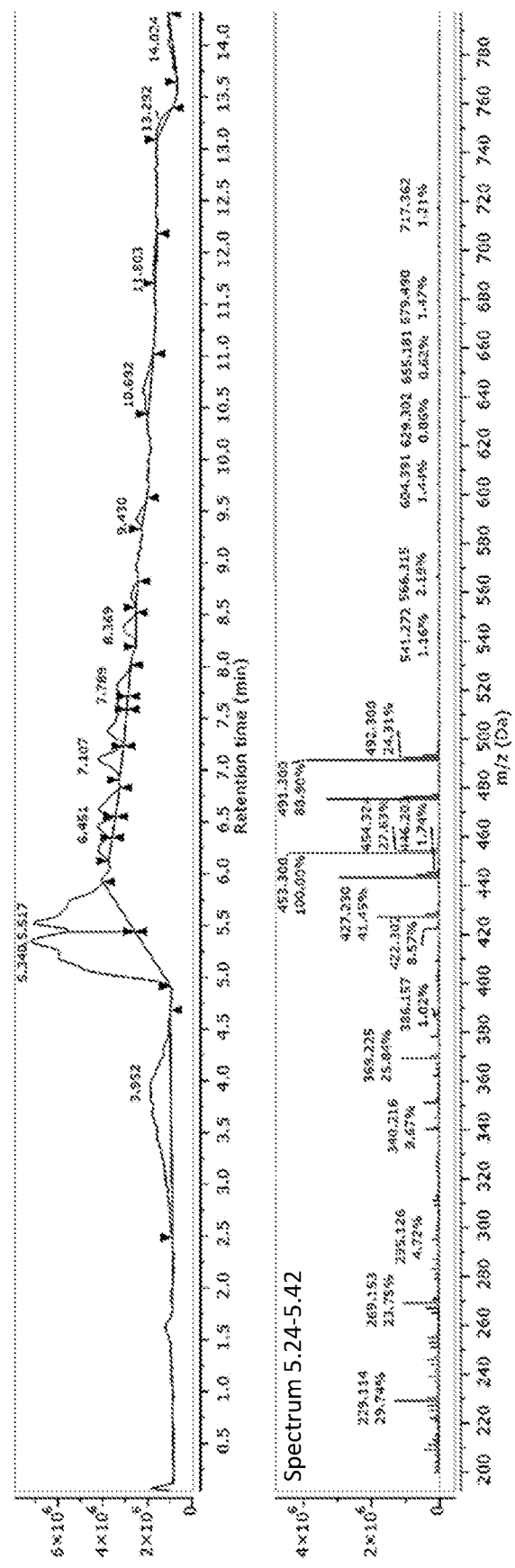
FIGS. 13A-13C. Retention time and mass spectra obtained from LC-MS analysis of 9,10,13-trihydroxy-(11E)-octadecenoic acid following before (FIG. 13C) and after (FIGS. 13 A and 13B) incubation under esterification conditions.
Figure 13B:
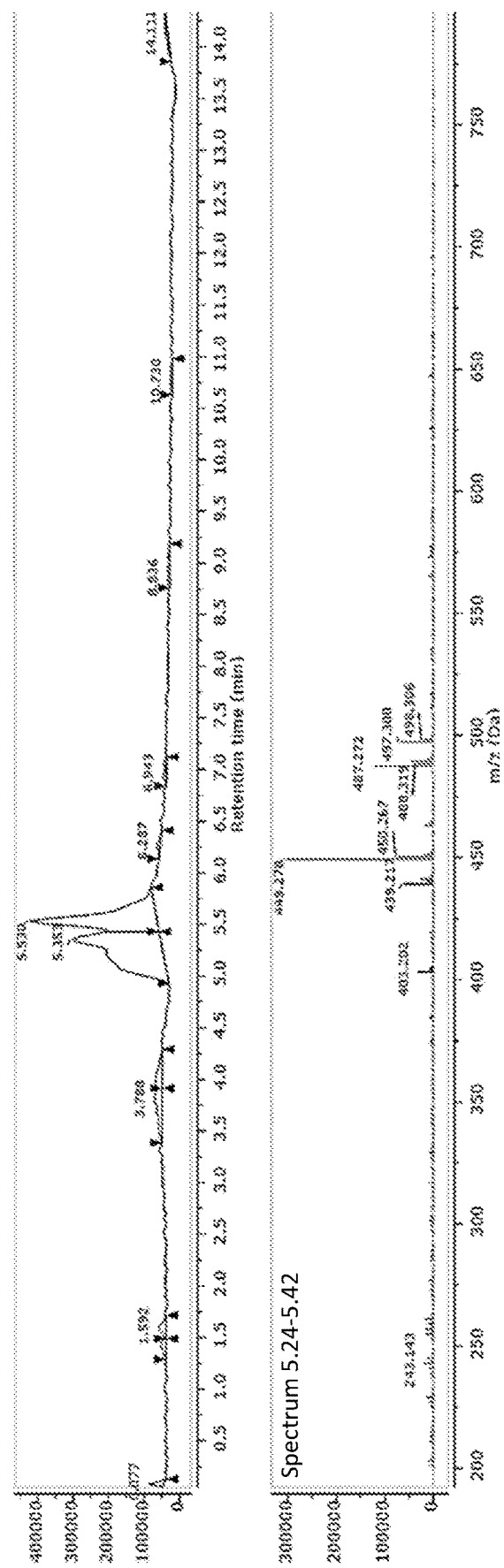
Figure 13C:
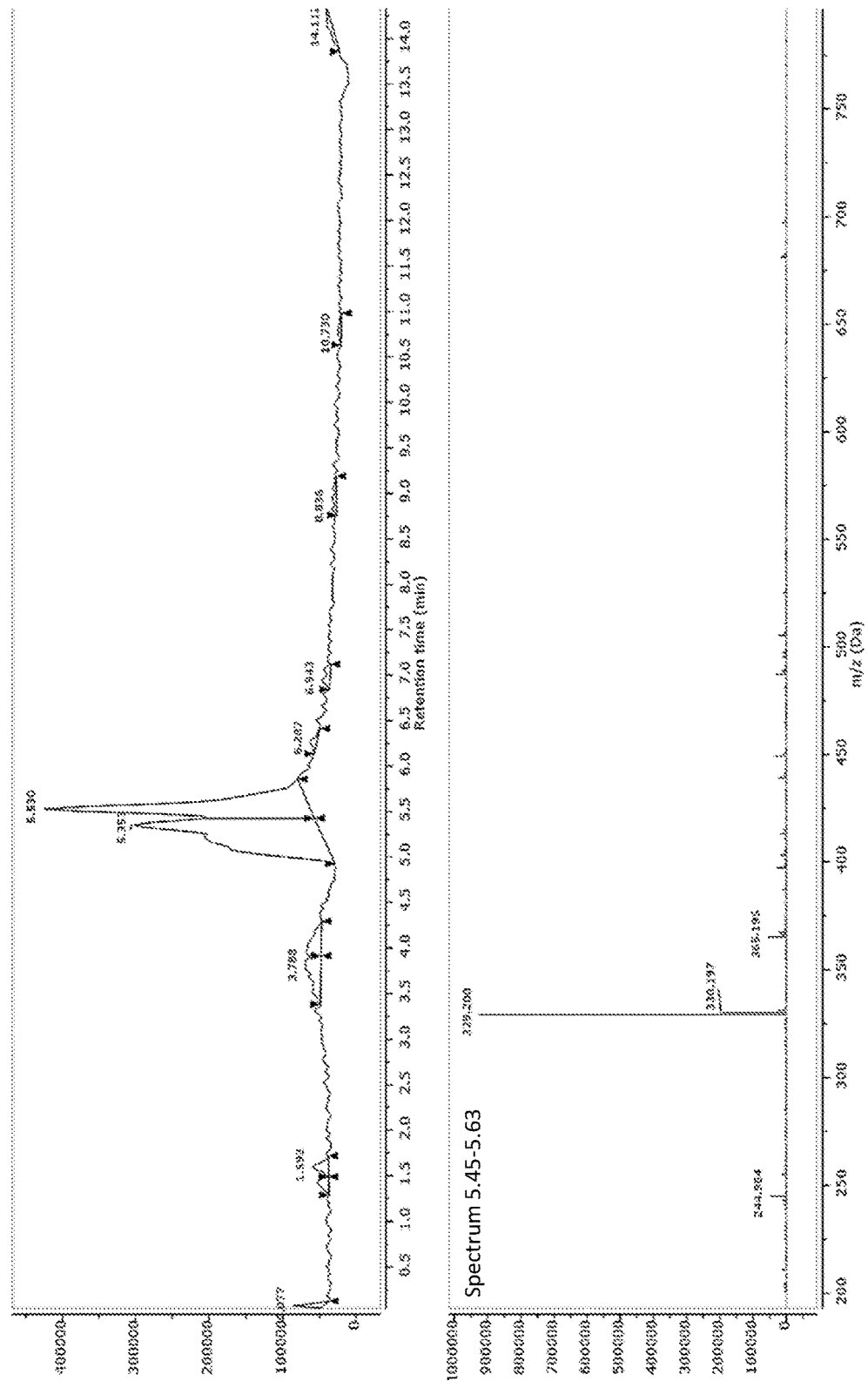

Glyceryl ester product RT=5.34-5.35 min, (m/z) 427.23 [M+Na]$^+$, 443.20 [M+K]$^+$ 403.2 [M–H]$^-$ 449 [M–H+HCOOH]$^-$ FIG. 13 shows retention time and mass spectrum for positive (FIG. 13A) and negative (FIG. 13B) LC-MS modes for 9,10,13-trihydroxy-(11E)-octadecenoic acid reacted under esterification conditions. FIG. 13C shows the negative LC-MS mode for unreacted free 9,10,13-trihydroxy-(11E)-octadecenoic acid (RT=5.53 min, (m/z) 329.20 [M–H]$^-$). The results show that the endogenous oxidized fatty acid was esterified.

133
2,2-dimethyl-13-hydroxy-9,10-trans-epoxy-(11E)-octadecenoic acid

134
4-hydroxy-DHA and 4-hydroxy-DHA lactone

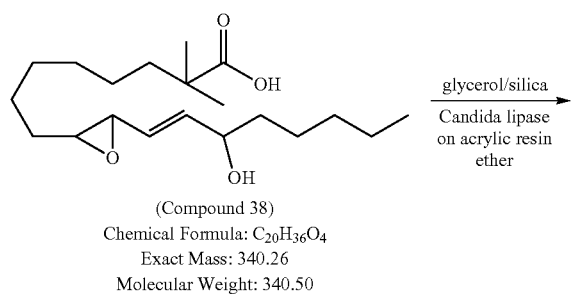

(Compound 38)
Chemical Formula: $C_{20}H_{36}O_4$
Exact Mass: 340.26
Molecular Weight: 340.50

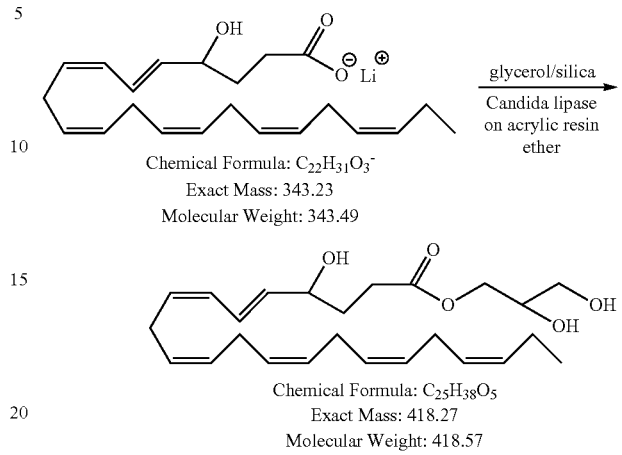

Chemical Formula: $C_{22}H_{31}O_3^-$
Exact Mass: 343.23
Molecular Weight: 343.49

Chemical Formula: $C_{25}H_{38}O_5$
Exact Mass: 418.27
Molecular Weight: 418.57

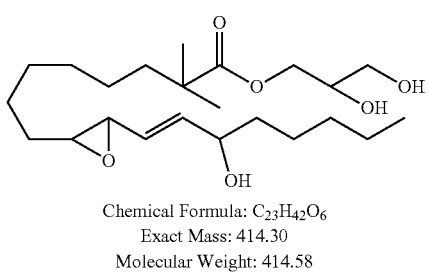

Chemical Formula: $C_{23}H_{42}O_6$
Exact Mass: 414.30
Molecular Weight: 414.58

Figure 14A:
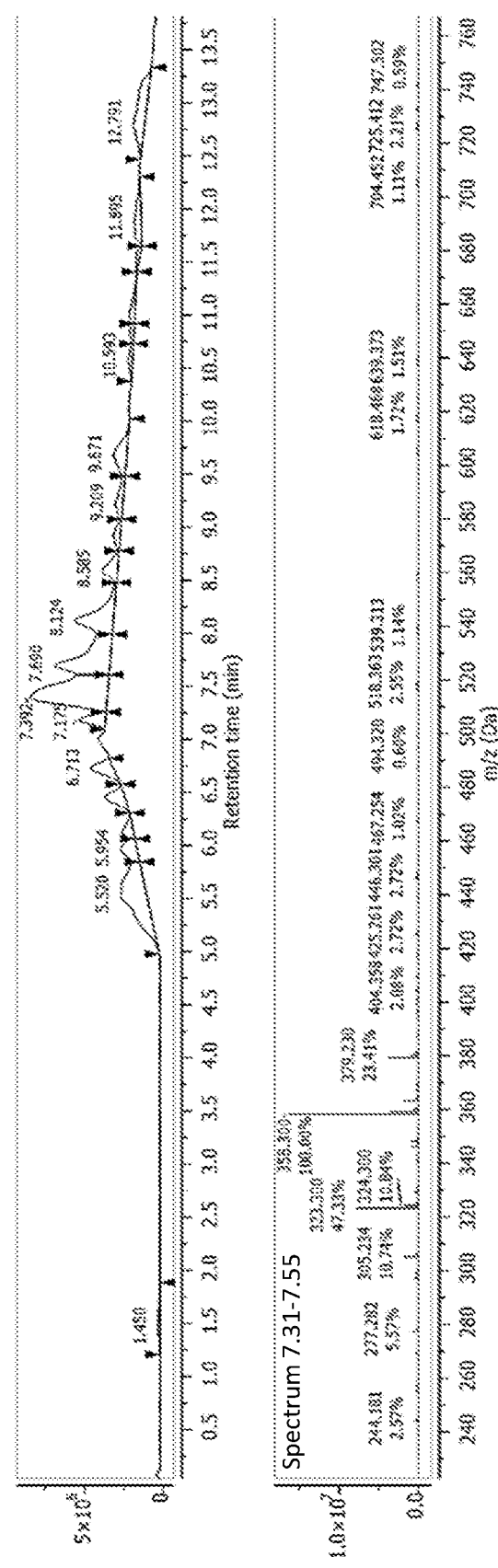
FIGS. 14A and 14B. Retention time and mass spectra obtained from LC-MS analysis of 2,2-dimethyl-13-hydroxy-9,10-trans-epoxy-(11E)-octadecenoic acid following incubation under esterification conditions.
Figure 14B:
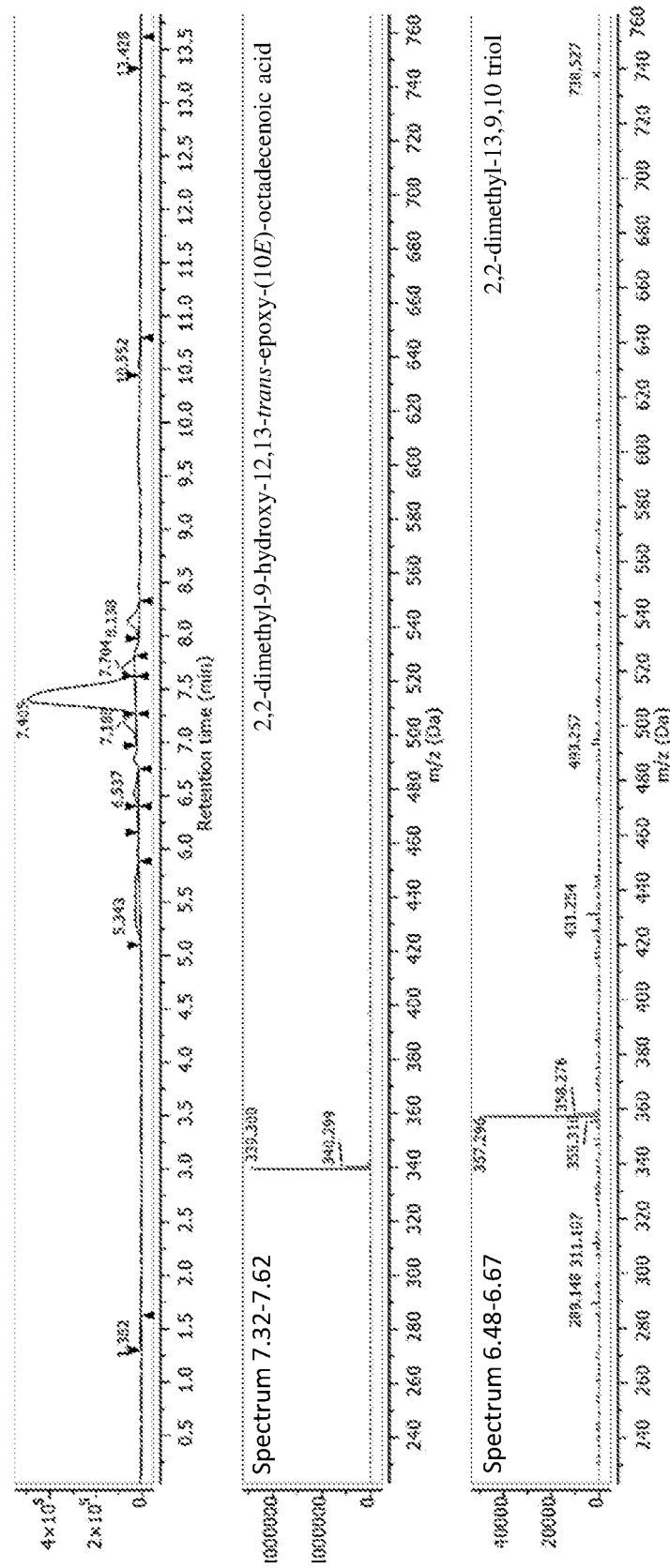

No esterification observed. Unreacted starting material RT=7.392 min, (m/z) 358.30 [M+H2O]$^+$, 323.30 [M+H−HO]$^+$ 339.30 [M−H]$^-$ FIG. 14 shows retention time and mass spectrum for positive (FIG. 14A) and negative (FIG. 14B) LC-MS modes for 2,2-dimethyl-13-hydroxy-9,10-trans-epoxy-(11E)-octadecenoic acid reacted under esterification conditions. The results show that the 2,2-dimethyl modified oxidized fatty acid was resistant to esterification.

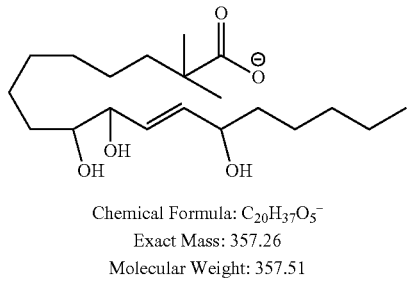 [SMILES: CCCCCC(O)/C=C/C(O)C(O)CCCCCCC(C)(C)C(=O)[O-]]

Chemical Formula: $C_{20}H_{37}O_5^-$
Exact Mass: 357.26
Molecular Weight: 357.51

The 2,2-dimethyl-13-hydroxy-9,10-trans-epoxy-(11E)-octadecenoic acid and 2,2-DM-13,9,10 triol were run as a mixture. The 2,2-dimethyl-13,9,10 triol eluted at RT=6.537 min, (m/z) 357.29 [M−H]$^-$. The results show that the 2,2-dimethyl modified oxidized fatty acid triol was resistant to esterification.

FIG. 15 shows retention time and mass spectrum for positive LC-MS mode for 4-hydroxy-DHA reacted under esterification conditions. The results show that the oxidized fatty acid rapidly undergoes internal lactonization.

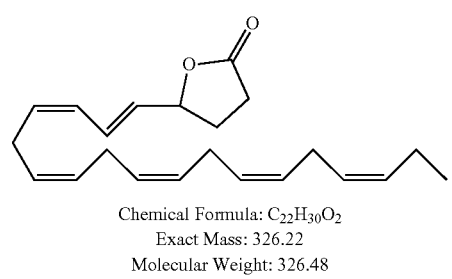 [SMILES: CC/C=C\C/C=C\C/C=C\C/C=C\C/C=C\C=C\C1CCC(=O)O1]

Chemical Formula: $C_{22}H_{30}O_2$
Exact Mass: 326.22
Molecular Weight: 326.48

4-HDHA lactone RT=8.73 min, (m/z) 327.23 [M+H]$^+$, 344.30 [M+NH4]$^+$ 2-methyl-4-hydroxy-DHA

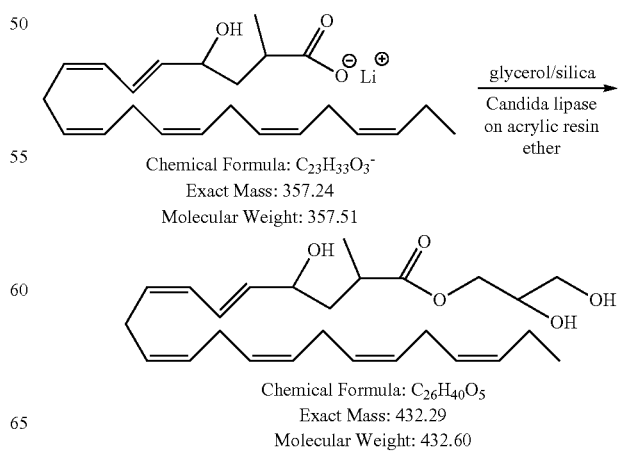

Chemical Formula: $C_{23}H_{33}O_3^-$
Exact Mass: 357.24
Molecular Weight: 357.51

Chemical Formula: $C_{26}H_{40}O_5$
Exact Mass: 432.29
Molecular Weight: 432.60

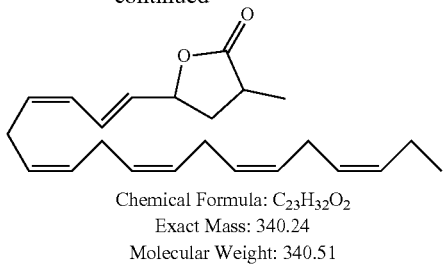

Chemical Formula: $C_{23}H_{32}O_2$
Exact Mass: 340.24
Molecular Weight: 340.51

Figure 16:
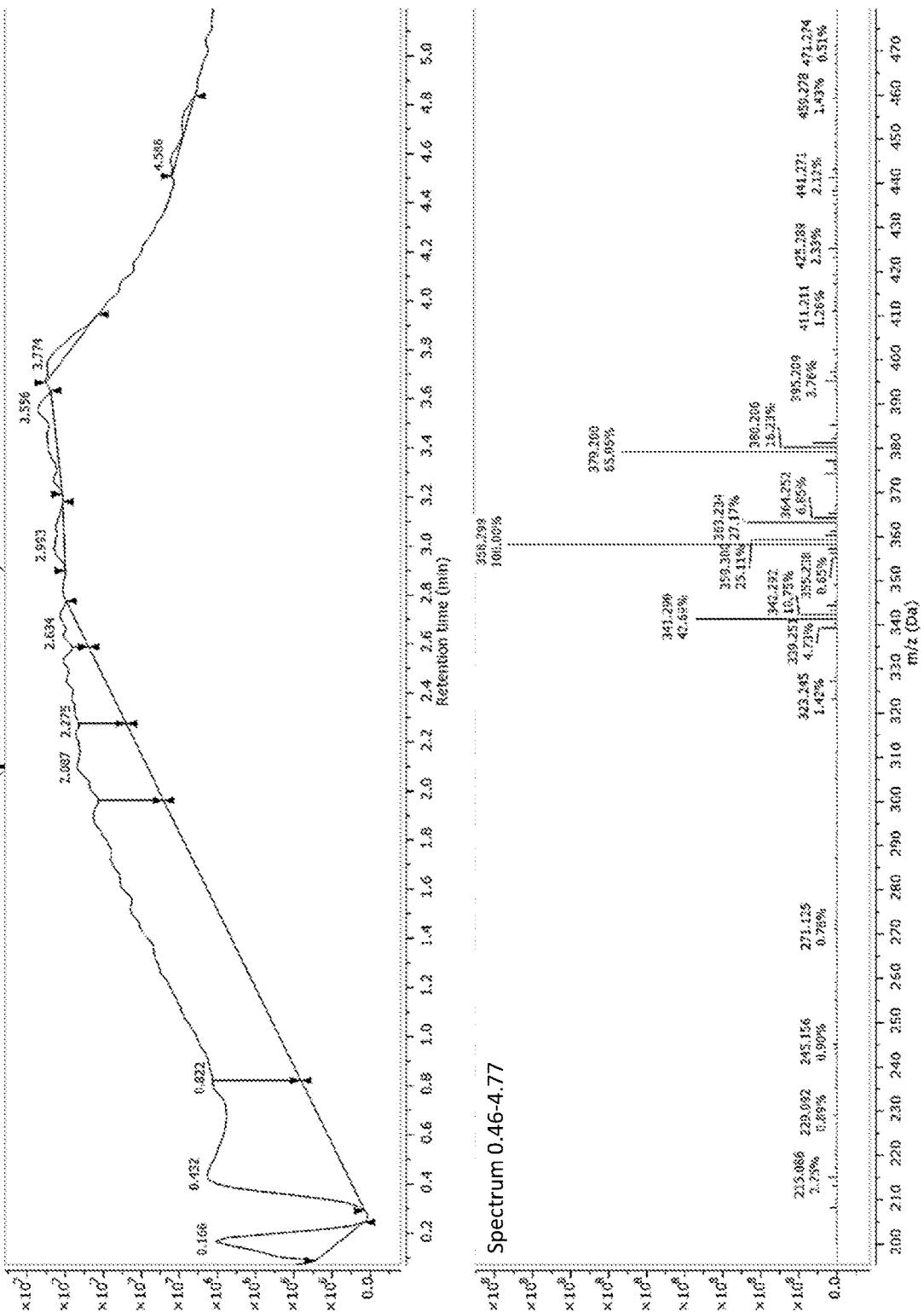
FIG. 16. Retention time and mass spectrum obtained from LC-MS analysis of 2-methyl-4-hydroxy-DHA and 2-methyl-4-hydroxy-DHA lactone following incubation under esterification conditions.

FIG. 16 shows retention time and mass spectrum for positive LC-MS mode for 2-methyl-4-hydroxy-DHA reacted under esterification conditions. The results show that the 2-methyl fatty acid analog was resistant to glycerol esterification due to competitive lactonization (direct infusion MS; (m/z) 341.30 [M+H]$^+$, 358.30 [M+H2O]$^+$, 379.2 [M+K]$^+$).

2,2-dimethyl-4-hydroxy-DHA

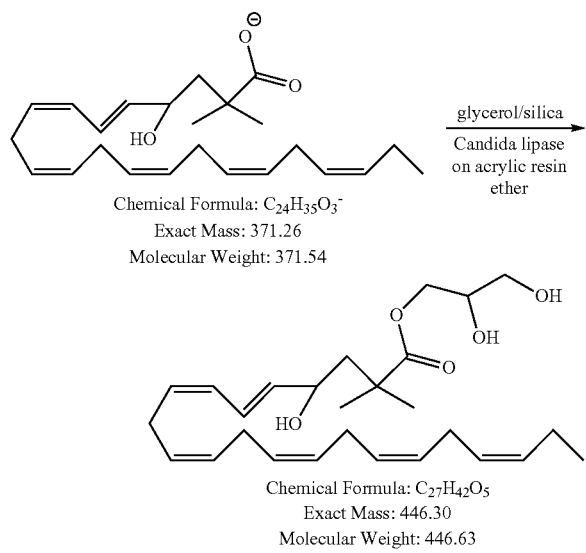

Chemical Formula: $C_{24}H_{35}O_3^-$
Exact Mass: 371.26
Molecular Weight: 371.54

Chemical Formula: $C_{27}H_{42}O_5$
Exact Mass: 446.30
Molecular Weight: 446.63

FIG. 17 shows retention time and mass spectrum for positive LC-MS mode for 2,2-dimethyl-4-hydroxy-DHA reacted under the esterification conditions. The results show that the 2,2-dimethyl 4-hydroxy-DHA analog was resistant to esterification, including internal lactonization. Unreacted starting material ran at RT=8.23 min, (m/z) 371.30 [M−H]$^-$.

The three experiments on 4-HDHA and analogs illustrate the increased reduction in esterification (including lactonization) of the 2,2-dimethyl modification compared to the 2-methyl and no modification (both of which rapidly lactonized). The 2,2-dimethyl modification thus serves to prevent esterification, including internal lactonization.

Example 39

Selective Manipulation of the Skin Free Acid and Esterified Lipid Pools Via Topical Administration of Analogs of Oxidized Derivatives of Linoleic Acid This example illustrates selective manipulation of the skin free acid and esterified lipid pools via topical administration of analogs of oxidized derivatives of linoleic acid.

Based on the observations that dietary linoleic acid deficiency and/or mutations in genes coding for linoleate hydroperoxidation and isomerization cause profound epidermal barrier dysfunction and transepidermal water loss, it was previously proposed that specific oxidized linoleic acid derivatives [13-hydroxy-9,10-epoxy-octadecenoate, 13,9,10-trihydroxy-octadecenoate and their metabolic derivatives] in the esterified lipid pool of skin are critical water barrier component (see, e.g., Zheng et al., J. Biol. Chem., 286(27):24046-24056, 2001; Munoz-Garcia et al., Biochim Biophys Acta, 1841(3):401-408, 2014; Nugteren et al., Biochim Biophys Acta, 834(3):429-436, 1985). These bioactive non-esterified lipids in the free pool may alternatively provide a chemical signal to induce water barrier formation or repair. Thus, targeted delivery of these specific oxidized lipids to either the free or esterified pool could have therapeutic implications for conditions characterized by barrier dysfunction including ichthyosis, atopic dermatitis/eczema, psoriasis, and other inflammatory or hyperproliferation conditions of skin and mucosal membranes. The results of the present studies provide proof of concept that the free pool of oxidized lipids can be selectively targeted with topical administration of the 2,2-dimethyl analog of oxidized linoleic acid metabolites, and that the esterified pool can be selectively targeted with topical administration of the free acid.

Analogs of 13-hydroxy-9,10-epoxy-octadecenoate and 9,10,13-trihydroxy-octadecenoate ("treatment") were topically applied to mice. In brief, to male, hairless mice (SKh1-e), 30 µL of treatment (10 mg/mL) was applied daily for 5 days to the same right dorsal side area, approximately 1.5×3.5 cm located 1 cm from the midline, between the shoulder and hip. The three treatment groups were 13-hydroxy-9,10-epoxy-octadecenoate-d5 (13-H-9,10-epoxy-LA-d5), 2,2-dimethyl-13-hydroxy-9,10-epoxy-octadecenoate, and a mixture containing 2,2-dimethyl-13-hydroxy-9,10-epoxy-octadecenoate and 2,2-dimethyl-9,10,13-trihydroxy-octadecenoate. On the sixth day, skin samples (0.02-0.05 g) were collected from within the treatment area and immediately frozen.

Skin samples were added to 7 ml ck50mix Precellys lysis tubes. Samples were shaken with a Precellys that was attached to a cryolys (Bertin Corp) for 6 cycles 10 s in length at 8000 rpm (2 min pause between cycles). A known amount of LTB4-d4 (Cayman Chemical) was added to each ground up skin sample and each sample was extracted from the lysis tube with 500 of ice cold methanol that contained (EDTA and BHT) into a new microcentrifuge tube. Emphasis was placed on ensuring all visible solid pieces of skin were extracted and another 500 of methanol (containing BHT and EDTA) was added to the original lysis tube to extract remainder of the sample. Extracts were stored in −80° C. for 2 hours and spun on a centrifuge to precipitate the proteins. Supernatant was collected and half was stored immediately in −80° C. under nitrogen gas. The remainder was hydrolyzed with sodium carbonate for 30 min (with acetic acid used to stop the reaction) and then stored under N$_2$ at −80° C. All samples were purified with solid phase extraction using a Phenomenex Strata X column where 10% methanol was used to load samples onto the columns and wash the columns. Samples were eluted with methanol containing BHT, dried under N$_2$ gas and reconstituted into GC vials.

LC-MS results are shown in FIG. 19. Compounds that were applied as epoxides were measured as their corresponding trihydroxy hydrolysis products due to presumed epoxide lability to skin pH. The 13-H-9,10-epoxy-octadecenoate-d5 was found in 4× greater abundance in the total pool than in the free pool, indicating that most of the sample that was applied topically had been incorporated into esterified (structural) lipids. The 2,2-dimethyl-13-H-9,10-epoxy-octadecenoate was found to be approximately equal in both the total and the free pools, indicating minimal to no esterification (FIG. 19).

Figure 19A:
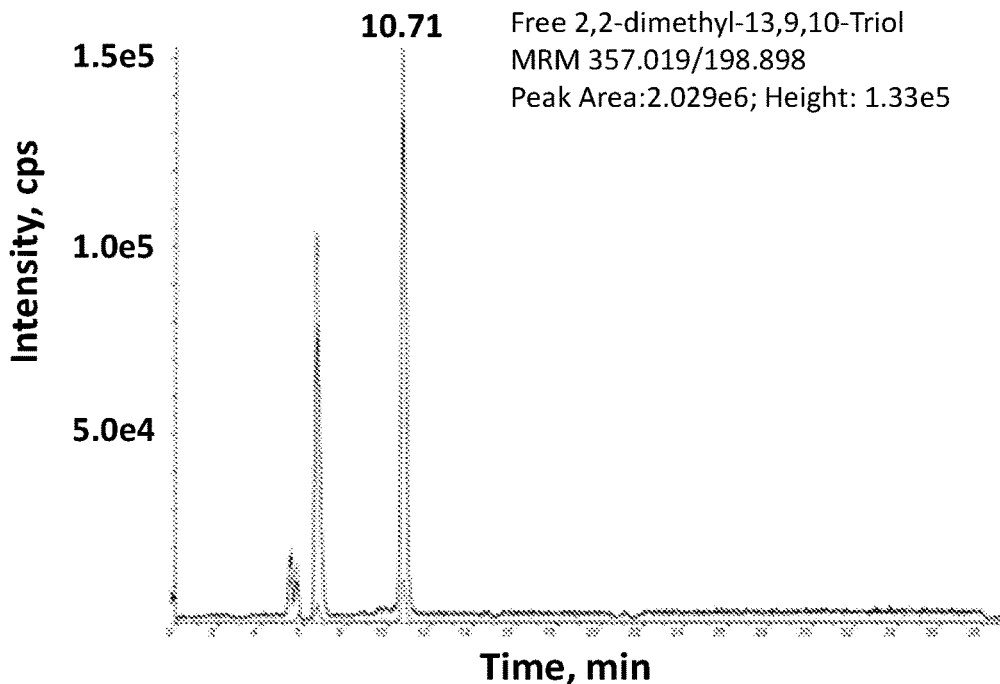
FIGS. 19A-19D. Selective manipulation of the skin free acid and esterified lipid pools via topical administration of a 2,2-dimethyl stable analog of oxidized derivatives of linoleic acid and labeled free acids. Topical administration of a 2,2-dimethyl derivative of an oxidized linoleic acid [2,2-dimethyl-13-hydroxy-9,10-epoxy-octadecenoate] to mouse skin selectively increased the 2,2-dimethyl-13,9,10-trihydroxy-octadecenaote derivative exclusively in the free acid pool without substantial incorporation into esterified lipids. This is evidenced by comparable peak areas for 2,2-dimethyl-13,9,10-trihydroxy-linoleate in the free acid pool (FIG. 19A) versus the total (free plus esterified) lipid pool (FIG. 19B). By contrast, topical administration of d5 labeled free acid of 13-hydroxy-9,10-epoxy-octadecenoate produced a major increase in its d5-13,9,10-trihydroxy-octadecenoate derivative in the total pool (FIG. 19D) compared to the free pool (FIG. 19C).
Figure 19B:
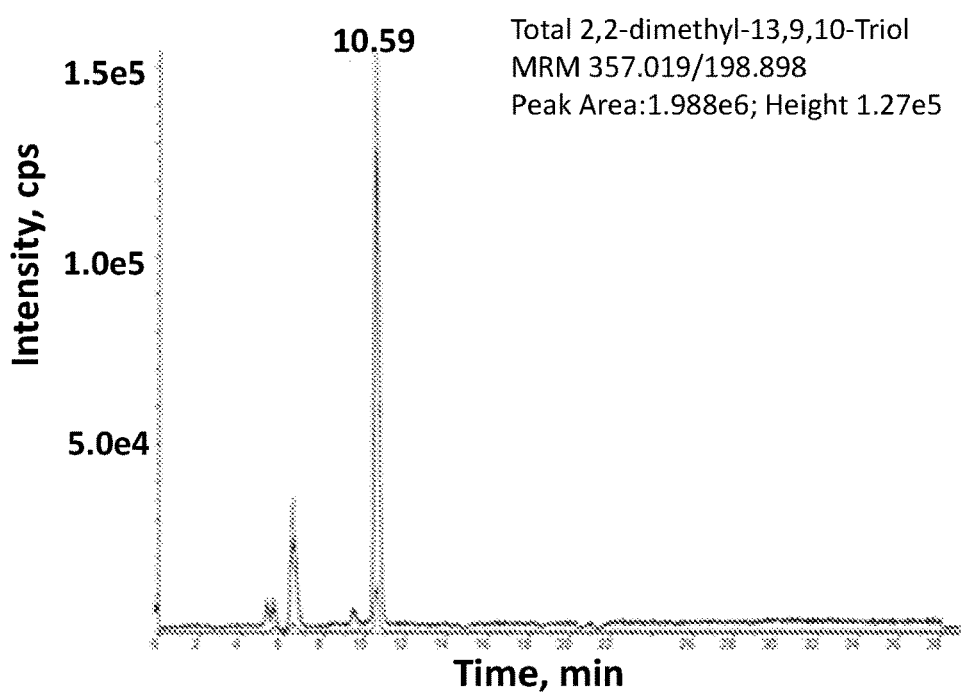
Figure 19C:
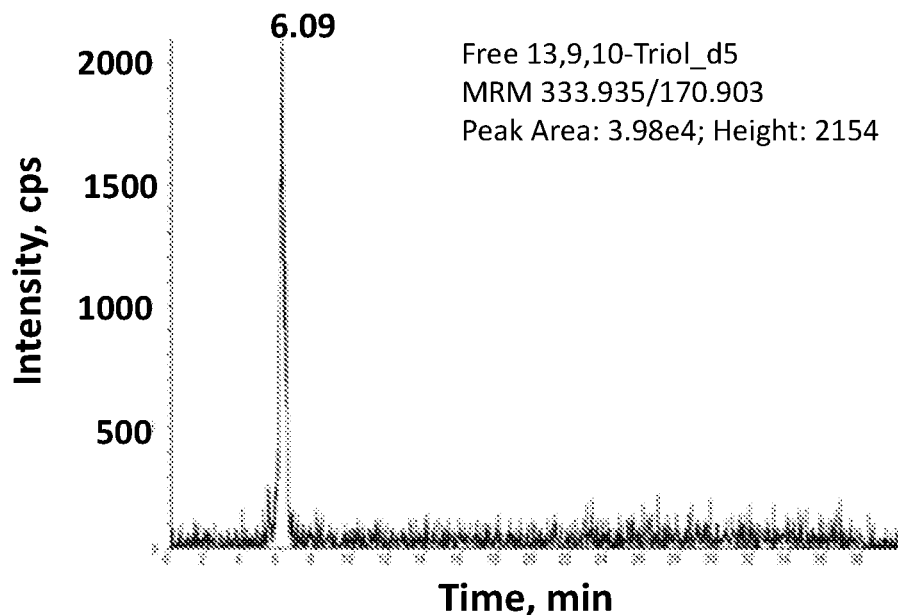
Figure 19D:
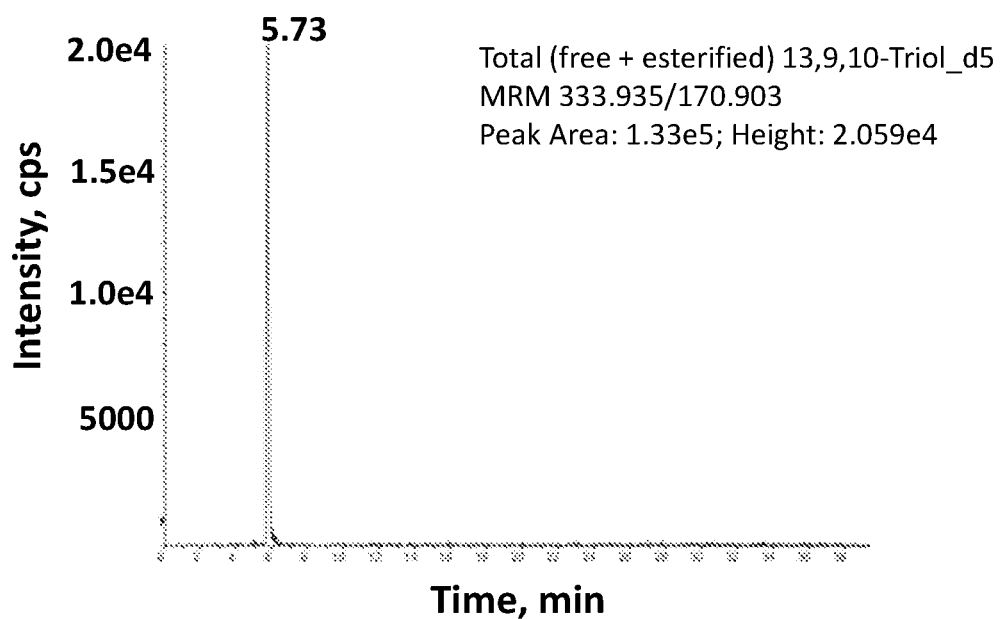

Endogenous oxidized linoleic acid derivatives are proposed to play essential roles in the formation of the epidermal water barrier by either: (1) acting as an essential structural component of esterified lipids forming the barrier; or (2) acting as labile, bioactive molecules that provide a chemical signal to induce water barrier formation (see, e.g., Zheng et al., J. Biol. Chem., 286(27):24046-24056, 2001; Munoz-Garcia et al., Biochim Biophys Acta, 1841(3):401-408, 2014; Nugteren et al., Biochim Biophys Acta, 834(3): 429-436, 1985). Here it is demonstrated that topical administration of a 2,2-dimethyl derivative of an oxidized linoleic acid [2,2-dimethyl-13-hydroxy-9,10-epoxy-octadecenoate] selectively increased the 2,2-dimethyl-13,9,10-trihydroxy-linoleate derivative exclusively in the free acid pool without substantial incorporation into esterified lipids. This is evidenced by comparable peak areas for 2,2-dimethyl-13,9,10-trihydroxy-linoleate in the free acid (FIG. 19A) pool versus the total (free plus esterified) lipid pool (FIG. 19B). By contrast, topical administration of d5 labeled free acid of 13-hydroxy-9,10-epoxy-octadecenoate (13-H-9,10-epoxy-LA-d5) produced a major increase in 13,9,10-trihydroxy-linoleate-d5 (9,10,13-trihydroxy-LA-d5) derivative in the total pool (FIG. 19D) compared to the free pool (FIG. 19C). Collectively, these in vivo findings show that: (1) addition of the 2,2-dimethyl moiety to an oxidized fatty acid prevents esterification allows for selective manipulation of the free acid pool in skin; and (2) that specific oxidized linoleic acid metabolites [13-hydroxy-9,10-epoxy-octadecenoate and 13,9,10-trihydroxy-octadecenoate] that are proposed to play key structural roles in the water barrier formation can be targeted to the esterified, structural lipid pool via topical administration of their free acids. Thus, both the free and esterified lipid pools can be selectively altered via topical administration of synthesized oxidized lipids or their stable analogs.

It will be apparent that the precise details of the methods or compositions described may be varied or modified without departing from the spirit of the described embodiments. We claim all such modifications and variations that fall within the scope and spirit of the claims below.

We claim:

1. A compound, or a stereoisomer, tautomer, or pharmaceutically acceptable salt thereof, having a structure according to:

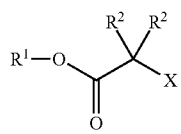

(CXI)

wherein
X is halogenated alkenyl or deuterium-substituted alkenyl, from 10-25 carbons in length and is substituted with one or more hydroxyl or carbonyl substitutions;
$R^1$ is hydrogen or $C_1$-$C_{10}$ alkyl; and
each $R^2$ is methyl.

2. A compound, or a stereoisomer, tautomer, or pharmaceutically acceptable salt thereof, having a structure according to any one of formulas:

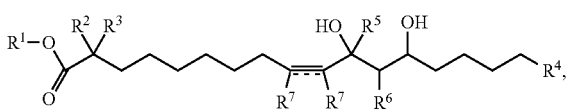
(X)

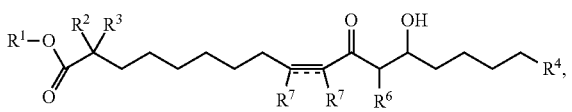
(XI)

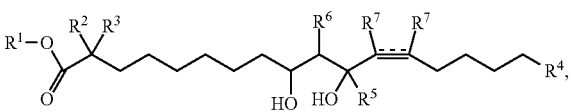
(XII)

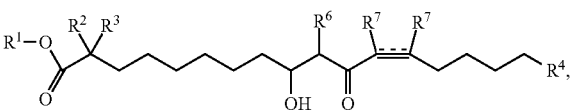
(XIII)

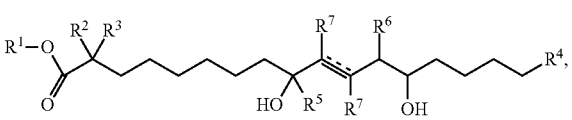
(XIV)

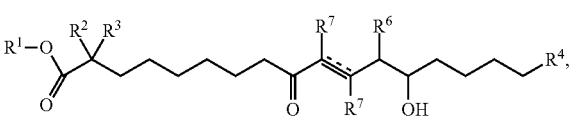
(XV)

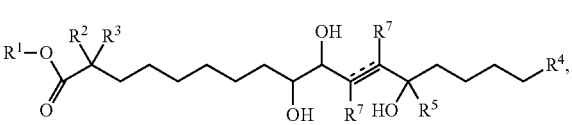
(XVI)

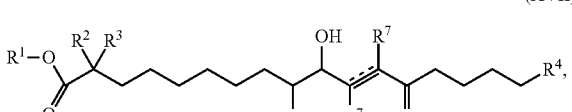
(XVII)

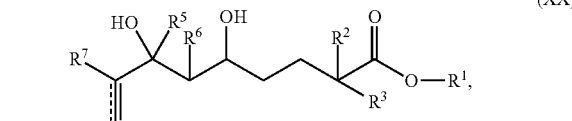
(XX)

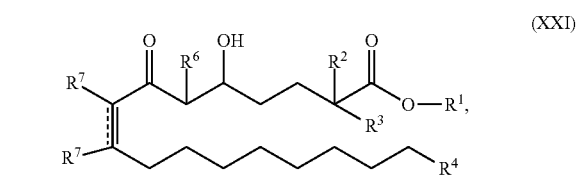
(XXI)

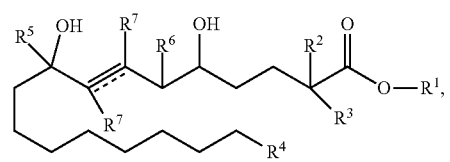
(XXIV)
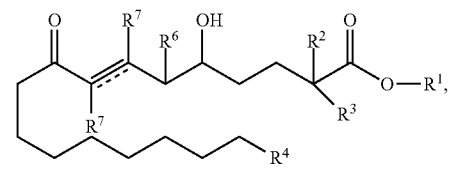
(XXV)
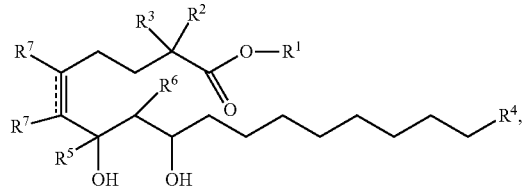
(XXVIII)
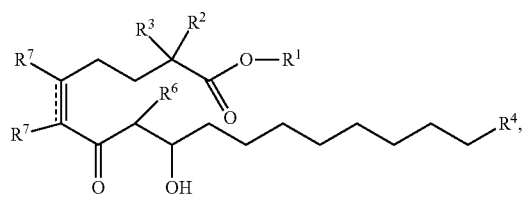
(XXIX)
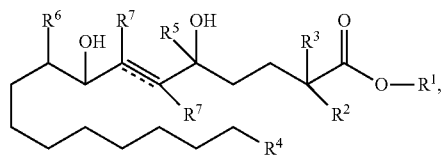
(XXXII)
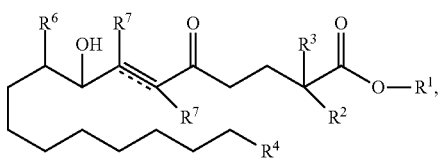
(XXXIII)
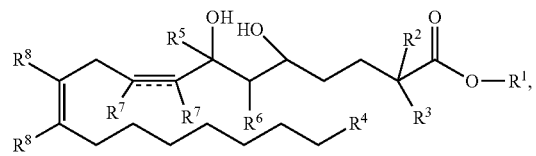
(XXXVI)
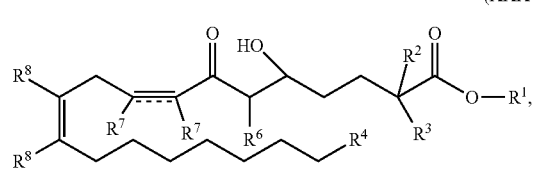
(XXXVII)
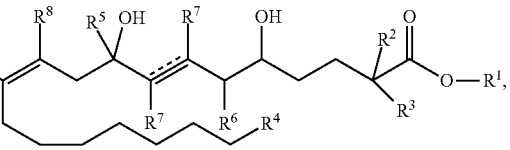
(XL)
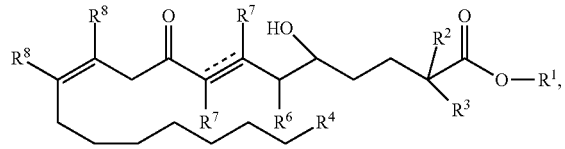
(XLI)
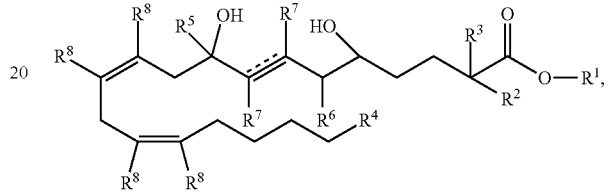
(XLIV)
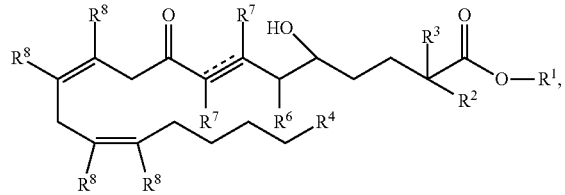
(XLV)
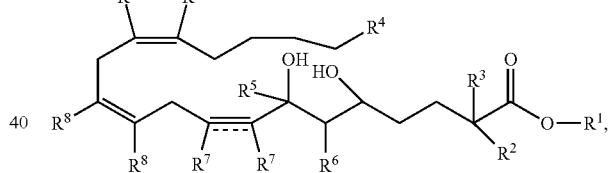
(XLVIII)
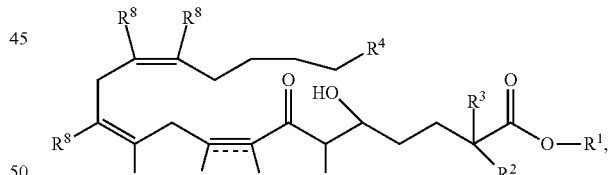
(XLIX)
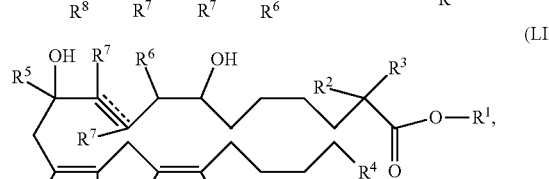
(LII)
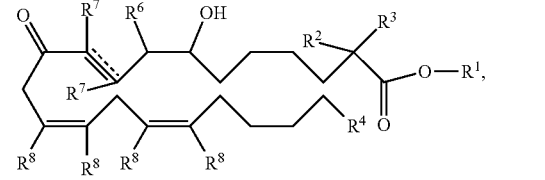
(LIII)

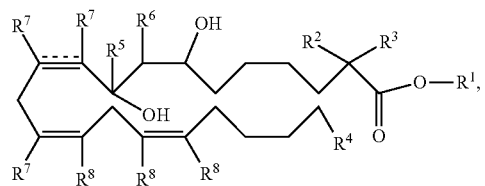
(LVI)
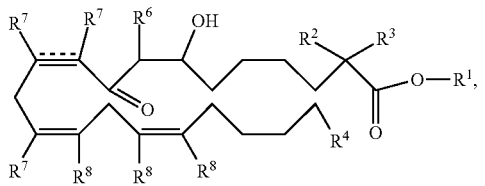
(LVII)
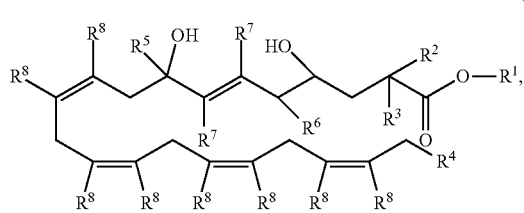
(LX)
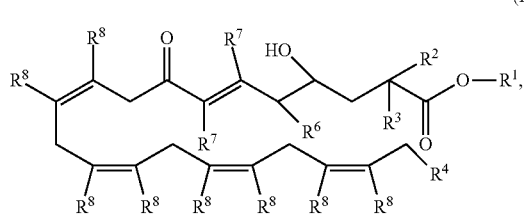
(LXI)
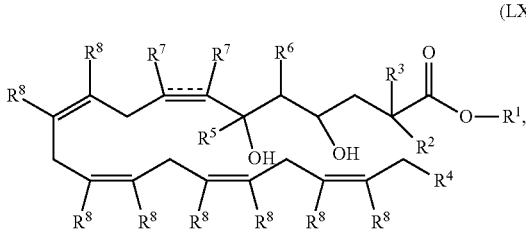
(LXIV)
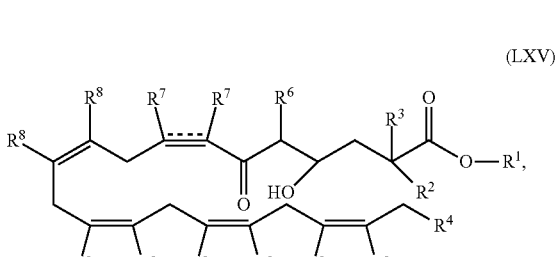
(LXV)
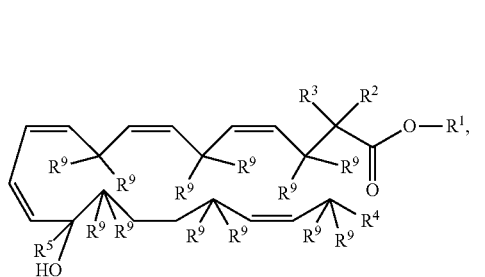
(LXVI)
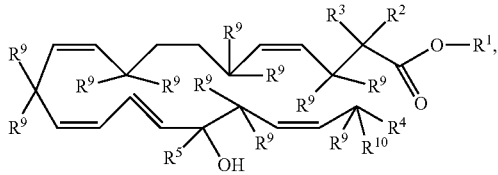
(LXVIII)
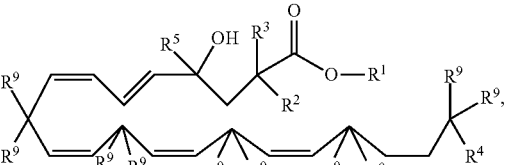
(LXX)
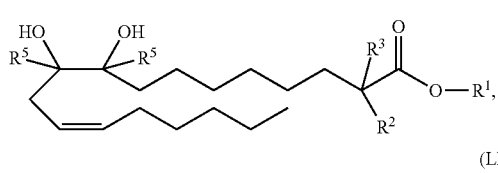
(LXXI)
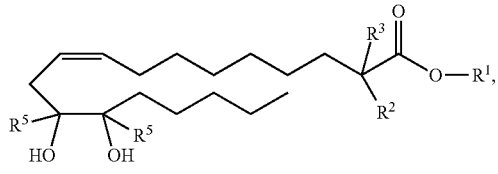
(LXXII)
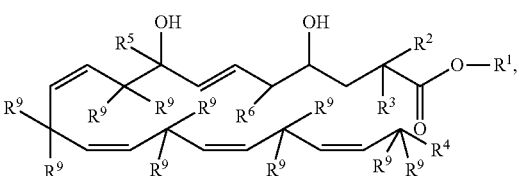
(LXXIX)
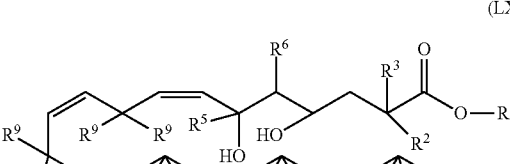
(LXXX)
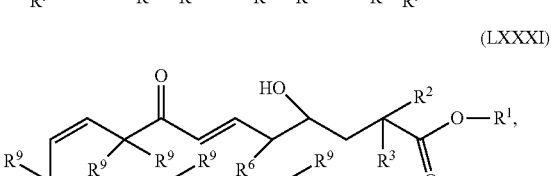
(LXXXI)
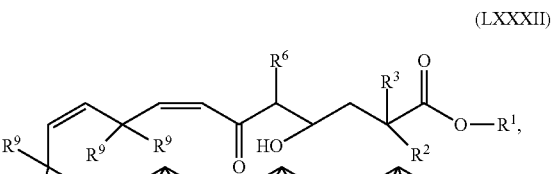
(LXXXII)

-continued (LXXXVII)
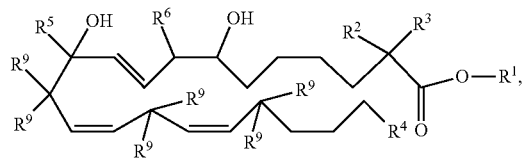

(LXXXVIII)
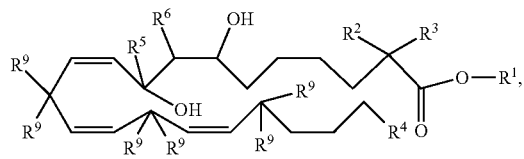

(LXXXIX)
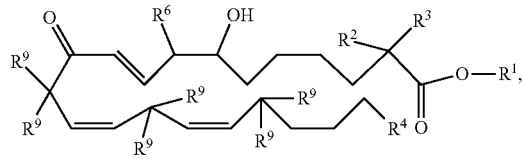

(XC)
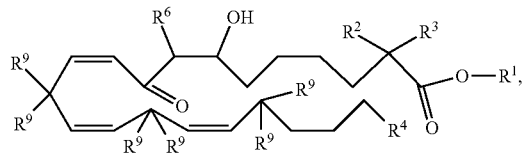

(XCV)
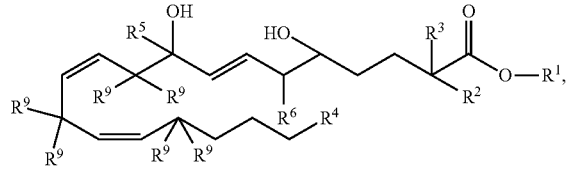

(XCVI)
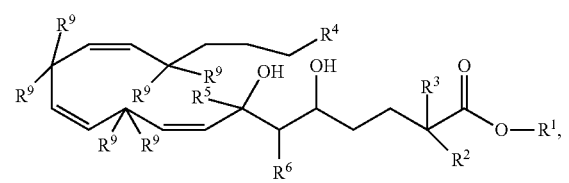

(XCVII)
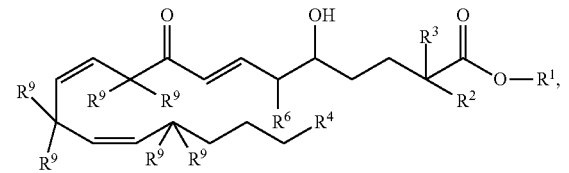

(XCVIII)
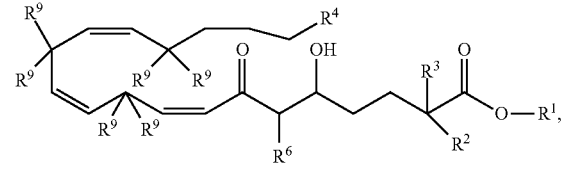

-continued (CI)
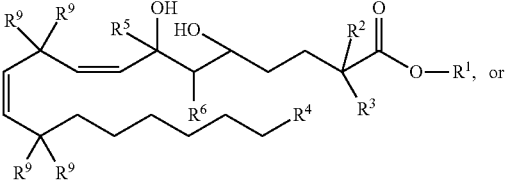

(CII)
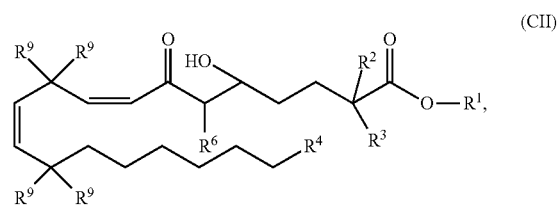

wherein $R^1$ is hydrogen or $C_1$-$C_{10}$ alkyl, $R^2$ and $R^3$ independently are $C_1$-$C_{10}$ alkyl, $R^4$ is $C_1$-$C_{10}$ alkyl, $R^5$ is hydrogen, $R^6$ is hydroxyl, each $R^7$ is independently hydrogen or is not present and the adjacent carbon atoms form an alkyne, and, if present, each $R^8$ is independently hydrogen or fluoride, and each $R^9$ is independently hydrogen or deuterium.

3. A compound, or a stereoisomer, tautomer, or pharmaceutically acceptable salt thereof, wherein the compound is:

(45)
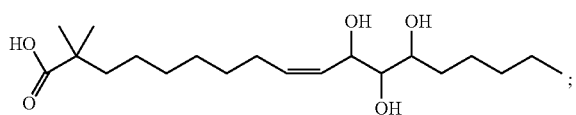

(46)
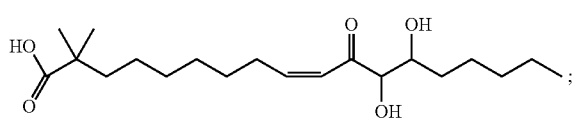

(52)
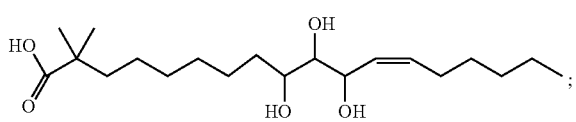

(53)
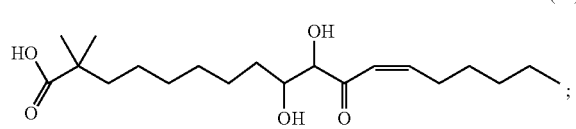

(59)
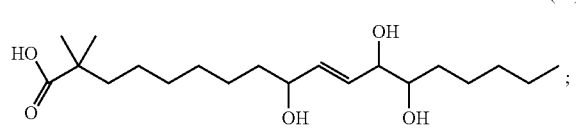

-continued
(60)
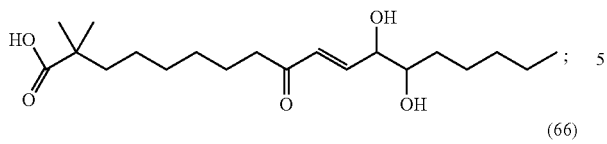
(66)
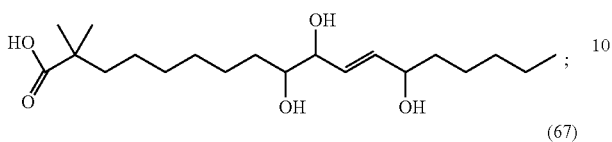
(67)
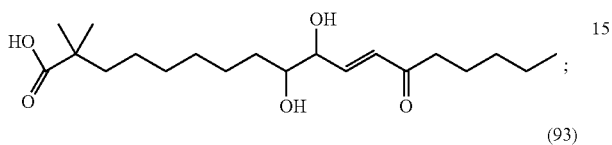
(93)
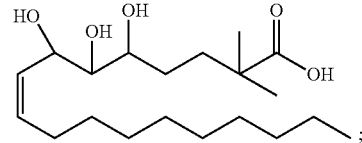
(94)
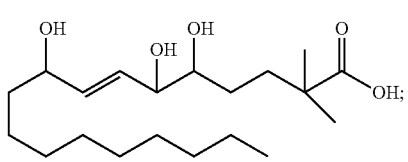
(104)
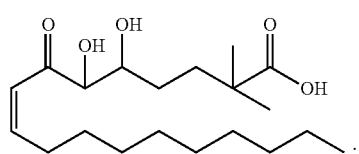
(107)
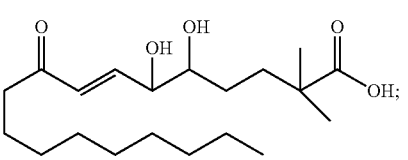
(128)
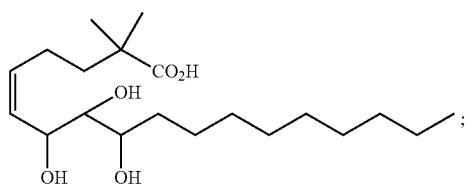
(131)
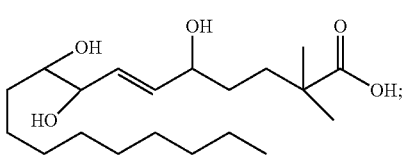
(134)
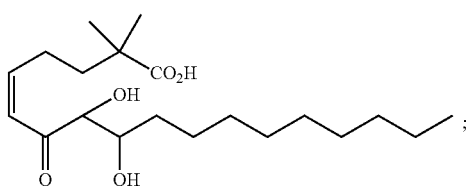
-continued
(137)
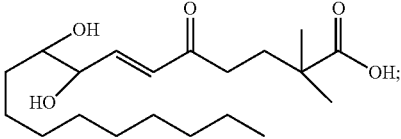
(200)
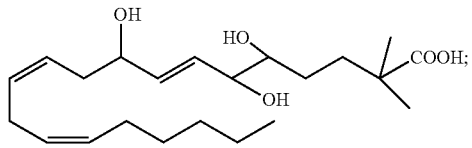
(203)
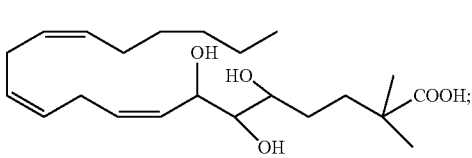
(212)
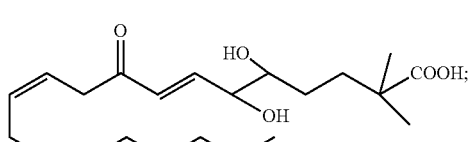
(215)
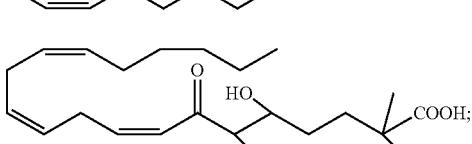
(240)
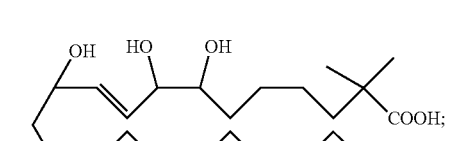
(252)
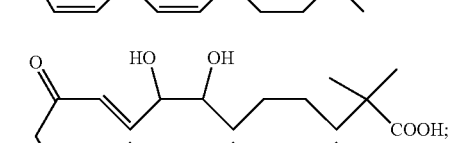
(255)
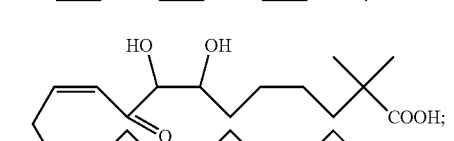
(257)
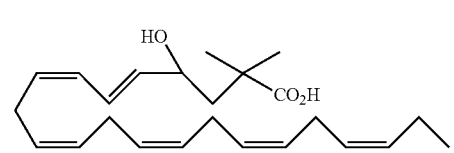
(314)
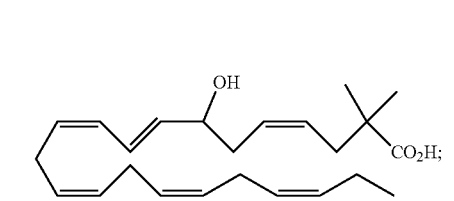

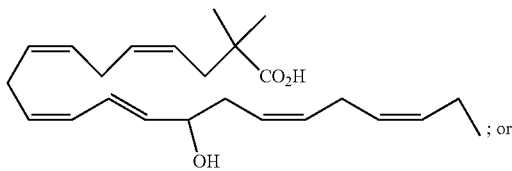
(317)

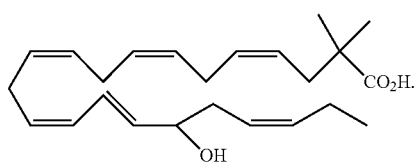
(320)

4. A compound, or a stereoisomer, tautomer, or pharmaceutically acceptable salt thereof, having a structure according to one of:

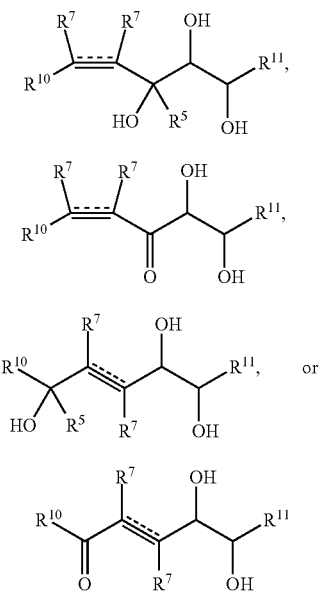

wherein:
R$^5$ is hydrogen, C$_1$-C$_{10}$ alkyl, or halide;
each R$^7$ is independently hydrogen or fluoride or not present and the adjacent carbons form alkyne; and
R$^{10}$ and R$^{11}$ are independently C$_1$-C$_{10}$ aliphatic.

5. A pharmaceutical composition comprising a compound of claim 1 and a pharmaceutically acceptable carrier.

6. The pharmaceutical composition of claim 5, formulated for topical, parenteral, or oral administration.

7. The compound of claim 2, having a structure according to formula LXX:

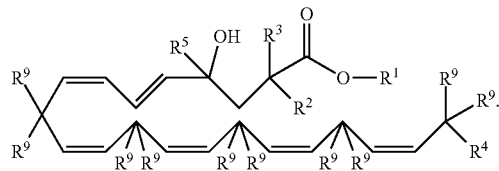
(LXX)

8. The compound of claim 7, wherein R$^1$ is hydrogen.

9. The compound of claim 7, wherein R$^2$, R$^3$, and R$^4$ are methyl.

10. The compound of claim 1, wherein X is substituted with one or more hydroxyl substitutions.

11. The compound of claim 1, wherein X is 15, 16, 17, 18, 19, 20, 21, 22, 23, 24, or 25 carbons in length.

12. A compound, or a stereoisomer, tautomer, or pharmaceutically acceptable salt thereof, having a structure according to:

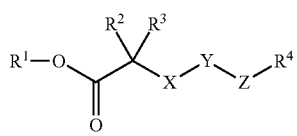
(I)

wherein
X is aliphatic from 1-16 carbons in length,
Z is aliphatic from 1-16 carbons in length, or is not present,
Y is selected from

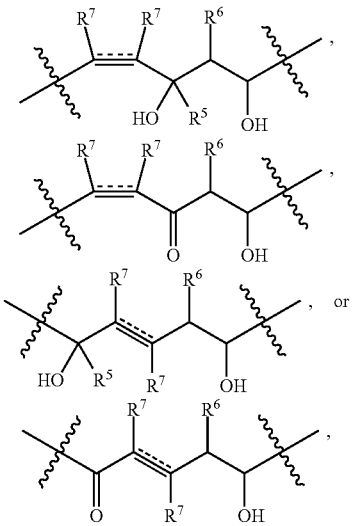

R$^1$ is hydrogen or C$_1$-C$_{10}$ alkyl;
R$^2$ and R$^3$ independently are C$_1$-C$_{10}$ alkyl;
R$^4$ is C$_1$-C$_{10}$ alkyl;
R$^5$ is hydrogen;
R$^6$ is hydroxyl; and
each R$^7$ is independently hydrogen or is not present and the adjacent carbon atoms form an alkyne.

13. A pharmaceutical composition comprising a compound of claim 12 and a pharmaceutically acceptable carrier.

14. The pharmaceutical composition of claim 13, formulated for topical, parenteral, or oral administration.

15. A pharmaceutical composition comprising a compound of claim 2 and a pharmaceutically acceptable carrier.

16. The pharmaceutical composition of claim 15, formulated for topical, parenteral, or oral administration.

* * * * *